(12) United States Patent
Arancio et al.

(10) Patent No.: US 7,947,279 B2
(45) Date of Patent: May 24, 2011

(54) PEPTIDE HAVING HYDROLASE ACTIVITY

(75) Inventors: Ottavio Arancio, New York, NY (US); Michael L. Shelanski, Brooklyn, NY (US); Bing Gong, Fort Lee, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 11/477,771

(22) Filed: Jun. 29, 2006

(65) Prior Publication Data

US 2007/0071724 A1  Mar. 29, 2007

Related U.S. Application Data

(60) Provisional application No. 60/695,303, filed on Jun. 30, 2005.

(51) Int. Cl.
*A61K 39/00* (2006.01)
*A61K 39/385* (2006.01)
*C07K 1/00* (2006.01)

(52) U.S. Cl. ............... 424/185.1; 424/192.1; 424/194.1; 530/350

(58) Field of Classification Search .................. None
See application file for complete search history.

(56) References Cited

U.S. PATENT DOCUMENTS

| | | | |
|---|---|---|---|
| 5,652,122 | A | 7/1997 | Frankel et al. |
| 5,670,617 | A | 9/1997 | Frankel et al. |
| 5,672,344 | A | 9/1997 | Kelley et al. |
| 5,753,502 | A | 5/1998 | Kilgannon et al. |
| 6,329,171 | B1 | 12/2001 | Kapeller-Libermann |
| 6,451,994 | B1 | 9/2002 | Kapeller-Libermann et al. |
| 6,504,010 | B1 * | 1/2003 | Wang et al. .................. 530/350 |
| 6,589,503 | B1 | 7/2003 | Piwnica-Worms |
| 6,610,287 | B1 | 8/2003 | Breakefield et al. |
| 6,841,535 | B2 | 1/2005 | Divita et al. |
| 6,900,044 | B2 | 5/2005 | Kapeller-Libermann |
| 2003/0037350 | A1 | 2/2003 | Glucksmann et al. |
| 2003/0082785 | A1 | 5/2003 | Libermann et al. |
| 2003/0100020 | A1 | 5/2003 | Meyers |
| 2003/0166244 | A1 | 9/2003 | Kapeller-Libermann et al. |
| 2004/0093630 | A1 | 5/2004 | Huh et al. |

FOREIGN PATENT DOCUMENTS

| | | |
|---|---|---|
| WO | WO-01/23589 A2 | 4/2001 |
| WO | WO-01/66763 C2 | 9/2001 |
| WO | WO-02/063031 A2 | 8/2002 |

OTHER PUBLICATIONS

Aarts et al., "Treatment of ischemic brain damage by perturbing NMDA receptor-PSD-95 proteins interactions," Science, vol. 298, pp. 846-850 (2002).
Akli et al., Nat. Genetics, vol. 3, pp. 224-228 (1993).
Almeida et al., "Beta-amyloid accumulation impairs multivesicular body sorting by inhibiting the ubiquitin-proteasome system," J Neurosci, vol. 26, pp. 4277-4288 (2006).
Antonova et al., "Rapid Increase in clusters of presynaptic proteins at onset of long-lasting potentiation," Science, vol. 294, pp. 1547-1550 (2001).
Araki et al., "Transgenic mouse lines expressing synatopHuorin in hippocampus and cerebellar cortex," Genesis, vol. 42, pp. 53-60 (2005).
Aravamudan et al., "Synaptic *Drosophila* UNC-13 is regulated by antagonistic G-protein pathways via a proteasome-dependent degradation mechanism," J. Neurobiol, vol. 54, pp. 417-438 (2003).
Arendash et al., "Progressive, age-related behavioral impairments in transgenic mice carrying both mutant amyloid precursor protein and presenilin-1 transgenes," Brain Res, vol. 891, pp. 42-53 (2001).
Arnaud et al., "Regulation of protein tyrosine kinase signaling by substrate degradation during brain development," Mol Cell Biol, vol. 23, pp. 9293-9302 (2003).
Barad et al., "Rolipram, a type IV-specific phosphodiesterase Inhibitor, facilitates the establishment of long-lasting ptotentiation and improves memory," Proc. Natl Acad Sci USA, vol. 95, pp. 15020-15025 (1998).
Barka et al., "Transduction of TAT-HA-beta-galactosidase fusion protein into salivary gland-derived cells and organ cultures of the developing gland, and into rat submandibular gland in vivo," J Histochem Cytochem, vol. 48, pp. 1453-1460 (2000).
Becker-Hapak et al., "TAT-mediated protein transduction into mammalian cells," Methods, vol. 24, pp. 247-256 (2001).
Bence et al., "Impairment of the ubiquitin-proteasome system by protein aggregation," Science, vol. 292, pp. 1552-1555 (2001).
Bock et al., "Apolipoprotein E receptors are required for reelin-Induced proteasomal degradation of the neuronal adaptor protein disabled-1," J Biol Chem, vol. 279, pp. 33471-33479 (2004).
Bourtchouladze et al., "A mouse model of Rubinstein-Taybi syndrome: defective long-term memory is ameliorated by inhibitors of phosphodiesterase 4," Proc Natl Acad Sci USA, vol. 100, pp. 10518-10522 (2003).
Bourtchuladze et al., "Deficient long-term memory in mice with a targeted mutation of the cAMP-responsive element-binding protein," Cell, vol. 79, pp. 59-68 (1994).
Buono et al., "Diverse human aldolase C gene promoter regions are required to direct specific Lacz expression in the hippocampus and purkinje cells of transgenic mice," FEBS Lett, vol. 578, pp. 337-344 (2004).
Cao et al., "In vivo Delivery of a Bcl-xL Fusion Protein Containing the TAT Protein Transduction Domain Protects against Ischemic BRain Injury and Neuronal Apoptosis," J Neurosci, vol. 22, pp. 5423-5431 (2002).
Chain et al., "Mechanisms for generating the autonomous cAMP-dependent protein kinase required for long-term facilitation in Alpysia," Neuron vol. 22, pp. 147-156 (1999).
Chain et al., "Ubiquitin-mediated proteolysis in learning and memory," Mol Neurobiol, vol. 20, pp. 125-142 (1999).

(Continued)

*Primary Examiner* — Olga N Chernyshev
(74) *Attorney, Agent, or Firm* — Wilmer Cutler Pickering Hale and Dorr, LLP

(57) ABSTRACT

The invention is directed to methods for increasing learning and memory in a subject with a neuropathological condition, specifically a condition related to elevated beta-amyloid deposition, the method comprising administering to the subject an effective amount of a compound capable of increasing the activity of Uch-L1. The invention is also directed to screening methods for identifying compounds that enhance the activity of the proteasome system, Uch-L1, or both.

8 Claims, 77 Drawing Sheets

OTHER PUBLICATIONS

Chen et al., A novel mechanism for the regulation of amyloid precursor protein metabolism, J. Cell Biol, vol. 158, pp. 79-89 (2002).
Choi et al., "Oxidative modifications and down-regulation of ubiquitin carboxyl-terminal hydrolase LI assocaited with idiopathic Parkinson's and Alzheimer's diseases," J Biol Chem, vol. 279, pp. 13256-13264 (2004).
Ciechanover et al., "The ubiquitin proteeasome system in neurodegenerative diseases: sometimes the chicken, sometimes the egg," Neuron, vol. 40, pp. 427-446 (2003).
Coleman et al., Physiol. Genomics, vol. 12, pp. 221-228 (2003).
Cui et al., Neuroreport, vol. 16, pp. 575-579 (2005).
Cullen et al., "Block of LTP in rat hippocampus in vivo by beta-amyloid precursor protein fragments," Neuroreport, vol. 8, pp. 3213-3217 (1997).
Dang et al., "Kinetic and mechanistic studies on the hydrolysis of ubiquitin C-terminal 7-amido-4-methylcoumarin by deubiquitinating enzymes," Biochemistry, vol. 37, pp. 1868-1879 (1998).
Davidson et al., "Highly efficient small interfering RNA delivery to primary mammalian neurons induces microRNA-like effects before mRNA degradation," J Neurosci, vol. 24, pp. 10040-10046 (2004).
de Vrij et al., "Protein quality control in Alzheimer's disease by the ubiquitin proteasome system," Prog Neurobiol, vol. 74, pp. 249-270 (2004).
Di Rosa et al., "Calpain inhibitors: a treatment for Izheimer's disease," J Mol Neurosci, vol. 19, pp. 135-141 (2002).
Dineley et al., "Beta-amyloid activates the mitogen-activated protein kinase cascade via hippocampal alpha7 nicotinic acetylcholine receptors: In vitro and in vivo mechanisms related to Alzheimer's disease," J Neurosci, vol. 21, pp. 4125-4133 (2001).
Dineley et al., "Accelerated plaque accumulation, associative learning deficits, and up-regulation of alpha 7 nicotinic receptor protein in transgenic mice co-expressing mutant human presenilin 1 and amyloid precursor proteins," J Biol Chem, vol. 277, pp. 22768-22780 (2002).
Dodart et al., "Immunization reverses memory deficits without reducing brain Abeta burden in ALzheimer's disease model," Nat Neurosci, vol. 5, pp. 452-457 (2002).
Duff et al., "Increased amyloid-beta42(43) in brains of mice expressing mutant presenilin 1," Nature, vol. 383, pp. 710-713 (1996).
Fenteany et al., "Inhibition of proteasome activities and subunit-specific amino-terminal threonine modification by lactacystin," Science, vol. 268, pp. 726-731 (1995).
Futaki, Adv Drug Deliv Rev, vol. 57, pp. 547-558 (2005).
Gil-Parrado et al., Biol Chem, vol. 384, pp. 395-402 (2003).
Gilon et al., "Degradation signals for ubiquitin system proteolysis in *Saccharomyces cerevisiae*," Embo J, vol. 17, pp. 2759-2766 (1998).
Gong et al., Persistent improvement in synaptice and cognitive functions in an Alzheimer mouse model following rolipram treatment, J Clin Invest, vol. 114, pp. 1624-1634 (2004).
Gouras et al., "Intraneuronal Abeta42 accumulation in humain brain," Am J Pathol, vol. 156, pp. 15-20 (2000).
Gregori et al., "Amyloid beta-protein inhibits ubiquitin-dependent protein degradation in vitro," J Biol Chem, vol. 270, pp. 19702-19708 (1995).
Grune et al., "Proteolysis in cultured liver epithelial cells during oxidative stree. ROle of the multicatalytic proteinase complex, proteasome," J Biol Chem, 270, pp. 2344-2351 (1995).
Hegde et al., "Ubiquitin C-terminal hydrolase is an immediate-early gene essential for long-term facilitation in Aplysia," Cell, vol. 89, pp. 115-126 (1997).
Hsiao et al., "Correlative memory deficits, Abeta elevation, and amyloid plaques in transgenic mice," Science, vol. 274, pp. 99-102 (1996).
Ichihara et al., "Axonal degeneration promotes adnornal accumulation of amyloid beta-protein in ascending gracile tract of gracile axonal dystrophy (GAD) mouse," Brain Res, vol. 695, pp. 173-178 (1995).
Itoh et al., "Impairments of long-term potentiation in Hippocampal slices of beta-amyloid-infused rats," Eur J Pharmacol, vol. 382, pp. 167-175 (1999).

Iwatsubo et al., "Amyloid beta protein (A beta) deposition: A beta 42(43) precedes A beta 40 in Down syndrome," Ann Neurol, vol. 37, pp. 294-299 (1995).
Kaspar et al., Molecular therapy, vol. 5, pp. 50-56 (2002).
Keck et al., "Proteasome inhibition by paired helical filament-tau in brains of patients with Alzheimer's disease," J Neurochem, vol. 85, pp. 115-122 (2003).
Keller et al., "Impaired proteasome function in Alzheimer's disease," J Neurochem, vol. 75, pp. 436-439 (2000).
Kim et al., "Endoproteolytic cleavage and proteasomal degradation of presenilin 2 in transfected cells," J Biol Chem, vol. 272, pp. 11006-11010 (1997).
Kim et al., "Sindbis vector SINrep (nsP2S726): a tool for rapid heterologous expression with attenuated cytotoxicity in neurons," J Neurosci Methods, vol. 133, pp. 81-90 (2004).
Krause et al., "Pharmacokinetics of rolipram in the rhesus and cynomolgus monkeys, the rat and the rabbit. Studies on species differences," Xenobiotica, vol. 18, pp. 561-571 (1988).
Kretz et al., Mol Ther, vol. 7, pp. 659-669 (2003).
LaFerla et al., "Neuronal cell death in Alzheimer's disease correlates with apoE uptake and intracellular Abeta stabilization," J Clin Invest, vol. 100, pp. 310-320 (1997).
Lerner et al.,J Bid Chem, vol. 280, pp. 20642-20650 (2005).
Leroy et al., "The ubiquitin pathway in PArkinson's disease," Nature 395, pp. 451-452 (1998).
Li et al., Mol Ther, vol. 10, pp. 1121-1129 (2004).
Lin et al., "A role for the PI-3 kinase signaling pathway in fear conditioning and synaptic plasticity in the amygdala," Neuron, vol. 31, pp. 841-851 (2001).
Lissy et al., "A common E2F-1 and P73 pathway mediates cell death induced by TCR activation," Nature, vol. 407, pp. 642-645 (2000).
Liu et al., "The UCH-L1 gene encodes two opposing enzymatic activities that affect alpha-synuclein degradatio and Parkinson's disease susceptibility," Cell, vol. 111, pp. 209-218 (2002).
Liu et al., "Discovery of Inhibitors that elicidate the role of UCH-LI activity in the H1299 lung cancer cell line," Chemistry & Biology, vol. 10, pp. 837-846 (2003).
Lopez et al., Defective ubiquitination of cerebral proteins in Alzheimer's disease, J Neurosci Res, vol. 62, pp. 302-310 (2000).
Lu et al., "Nitric oxide signaling contributes to late-phase LTP and CREB phosphorylation in the hippocampus," J. Neurosci, vol. 19, pp. 10250-10261 (1999).
Malgaroli et al., "Glutamate-induced long-term potentiation of the freqency of miniature synaptic currents in cultured hippocampal neurons," nature, vol. 357, pp. 134-139 (1992).
Maraganore et al, Neurology, vol. 53, pp. 1858-1860 (1999).
Markesbery, "Oxidative stress hypothesis in Alzheimer's disease," Free Radic Biol Med, vol. 23, pp. 134-147 (1997).
Masliah, "Mechanisms of synaptic dysfunction in Alzheimer's disease," Histol Histopathol, vol. 10, pp. 509-519 (1995).
Mattson, "Cellular actions of beta-amyloid precursor protein and its soluble and fibrillogenic derivatives," Physiol Rev, vol. 77, pp. 1081-1132 (1997).
Morgan et al., "A beta peptide vaccination prevents memory loss in an aminal model of Alzheimer's disease," Nature, vol. 408, pp. 982-985 (2000).
Nakagawa et al., "Regulation of neurogenesis in adult mouse hippocampus by cAMP and the cAMP response element-binding protein," J Neurosci, vol. 22, pp. 3673-3682 (2002).
Nakano et al., "Identification of a conserved 125 base-pair Hb9 enhancer that specifies gene expression to spinal motor neurons," Dev Biol, vol. 283, pp. 474-485 (2005).
Nishikawa et al., "Alterations of structure and Hydrolase activity of parkinsonism-associated human ubiquitin carboxyl-terminal hydrolase L1 variants," Biochem Biophys Res Commun, vol. 304, pp. 176-183 (2003).
Oddo et al, "Triple-transgenic model of Alzheimer's disease with plaques and tangles: intracellular Abeta and synaptic dysfunction," Neuron, vol. 39, pp. 409-421 (2003).
Parveen et al., "Cell-type-specific gene delivery into neuronal cells in vitro and in vivo," Virology, vol. 314, pp. 74-83 (2003).

Patrick et al., "p35, the neuronal-specific activator of cyclin-dependent kinase (Cdk5) is degraded by the ubiquitin-proteasome pathway," J Biol Chem, vol. 273, pp. 24057-24064 (1998).

Petrucelli et al., Parkin protects against the toxicity associated with mutant alpha-synuclein: proteasome dysfunction selectively affects catecholaminergic neurons, Neuron, vol. 36, pp. 1007-1019 (2002).

Philips et al., Differential contribution of amygdala and hippocampus to cued and contextual fear conditioning, Behav Neurosci, vol. 106, pp. 274-285 (1992).

Puzzo et al., "Amyloid-beta peptide inhibits activation of the nictric oxide/cGMP/cAMP-responsive element-binding protein pathway during hippocampal synaptic plasticity," J Neurosci, vol. 25, pp. 6887-6897 (2005).

Qiu et al., Recognition and ubiquination of Notch by Itch, a hect-type E3 ubiquitin ligase, J Biol Chem, vol. 275, pp. 35734-35737 (2000).

Reinheckel et al., "Comparative resistance of the 20S and 26S proteasome to oxidative stress," Biochem J, vol. 335 (Pt 3), pp. 637-642 (1998).

Saigoh et al., "Intraenic deletion in the gene encoding ubiquitin carboxy-terminal hydrolase in gad mice," Nat Genet, vol. 23, pp. 47-51 (1999).

Schwarze et al., "In vivo protein transduction: delivery of a biologically active protein into the mouse," Science, vol. 285, pp. 1569-1572 (1999).

Selkoe et al., "Alzheimer's disease in a synaptic failure," Science, vol. 298, pp. 789-791 (2002).

Snyder et al., "A role for adult neurogenesis in spatial long-term memory," Neuroscience, vol. 130, pp. 843-852 (2005).

Soudais et al., FASEB J, vol. 15, pp. 2283-2285 (2001).

Stine et al., In vitro characterization of conditions for amyloid-beta peptide oligomerization and fibrillogenesis, J Biol Chem, vol. 278, pp. 11612-11622 (2003).

Tanaka, "Proteasomes: structure and biology," J Biochem (Tokyo), vol. 123, pp. 195-204 (1998).

Terrone et al., Biochemistry, vol. 42, pp. 13787-13799 (2003).

Trinchese et al., "Progressive age-related development of Alzheimer-like pathology in APP/PSI mice," Ann Neurol, vol. 55, pp. 801-814 (2004).

Trommer et al., "ApoE isoform-specific effects on LTP: blockade by oligomeric amyloid-beta 1-42," Neurobiol Dis, vol. 18, pp. 75-82 (2005).

Troy et al., "Downregulation of Cu/Zn superoxide dismutase leads to cell death via the nitric oxide-peroxynitrite pathway," J Neurosci, vol. 16, pp. 253-261 (1996).

Tully et al., "Targeting the CREB pathway for memory enhancers," Nat Rev Drug Discov, vol. 2, pp. 267-277 (2003).

Van Leeuwen et al., "Frameshift mutants of beta amyloid precursor protein and ubiquitin-B in Alzheimer's and Down patients," Science, vol. 279, pp. 242-247 (1998).

van Leeuwen et al., "Molecular misreading. A new type of transcript mutation in gerontology," Ann N Y Acad Sci, vol. 908, pp. 267-281 (2000).

Vitolo et al., "Amyloid beta-peptide inhibition of the PKA/CREB pathway and long-term potentiation: resersibility by drugs that enhance cAMP signaling," Proc. Natl Acad Sci USA, Vol, pp. 13217-13221 (2002).

Wada et al., "The ubiquitin-proteasome system and neurodegeration," Rinsho Shinkeigaku, vol. 41, pp. 1072-1074 (2001).

Wada et al., Cleavage of the C-terminus of NEDD8 by UCH-L3, Biochem Biophys Res Commun, vol. 251, pp. 688-692 (1998).

Wadia et al., "Protein transduction technology," Curr Opin Biotechnol, vol. 13, pp. 52-56 (2002).

Wadia et al., Modulation of cellular function by TAT mediated transduction of full length proteins, Curr Protein Pept Sci, vol. 4, pp. 97-104 (2003).

Wadia et al., "Transductible TAT-Ha fusogenic peptide enhances escape of TAT-fusion proteins after lipid raft macropinocytosis," Nat Med, vol. 10, pp. 310-315 (2004).

Walsh et al., "Naturally secreted oligmers of amyloid beta protein potently inhibit hippocampal long-term potentiation in vivo," Nature, vol. 416, pp. 535-539 (2002).

Wang et al., "Block of long-term potentiation by naturally secreted and synthetic amyloid beta-peptide in hippocampal slices is mediated via activation of the kinases c-Jun N-terminal kinase cyclin-dependent kinase 5, and p38 mitogen-activated protein kinase as well as metabotropic glutmate receptor type 5," J Neurosci, vol. 24, pp. 3370-3378 (2004).

Wen et al., "The presinilin-1 familial Alzheimer disease mutant P117L impairs neurogenesis in the hippocampus of adult mice," Exp Neurol, vol. 188, pp. 224-237 (2004).

Wilkinson et al., "Ubiquitination and deubiquitination: targeting of proteins for degradation by the proteasame," Semin Cell Dev Biol., vol. 11, pp. 141-148 (2000).

Wilkinson et al., "The neuron-specific protein PGP 9.5 is a ubiquitin carboxy-terminal hydrolase," Science, vol. 246, pp. 670-673 (1989).

Mammalian Gene Collection (MGC Program Team, "Generation and Initial analysis of more than 15,000 full-length human and mosue cDNA sequences," PNAS, Dec. 24, 2002, vol. 99, No. 26, 16899-16903.

* cited by examiner

A.

B.

A.

B.

A.

B.

A.

B.

F.

G.

A.

B.

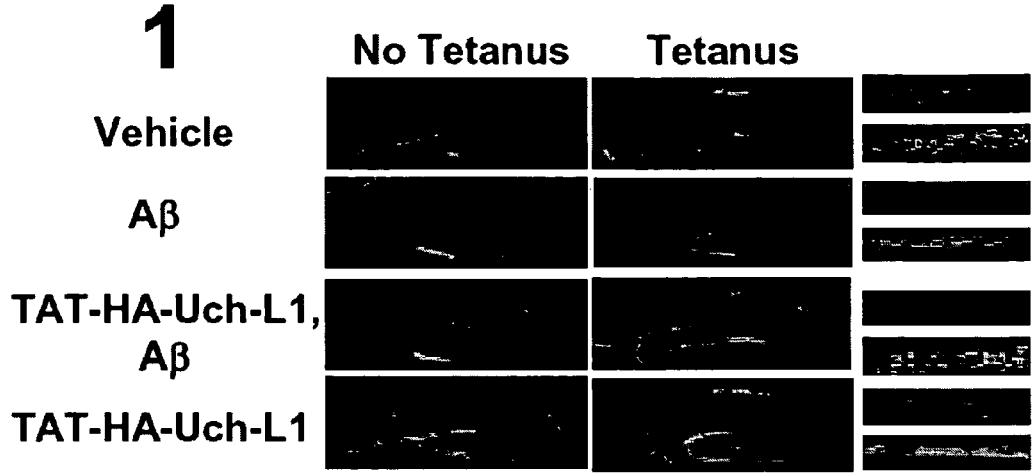
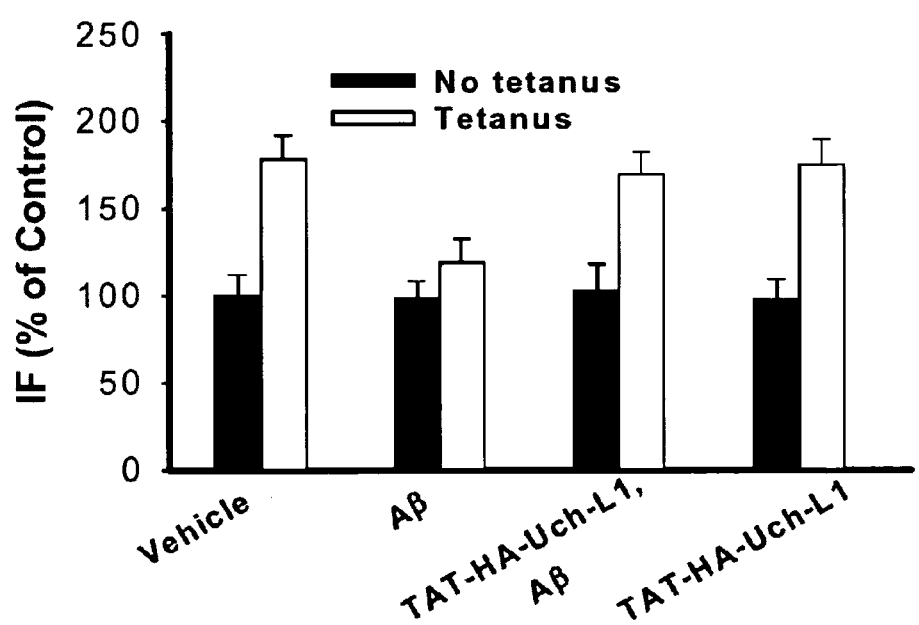
Figure 31C

```
   1 cttccctagg ctatttctgc cgggcgctcc gcgaagatgc agctcaagcc gatggagatc
  61 aaccccgaga tgctgaacaa agtgctgtcc cggctggggg tcgccggcca gtggcgcttc
 121 gtggacgtgc tggggctgga agaggagtct ctgggctcgg tgccagcgcc tgcctgcgcg
 181 ctgctgctgc tgtttcccct cacggcccag catgagaact tcaggaaaaa gcagattgaa
 241 gagctgaagg acaagaagt tagtcctaaa gtgtacttca tgaagcagac cattgggaat
 301 tcctgtggca caatcggact tattcacgca gtggccaata atcaagacaa actgggattt
 361 gaggatggat cagttctgaa acagtttctt tctgaaacag agaaaatgtc ccctgaagac
 421 agagcaaaat gctttgaaaa gaatgaggcc atacaggcag cccatgatgc cgtggcacag
 481 gaaggccaat gtcgggtaga tgacaaggtg aatttccatt ttattctgtt taacaacgtg
 541 gatggccacc tctatgaact tgatggacga atgccttttc cggtgaacca tggcgccagt
 601 tcagaggaca ccctgctgaa ggacgctgcc aaggtctgca gagaattcac cgagcgtgag
 661 caaggagaag tccgcttctc tgccgtggct ctctgcaagg cagcctaatg ctctgtggga
 721 gggactttgc tgatttcccc tcttcccttc aacatgaaaa tatataccccc cccatgcagt
 781 ctaaaatgct tcagtacttg tgaaacacag ctgttcttct gttctgcaga cacgccttcc
 841 cctcagccac acccaggcac ttaagcacaa gcagagtgca cagctgtcca ctgggccatt
 901 gtggtgtgag cttcagatgg tgaagcattc tccccagtgt atgtcttgta tccgatatct
 961 aacgctttaa atggctactt tggtttctgt ctgtaagtta agaccttgga tgtggtttaa
1021 ttgtttgtcc tcaaaggaa taaaactttt ctgctgataa aaaaaaaaaa aaaaaaaa
1081 aaaaaaaaaa aaaaaaaaa a(SEQ ID NO:1)
```

Figure 41

```
  1 MQLKPMEINP EMLNKVLSRL GVAGQWRFVD VLGLEEESLG SVPAPACALL LLFPLTAQHE
 61 NFRKKQIEEL KGQEVSPKVY FMKQTIGNSC GTIGLIHAVA NNQDKLGFED GSVLKQFLSE
121 TEKMSPEDRA KCFEKNEAIQ AAHDAVAQEG QCRVDDKVNF HFILFNNVDG HLYELDGR
181 FPVNHGASSE DTLLKDAAKV CREFTEREQG EVRFSAVALC KAA (SEQ ID NO:2)
```

Figure 42

SEQUENCE LISTING

<160> NUMBER OF SEQ ID NOS: 10

<210> SEQ ID NO 1
<211> LENGTH: 1101
<212> TYPE: DNA
<213> ORGANISM: Homo sapiens

<400> SEQUENCE: 1

```
cttccctagg ctatttctgc cgggcgctcc gcgaagatgc agctcaagcc gatggagatc      60 aacccgaga tgctgaacaa agtgctgtcc cggctggggg tcgccggcca gtggcgcttc     120
gtggacgtgc tggggctgga agaggagtct ctgggctcgg tgccagcgcc tgcctgcgcg     180
ctgctgctgc tgtttcccct cacggcccag catgagaact tcaggaaaaa gcagattgaa     240
gagctgaagg gacaagaagt tagtcctaaa gtgtacttca tgaagcagac cattgggaat     300
```

```
tcctgtggca caatcggact tattcacgca gtggccaata atcaagacaa actgggattt    360
gaggatggat cagttctgaa acagtttctt tctgaaacag agaaaatgtc ccctgaagac    420
agagcaaaat gctttgaaaa gaatgaggcc atacaggcag cccatgatgc cgtggcacag    480
gaaggccaat gtcgggtaga tgacaaggtg aatttccatt ttattctgtt taacaacgtg    540
gatggccacc tctatgaact tgatggacga atgccttttc cggtgaacca tggcgccagt    600
tcagaggaca ccctgctgaa ggacgctgcc aaggtctgca gagaattcac cgagcgtgag    660
caaggagaag tccgcttctc tgccgtggct ctctgcaagg cagcctaatg ctctgtggga    720
gggactttgc tgatttcccc tcttcccttc aacatgaaaa tatataccccc cccatgcagt    780
ctaaaatgct tcagtacttg tgaaacacag ctgttcttct gttctgcaga cacgccttcc    840
cctcagccac acccaggcac ttaagcacaa gcagagtgca cagctgtcca ctgggccatt    900
gtggtgtgag cttcagatgg tgaagcattc tccccagtgt atgtcttgta tccgatatct    960
aacgctttaa atggctactt tggtttctgt ctgtaagtta agaccttgga tgtggtttaa   1020
ttgtttgtcc tcaaaaggaa taaaactttt ctgctgataa aaaaaaaaaa aaaaaaaaa    1080
aaaaaaaaaa aaaaaaaaaa a                                             1101
```

<210> SEQ ID NO 2
<211> LENGTH: 221
<212> TYPE: PRT
<213> ORGANISM: Homo sapiens

<400> SEQUENCE: 2

```
Met Gln Leu Lys Pro Met Glu Ile Asn Pro Glu Met Leu Asn Lys Val
1               5                   10                  15

Leu Ser Arg Leu Gly Val Ala Gly Gln Trp Arg Phe Val Asp Val Leu
            20                  25                  30

Gly Leu Glu Glu Glu Ser Leu Gly Ser Val Pro Ala Pro Ala Cys Ala
        35                  40                  45

Leu Leu Leu Leu Phe Pro Leu Thr Ala Gln His Glu Asn Phe Arg Lys
    50                  55                  60

Lys Gln Ile Glu Glu Leu Lys Gly Gln Glu Val Ser Pro Lys Val Tyr
65                  70                  75                  80

Phe Met Lys Gln Thr Ile Gly Asn Ser Cys Gly Thr Ile Gly Leu Ile
                85                  90                  95

His Ala Val Ala Asn Asn Gln Asp Lys Leu Gly Phe Glu Asp Gly Ser
            100                 105                 110

Val Leu Lys Gln Phe Leu Ser Glu Thr Glu Lys Met Ser Pro Glu Asp
        115                 120                 125

Arg Ala Lys Cys Phe Glu Lys Asn Glu Ala Ile Gln Ala Ala His Asp
    130                 135                 140

Ala Val Ala Gln Glu Gly Gln Cys Arg Val Asp Asp Lys Val Asn Phe
145                 150                 155                 160

His Phe Ile Leu Phe Asn Asn Val Asp Gly His Leu Tyr Glu Leu Asp
                165                 170                 175

Gly Arg Phe Pro Val Asn His Gly Ala Ser Ser Glu Asp Thr Leu Leu
            180                 185                 190

Lys Asp Ala Ala Lys Val Cys Arg Glu Phe Thr Glu Arg Glu Gln Gly
        195                 200                 205

Glu Val Arg Phe Ser Ala Val Ala Leu Cys Lys Ala Ala
    210                 215                 220
```

```
<210> SEQ ID NO 3
<211> LENGTH: 28
<212> TYPE: DNA
<213> ORGANISM: Artificial
<220> FEATURE:
<223> OTHER INFORMATION: Synthetic oligonucleotide

<400> SEQUENCE: 3
ccgctcgagc gagatataca tatgcagc                                            28

<210> SEQ ID NO 4
<211> LENGTH: 30
<212> TYPE: DNA
<213> ORGANISM: Artificial
<220> FEATURE:
<223> OTHER INFORMATION: Synthetic oligonucleotide

<400> SEQUENCE: 4
acatgcatgc atgtagagca ttaggctgcc                                          30

<210> SEQ ID NO 5
<211> LENGTH: 21
<212> TYPE: DNA
<213> ORGANISM: Artificial
<220> FEATURE:
<223> OTHER INFORMATION: Synthetic oligonucleotide

<400> SEQUENCE: 5
tgtctgaaac ggagaagctg t                                                   21

<210> SEQ ID NO 6
<211> LENGTH: 21
<212> TYPE: DNA
<213> ORGANISM: Artificial
<220> FEATURE:
<223> OTHER INFORMATION: Synthetic oligonucleotide

<400> SEQUENCE: 6
tgaattctct gcagaccttg g                                                   21

<210> SEQ ID NO 7
<211> LENGTH: 39
<212> TYPE: DNA
<213> ORGANISM: Artificial
<220> FEATURE:
<223> OTHER INFORMATION: Synthetic oligonucleotide

<400> SEQUENCE: 7
cagaccattg ggaattccag cggcacaatc ggacttatt                                39

<210> SEQ ID NO 8
<211> LENGTH: 35
<212> TYPE: DNA
<213> ORGANISM: Artificial
<220> FEATURE:
<223> OTHER INFORMATION: Synthetic oligonucleotide

<400> SEQUENCE: 8
gaccattggg aattccagtg gcacaatcgg actta                                    35

<210> SEQ ID NO 9
<211> LENGTH: 29
<212> TYPE: DNA
<213> ORGANISM: Artificial
<220> FEATURE:
<223> OTHER INFORMATION: Synthetic oligonucleotide
```

```
<400> SEQUENCE: 9
ctgaacaaag tgctgtaccg gctgggggt                                    29

<210> SEQ ID NO 10
<211> LENGTH: 29
<212> TYPE: DNA
<213> ORGANISM: Artificial
<220> FEATURE:
<223> OTHER INFORMATION: Synthetic oligonucleotide

<400> SEQUENCE: 10
acccccagcc ggtacagcac tttgttcag                                    29
```

PEPTIDE HAVING HYDROLASE ACTIVITY

This application claims priority to U.S. Provisional Application No. 60/695,303 filed on Jun. 30, 2005, which is hereby incorporated by reference in its entirety.

The invention disclosed herein was made with U.S. Government support under NIH Grant No. NS-15076. Accordingly, the U.S. Government may have certain rights in this invention.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

Overproduction or diminished removal of the amyloid β-protein (Aβ) in the brain are likely to play a key role in several aspects of Alzheimer's Disease (AD)-like pathology and other neuropathological conditions associated with deposition of Aβ in the brain. Endstage AD shows accumulation of large numbers of senile plaques composed of Aβ together with intraneuronal neurofibrillary tangles and loss of neurons and of white matter. In most cases, the development of the symptoms in AD is a very gradual process in which the earliest symptoms of memory loss are often slight and where AD can be extremely difficult to differentiate from benign forms of memory loss. However, about one out of three patients diagnosed with minimal cognitive impairment progress to frank AD in a period of two years. It appears that memory deficits precede massive cell loss and it is clear that synaptic dysfunction occurs far in advance of cellular loss. Therefore, it is important to better define the mechanisms underlying the early memory impairment and develop therapeutic interventions to minimize the progression of lesser memory deficits to more severe neurodegenerative diseases.

SUMMARY OF THE INVENTION

This invention provides for an isolated nucleic acid having a nucleotide sequence from about nucleotide 253 to about nucleotide 564 of SEQ ID NO:1 or a nucleotide sequence about 75% identical thereto, wherein the isolated nucleic acid encodes a peptide having hydrolase activity. In one embodiment, the nucleotide sequence is about 75%, about 80%, about 85%, about 90%, about 95%, about 96%, about 97%, about 98% or about 99% identical to the sequence from about nucleotide 253 to about nucleotide 564 of SEQ ID NO:1 (FIG. 41).

In one aspect, the invention provides for an isolated nucleic acid encoding a mutated Uch-L1 protein. In one embodiment of the invention the mutated version of Uch-L1 comprises an S18Y mutation. In another embodiment, the nucleic acid is operably-linked to a neuronal-specific promoter. In a further embodiment, the nucleic acid further comprises a brain-specific vector or a neuronal-specific viral vector.

The invention also provides for an isolated peptide comprising an amino acid sequence from about amino acid 73 to about amino acid 176 of SEQ ID NO:2 (FIG. 42). In one embodiment, the peptide is a peptidomimetic. The invention provides for an isolated peptide comprising an amino acid sequence that is about 75%, about 80%, about 85%, about 90%, about 95%, about 96%, about 97%, about 98% or about 99% identical to the amino acid sequence from about amino acid 73 to about amino acid 176 of SEQ ID NO:2. In one embodiment, the peptide is linked to a carrier.

The invention provides a method for increasing learning, memory, or both in a subject with a neuropathological condition, the method comprising administering to the subject an effective amount of a compound capable of increasing Uch-L1 activity in neural tissue of the subject. The invention also provides for a method for increasing synaptic plasticity in a subject with a neuropathological condition, the method comprising administering to the subject an effective amount of a compound capable of increasing Uch-L1 activity in neural tissue of the subject. The invention further provides for a method for increasing long term potentiation in a subject with a neuropathological condition, the method comprising administering to the subject an effective amount of a compound capable of increasing Uch-L1 activity in neural tissue of the subject. In one embodiment, the neuropathological condition comprises neurodegeneration. In another embodiment, the neuropathological condition comprises elevated amyloid deposition.

The invention also provides that the neuropathological condition comprises Alzheimer's disease, Parkinson's disease, Pick's disease, a Lewy body disease, amyotrophic lateral sclerosis, Huntington's disease, Creutzfeld-Jakob disease, Down syndrome, multiple system atrophy, neuronal degeneration with brain iron accumulation type I (Hallervorden-Spatz disease), pure autonomic failure, REM sleep behavior disorder, mild cognitive impairment (MCI), cerebral amyloid angiopathy (CAA), vascular dementias mixed with Alzheimer's disease, a neurodegenerative disease characterized by abnormal amyloid deposition, or any combination thereof.

In an embodiment of the invention, the compound comprises a Uch-L1 peptide, a fragment of the Uch-L1 protein (SEQ ID NO:2), a Uch-L1 peptide having hydrolase activity, a fusion peptide of a Uch-L1 peptide and a carrier, a nucleic acid encoding a Uch-L1 peptide, a nucleic acid encoding a fragment of a Uch-L1 peptide, a nucleic acid encoding a Uch-L1 peptide with hydrolase activity, a nucleic acid encoding a promoter of a Uch-L1 gene, an activator of a promoter of a Uch-L1 gene, or any combination thereof. In one embodiment, the compound further comprises a carrier capable of transporting the compound into a cell. In a further embodiment, the carrier comprises a peptide transduction signal, a non-protein molecule, and/or a combination thereof. In another embodiment, the peptide transduction signal comprises an HIV-transactivator protein (TAT) domain, a penetratin 1 protein or transducing domain thereof, an HSV VP22 protein or transducing domain thereof. In another embodiment, the compound comprises a nucleic acid consisting essentially of (a) a promoter; and (b) a nucleic acid encoding a peptide having Uch-L1 hydrolase activity; and wherein (a) is operably linked to (b) and to (c). In a further embodiment, the compound further comprises (c) a neural specific nucleic acid that specifically targets the compound to a neural cell. In one aspect of the invention, the promoter is a constitutive promoter. In another aspect, the promoter is a neural cell-specific promoter. In another embodiment, the promoter is operably linked to an activator. In another embodiment, the Uch-L1 hydrolase activity comprises a Uch-L1 polypeptide, or a peptide fragment thereof. In a further embodiment, the compound further comprises a brain-specific vector or a neuron-specific viral vector.

The invention also provides for a method for identifying whether a test compound is capable of increasing activity of a proteasome, or is capable of increasing activity of a Uch-L1 protein, or both, the method comprising (a) contacting a cell expressing a proteasome, or a Uch-L1 protein, or both, with (i) a proteasome inhibitor; and (ii) a test compound, and (b) determining whether activity of the proteasome, the Uch-L1 protein, or both in (a) is increased as compared to the activity of the proteasome, the Uch-L1 protein, or both, respectively, in the absence of the test compound, so as to identify whether the test compound is capable of increasing activity of the proteasome, the Uch-L1 protein, or both.

In one embodiment, the cell is a neural cell or a neural cell line. In another embodiment, the proteasome inhibitor comprises amyloid-beta, LDN-57444, compound 50, compound 51, lactacystin, MG132, Adaahx3L3VS, AdaLys(Bio) Ahx3L3VS, Epoximicin, clasto-Lactacystin β-Lactone, α-methylomuralide, MG-115, NLVS, MP-LLL-VS, PR-11, PR-39, Proteasome inhibitor I, Proteasome inhibitor II, Proteasome inhibitor III, Proteasome inhibitor IV, O106-9920, Tyropeptine A, Ubiquitin Aldehyde, and/or YU101. In a further embodiment, the cell expresses a reporter protein and wherein the determining comprises measuring the reporter protein. In another embodiment, the cell comprises an SY5Y neuroblastoma cell transfected with Green Flourescent Protein reporter expression vector. Within the scope of the invention is an SY5Y neuroblastoma cell that expresses a reporter protein other than green fluorescent protein, including, but not limited to luciferase, beta galactosidase or chloramphenicol acetyltransferase. In another embodiment, the method provides for a decrease in reporter expression that indicates increased activity of the proteasome, the Uch-L1 protein, or both. In a further embodiment, the reporter protein comprises green fluorescent protein. In yet another embodiment, the method further comprises testing whether or not application of the test compound to a neuronal hippocampal culture in the presence and absence of glutamate and beta-amyloid, so as to determine whether or not the test compound is capable of increasing phosphorylation of cAMP-response element-binding protein (CREB) within a neuronal cell. In another embodiment, if there is an increase in phosphorylation of the CREB determined, then the test compound is determined to increase the activity of the proteasome, the Uch-L1 in the cell, or both. In another embodiment, the cell expresses a CRE reporter construct. In another embodiment, the CRE reporter construct comprises luciferase, beta galactosidase, chloramphenicol acetyltransferase, or green fluorescent protein. In a further embodiment, the method is carried out in a high throughput manner.

The invention provides for a method for identifying a compound that is capable of (i) increasing proteasome activity in a cell, and (ii) improving synaptic activity in a hippocampal neuron, the method comprising (a) contacting a neuroblastoma cell with the compound, wherein the neuronal cell constitutively expresses a reporter-protein that is constitutively degraded by a proteasome in the cell; (b) measuring reporter-protein level in the cell, wherein a decrease in the level of the reporter-protein, as compared to the level of reporter-protein measured in the absence of the compound, indicates that the compound increases proteasome activity in the cell; (c) contacting a second hippocampal neuronal cell with the compound in the presence of (i) glutamate and (ii) amyloid-beta so that CREB phosphorylation is inhibited; and (d) determining inhibition of CREB phosphorylation, as compared to CREB phosphorylation in the absence of the compound, wherein a reduction in inhibition of CREB phosphorylation indicates that the compound improves synaptic activity in the second hippocampal neuronal cell.

The invention also provides for a method for identifying a compound that is capable of (i) increasing proteasome activity in a cell, and (ii) improving synaptic activity in a neuron, the method comprising (a) contacting a neuronal cell with a compound, wherein the neuronal cell constitutively expresses a reporter-protein that is constitutively degraded by a proteasome in the cell; (b) measuring reporter-protein level in the cell, wherein a decrease in the level of the reporter-protein, as compared to the level of reporter-protein measured in the absence of the compound, indicates that the compound increases proteasome activity in the cell; (c) contacting a second neuronal cell with the compound in the presence of (i) an excitatory neuronal stimulus and (ii) an inhibitor of CREB phosphorylation; (d) determining inhibition of CREB phosphorylation, as compared to CREB phosphorylation in the absence of the compound, wherein a reduction in inhibition of CREB phosphorylation indicates that the compound improves synaptic activity in the second neuronal cell. In one aspect, the neuronal cell comprises a cortical neuron or hippocampal neuron. In another aspect, the excitatory neuronal stimulus comprises a chemical stimulus, a mechanical stimulus, an electrical stimulus, or any combination thereof. In another embodiment, the synaptic plasticity of the neuronal cells can be determined by measuring CREB phosyphorylation, PKA activity, and/or expression of genes that are downstream of CREB. For example, instead of measuring the inhibition of CREB phosphorylation the method can comprise measuring of (i) PKA regulatory subunit IIα, (ii) PKA activity, (iii) expression of genes downstream of CREB, or (iv) any combination thereof. In another embodiment, the inhibitor of CREB phosphoylation comprises beta-amyloid, a PKA inhibitor, a MAP-kinase inhibitor, a CamKII inhibitor, or any combination thereof.

The administration of the composition of the invention may be effected by intralesional, intraperitoneal, intramuscular or intravenous injection; by infusion; or may involve liposome-mediated delivery; or topical, nasal, oral, anal, ocular or otic delivery.

In the practice of the method, administration of a compound may comprise daily, weekly, monthly or hourly administration, the precise frequency being subject to various variables such as age and condition of the subject, amount to be administered, half-life of the agent in the subject, area of the subject to which administration is desired and the like.

In connection with the method of this invention, a therapeutically effective amount of the inhibitor may include dosages which take into account, the size and weight of the subject, the age of the subject, the severity of the symptoms, the method of delivery of the agent and the history of the symptoms in the subject.

BRIEF DESCRIPTION OF THE FIGURES

FIG. 9A, 20 nM TAT-Uch-L1 fusion protein reverses the decrease of LTP in 12-18 month old APP/PS1 mice. FIG. 9B, TAT-Uch-L1 fusion protein does not affect LTP in WT littermate mice.

(FIG. 14A) Ubiquitin-C-Terminal hydrolase activity was decreased in 4-6 month old APP/PS1 mice compared to WT littermates (n=3 for both WT and APP/PS1 mice; $p<0.01$). (FIG. 14B) Quantitative RT-PCR analysis showed no difference in the expression levels of Uch-L1 mRNA purified from the hippocampi of 4-6 month old APP/PS1 mice and their WT littermates. β-actin (open bar) or GAPDH (solid bar) were used to normalize results (n=9 for both genotypes; $p>0.05$). (FIG. 14C) Quantitative Western blot analysis showed no difference in hippocampal Uch-L1 protein levels from 4-6 month old APP/PS1 mice and their WT littermates (n=3 for both genotypes; data were normalized to the level of ERK).

(FIG. 15A) BST at the Schaffer collateral/CA1 connection of hippocampal slices was strongly reduced by exposure to the 20S-proteasome inhibitor lactacystin (10 µM) for 2-4 hrs (n=11 lactacystin-treated slices from 9 mice and 14 vehicle-treated slices from 12 mice; two-way ANOVA $F(1, 23)=54.48$, $p<0.001$; similar results were obtained when the fEPSP slope was plotted versus the amplitude of the fiber afferent volley). (FIG. 15B) CA1-LTP was blocked by exposure to 10 µM lactacystin for 2-4 hrs. The inhibitor did not affect baseline transmission in slices that did not receive tetanic stimulation. The three arrows indicate time and pattern of the tetani in this and the following figures (n=11 lactacystin-treated slices from 9 mice and 14 vehicle-treated slices from 12 mice; two-way ANOVA $F(1, 23)=45.68$, $p<0.001$ and planned comparison showed that the groups were significantly different at each time point after tetanus; $p<0.001$). (FIG. 15C) Ubiquitin-C-Terminal hydrolase activity was decreased in hippocampal slices treated with the very specific Uch-L1 inhibitor LDN-57444 (5 µM) for 4 hrs (n=10 for each group, $p<0.01$) as well as in hippocampi from adult mice injected with 0.4 mg/kg inhibitor and sacrificed 4 hrs after the injection (n=3 for each group, $p<0.01$). (FIG. 15D) CA1-LTP was blocked by exposure to LDN-57444 (5 µM) for 2 hrs (n=6 slices from 6 mice for both LDN-57444- and vehicle-treated slices; two-way ANOVA $F(1,10)=25.04$, $p<0.001$ and planned comparison showed that the groups were significantly different at each time point after tetanus; $p<0.001$). The inhibitor did not affect baseline transmission in slices that did not receive tetanic stimulation (n=3 slices from 2 mice). (FIG. 15E) CA1-BST was not affected by 2 hrs exposure to 5 µM LDN-57444 (n=6 slices from 6 mice for both LDN-57444- and vehicle-treated slices; two-way ANOVA $F(1,10)=8.14$, $p>0.05$; similar results were obtained when the fEPSP slope was plotted versus the amplitude of the fiber afferent volley). (FIG. 15F) CA1-BST was strongly reduced by 4 hrs exposure to 5 µM LDN-57444 (n=6 slices from 6 mice for both LDN-57444- and vehicle-treated slices; two-way ANOVA $F(1,10)=8.14$, $p<0.05$; similar results were obtained when the fEPSP slope was plotted versus the amplitude of the fiber afferent volley). (FIG. 15G) LTP is strongly reduced by 4 hrs exposure to 5 µM LDN-57444 (n=6 slices from 6 mice for both LDN-57444- and vehicle-treated slices; two-way ANOVA $F(1,10)=45.76$, $p<0.001$ and planned comparison showed that the groups were significantly different at each time point after tetanus, $p<0.001$). The inhibitor did not affect baseline transmission in slices that did not receive tetanic stimulation (n=4 slices from 2 mice). (FIG. 15H) LDN-57444 (0.4 mg/kg) injections worsened contextual conditioning performance and its decay as the mice were exposed to the context at 1, 7, 14 and 21 days after training (n=19, 6 males 13 females in LDN-57444-injected mice versus n=19, 7 males 12 females in vehicle-treated mice; two-way ANOVA $F(1,180)=4.58$, $p<0.05$ and planned comparisons showed a statistically significant difference at each time point between LDN-57444- and vehicle-injected mice, $p<0.05$).

(FIG. 16A) TAT-HA-Uch-L1 and TAT-HA fusion proteins were purified from Ecoli BL21(DE3)pLysS cells and separated on SDS-PAGE. The immunoblot was performed with anti-Uch-L1 and anti-HA antibodies. The molecular weights of TAT-HA-Uch-L1 and TAT-HA were about 40 KD and 15 KD, respectively. (FIG. 16B) Hippocampal slices showed immunofluorescence for TAT-HA-Uch-L1 and TAT-HA fusion proteins when they were perfused with the fusion proteins. In B1, representative examples of hippocampal slices stained with antibodies against Uch-L1 or HA. The slices were fixed after 1 hr perfusion with 20 nM TAT-HA-Uch-L1, TAT-HA or vehicle. In B2, quantification of the immunofluorescence intensity in the CA1 region revealed a significant immunofluorescence increase in TAT-HA-Uch-L1- and TAT-HA-treated slices compared to vehicle-treated control slices from the same animals (n=3 for TAT-HA-Uch-L1 and n=4 for TAT-HA, $p<0.01$ for both). The intensity of staining was time-dependent with slices treated with TAT-HA-Uch-L1 and TAT-HA showing a four fold increase after 4 hrs (n=3 for both). (FIG. 16C) Hippocampal cultured neurons (5 DIV) showed strong immunofluorescence for TAT-HA-Uch-L1 and TAT-HA fusion proteins when they were perfused with the fusion proteins for 1 hr at a concentration of 100 nM. Following fixation, antibodies against Uch-L1 or HA paired with the specific neuronal marker MAP2 were used to probe the fusion protein penetration inside neurons. Scale bar=50 µm. (FIG. 16D) Hippocampal slices showed immunofluorescence for TAT-HA-Uch-L1 and TAT-HA fusion proteins when animals were injected with the fusion proteins. In D1, representative examples of hippocampal slices stained with anti-bodies against Uch-L1 or HA. The animals were sacrificed 4 hrs after the i.p. injection of 0.02-0.04 g/kg TAT-HA-Uch-L1, TAT-HA or vehicle. In D2, quantification of the immunofluorescence intensity in the CA1 region revealed a significant immunofluorescence increase in slices from TAT-HA-Uch-L1- and TAT-HA-injected mice compared to control slices from vehicle-injected animals (n=4 and p<0.01 for both). (FIG. 16E) Quantitative Western blot analysis showed that 1 hr pre-incubation with TAT-A-Uch-L1 peptide (20 nM) annulled the decrease of monoubiquitin levels in hippocampal slices treated with 200 nM Aβ for 20 min. Band intensities were measured and normalized for ERK intensities (n=5 in all groups). (FIG. 16F) Pre-incubation for 1 hr with TAT-HA-Uch-L1 (20 nM) re-established normal ubiquitin-C-terminal hydrolase activity in slices exposed to 200 nM A, for 20 min (n=6 in all groups). (FIG. 16G) Quantitative Western blot analysis showed that 2 hrs pre-incubation with TAT-HA-Uch-L1 peptide (20 nM) blocked the increase of GFP$^u$ in SY5Y neuroblastoma cells transfected with GFP treated with 200 μM Aβ for 24 hrs. Band intensities were measured and normalized for ERK intensities (n=3 in all groups).

(FIG. 17A) Pre-incubation for 1 hr with TAT-HA-Uch-L1 (20 nM) followed by Aβ (200 nM) plus TAT-HA-Uch-L1 (20 nM) for 20 min completely reversed the Aβ-induced impairment of CA1-LTP in hippocampal slices. The fusion protein did not affect the amounts of potentiation in slices that were not treated with Aβ. Aβ alone markedly reduced the amounts of potentiation (Aβ n=11 slices from 11 mice, TAT-HA-Uch-L1 plus Aβ n=12 slices from 12 mice, TAT-HA-Uch-L1 n=9 slices from 9 mice; a two-way ANOVA revealed a significant difference between the TAT-HA-Uch-L1 plus Aβ group compared to the Aβ alone group [$F(1, 21)=40.89$, $p<0.001$], and planned comparisons showed that the groups were significantly different at each time point after the tetanus ($p<0.001$). (FIG. 17B) Pre-incubation for 1 hr with TAT-HA (20 nM) followed by Aβ (200 nM) plus TAT-HA (20 nM) for 20 min did not reverse the Aβ-induced impairment of CA1-LTP, nor affected the amounts of potentiation in slices that were not treated with Aβ. These experiments were interleaved with those described in (A) [vehicle n=10 slices from 10 mice, TAT-HA n=6 slices from 6 mice, TAT-HA plus Aβ n=9 slices from 9 mice; a two-way ANOVA showed similar values between the TAT-HA plus Aβ group and the Aβ alone group $F(1, 18)=1.66$, $p>0.05$].

(FIG. 18A) TAT-HA-Uch-L1, TAT-HA-Uch-L1(C90S) and TAT-HA-Uch-L1 (S18Y) fusion proteins were purified from *E coli* BL21 (DE3)pLysS cells and separated on SDS-PAGE. Immunoblot was performed using antibodies anti-HA and anti-Uch-L1. (FIG. 18B) Pre-incubation for 1 hr with TAT-HA-Uch-L1(C90S) (20 nM) failed to reverse the Aβ-induced impairment of CA1-LTP in slices that were co-treated with Aβ (200 nM) and TAT-HA-Uch-L1(C90S) (20 nM) for 20 min (n=12 slices from 12 mice). The fusion protein severely impaired potentiation in slices that were not treated with Aβ (n=10 slices from 8 mice) compared to slices that were treated with vehicle alone [n=9 slices from 6 mice, $F(1, 17)=23.41$, $p<0.001$ and planned comparisons showed that the groups were significantly different at each time point after the tetanus, $p<0.001$]. A two-way ANOVA did not reveal a significant difference between the TAT-HA-Uch-L1(C90S) plus Aβ group compared to the TAT-HA plus Aβ group [n=9 slices from 9 mice, $F(1, 19)=1.37$, $p>0.05$]. (FIG. 18C) Pre-incubation for 1 hr with TAT-HA-Uch-L1(S18Y) (20 nM) completely reversed the Aβ-induced impairment of CA1-LTP in slices that were co-treated with Aβ (200 nM) and TAT-HA-Uch-L1(S18Y) (20 nM) for 20 min (n=11 slices from 11 mice). A two-way ANOVA revealed a significant difference between the TAT-HA-Uch-L1(S18Y) plus Aβ group compared to the TAT-HA plus Aβ group, $F(1, 18)=43.40$, $p<0.001$ and planned comparisons showed that the groups were significantly different at each time point after the tetanus ($p<0.001$). The fusion protein did not affect the amounts of potentiation in slices that were not treated with Aβ (n=13 slices from 8 mice). These experiments were interleaved with those described in (FIG. 18B).

(FIG. 19A) Incubation for 1 hr with TAT-HA-Uch-L1 (20 nM) completely reversed the impairment of CA1-LTP in slices from 4 month-old APP/PS1 mice (n=12 slices from 10 males), whereas TAT-HA (20 nM) did not reverse the impairment of LTP n=10 slices from 9 males). Two-way ANOVA revealed a significant difference between the 2 APP/PS1 groups [$F(1, 20)=76.26$, $p<0.001$], and planned comparisons showed that the groups were significantly different at each time point after the tetanus ($p<0.001$). Both TAT-HA-Uch-L1 and TAT-HA did not affect baseline transmission in slices that did not receive tetanic stimulation (n=5 slices from 3 males for both treatments, $F(1,8)=0.24$, $p>0.05$). Amounts of potentiation were similar in slices treated with TAT-HA and TAT-free vehicle-treated slices. (FIG. 19B) Incubation for 1 hr with TAT-HA-Uch-L1 (20 nM) or TAT-HA (20 nM) gave similar amounts of potentiation in slices from 4 month-old WT mice (n=13 slices from 10 males and 11 slices from 11 males, respectively; $F(1,18)=1.65$, $p>0.05$), nor affected baseline transmission in slices that did not receive tetanic stimulation (n=4 slices from 3 males and 5 slices from 4 males, respectively; $F(1,7Y)=0.35$, $p>0.05$). (FIG. 19C) Incubation for 1 hr with TAT-HA-Uch-L1 (20 nM) had a beneficial effect on the impairment of LTP in slices from 12-18 month-old APP/PS1 mice (n=12 slices from 10 males), whereas TAT-HA (20 nM) did not reverse the impairment of LTP (n 9 slices from 7 males). Two-way ANOVA revealed a significant difference between the 2 APP/PS1 groups [$F(1, 20)=11.55$, $p<0.001$], and planned comparisons showed that the groups were significantly different at each time point after the tetanus ($p<0.001$). Both TAT-HA-Uch-L1 and TAT-HA did not affect baseline transmission in slices that did not receive tetanic stimulation (n=4 slices from 3 males for both treatments; $F(1,6)=0.64$, $p>0.05$). Amounts of potentiation were similar in slices treated with TAT-HA and TAT-free vehicle-treated slices. (FIG. 19D) Incubation for 1 hr with TAT-HA-Uch-L1 (20 nM) or TAT-HA (20 nM) did not vary the amounts of potentiation in slices from 12-18 month-old WT mice [n=11 slices from 9 males and 9 slices from 9 males, respectively; $F(1,18)=0.09$, $p>0.05$], nor affected baseline transmission in slices that did not receive tetanic stimulation [n=5 slices from 3 males and 5 slices from 4 males, respectively; $F(1,8)=0.85$, $p>0.05$]. (FIG. 19E) Incubation for 1 hr with TAT-HA-Uch-L1 (20 nM) improved BST at the CA3-CA1 connection of slices from 12-18 month-old APP/PS1 mice whereas TAT-HA (20 nM) did not reverse it [n=12 slices from 10 males and 9 slices from 7 males, respectively; $F(1, 9)=20.66$; $p<0.001$; planned comparisons showed that the groups were significantly different between 7 and 35 V; $p<0.01$]. No statistically significant difference was found in the fEPSP slope values of TAT-HA-Uch-L1-treated APP/PS1 mice compared with those of TAT-HA-treated and TAT-HA- Uch-L1-treated WT mice [F(2, 29)=0.34; p>0.05]. TAT-HA treated slices had similar BST as TAT-free vehicle-treated slices both in APP/PS1 mice and WT littermates. (FIG. 19F) A single injection of TAT-HA-Uch-L1 (0.02-0.04 g/kg, i.p) 4 hrs prior to training of fear conditioning re-established normal freezing time during decay of the contextual learning at 7-, 14-, and 21-days after the training (TAT-HA-Uch-L1 n=15, 3 males plus 12 females; TAT-HA n=13, 3 males plus 10 females). TA-HA-Uch-L1 had no effect on the freezing responses of WT mice (TAT-HA-Uch-L1 n=12, 3 males plus 9 females; TAT-HA n=18, 4 males plus 14 females). Two-way ANOVA followed by the Bonferroni test revealed a statistically significant difference among the 4 groups [F(3, 58)=18.53; p<0.001]. Post-hoc analysis showed a statistically significant difference between TAT-HA-treated APP/PS1 and WT littermates (p<0.01 at 1, 7, 14 and 21 days), as well as between TAT-HA-Uch-L1-treated and TAT-HA-treated APP/PS1 mice (p<0.01 at 7, 14 and 21 days). A single injection of TAT-HA (0.02-0.04 g/kg, i.p) produced similar freezing responses as TAT-free vehicle solution alone in APP/PS1 and WT mice.

(FIG. 20A) PKA activity was reduced in slices treated with 200 nM $A\beta$ for 20 min (n=5 for both, p<0.01). However, pre-incubation with TAT-HA-Uch-L1 (20 nM) for 1 hr increased levels of kinase activity despite the presence of $A\beta$ (n=5, p<0.01 compared to $A\beta$ alone). (FIG. 20B) PKA activity was reduced in cultures treated with 3 $\mu$M $A\beta$ for 24 hrs (n=5 for both $A\beta$- and vehicle-treated cultures, p<0.01). However, incubation with TAT-HA-Uch-L1 (100 nM) for 24 hrs increased levels of kinase activity despite the presence of $A\beta$ (n=5, p<0.01 compared to $A\beta$ alone). The glutamate-induced increase in PKA activity (50 $\mu$M for 15 min, n=5) was blocked by 3 $\mu$M $A\beta$ for 24 hrs (n=5, p<0.01). However, pre-incubation with TAT-HA-Uch-L1 (100 nM for 24 hrs) rescued the glutamate-induced increase in kinase activity despite the presence of $A\beta$ (n=5, p>0.05 compared to glutamate alone). Lactacystin (10 $\mu$M for 1 hr) blocked the beneficial effect of TAT-HA-Uch-L1 (n=5). (FIG. 20C) Quantitative Western blot analysis of protein extracts from hippocampal slices showed an increase in PKA RII$\alpha$ levels after treatment with 200 nM $A\beta$ for 20 min (n=5 for both $A\beta$- and control-vehicle-treated slices, p<0.01). However, pre-incubation with TAT-HA-Uch-L1 (20 nM) for 1 hr re-established normal levels of regulatory subunit despite the presence of $A\beta$ (n=5). All samples are normalized against unphosphorylated ERK. (FIG. 20D) In D1, representative examples of hippocampal slices stained with a phospho-CREB antibody. The slices were fixed 60 min. after either TAT-HA, $A\beta$, TAT-HA-Uch-L1 plus $A\beta$, TAT-HA-Uch-L1 with and without tetanus. Left, lower-power (4×) view of the entire slice. Right, higher power (16×) view of CA1 cell pyramidal area. In D2, cumulative plot showing that TAT-HA-Uch-L1 (20 nM for 1 hr) followed by 200 nM $A\beta$ plus TAT-HA-Uch-L1 (20 nM) for 20 min re-established the tetanus-induced increase in CREB phosphorylation in the CA1 pyramidal area of hippocampal slices (n=5, p<0.01 compared to tetanized slices treated with $A\beta$ alone). $A\beta$ blocked the increase in phospho-CREB (n=5 both for vehicle- and $A\beta$-alone-treated-slices, p<0.01), whereas TAT-HA-Uch-L1 alone did not affect the increase (n=5). TAT-HA treated slices showed similar amounts of tetanus-induced phospho-CREB increase as TAT-free vehicle treated slices (n=5 for both). $A\beta42$ alone or TAT-HA-Uch-L1 alone or TAT-HA-Uch-L1 paired with $A\beta42$ without theta-burst did not modify immunofluorescence (n=3 for all treatments). (FIG. 20E) Western blot for phospho-CREB at Ser-133. Phosphorylation was increased by treatment with 50 M glutamate for 15 min (n=3). $A\beta$ (3 $\mu$M) for 24 hrs annulled the increase in phospho-CREB (n=3). This effect was completely opposed by the addition of TAT-HA-Uch-L1 (n=3) or TAT-HA-Uch-L1(S18Y) (100 nM) (n=3) during the exposure to $A\beta$. The presence of LDN-57444 (10 $\mu$M, n=3) and TAT-HA-Uch-L1(C90S) (100 nM) (n=3) did not allow the enhancement of phospho-CREB.

(FIG. 21A) A brief 15 min. exposure to the 20S proteasomal inhibitor lactacystin (10 $\mu$M) did not affect BST at the Schaffer collateral/CA1 connection in hippocampal slices (n=13 lactacystin-treated slices from 11 mice and 15 vehicle-treated slices from 12 mice; two-way ANOVA F(1,26)=0.15, p>0.05; similar results were obtained when the fEPSP slope was plotted versus the amplitude of the fiber afferent volley). (FIG. 21B) A brief 15 min. exposure to lactacystin (10 $\mu$M) did not affect CA1-LTP in hippocampal slices (n=13 lactacystin-treated slices from 11 mice and 15 vehicle-treated slices from 12 mice; two-way ANOVA F(1, 26)=0.95, p>0.05). (21C) A brief 15 min. exposure to the Uch-L1 inhibitor LDN-57444 (5 $\mu$M) did not affect CA1-BST in hippocampal slices (n=6 slices from 6 mice for both lactacystin- and vehicle-treated slices; two-way ANOVA F(1,10)=0.45, p>0.05; similar results were obtained when the fEPSP slope was plotted versus the amplitude of the fiber afferent volley). (FIG. 21D) A brief 15 min. exposure to LDN-57444 (5 $\mu$M) did not affect CA1-LTP in hippocampal slices (n=6 slices from 6 mice for both lactacystin- and vehicle-treated slices; two-way ANOVA F(1, 10)=0.65, p>0.05).

(FIG. 23A) A single injection of TAT-HA-Uch-L1 (0.02-0.04 g/kg, i.p.) did not change $A\beta$ levels in 4 month old transgenic mice that were sacrificed 4 hrs after the injection (hippocampal and cortex values were 6.35±0.54 and 4.17±0.68 pmol/mg protein, respectively, in TAT-HA-Uch-L1-treated APP/PS1 mice, n=6, versus 6.78±0.46 and 3.98±0.44 pmol/mg protein in TAT-HA-treated APP/PS1 mice, n=6; p>0.05). (FIG. 23B) A single injection of TAT-HA-Uch-L1 (0.02-0.04 g/kg, i.p.) did not change $A\beta$ levels in 3-5 month old transgenic mice that were sacrificed 3 weeks after the injection (hippocampal and cortex values were 178.60±18.24 and 90.28±17.38 pmol/mg protein, respectively, in TAT-HA-Uch-L1-treated APP/PS1 mice, n=8, versus 168.40±16.57 and 87.45±15.83 pmol/mg protein in TAT-HA-treated APP/PS1 mice, n=7; p>0.05).

(FIG. 25A) Reduction of Uch activity by exposure to different concentrations of the Uch-L1 inhibitor LDN-57444 (LDN) for 2 hrs (n=10/group; p<0.05 at 0.9 $\mu$M and p<0.01 at concentrations above 2.7 $\mu$M). (FIG. 25B) Time-course of the reduction of Uch activity by exposure of hippocampal slices to 5 µM LDN (n=5/group; p<0.05 at 15 min and p<0.01 after 30 min). (FIG. 25C) BST at the Schaffer collateral/CA1 connection of hippocampal slices was not affected by 2 hr exposure to 5 µM LDN (n=6 slices from 6 mice per condition; two-way ANOVA F(1,10)=1.04, p>0.05). (FIG. 25D) CA1-LTP was reduced by exposure to LDN (5 µM) for 2 hrs (n=6 slices from 6 mice per condition; two-way ANOVA F(1,10)=25.04, p<0.001 and planned comparison showed that the groups were significantly different at each time point after tetanus, p<0.001). The inhibitor did not affect baseline transmission in non-tetanized slices (n=3 slices from 2 mice). The three arrows indicate time and pattern of the tetani in this and the following figures. (FIG. 25E) CA1-BST was strongly reduced by 4 hr exposure to 5 µM LDN (n=6 slices from 6 mice for each condition, two-way ANOVA F(1,10)=8.14, p<0.05). (FIG. 25F) LTP is strongly reduced by 4 hr exposure to 5 µM LDN (n=6 slices from 6 mice for each condition; two-way ANOVA F(1,10)=45.76, p<0.001 and planned comparison showed that the groups were significantly different at each time point after tetanus, p<0.001). The inhibitor did not affect baseline transmission in non-tetanized slices (n=4 slices from 2 mice).

(FIG. 26A) Pre-incubation for 1 hr with TAT-HA-Uch-L1 (20 nM) re-established normal Uch activity in slices exposed to 200 nM Aβ for 20 min (n=9 in all groups, p<0.01 in the Aβ group compared to the vehicle group). (FIG. 26B) Quantitative Western blot analysis shows that 1 hr pre-incubation with TAT-HA-Uch-L1 (20 nM) blocks the decrease of monoubiquitin levels in hippocampal slices treated with 200 nM Aβ for 20 min. Band intensities were measured and normalized for ERK1/2 intensities (n=8 in all groups, p<0.01 in Aβ group compared to the vehicle group).

(FIG. 27A) Pre-treatment with TAT-HA-Uch-L1 (20 nM) alone for 1 hr followed by perfusion with TAT-HA-Uch-L1 (20 nM) plus Aβ (200 nM) for 20 min completely reversed the Aβ-induced impairment of CA1-LTP in hippocampal slices. The fusion protein did not affect LTP in slices that were not treated with Aβ and did not affect basal transmission in non-tetanized slices. Aβ alone markedly reduced the amounts of potentiation (Aβ n=14 slices from 14 mice, TAT-HA-Uch-L1 plus Aβ n=15 slices from 15 mice, TAT-HA-Uch-L1 n=9 slices from 9 mice, TAT-HA-Uch-L1 with no tetanus n=5 from 3 mice; a two-way ANOVA revealed a significant difference between the TAT-HA-Uch-L1 plus Aβ group compared to the Aβ alone group [F(1, 29)=42.75, p<0.001], and planned comparisons showed that the groups were significantly different at each time point after tetanus (p<0.001). (FIG. 27B) Pre-treatment with TAT-HA-iUch-L1 (20 nM) for 1 hr followed by TAT-HA-iUch-L1 (20 nM) plus Aβ (200 nM) for 20 min did not reverse the Aβ-induced impairment of CA1-LTP, or affect LTP in slices that were not treated with Aβ, or affect basal transmission in non-tetanized slices. These experiments were interleaved with those described in (FIG. 27A) [vehicle n=13 slices from 12 mice, TAT-HA-iUch-L1 n=8 slices from 8 mice, TAT-HA-iUch-L1 plus Aβ n=$^9$ slices from 9 mice, TAT-HA-iUch-L1 with no tetanus n=5 slices from 4 mice; a two-way ANOVA showed similar values with TAT-HA-iUch-L1 plus Aβ and with Aβ alone F(1, 21)=1.58, p>0.05]. Similar results were obtained with TAT-HA (20 nM) with or without Aβ. (FIG. 27C) Uch activity of mutant TAT-HA-Uch-L1 constructs. TAT-HA-Uch-L1(S18Y) is similar in activity to TAT-HA-Uch-L1 (p>0.05), while TAT-HA-Uch-L1 (C90S), TAT-HA and TAT-HA-iUch-L1 are inactive (p<0.001) (n=3/group). (FIG. 27lD) Pre-treatment with TAT-HA-Uch-L1(C90S) (20 nM) for 1 hr followed by TAT-HA-Uch-L1(C90S) (20 nM) plus Aβ (200 nM) for 20 min failed to reverse the Aβ-induced impairment of CA1-LTP (n=15 slices from 14 mice). The fusion protein severely impaired potentiation in slices even in the absence of Aβ (n=13 slices from 10 mice) compared to slices that were treated with vehicle alone [n=12 slices from 8 mice, F(1, 23)=23.41, p<0.001 and planned comparisons showed that the groups were significantly different at each time point after the tetanus, p<0.001], whereas it did not affect basal transmission in non-tetanized slices (n=5 from 3 mice). These experiments were interleaved with those described in (E). A two-way ANOVA did not reveal a significant difference between the TAT-HA-Uch-L1(C90S) plus Aβ group compared to the TAT-HA-iUch-L1 plus Aβ group [n=9 slices from 9 mice, F(1, 22)=1.44, p>0.05]. (FIG. 27E) Pre-treatment with TAT-HA-Uch-L1(S18Y) (20 nM) for 1 hr followed by TAT-HA-Uch-L1(S18Y) (20 nM) plus Aβ (200 nM) for 20 min completely reversed the Aβ-induced impairment of CA1-LTP (n=14 slices from 13 mice). A two-way ANOVA revealed a significant difference between the TAT-HA-Uch-L1(S18Y) plus Aβ group compared to the TAT-HA-iUch-L1 plus Aβ group, F(1, 21)=42.08, p<0.001 and planned comparisons showed that the groups were significantly different at each time point after the tetanus (p<0.001]. The fusion protein did not affect the amounts of potentiation in slices that were not treated with Aβ (n=15 slices from 9 mice), nor affected basal transmission in non-tetanized slices (n=6 slices from 4 mice). (FIG. 27F) Pre-treatment with different concentrations of TAT-HA-Uch-L1(S18Y) and TAT-HA-Uch-L1 for 1 hr followed by co-treatment with TAT-fusion proteins and Aβ (200 nM) and for 20 min produced similar amounts of rescue of LTP (n=12 for each group). Nonlinear regression analysis was used to generate the best fitting curve for different concentrations using GraphPad Prism software (GraphPad Software Inc., San Diego, Calif.). A two-way ANOVA did not reveal a significant difference between the two groups [F(6, 168)=0.3, p>0.05].

(FIG. 28A) Quantitative RT-PCR analysis showed no difference in the expression levels of Uch-L1 mRNA purified from the hippocampi of 4-6 month old APP/PS1 mice and their WT littermates. GAPDH was used to normalize results (n=9 for both genotypes; p>0.05). (FIG. 28B) Quantitative Western blot analysis showed a reduction of the soluble fraction of Uch-L1 protein levels in hippocampi from 4-6 month old APP/PS1 mice compared to WT littermates (n=3 for both genotypes; p<0.01, data were normalized to the level of ERK1/2). (FIG. 28C) Quantitative Western blot analysis showed an increase of the insoluble fraction of Uch-L1 protein levels in hippocampi from 4-6 month old APP/PS1 mice compared to WT littermates (n=3 for both genotypes; p<0.01, data were normalized to the level of ERK1/2). (FIG. 28D) Hippocampal Uch activity was measured in soluble, insoluble and total extracts of 4-6 month old APP/PS1 mice and WT littermates (n=3 for all the groups). Both soluble and total extracts showed a decrease in activity in APP/PS1 mice compared to WT mice (p<0.01), while insoluble fraction showed no significant change in activity between genotypes (p>0.05). The activity of Uch-L1 in the insoluble fraction was markedly lower than that in the soluble fraction in the WT mice (p<0.001). Activity was normalized with respect to the activity of WT soluble protein. (FIG. 28E) Total hippocampal Uch activity was decreased in APP/PS1 mice of different ages compared to WT littermates (n=3 for both WT and APP/PS1 mice; p<0.01). Single transgenic APP mice showed a significant decrease of Uch activity at 15-18 months of age (p<0.01). A slight reduction in Uch activity is also present in WT and single Tg PS1 mice at 15-18 months of age. (FIG. 28F) TAT-HA-Uch-L1 re-established normal total Uch activity in APP/PS1 mice; TAT-HA-Uch-L1 increased total Uch activity in WT mice (n=3 for each group, p<0.01 for both genotypes when comparing vehicle treated animals with TAT-HA-Uch-L1 treated mice).

(FIG. 29A) Incubation for 1 hr with TAT-HA-Uch-L1 (20 nM) completely reversed the impairment of CA1-LTP in slices from 4 month-old APP/PS1 mice (n=15 slices from 12 males), whereas TAT-HA-iUch-L1 (20 nM) had no effect (n=10 slices from 9 males). Two-way ANOVA revealed a significant difference between the groups [F(1, 23)=73.81, p<0.001], and planned comparisons showed that the groups were significantly different at each time point after the tetanus (p<0.001). Neither TAT-HA-Uch-L1 nor TAT-HA-iUch-L1 affected baseline transmission in slices that did not receive tetanus (n=7 slices from 5 males for each group). TAT-HA (20 nM) produced similar results as TAT-HA-iUch-L1 in this and the following experiments. (FIG. 29B) Incubation for 1 hr with TAT-HA-Uch-L1 (20 nM) or TAT-HA-iUch-L1 (20 nM) had no effect on LTP (n=15 slices from 10 males and 10 slices from 10 males, respectively; F(1,23) =2.04, p>0.05) or baseline transmission (n=4 slices from 3 males and 5 slices from 4 males, respectively) in slices from 4 month-old WT mice. (FIG. 29C) Incubation for 1 hr with TAT-HA-Uch-L1 (20 nM) reversed the impairment of LTP in slices from 12-18 month-old APP/PS1 mice (n=14 slices from 11 males). TAT-HA-iUch-L1 (20 nM) had no effect (n=9 slices from 6 males). Two-way ANOVA revealed a significant difference between the 2 APP/PS1 groups [F(1, 21)=16.21, p<0.001], and planned comparisons showed that the groups were significantly different at each time point after the tetanus (p<0.001). Neither TAT-HA-Uch-L1 nor TAT-HA-iUch-L1 affected baseline transmission in non-tetanized slices (n=6 slices from 5 males for both treatments). (FIG. 29D) Incubation for 1 hr with TAT-HA-Uch-L1 (20 nM) or TAT-HA-iUch-L1 (20 nM) did not affect LTP [n=13 slices from 11 males and 13 slices from 11 males, respectively; F(1,24)=1.38, p>0.05] or baseline transmission in slices from 12-18 month-old WT mice (n=7 slices from 4 males and 7 slices from 5 males, respectively). (FIG. 29E) Incubation for 1 hr with TAT-HA-Uch-L1 (20 nM) improved BST at the CA3-CA1 connection of slices from 12-18 month-old APP/PS1 mice whereas TAT-HA-iUch-L1 (20 nM) did not [F(1, 21)=18.05, p<0.001; planned comparisons showed that the groups were significantly different between 7 and 35 V, p<0.01]. No statistically significant difference was found in the fEPSP slope values of TAT-HA-Uch-L1-treated APP/PS1 mice compared with those of TAT-HA-iUch-L1-treated and TAT-HA-Uch-L1-treated WT mice, F(1, 25)=1.68 and F(1, 25)=2.74, respectively, p>0.05 for both]. TAT-HA-iUch-L1 treated slices had similar BST as TAT-free vehicle-treated slices both in APP/PS1 mice and WT littermates (p>0.05).

(FIG. 30A) Time course of reduction in hippocampal Uch activity following a single injection of LDN (0.4 mg/kg) in adult mice sacrificed at different intervals after injection (n=3 for each group, p<0.01 at 30 min, 1 hr and 4 hrs compared to controls). (FIG. 30B) LDN (0.4 mg/kg) injections worsened contextual conditioning performance as the mice were exposed to the context at 1, 7, 14 and 21 days after training (n=19, 6 males 13 females in LDN-injected mice versus n=19, 7 males 12 females in vehicle-treated mice; two-way ANOVA F(1,36)= 4.97, p<0.05 and planned comparisons showed a statistically significant difference at each time point between LDN- and vehicle-injected mice, p<0.05). (FIG. 30C) A single injection of TAT-HA-Uch-L1(C90S) (0.02-0.04 g/kg, i.p) 4 hrs prior to training of fear conditioning worsened contextual conditioning performance in mice exposed to the context at 1, 7, 14 and 21 days after training [n=13, 9 males 4 females in TAT-HA-Uch-L1(C90S)-injected mice versus n=15, 10 males 5 females in vehicle-treated mice; two-way ANOVA F(1, 26)=4.69, p<0.05 and planned comparisons showed a statistically significant difference at each time point between TAT-HA-Uch-L1(C90S)— and vehicle-injected mice, p<0.05]. (FIG. 30D) A single injection of TAT-HA-Uch-L1, but not TAT-HA-iUch-L1 (0.02-0.04 g/kg, i.p) 4 hrs prior to training of fear conditioning re-established normal freezing time during retention of contextual learning at 7-, 14-, and 21-days after training in APP/PS1 mice (TAT-HA-Uch-L1 n=22, 10 males plus 12 females; TAT-HA-iUch-L1 n=12, 5 males plus 7 females). TAT-HA-Uch-L1 had no effect on the freezing responses of WT mice (TAT-HA-Uch-L1 n=18, 9 males plus 9 females; TAT-HA-iUch-L1 n=14, 7 males plus 7 females). Two-way ANOVA followed by the Bonferroni test revealed a statistically significant difference among the 4 groups [F(3, 64)=19.53; p<0.001]. TAT-HA produced similar results as TAT-HA-iUch-L1.

FIGS. 31A-31D. Effect of Uch-L1 on Aβ-induced hippocampal synaptic dysfunction is associated with restoration of the PKA-CREB pathway. (FIG. 31A) PKA activity was reduced in slices treated with 200 nM AD for 20 min (n=5, p<0.01). Pre-incubation with TAT-HA-Uch-L1 (20 nM) for 1 hr increased levels of kinase activity despite the presence of Aβ (n=8, p<0.01 compared to Aβ alone) (vehicle and TAT-HA-Uch-L1 alone n=5). (FIG. 31B) Quantitative Western blot analysis of protein extracts from hippocampal slices showed an increase in PKA RIIα levels after treatment with 200 nM Aβ for 20 min (n=8, p<0.01). Pre-incubation with TAT-HA-Uch-L1 (20 nM) for 1 hr re-established normal levels of RIIα despite the presence of Aβ (n=7, p<0.01 compared to Aβ alone) (vehicle and TAT-HA-Uch-L1 alone n=8). All samples are normalized against unphosphorylated ERK. (FIG. 31C) Upper panel: representative examples of hippocampal ice stained with a phospho-CREB antibody. The slices were fixed 60 min. after vehicle, Aβ, TAT-HA-Uch-L1 plus Aβ, TAT-HA-Uch-L1 with and without tetanus. Left, lower-power (4x) view of the entire slice. Right, higher power (16x) view of CA1 cell pyramidal area. Lower panel: plot of fluorescence intensities showing Aβ blockade of the increase in CA1-phospho-CREB after tetanus (n=7 both for vehicle- and Aβ-alone-treated-slices, p<0.01), whereas TAT-HA-Uch-L1 (20 nM for 1 hr) followed by 200 nM Aβ plus TAT-HA-Uch-L1 (20 nM) for 20 min re-established the tetanus-induced increase in phospho-CREB (n=7, p<0.01 compared to tetanized slices treated with Aβ alone). TAT-HA-Uch-L1 alone had no effect (n=7). In the absence of theta burst neither Aβ42 alone nor TAT-HA-Uch-L1 alone nor TAT-HA-Uch-L1 paired with Aβ42 induced changes (n=5 for each group). (FIG. 31D) Schematic representation of Aβ modulation of the ubiquitin-proteasome-PKA-CREB pathway: a working hypothesis showing that exogenous Uch-L1 re-establishes normal memory. After binding with a putative membrane receptor Aβ inhibits adenylate cyclase (AC) (Vitolo et al., 2002) and proteasomal degradation of the RIIα-subunit (R), resulting in its accumulation and a shift of the equilibrium in the PKA complex toward the inactive tetramer. As a consequence, the transcription factor CREB cannot be phosphorylated and initiate transcription. Transduction of Uch-L1 re-establishes normal proteasomal activity leading to normal levels of RIIα-subunit. The freed catalytic subunit is activated and can phosphorylate CREB at Ser-133.

(FIG. 32A) LDN-57444 (LDN) does not affect Uch-L3 hydrolase activity. Nedd8-AMC 400 nM was mixed with 20 nM Uch-L3 with or without 5 μM LDN (n=3 for both Uch-L3 alone and Uch-L3 plus LDN groups; two-way ANOVA F(1,64)=0.20, p>0.05). (FIG. 32B) A brief (15 min) exposure to the Uch-L1 inhibitor LDN (5 μM) does not affect CA1-BST in hippocampal slices (n=6 slices from 6 mice for both inhibitor- and vehicle-treated slices; two-way ANOVA F(1,10)=0.45, p>0.05; similar results were obtained when the fEPSP slope was plotted versus the amplitude of the fiber afferent volley). (FIG. 32C) A brief (15 min) exposure to LDN (5 μM) did not affect CA1-LTP in hippocampal slices (n=6 slices from 6 mice for both inhibitor- and vehicle-treated slices; two-way ANOVA F(1, 10)=0.65, p>0.05). The inhibitor did not affect baseline transmission in non-tetanized slices (n=5 slices from 3 mice). (FIG. 32D) A 2-4 hr exposure to LDN (2.7 μM) reduces CA1-LTP in hippocampal slices (n=9 slices from 9 mice for both inhibitor- and vehicle-treated slices; two-way ANOVA F(1, 16)=9.27, p<0.01) whereas a concentration of 1 μM has no effect (n=6 slices from 6 mice, F(1, 13)=2.18, p>0.05). The two concentrations of inhibitor did not affect CA1-BST.

(FIG. 33A) Hippocampal slices showed immunofluorescence for TAT-HA-Uch-L1, TAT-HA-iUch-L1 and TAT-HA fusion proteins when they were perfused with the fusion proteins. In A1, representative examples of hippocampal slices stained with antibodies against Uch-L1 or HA. The slices were fixed after 1 hr perfusion with 20 nM TAT fusion proteins or vehicle. In A2, quantification of the immunofluorescence intensity in the CA1 region revealed a significant immunofluorescence increase in TAT fusion protein-treated slices compared to vehicle-treated control slices from the same animals (n=4 and p<0.01 in all groups). (FIG. 33B) Hippocampal slices showed immunofluorescence for TAT-HA-Uch-L1, TAT-HA-iUch-L1 and TAT-HA fusion proteins when animals were injected with the fusion proteins. In FIG. 33B1, representative examples of hippocampal slices stained with antibodies against Uch-L1 or HA. The animals were sacrificed 4 hrs after the i.p. injection of 0.02-0.04 g/kg TAT fusion proteins or vehicle. In FIG. 33B2, quantification of the immunofluorescence intensity in the CA1 region revealed a significant immunofluorescence increase in slices from TAT fusion protein-injected mice compared to control slices from vehicle-injected animals (n=4 and p<0.01 in all groups). (FIG. 33C) Rat hippocampal cultured neurons (5 DIV) showed strong immunofluorescence for TAT-HA-Uch-L1, TAT-HA-iUch-L1 and TAT-HA fusion proteins when they were perfused with the fusion proteins for 1 hr at a concentration of 100 nM. Following fixation, antibodies against Uch-L1 or HA paired with the specific neuronal marker MAP2 were used to probe the fusion protein penetration inside neurons. Scale bar=50 μm. (FIG. 33D) Exogenous TAT-HA-Uch-L1 is localized to the soluble fraction of protein extracts. Hippocampal slices from WT animals were incubated with TAT-HA-Uch-L1 for 1 hr. Soluble and insoluble fractions of protein extracts were analyzed using Western blot with anti-Uch-L1 antibodies that detected both exogenous TAT-HA-Uch-L1 and endogenous Uch-L1. TAT-HA-Uch-L1 was localized to the soluble fraction. No fusion protein was detected in the insoluble fraction. Similar results were obtained in APP/PS1 slices treated with TAT-HA-Uch-L1. The presence of exogenous Uch-L1 in the soluble fraction but not in the insoluble fraction was confirmed using HA antibodies.

(FIG. 37A) Quantitative RT-PCR analysis showed no difference in the expression levels of Uch-L3 mRNA purified from the hippocampi of 4-6 month old APP/PS1 mice and their WT littermates. GAPDH was used to normalize results (n=9 for both genotypes; p>0.05). (FIGS. 37B and 37C) Quantitive Western blot analysis showed similar soluble and insoluble Uch-L3 protein levels in 4-6 month old APP/PS1 mice compared to WT littermates (n=3 for both genotypes; p>0.05, data were normalized to the level of ERK1/2). (FIG. 37D) Nedd8-AMC hydrolysis is normal in 4-6 month old APP/PS1 mice compared to WT littermates (n=3 for both genotypes, p>0.05).

(FIG. 38A) LDN (5 μM for 2 hrs) further reduced Uch activity in APP/PS1 slices (p<0.01) (n=3 for both WT and APP/PS1 mice either treated with the inhibitor or with vehicle). (FIG. 38B) LDN (5 μM for 2 hrs) did not further reduce LTP in APP/PS1 slices (n=7 for both groups, F(1, 12)=0.98, p>0.05). (FIG. 38C) LDN (5 μM for 2 hrs) did not further reduce LTP in Aβ-treated slices (n=8 for all groups, F(1, 14)=1.67 and F(1, 14)=2.05 respectively, p>0.05 for both the LDN plus Aβ group compared to Aβ alone or LDN alone).

(FIG. 39A) A single injection of TAT-HA-Uch-L1 (0.02-0.04 g/kg, i.p.) did not change Aβ levels in 4 month old transgenic mice that were sacrificed 4 hrs after the injection (hippocampal and cortex values were 6.35±0.54 and 4.17±0.68 pmol/mg protein, respectively, in TAT-HA-Uch-L1-treated APP/PS1 mice, n=6, versus 6.78±0.46 and 3.98±0.44 pmol/mg protein in TAT-HA-treated APP/PS1 mice, n=6; p>0.05). (FIG. 39B) A single injection of TAT-HA-Uch-L1 (0.02-0.04 g/kg, i.p.) did not change Aβ levels in 3-5 month old transgenic mice that were sacrificed 3 weeks after the injection (hippocampal and cortex values were 178.60±18.24 and 90.28±17.38 pmol/mg protein, respectively, in TAT-HA-Uch-L1-treated APP/PS1 mice, n=8, versus 168.40±16.57 and 87.45±15.83 pmol/mg protein in TAT-HA-treated APP/PS1 mice, n=7; p>0.05).

(FIG. 40A) PKA activity was reduced in cultures treated with 3 μM Aβ for 24 hrs (p<0.01). However, incubation with TAT-HA-Uch-L1 (100 nM) for 24 hrs increased levels of kinase activity despite the presence of Aβ (p<0.01 compared to Aβ alone). The glutamate-induced increase in PKA activity (50 μM for 15 min) was blocked by 3 μM Aβ for 24 hrs (p<0.01). However, pre-incubation with TAT-HA-Uch-L1 (100 nM for 24 hrs) rescued the glutamate-induced increase in kinase activity despite the presence of Aβ (p<0.01 compared to Aβ plus glutamate). Addition of lactacystin, an irreversible membrane permeable inhibitor of the 20S-proteasome (Fenteany et al., 1995) at 10 μM for 1 hr, blocked the beneficial effect of TAT-HA-Uch-L1 (n=5 for each group). (FIG. 40B) Western blot for phospho-CREB at Ser-133. Phosphorylation was increased by treatment with 50 μM glutamate for 15 min. Aβ (3 μM) for 24 hrs annulled the increase in phospho-CREB. This effect was completely opposed by the addition of TAT-HA-Uch-L1 or TAT-HA-Uch-L1 (S18Y) (100 nM) during the exposure to Aβ. The presence of LDN (10 μM) and TAT-HA-Uch-L1(C90S) (100 nM) did not allow the enhancement of phospho-CREB. TAT-HA alone and TAT-HA-Uch-L1 alone with no glutamate did not affect levels of phospho-CREB (n=3 for all groups).

FIG. 41. *Homo sapiens* (human) ubiquitin carboxyl-terminal esterase L1 mRNA (Accession No. BC006305); coding sequence from about 37 to about 708 (SEQ ID NO:1) (Strausberg et al., Proc. Natl. Acad. Sci. U.S.A. 99 (26): 16899-16903 (2002)).

FIG. 42. *Homo sapiens* (human) ubiquitin carboxyl-terminal esterase L1 amino acid sequence (SEQ ID NO: 2) (Accession No. AAH06305) encoded by nucleotides from about 37 to about 708 of SEQ ID NO:1

DETAILED DESCRIPTION OF THE INVENTION

Figure 1A:
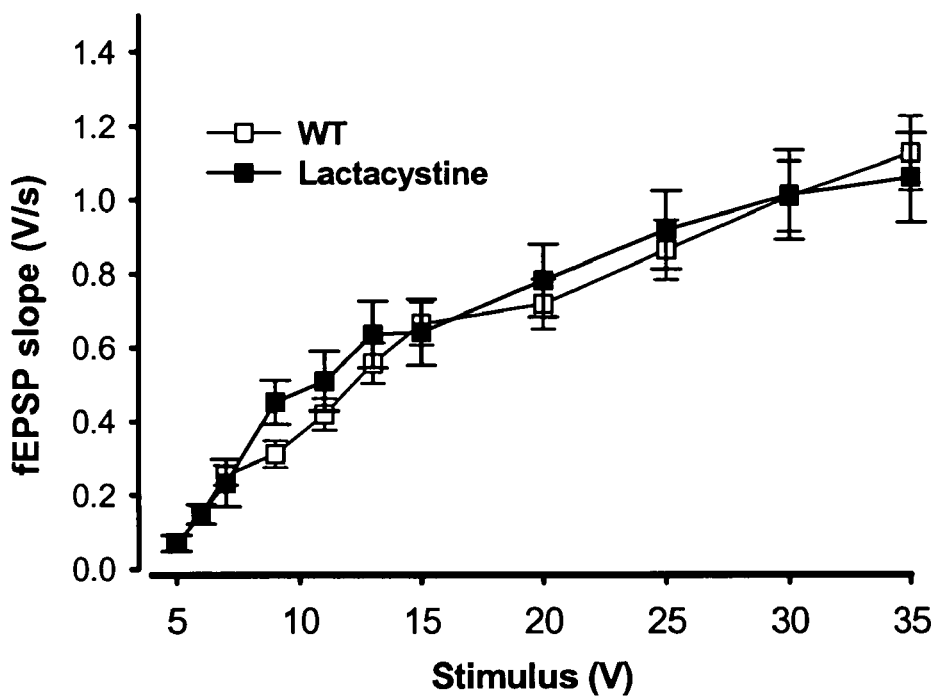
FIGS. 1A-1B. The cumulative plot of the input/output and potentiation curves shows 10 µM lactacystin 15 min does not affect BST (FIG. 1A) and LTP (FIG. 1B).

The patent and scientific literature referred to herein establishes knowledge that is available to those skilled in the art. The issued patents, applications, and other publications that are cited herein are hereby incorporated by reference to the same extent as if each was specifically and individually indicated to be incorporated by reference. In the case of inconsistencies, the present disclosure will prevail.

The ubiquitin-proteasome system is responsible for degradation of proteins that have been specifically marked for destruction by the attachment of ubiquitin. In the brains of deceased Alzheimer's disease patients, there is an accumulation of ubiquitinated proteins, indicating a role for the proteasome system in the pathogenesis of AD. A discovery of this invention is that dysfunction of the proteasome occurs early in AD and contributes significantly to the pathophysiology and progression of the disease.

Ubiquitin carboxy-terminal hydrolase (Uch) is one of many components of the neuronal ubiquitin-proteasome system. The Uch family of enzymes includes the isozymes Uch-L1 (also referred to as PGP9.5), Uch-L3, Uch-L4 and Uch-L5. Uch-L1 is expressed specifically in neurons as well as ovaries and testis. The mRNA sequence for human Uch-L1 (Accession No. BC006305) is shown as SEQ ID NO:1 (Strausberg et al., Proc. Natl. Acad. Sci. U.S.A. 99 (26): 16899-16903 (2002)). The human Uch-L1 polypeptide (SEQ ID NO:2) is encoded by from about nucleotide 37 to about nucleotide 708 of SEQ ID NO:1. The Uch-L1 gene encodes two separate enzymatic activities a hydrolase function and a ligase function. The hydrolase domain of Uch-L1 comprises from about nucleotide 253 to about nucleotide 564 of SEQ ID NO:1 and from about amino acid 73 to about amino acid 176 of SEQ ID NO:2. After a ubiquitin-tagged protein is targeted to the proteasome, Uch-L1 removes the mono-ubiquitin tag from the targeted protein and the targeted protein is degraded by the proteasome machinery. A decrease in Uch-L1 hydrolase activity results in the accumulation of ubiquitin-tagged proteins which are not further processed by the proteasome. Endstage AD brains display accumulation of intraneuronal neurofibrillary tangles and senile plaques composed of ubiquitinated proteins and amyloid-β. Amyloid-β is a sticky, fibrous, extracellular protein that forms the core of a senile plaque, which is surrounded by degenerating nerve endings. Neurofibrillary tangles are dense bundles of abnormal helical filaments that accumulate in affected neurons. These lesions result in loss of neurons and white matter and cognitive impairment in numerous neurodegenerative conditions.

Studies in the marine snail Aplysia, demonstrated that antibodies or antisense oligonucleotides specific for a neuron-specific Uch inhibited the recycling of ubiquitin and blocked long-term facilitation, demonstrating that an increase in Uch activity is essential for the switch from short-term to long-term facilitation in Aplysia (Hegde et al., Cell 89:115-126 (1997)).

It is a discovery of this invention that Uch-L1 is involved in hippocampal long-term potentiation (LTP), a synaptic phenomenon that is related to learning and memory, and in associative memory in vertebrates. It is also a discovery of the invention that administration of a cell-membrane-transducible Uch-L1 fusion protein increases Uch-L1 hydrolase activity in vivo thereby rescuing amyloid-beta-induced synaptic dysfunction and re-establishing normal cognitive functions in a mouse model of Alzheimer's disease.

The invention provides for a method for increasing learning, memory, or both in a subject with a neuropathological condition, the method comprising administering to the subject an effective amount of a compound capable of increasing Uch-L1 activity in neural tissue of the subject. Learning and memory are initially stored by means of persistent changes in the activity of existing neurons in which brain hippocampus plays a fundamental role. This initial storage of information is accomplished by means of long-term potentiation (LTP), which refers to an increase in strength of existing synaptic connections following brief periods of stimulation.

The invention also provides for a method for increasing synaptic plasticity in a subject with a neuropathological condition, the method comprising administering to the subject an effective amount of a compound capable of increasing Uch-L1 activity in neural tissue of the subject. The development of LTP involves simultaneous changes in both presynaptic and postsynaptic neurons at any given synapse. This synaptic plasticity allows for increases in the strength of the synaptic connection.

The invention provides for a method for increasing long-term potentiation in a subject with a neuropathological condition, the method comprising administering to the subject an effective amount of a compound capable of increasing Uch-L1 activity in neural tissue of the subject. LTP, an increase in the strength of synaptic connections, can last for days or weeks; long enough for short-term memory to be consolidated into long-term memory.

In one embodiment, the invention provides a method to counteract the effects of a reduction in Uch-L1 protein levels.

In certain embodiments of the inventive methods, the neuropathological condition comprises neurodegeneration. In various embodiments, the neuropathological condition comprises elevated amyloid deposition in the brain. In additional embodiments, the neuropathological condition comprises Alzheimer's disease, Parkinson's disease, Pick's disease, a Lewy body disease, amyotrophic lateral sclerosis, Huntington's disease, Creutzfeld-Jakob disease, Down syndrome, multiple system atrophy, neuronal degeneration with brain iron accumulation type I (Hallervorden-Spatz disease), pure autonomic failure, REM sleep behavior disorder, mild cognitive impairment (MCI), cerebral amyloid angiopathy (CAA), vascular dementias mixed with Alzheimer's disease, and any other neurodegenerative disease characterized by abnormal amyloid deposition, or any combination of these diseases or conditions. The methods of the invention provide for compounds that are capable of increasing Uch-L1 activity in neural tissue of a subject with a neuropathological condition, thereby increasing cognitive function in the subject. Within the context of the invention, the increased Uch-L1 activity is Uch-L1 hydrolase activity. The compounds provided for by the methods of the invention comprise Uch-L1, a fragment of Uch-L1, a Uch-L1 peptide with hydrolase activity, a fusion peptide of Uch-L1 and a carrier, a nucleic acid encoding Uch-L1, a nucleic acid encoding a fragment of Uch-L1, a nucleic acid encoding a Uch-L1 peptide with hydrolase activity, an activator of Uch-L1 activity, or any combination thereof. In certain embodiments, the compound comprises a carrier capable of translocating the compound across a cell membrane. In other embodiments, the carrier comprises a transduction signal, such as, but not limited to, an HIV-transactivator protein (TAT) domain, a penetratin 1 domain (also referred to as antennapedia), an HSV VP22 protein domain, or any combinations thereof. In another embodiment, the carrier is a neuronal-cell specific transducer or a signal that specifically targets neural cells, such as taurine.

Figure 12:
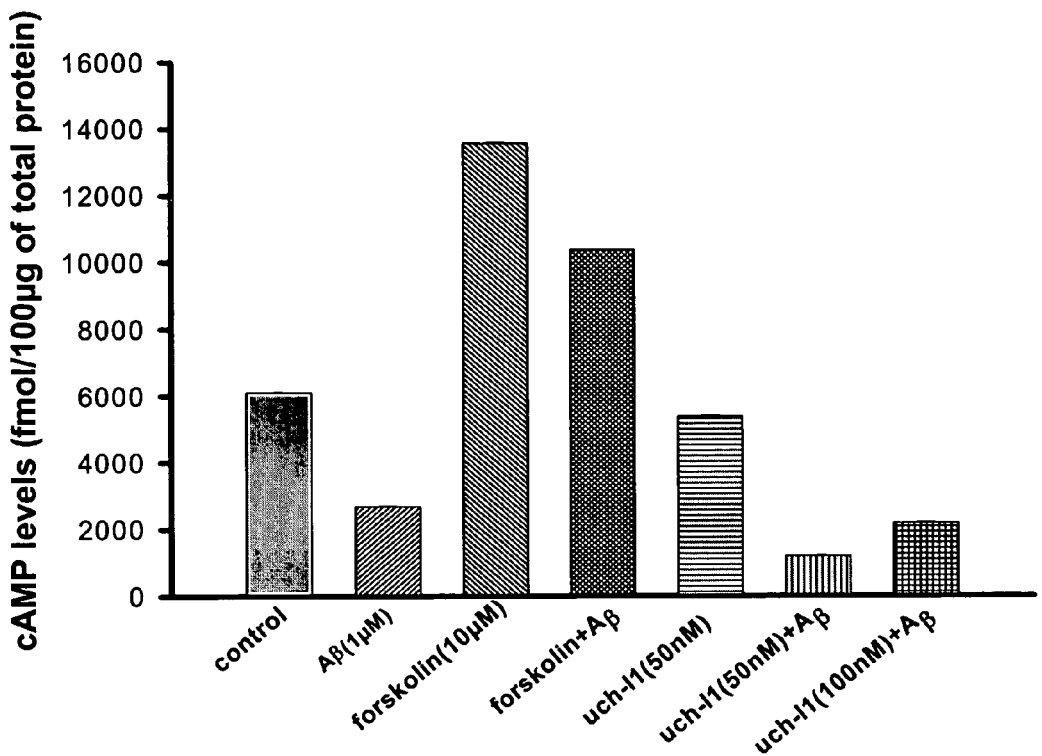
FIG. 12. Preliminary data show that TAT-Uch-L1 fusion protein does not re-establish normal cAMP levels in Aβ treated cultured hippocampal neurons.
Figure 13:
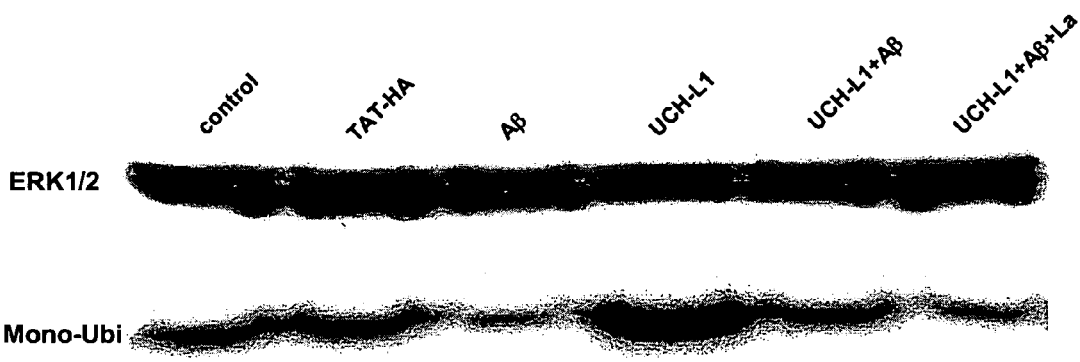
FIG. 13. Mono-ubiquitin levels are reduced in hippocampal cultures treated with Aβ. TAT-Uch-L1 fusion protein re-establishes normal mono-ubiquitin levels.

The invention provides for an isolated nucleic acid having a sequence from about nucleotide 253 to about nucleotide 564 of SEQ ID NO:1 or a nucleotide sequence about 75% identical thereto, wherein the isolated nucleic acid encodes a peptide having hydrolase activity. In certain embodiments, the nucleotide sequence is about 75%, about 80%, about 85%, about 90%, about 95%, about 96%, about 97%, about 98% or about 99% identical to the sequence from about 253 to about 564 of SEQ ID NO:1. Also provided for by the invention is the peptide encoded for by the isolated nucleic acids. The corresponding peptide encompasses from about amino acid 73 to about amino acid 176 of SEQ ID NO:2. The invention also provides an isolated nucleic acid encoding a mutated version of Uch-L1. In one embodiment, the mutated Uch-L1 is a Uch-L1 truncated so that the hydrolase domain is retained. Within the scope of the invention are one or more conservative amino acid substitutions within the peptide, wherein the peptide retains hydrolase activity. For example, the encoded mutated version of Uch-L1 may comprise a substitution of serine-18 to tyrosine (S18Y) in SEQ ID NO:2. The S18Y mutation is a polymorphic variant of the Uch-L1 gene associated with a decreased risk of Parkinson's disease (Maraganore et al., Neurology 53:1858-1860 (1999)). The S18Y mutant Uch-L1 enzyme is characterized by diminished ligase activity (the mutation is in the ligase domain), while retaining hydrolase activity. It is a discovery of the invention that this mutated Uch-L1 with diminished ligase activity still improves LTP in slices as well as synaptic plasticity in cultures (see Example 2, FIG. 12).

The methods of the invention provide for a compound comprising a compound consisting essentially of (a) a promoter; (b) a nucleic acid encoding a peptide having Uch-L1 hydrolase activity; and (c) a nucleic acid encoding a peptide capable of specifically targeting the compound to a neural cell, wherein (a) is operably linked to (b) and to (c) and wherein the nucleic acid is capable of producing expression of Uch-L1 hydrolase activity in the neural cell. In one embodiment, the promoter is constitutive. In another embodiment, the promoter is a neural cell specific promoter. In yet another embodiment, the Uch-L1 hydrolase activity comprises a Uch-L1 polypeptide, or a peptide fragment thereof. For example, a peptide encompassing from about amino acid 73 to about amino acid 176 of SEQ ID NO:2. In an additional embodiment, the compound further comprises a brain-specific vector or carrier or a neuron-specific viral vector or carrier.

To achieve an intracellular increase in Uch-L1 activity, the compound must traverse the cell membrane. The methods of the invention provide for carriers or internalization factors which facilitate the transport of the compound across the cell membrane. Transduction domain peptides and transmembrane carrier peptides allow entry of proteins into cells. U.S. Pat. Nos. 5,652,122, 5,670,617, 6,589,503 and 6,841,535 describe non-limiting examples of membrane-permeable peptides that are useful as agents to facilitate the efficient cellular internalization of a broad range and size of compounds including nucleic acids and proteins. The transduction domain of the HIV-transactivator protein (TAT) has been used to efficiently deliver a wide variety of biologically active cargo both in vitro and in vivo (Aarts et al., Science 298:846-850 (2002); Cao et al., J Neurosci 22:5423-5431 (2002); Lissy et al., Nature 407:642-645 (2000); Wadia and Dowdy, Curr Protein Pept Sci 4:97-104 (2002)), including Uch-L1 (Wada et al., Rinsho Shinkeigaku 41:1072-1074 (2001)). The TAT domain and other arginine-rich membrane-permeable peptides are reviewed in Futaki, Adv Drug Deliv Rev 57:547-58 (2005). Other exemplary carrier peptides comprise fragments of the *Drosophilia* Antennapedia homeodomain (Terrone et al., Biochemistry 42:13787-99 (2003), Troy et al., J Neurosci 16:253-261 (1996)). A specific Antennapedia peptide, penetratin 1, has been used to translocate oligonucleotides and peptides across cell membranes (Davidson et al., J Neurosci 24:10040-10046 (2004); Gil-Parrado et al., Biol Chem; 384:395-402 (2003)). In another example, the VP22 protein of HSV has been used to facilitate the transfer of viral vectors into brain neurons (Kretz et al., Mol Ther 7:659-69 (2003)).

Uch-L1 activity may also be increased in a cell using targeted expression of a gene encoding Uch-L1. As provided for in the methods of the invention, methods to target gene expression include cell specific promoters and cell- or tissue-specific viral vectors. In the context of this invention, non-limiting examples of neuronal cell-specific promoters include a Thy-1.2 promoter (Araki et al., Genesis 42:53-60 (2005)), an aldolase C promoter (Buono et al., FEBS Lett 578:337-344 (2004)), and a neuron-specific enolase promoter (Wen et al., Exp Neurol 188:224-237 (2004)). Other exemplary promoters include a CamKIIα promoter, a PDGF promoter, a Hb9 promoter (Nakano et al, Dev. Biol. In press), a Sp4 promoter (Lerner et al, J. Biol. Chem. 280: 20642-20650, 2005), and a cyclooxygenase-2 (Cui et al, Neuroreport 16: 575-579, 2005). U.S. Pat. No. 5,753,502 describes the use of an ICAM-4 promoter for directing gene expression in neuronal cells. U.S. Publication No. 2004/0093630 A1 is directed a zebrafish HuC promoter to direct neuron-specific expression of genes.

Viral vectors may also be used within the context of this invention to deliver nucleic acids encoding Uch-L1, or fragments thereof. A brain- or neural-cell specific viral vector is used to target Uch-L1 nucleic acid delivery to neural cells. For example, cell-type-specific gene delivery into neurons was accomplished in vivo using engineered avian retroviruses (Parveen et al., Virology 314:74-83 (2003)), adenoviral vectors (Akli et al, Nat. Genetics 3: 224-228, 1993), lentiviral vectors (Coleman et al, Physiol. Genomics 12: 221-228, 2003), canine adenoviral vectors (Soudais et al, FASEB J. 15: 2283-2285, 2001), adeno-associated virus vectors (Kaspar et al, Molecular therapy 5: 50-56, 2002), and Cy3-labeled baculovirus vectors (Li et al, Mol. Ther. 10: 1121-1129, 2004).

U.S. Pat. No. 6,610,287 describes the use of a mutated herpes simplex virus (HSV-1) comprising a neuronal-cell specific promoter to achieve specific expression of a gene in a neuronal cell.

Screening Methods

The invention provides for a method for identifying whether a test compound is capable of increasing activity of a proteasome, or is capable of increasing activity of a Uch-L1 protein, or both, the method comprising (a) contacting a cell expressing a proteasome, or a Uch-L1 protein, or both, with (i) a proteasome inhibitor; and (ii) a test compound, and (b) determining whether activity of the proteasome, the Uch-L1 protein, or both in (a) is increased as compared to the activity of the proteasome, the Uch-L1 protein, or both, respectively, in the absence of the test compound, so as to identify whether the test compound is capable of increasing activity of the proteasome, the Uch-L1 protein, or both.

In one embodiment, the cell is a neural cell or a neural cell line. In other embodiments, the proteasome inhibitor comprises amyloid-beta, LDN-57444, compound 50, compound 51, lactacystin, MG132, Adaahx3L3VS, AdaLys(Bio) Ahx3L3VS, Epoximicin, clasto-Lactacystin β-Lactone, α-methylomuralide, MG-115, NLVS, MP-LLL-VS, PR-11, PR-39, Proteasome inhibitor I, Proteasome inhibitor II, Proteasome inhibitor III, Proteasome inhibitor IV, O106-9920, Tyropeptine A, Ubiquitin Aldehyde, and/or YU101. In another embodiment, the cell expresses a reporter protein and the determining of the activity of the proteasome, the Uch-L1 protein, or both comprises measuring the reporter protein.

In another embodiment, the cell of the method comprises SY5Y neuroblastoma cell transfected with Green Flourescent Protein reporter expression vector. In an additional embodiment, a decrease in reporter expression indicates increased activity of the proteasome, the Uch-L1 protein, or both. In a specific embodiment, the reporter protein comprises green fluorescent protein.

Other embodiments of the method provide for application of the test compound to a neuronal hippocampal culture in the presence and absence of glutamate and beta-amyloid, so as to determine whether or not the test compound is capable increasing phosphorylation of cAMP-response element-binding protein (CREB) within a neuronal cell. In one embodiment, if there is an increase in phosphorylation of the CREB determined, then the test compound is determined to increase the activity of the proteasome, the Uch-L1 in the cell, or both. In one embodiment of the method, the cell expresses a CRE reporter construct. In other embodiments, the CRE reporter construct comprises luciferase, beta galactosidase, chloramphenicol acetyltransferase, or green fluorescent protein. In an additional embodiment, the method is carried out in a high throughput manner.

The invention provides for a method for identifying a compound that is capable of (i) increasing proteasome activity in a cell, and (ii) improving synaptic activity in a hippocampal neuron, the method comprising (a) contacting a neuroblastoma cell with the compound, wherein the neuronal cell constitutively expresses a reporter-protein that is constitutively degraded by a proteasome in the cell; (b) measuring reporter-protein level in the cell, wherein a decrease in the level of the reporter-protein, as compared to the level of reporter-protein measured in the absence of the compound, indicates that the compound increases proteasome activity in the cell; (c) contacting a second hippocampal neuronal cell with the compound in the presence of (i) glutamate and (ii) amyloid-beta so that CREB phosphorylation is inhibited; and (d) determining inhibition of CREB phosphorylation, as compared to CREB phosphorylation in the absence of the compound, wherein a reduction in inhibition of CREB phosphorylation indicates that the compound improves synaptic activity in the second hippocampal neuronal cell.

Also provided for by the invention is a method for identifying a compound that is capable of (i) increasing proteasome activity in a cell, and (ii) improving synaptic activity in a neuron, the method comprising (a) contacting a neuronal cell with a compound, wherein the neuronal cell constitutively expresses a reporter-protein that is constitutively degraded by a proteasome in the cell; (b) measuring reporter-protein level in the cell, wherein a decrease in the level of the reporter-protein, as compared to the level of reporter-protein measured in the absence of the compound, indicates that the compound increases proteasome activity in the cell; (c) contacting a second neuronal cell with the compound in the presence of (i) an excitatory neuronal stimulus and (ii) an inhibitor of CREB phosphorylation; and (d) determining inhibition of CREB phosphorylation, as compared to CREB phosphorylation in the absence of the compound, wherein a reduction in inhibition of CREB phosphorylation indicates that the compound improves synaptic activity in the second neuronal cell. In one embodiment, the neuronal cell comprises a cortical neuron or hippocampal neuron. In other embodiments, the excitatory neuronal stimulus comprises a chemical stimulus, a mechanical stimulus, an electrical stimulus, or any combination thereof. In additional embodiments, synaptic plasticity of the neuronal cells can be measured in a variety of ways. For example, instead of measuring the inhibition of CREB phosphorylation the method will comprise measuring of (i) PKA regulatory subunit IIα, (ii) PKA activity, (iii) expression of genes downstream of CREB, or (iv) any combination thereof. In further embodiments, the inhibitor of CREB phosphoylation comprises beta-amyloid, a PKA inhibitor, a MAP-kinase inhibitor, a CamKII inhibitor, or any combination thereof.

In one aspect of the invention, the compound can be combined with a carrier. The term "carrier" is used herein to refer to a pharmaceutically acceptable vehicle for a pharmacologically active agent. The carrier facilitates delivery of the active agent to the target site without terminating the function of the agent. Non-limiting examples of suitable forms of the carrier include solutions, creams, gels, gel emulsions, jellies, pastes, lotions, salves, sprays, ointments, powders, solid admixtures, aerosols, emulsions (e.g., water in oil or oil in water), gel aqueous solutions, aqueous solutions, suspensions, liniments, tinctures, and patches suitable for topical administration.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of $\leq 20\%$.

The term "effective" is used herein to indicate that the inhibitor is administered in an amount and at an interval that results in the desired treatment or improvement in the disorder or condition being treated (e.g., an amount effective to modulate the growth of kidney tissue). In some embodiments, the subject is a human, mouse, rabbit, monkey, rat, bovine, pig, sheep, goat or dog.

Pharmaceutical formulations include those suitable for oral or parenteral (including intramuscular, subcutaneous and intravenous) administration. Forms suitable for parenteral administration also include forms suitable for administration by inhalation or insufflation or for nasal, or topical (including buccal, rectal, vaginal and sublingual) administration. The formulations may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combinations thereof, and then, if necessary, shaping the product into the desired delivery system.

The following examples illustrate the present invention, and are set forth to aid in the understanding of the invention, and should not be construed to limit in any way the scope of the invention.

EXAMPLES

Example 1

Beta-Amyloid Protein Causes Impairment of the Ubiquitin-Proteasome Pathway and Synaptic Plasticity Synaptic dysfunction is one of the major causes of the memory loss that characterizes the early clinical stages of Alzheimer's disease (AD). High levels of amyloid β-42 (Aβ42) impair synaptic function by inhibition of protein kinase A (PKA) activity and CREB phosphorylation. This is in part achieved through the down-regulation of the synthesis of ubiquitin carboxyterminal hydrolase mRNA, a key enzyme in the ubiquitin proteasome system, which also plays a critical role in PKA activation. These findings have also been shown in human brain tissues from patients affected by AD [Choi et al, J Biol Chem 279:13256-13264 (2004)], thus further stressing the importance of the ubiquitin-proteasome system in the pathogenesis of the disease.

Experimental methods were carried out as described in Example 5. Prolonged exposure to a specific 20S proteasome inhibitor, lactacystin (10 µM) produced pronounced depression of both basal synaptic transmission (BST) (1.13±0.01 vs 0.93±0.06 mV/ms at 35V stimulation, P<0.01) and LTP (231.90±12.90% vs 116.17±14.69% at 60 min and 225.20±7.40% vs 119.25±12.82% of baseline at 120 min P<0.01) in CA1 area to levels similar to those observed in parallel experiments performed on slices from 3-4 month-old APP/PS1 transgenic mice that overproduce Aβ42. The fact that lactacystin affected also PPF (248.90±32.66% vs 150.96±10.18% at 50 ms interval and 142.61±10.91% vs 119.11±5.43% at 300 ms interval) shows that the proteasome system is also involved in regulating molecular pathways active at the presynaptic terminals. A functional ubiquitin-proteasome pathway is essential to preserve neuronal plasticity and its impairment, as that caused by Aβ42, may be a cause of the memory loss process typical of AD.

When brain slices were perfused with 200 nM Aβ, LTP was reduced. However, when TAT-Uch-L1 fusion protein at 20 nM was added to the bath solution for 1 hr before adding Aβ, the depressed LTP was rescued. Furthermore, the reversal of LTP reduction by Uch-L1 fusion protein was blocked by 1 µM KT5720, a specific PKA inhibitor. This shows that functional ubiquitin-proteasome is essential to produce LTP. These studies show also that the ubiquitin-proteasome system is involved in the Aβ-induced LTP deficit through down-regulation of the cAMP-PKA pathway. Thus, drugs that enhance the activity of the ubiquitin-proteasome system can have a beneficial effect in AD.

This Example shows that the proteasome system is involved in regulating molecular pathways active both at the pre- and post-synaptic level. It also shows that the TAT-HA-Uch-L1 fusion protein provided by the invention is membrane transducable and the fusion protein is capable of rescuing the deficits of synaptic plasticity caused by Aβ toxicity. The mechanism of the effect of the fusion protein on synaptic plasticity is through improvement of the cAMP-PKA-CREB pathway.

Example 2

Transduction of TAT-Uch-L1 Fusion Protein Reverses Impairment of Synaptic Plasticity by Beta-Amyloid Evidence supports a direct link between the neuronal ubiquitination/de-ubiquitination machinery and the pathogenesis of Alzheimer's disease (AD). High levels of amyloid β-42 (Aβ42) impair synaptic function by inhibition of protein kinase A (PKA) activity and CREB phosphorylation. This is in part due to down-regulation of the synthesis of ubiquitin carboxy-terminal hydrolase 1 (Uch-L1) mRNA, a key enzyme in the ubiquitin proteasome system. To further study if the ubiquitin-proteasome system is involved in the Aβ-induced synaptic dysfunction, an 11-amino acid transduction domain of HIV-transactivator protein (TAT) was fused with the Uch-L1 protein to allow rapid transduction of full-length functionally exogenous active proteins into intact tissue.

Methods were carried out as described in Example 5. Human Uch-L1 gene was subcloned into the XhoI/SphI site of the pTAT-HA vector. TAT-HA-Uch-L1, TAT-HA and TAT-GFP vector were expressed in *Escherichia coli* strain BL21 pLysS. Mouse hippocampal slices were perfused with purified TAT-Uch-L1 protein (20 nM) for 1 hr, while amyloid-beta was added 20 min before induction of LTP through a theta-burst stimulation (4 pulses at 100 Kz, with the bursts repeated at 5 Hz and each tetanus including 3 ten-burst trains separated by 15 seconds). The LTP deficit in hippocampal CA1 region caused by Aβ was reversed by TAT-Uch-L1 fusion protein (220 15% of baseline at 120 min after burst vs. 158 14% of baseline in slices that did not receive TAT-Uch-L1 protein). TAT-HA could not rescue the reduction of LTP. The two TAT-proteins did not vary amounts of LTP in vehicle-treated slices. Similar to Aβ, perfusion of the hippocampal slices with a mutant (C90S) TAT-Uch-L1- dramatically reduced LTP. Thus, block of the Uch-L1 hydrolase function causes synaptic dysfunction similar to beta amyloid. These studies show that the ubiquitin-proteasome system is involved in the Aβ-induced LTP deficit. Thus, drugs that enhance the activity of the ubiquitin-proteasome system can have a beneficial effect in AD.

The results presented in this Example show that block of the Uch-L1 hydrolase function causes synaptic dysfunction similar to beta-amyloid. They also show that the TAT-Uch-L1 fusion protein is capable of rescuing the deficits of synaptic plasticity caused by overexpression of mutated APP and PS1 transgenes in transgenic AD mouse models. Finally, the data demonstrate that the effect of Aβ on the ubiquitin-proteasome system is due to a reduction of the degradation of the PKA RIIα levels, PKA activity and monoubiquitin levels.

Example 3

Transduction of Uch-L1 Protein Reverses Cognitive Impairments in a Mouse Model of Alzheimer's Disease The neuronal proteasomal system is involved in the pathogenesis of sporadic Alzheimer's disease (AD). This Example shows that the ubiquitin C-terminal hydrolase (Uch) activity is reduced in the APP/PS1 mouse model of the disease. The invention provides that transduction of Uch-L1 protein fused to the 11-amino acid transduction domain of HIV-transactivator protein (TAT) re-establishes normal synaptic function both in hippocampal slices treated with oligomeric Aβ and in APP/PS1 animals. Moreover, intraperitoneal injections with the fusion protein are capable of re-establishing normal decay of the contextual learning in APP/PS1 mice. The beneficial effect of the Uch-L1 fusion protein is linked to restoration of normal levels of PKA regulatory subunit IIα leading to normal kinase activity and CREB phosphorylation. Thus, drugs that enhance the activity of the proteasome system can have a beneficial effect in AD.

In the brains of patients dying from AD there is an accumulation of ubiquinated proteins (de Vrij et al., 2004) showing that the protein degradation mechanisms of the brain have been inhibited. Analysis of proteasome function in post-mortem human AD brains has shown little change in the levels of mRNA or protein for the major proteasomal components but a strong inhibition of degradative activity (Keller et al., 2000; Lopez Salon et al., 2000).

Animal studies have shown that cognitive deficits occur in double transgenic animals overexpressing APP (K670N: M671L) together with PS1 (M146L). These mice overproduce Aβ in advance of plaque deposition and show inhibition of LTP, an electrophysiological correlate of memory storage, at relatively young ages (Trinchese et al., 2004). The role of Aβ in these effects is confirmed by the demonstration of direct LTP inhibition by Aβ applied to hippocampal slices from wild-type animals (Cullen et al., 1997; Itoh et al., 1999; Walsh et al., 2002). This inhibition of LTP in slices is reversible by treatments that raise the intracellular concentration of cyclic AMP (cAMP) (Vitolo et al., 2002). It has been proposed that the effects of A-beta on LTP are mediated by the α-7 nicotinic receptor and by the inhibition of PKA dissociation leading to the inhibition of phosphorylation of the cyclic AMP response element (CREB) and the blockade of transcription (Dineley et al., 2001; Dineley et al., 2002; Gong et al., 2004; Vitolo et al., 2002). PKA activity is regulated both by the dissociation of its catalytic and regulatory subunits and by the degradation of the regulatory subunits by the proteasome (Chain et al., 1999). In Aplysia, long-term facilitation is mediated by a concurrent increase in cAMP and of a neuron-specific ubiquitin C-terminal hydrolase (Uch) (Hegde et al., 1997). This enzyme enhances the recycling of ubiquitin and its inhibition by either antibody injection or antisense oligonucleotides blocks long-term facilitation (Hegde et al., 1997).

In this Example, experiments were designed to determine whether Uch enzymatic activity and/or its synthesis are modified in the double transgenic APP/PS1 mouse model of AD. Methods were carried out as described in Example 5. The experiments determined whether increasing the Uch activity through application of a fusion protein containing the Uch-L1 isozyme exclusively expressed in neurons and testis/ovary (Leroy et al., 1998; Wilkinson et al., 1989), rescues synaptic dysfunction in hippocampal slices treated with oligomeric Aβ, as well as re-establishes normal synaptic and cognitive functions in the double transgenic mice. The mechanism of action of exogenously applied Uch-L1 was examined by examining its effects on the different components of the PKA/CREB pathway.

Ubiquitin C-Terminal Hydrolase Activity is Down-Regulated in APP/PS1 Mice

Figure 14A:
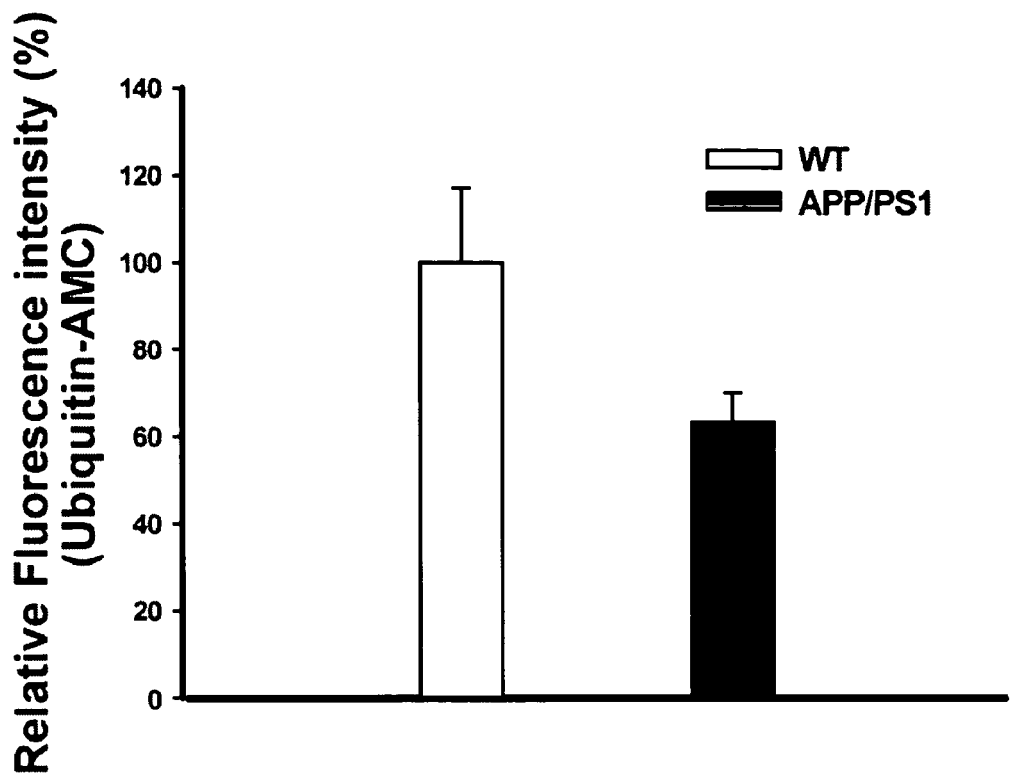
FIGS. 14A-14C. Ubiquitin C-terminal Hydrolase Activity is Down-regulated in APP/PS1 Mice.
Figure 14B:
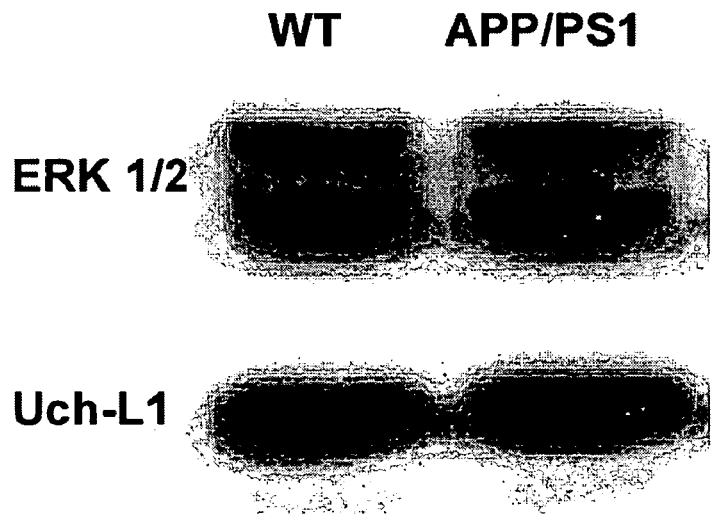
Figure 14C:
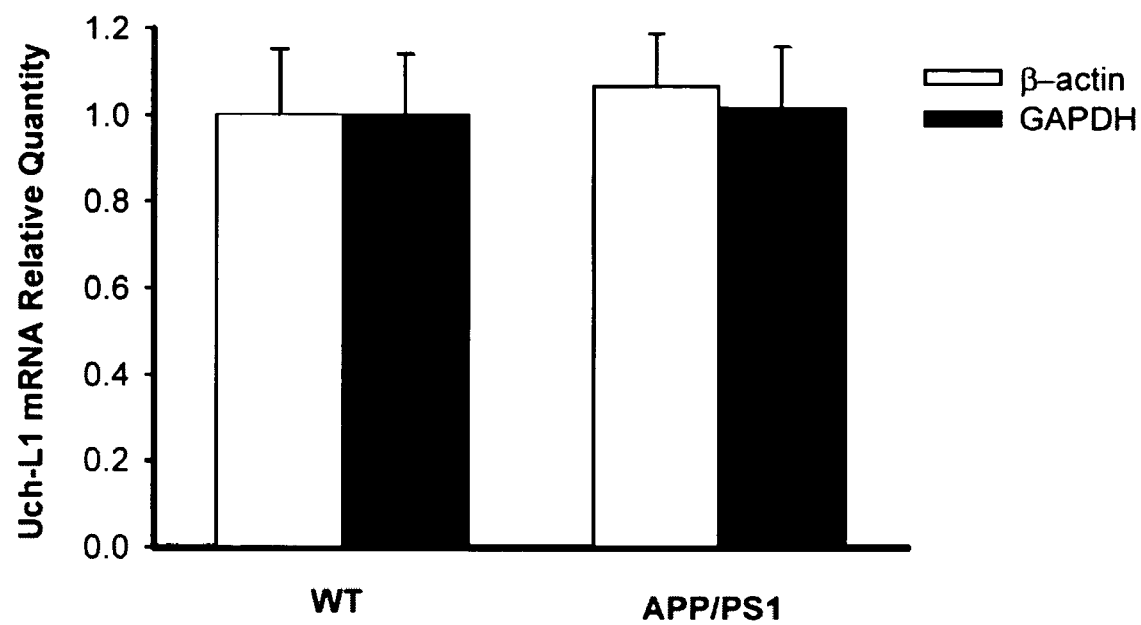

Ubiquitin C-terminal hydrolase (Uch) has been implicated in learning and memory in Aplysia (Hegde et al., 1997). To determine whether alterations in the synthesis and/or enzymatic activity of Uch might be involved in the memory loss of AD, Uch activity was measured using an assay for deubiquitinating enzymes based on the substrate ubiquitin C-terminal 7-amido-4-methylcoumarin (Ub-AMC) (Dang et al., 1998). There was a decrease of almost 40% in hydrolase activity in APP/PS1 mice compared to WT littermates (FIG. 14A). Next, the expression level of Uch-L1 mRNA was measured by using quantitative real-time RT-PCR analysis. The primer probe set was designed for the Uch-L1 gene, and total RNA was prepared from the hippocampus of APP/PS1 mice and WT littermates. The expression level of Uch-L1 mRNA in double transgenic mice was similar to that of WT littermates (FIG. 14B). Similar results were obtained when the cortices of APP/PS1 mice were compared to WT littermates. Measurement of the levels of Uch-L1 protein by using quantitative Western blot analysis on hippocampal slices showed normal levels of Uch-L1 in APP/PS1 mice as compared to WT littermates (FIG. 14C). Taken together, these results indicate that the Uch enzymatic activity is down-regulated in transgenic mice overexpressing APP and PS1 transgenes. Moreover, it is likely that the loss of enzymatic activity is due to changes occurring at post-translational level. Consistent with these observations, post-translational changes that reduce ubiquitin-proteasome activity including increased aggregation of proteasome substrates and direct oxidative change of the ubiquitin-proteasome complex have been reported (Grune et al., 1995; Reinheckel et al., 1998; Tanaka, 1998).

Uch-L1 Activity is Essential for Normal Synaptic and Cognitive Function

Figure 15A:
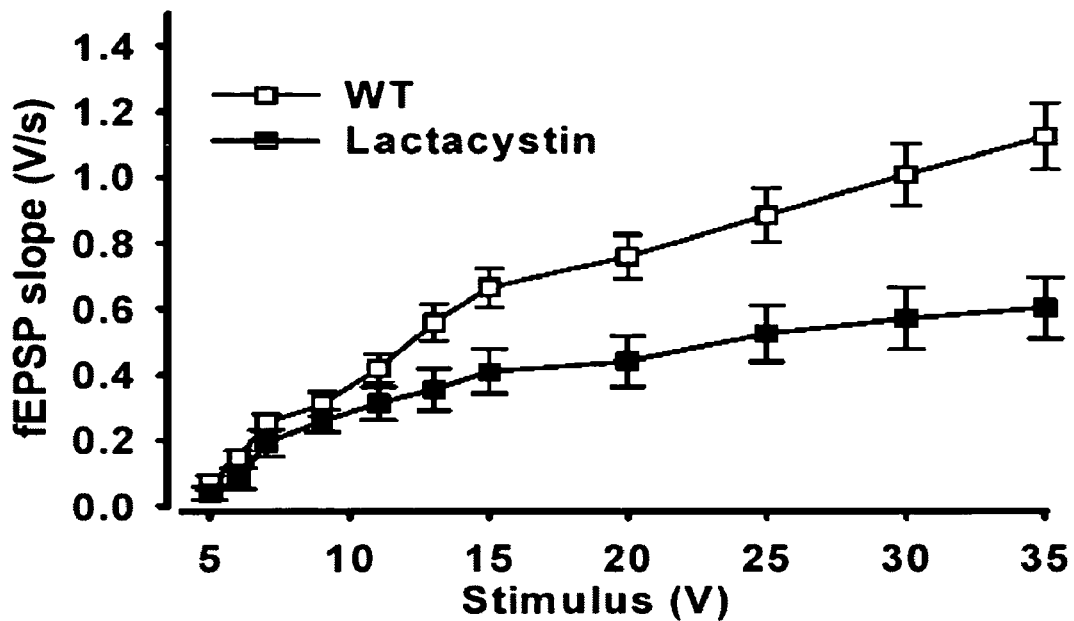
FIGS. 15A-15H. Activation of Uch-L1 is Essential for Synaptic and Cognitive Function.
Figure 15B:
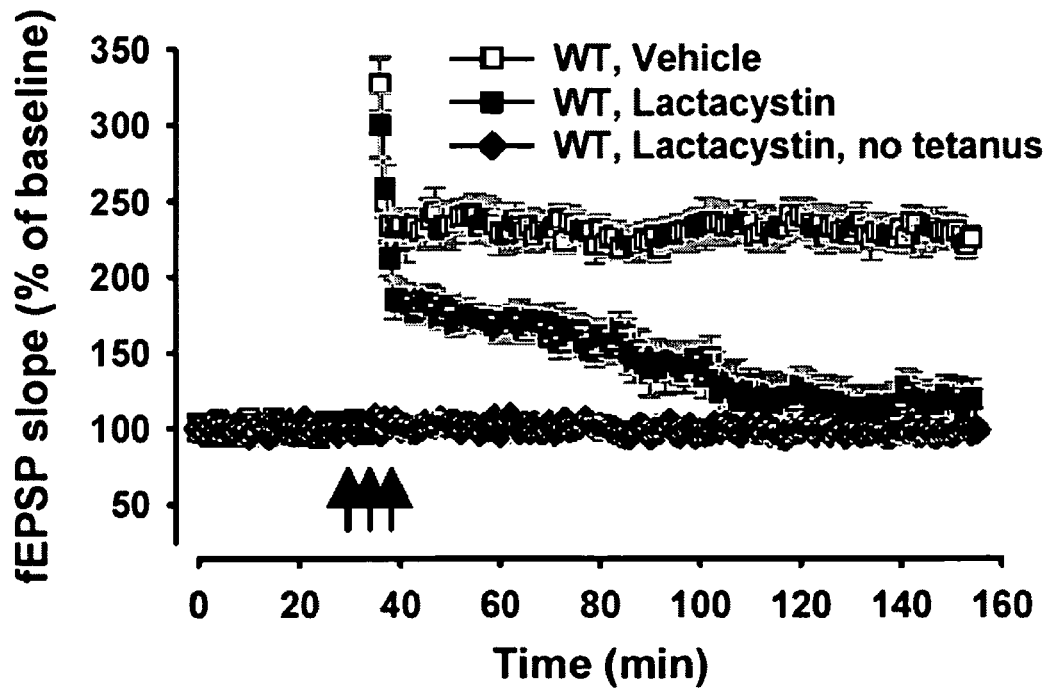
Figures 21A, 21B:
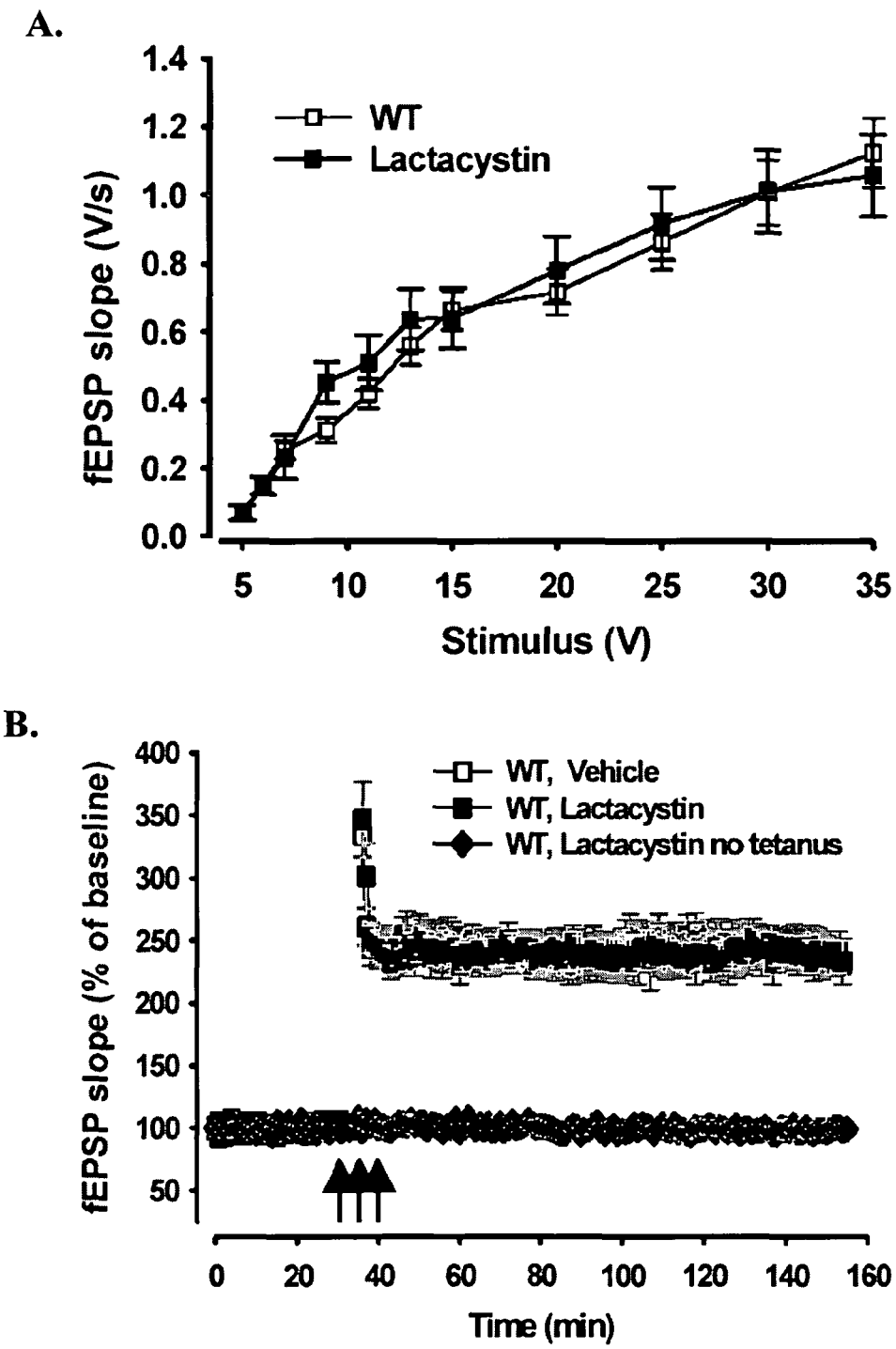
FIGS. 21A-21D. A Brief Inhibition of the Proteasome System does not Affect Synaptic Function.
Figure 21C:
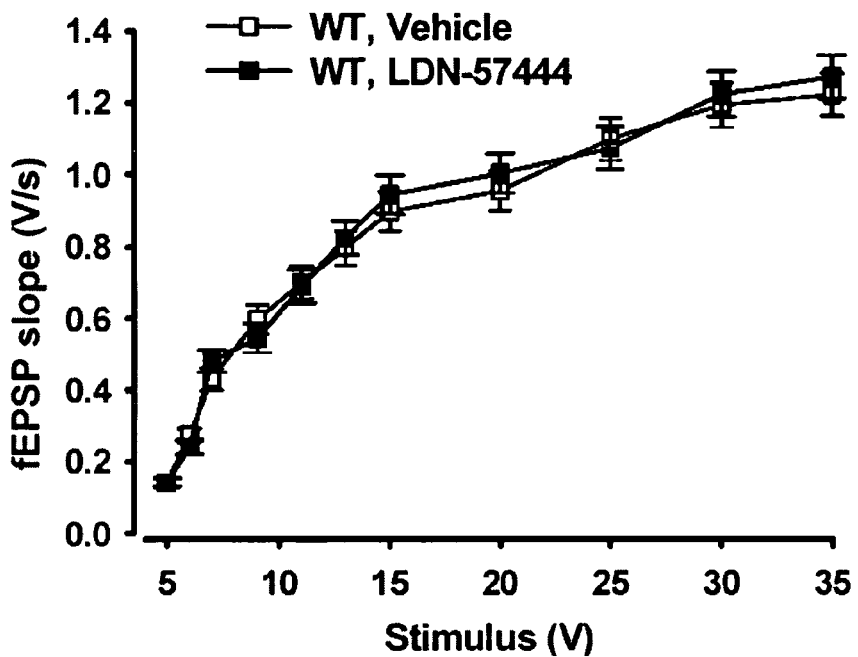

An increase in Uch activity regulates the switch from short-term to long-term facilitation in Aplysia (Hegde et al., 1997). To determine if proteasome function was also critical for these functions in mammalian brain, hippocampal slices were perfused with lactacystin (10 µM), an irreversible membrane permeable inhibitor of the 20S-proteasome (Fenteany et al., 1995). A brief 15 min exposure to the inhibitor did not change basal synaptic transmission (BST) (FIG. 21A) or LTP (FIG. 21B). A longer 2 to 4 hour exposure to the inhibitor reduced both BST (slope of the input-output curve at 35 V) and LTP to approximately 50% that of vehicle treated slices (FIGS. 15A and 15B).

Figure 15C:
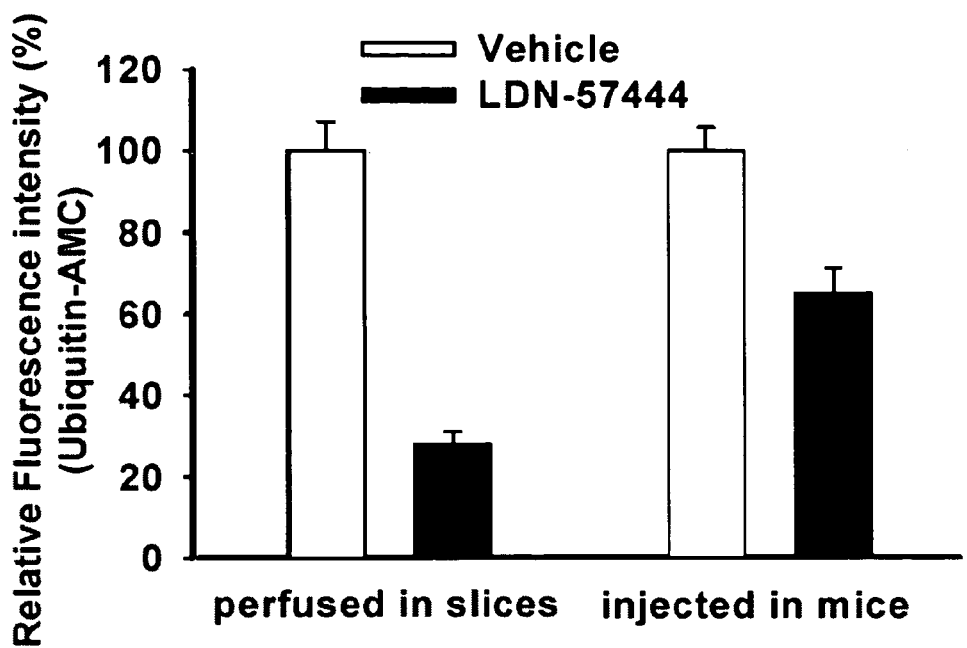
Figure 15D:
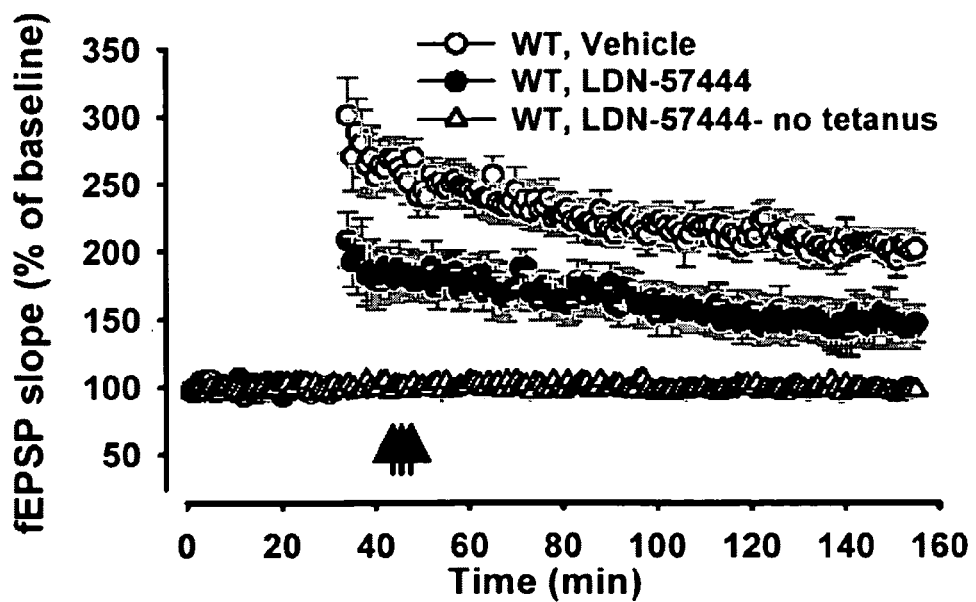
Figure 15E:
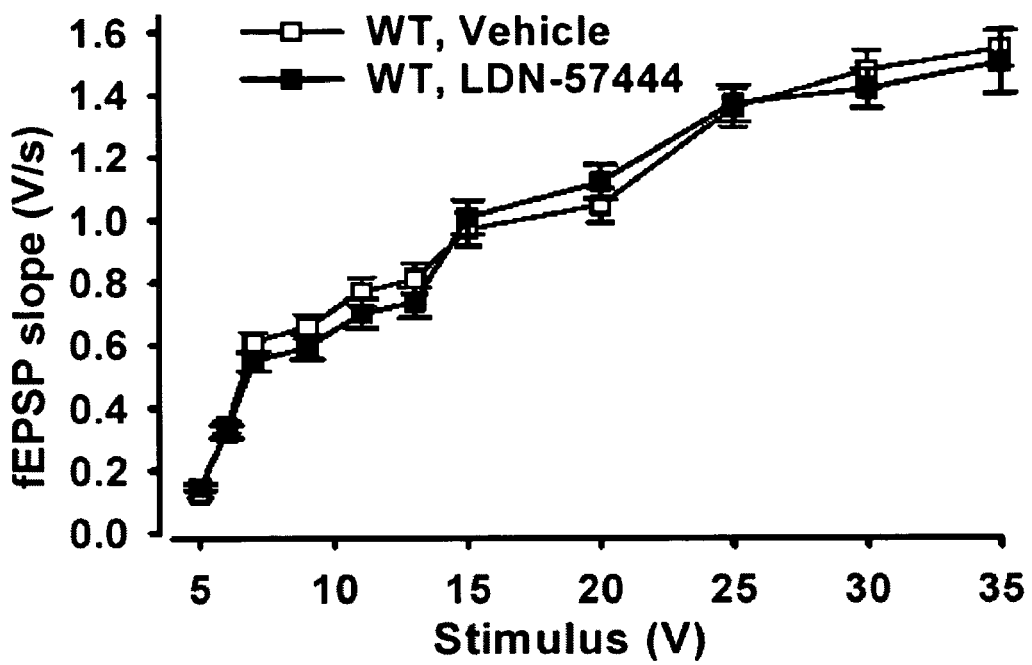
Figure 15F:
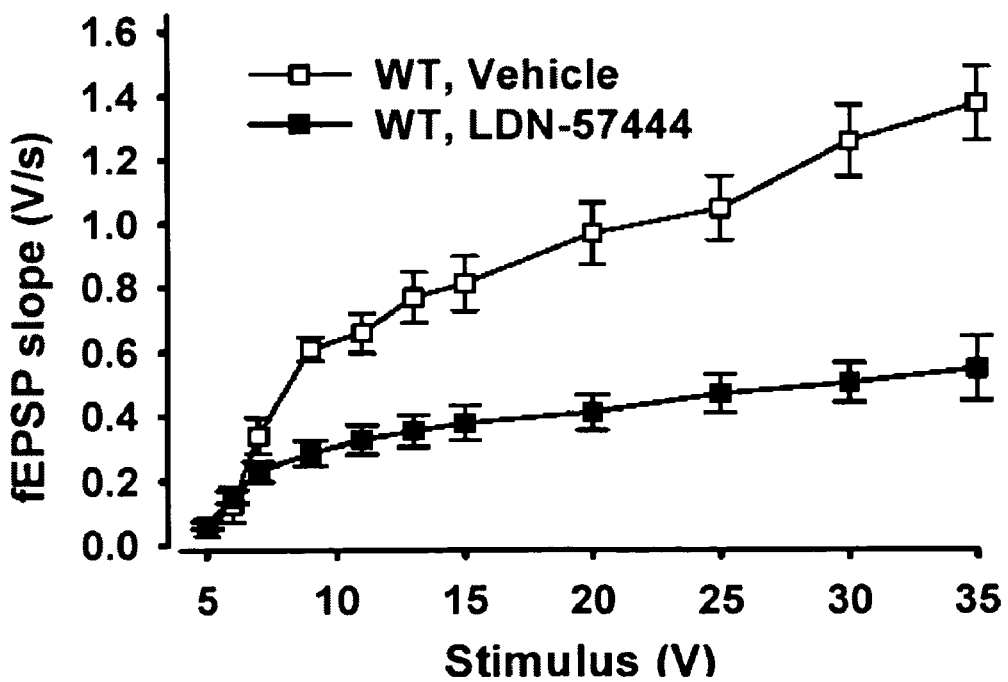
Figure 15G:
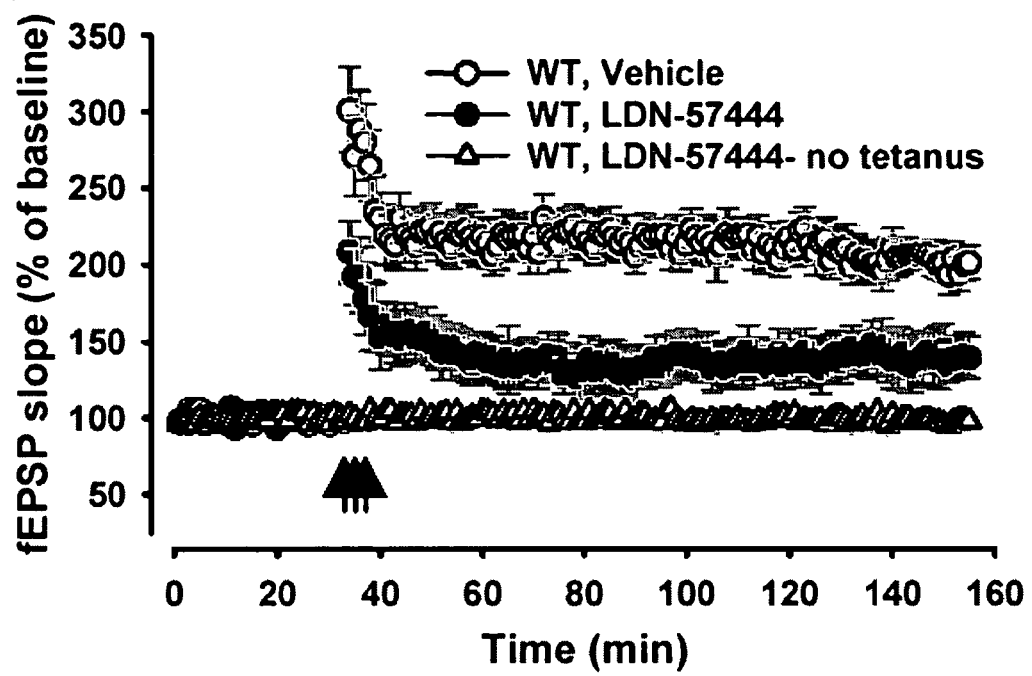
Figure 21D:
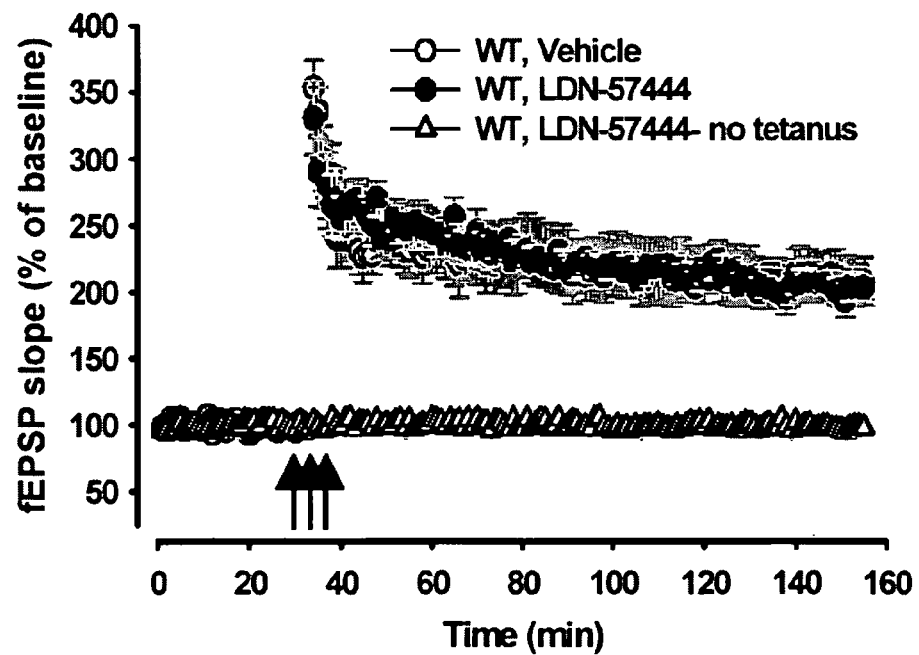

Uch-L1 is one of the many components of the ubiquitin-proteasome system. To demonstrate that Uch-L1 itself is essential for normal synaptic function, the same experimental protocol as for lactacystin was repeated by using the highly specific Uch-L1 inhibitor, LDN-57444 (Liu et al., 2002). This compound is a reversible, competitive and active site directed isatin oxime with an $IC_{50}$ value of 0.88 µM for Uch-L1 and 25 µM for its systemic isoform, Uch-L3. Experiments showed that perfusion with LDN-57444 was capable of reducing Uch-L1 hydrolase activity in hippocampal slices to less than 30% of vehicle-treated controls (FIG. 15C). When adult mice were injected with 0.4 mg/kg of the inhibitor and sacrificed 4 hrs after the injection, their Uch-L1 activity was reduced to 65% of vehicle injected controls (FIG. 15C). Exposure of hippocampal slices to the inhibitor for 15 minutes period did not affect BST or LTP (FIG. 21D). However, a longer 2 hour exposure to the inhibitor reduced LTP to approximately 70% of vehicle treated slices (FIG. 15D) without affecting BST (FIG. 15E). A 4 hour exposure reduced both BST (FIG. 15F) and LTP (FIG. 15G) to approximately 40% and 65% of vehicle treated slices, respectively. These data show that proteasomal and Uch-L1 activity are critical for normal hippocampal synaptic function in mice.

Figure 15H:
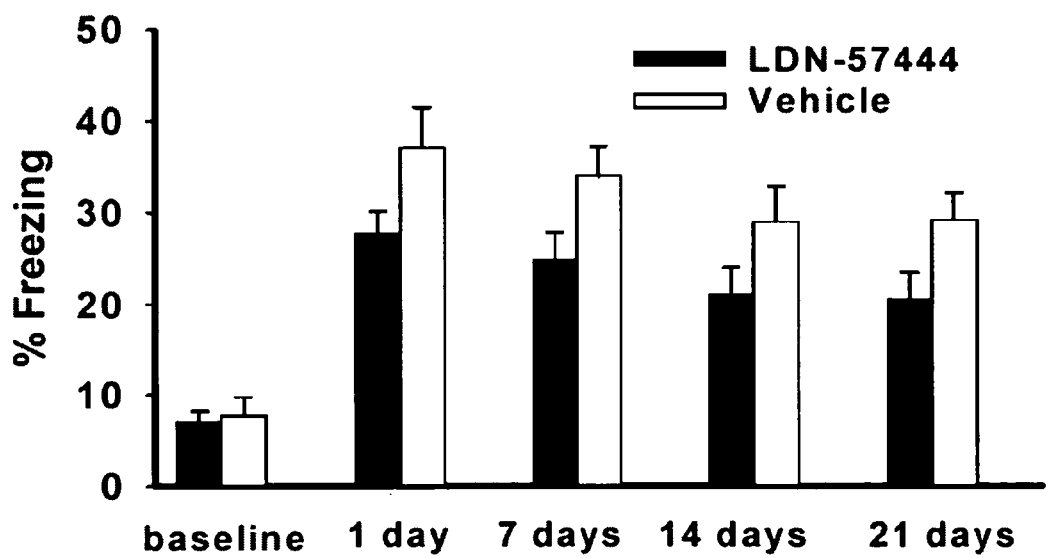

Because the electrophysiological studies showed that inhibition of Uch-L1 impairs synaptic function in hippocampus, an area of the brain required for learning and memory, fear-conditioning, a form of explicit learning that has been found to be impaired in different AD mouse models (Dineley et al., 2002; Gong et al., 2004) was used to determine whether Uch-L1 is essential for learning and memory in mice. The fear-conditioning learning paradigm depends on the hippocampus and amygdala. The hippocampus, is indispensable for contextual fear learning (Phillips and LeDoux, 1992), a form of associative memory in which mice must associate a neutral stimulus with an aversive one. LDN-57444-(0.4 mg/kg i.p. at 4 hrs after the electric shock) and vehicle-injected mice were subjected to a standard fear-conditioning paradigm (Bourtchuladze et al., 1994). The animals were placed in a novel context (fear-conditioning box) and were exposed to a tone (conditioned stimulus [CS]) paired with a mild foot shock (unconditioned stimulus [US]) (training phase of the fear conditioning). Conditioning was assessed 24 hours later by measuring "freezing" behavior—the absence of all movement except for that necessitated by breathing—in response to the context (contextual conditioning) or the auditory cue (CS) within a completely different context (cued conditioning). During the training phase, no difference in the freezing of LDN-57444- or vehicle-injected mice was seen. Twenty-four hours later there was a decrease in the freezing time of LDN-57444-treated mice to 74% of that of vehicle-treated mice in contextual conditioning (FIG. 15H). Cued fear conditioning, did not show a difference in freezing behavior between the 2 groups (p>0.05) suggesting that the amygdala, which is involved mainly in cued conditioning (Phillips and LeDoux, 1992), is not impaired by Uch-L1 inhibition. The difference in the freezing time persisted when contextual learning was assessed 7- 14- and 21 days following exposure to the electric shock with LDN-57444-injected mice having values of about 70% of vehicle-treated mice at 21 days (FIG. 15H). These data show that Uch-L1 activity is essential for normal cognitive function.

Exogenous Uch-L1 Rescues the Deficit of LTP by Aβ

Figure 16A:
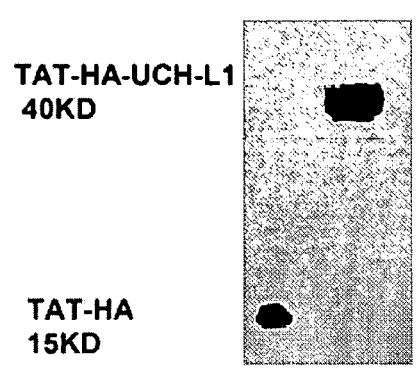
FIGS. 16A-16G. The 11-Amino Acid Transduction Domain of HIV-Transactivator Protein (TAT) Carries Functional Uch-L1 Protein into Tissue both in Vitro and in Vivo.

To allow entry of Uch-L1 into cells, the invention provides a fusion protein in which an 11-amino acid transduction domain of the HIV-transactivator protein (TAT) is fused with Uch-L1 (Wadia and Dowdy, 2003; Wadia et al., 2004). The TAT protein transduction domain has been used to deliver a wide variety of biologically active cargo with high efficiency (≈100%) both in vitro and in vivo (Aarts et al., 2002; Cao et al., 2002; Lissy et al., 2000; Wadia and Dowdy, 2002) including Uch-L1 (Wada et al., 2001). Following subcloning of human Uch-L1 cDNA and its insertion into a pTAT-HA vector, TAT-HA and TAT-HA-Uch-L1 fusion proteins were expressed in *Escherichia coli* strain BL21(DE3)pLysS cells and purified (See Example 5). Western blotting using anti-HA as well as anti-human Uch-L1 antibody showed molecular weights for TAT-HA and TAT-HA-Uch-L1 fusion protein of approximately 15 KD and 40 KD respectively, confirming the presence of TAT-HA and TAT-HA-Uch-L1 fusion proteins (FIG. 16A).

Figure 1B:
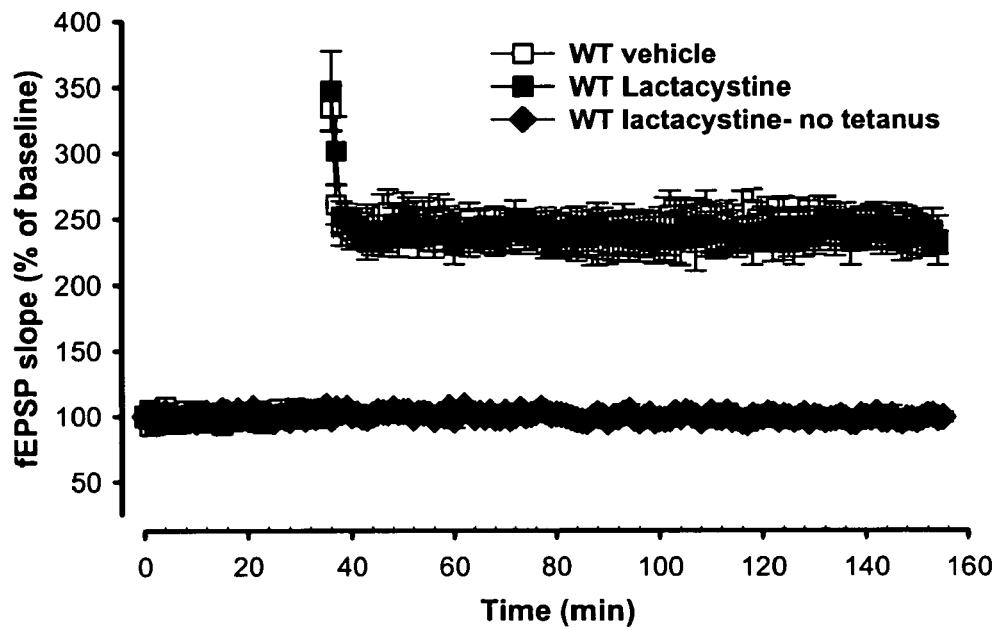
Figure 2A:
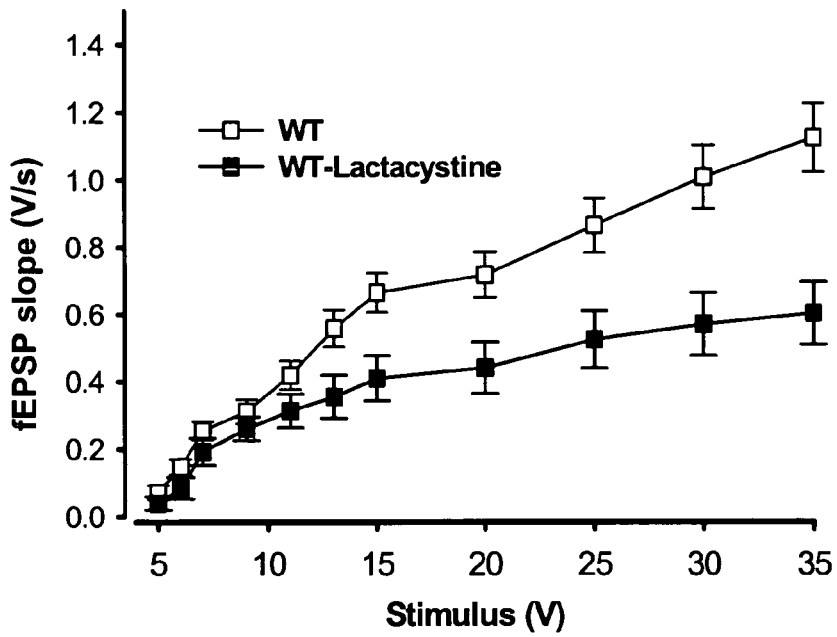
FIGS. 2A-2C. After 2-4 hrs treatment of 10 µM lactacystin, both BST (FIG. 2A) and LTP (FIG. 2B) as well as PPF (FIG. 2C) were markedly reduced.
Figure 2B:
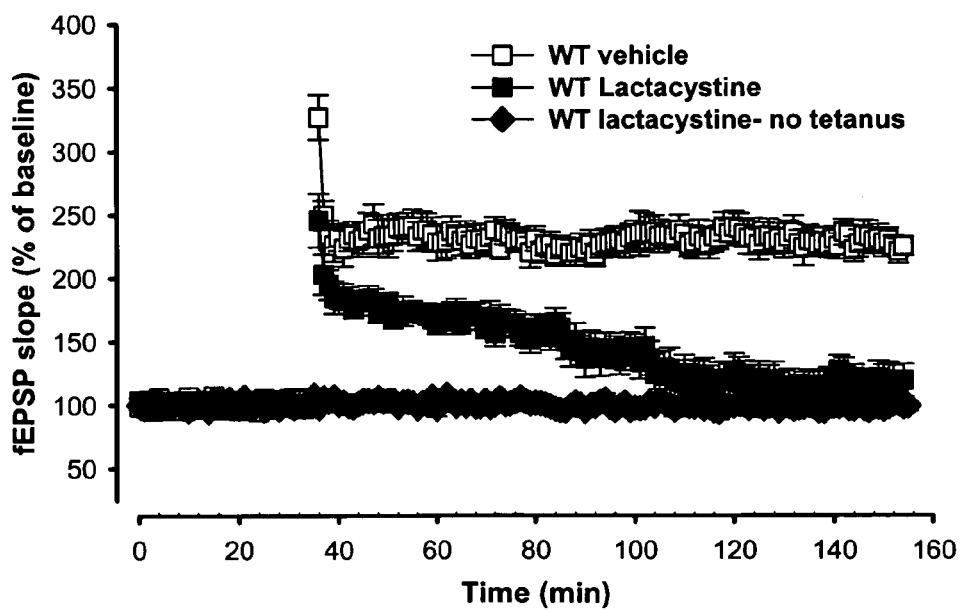
Figure 2C:
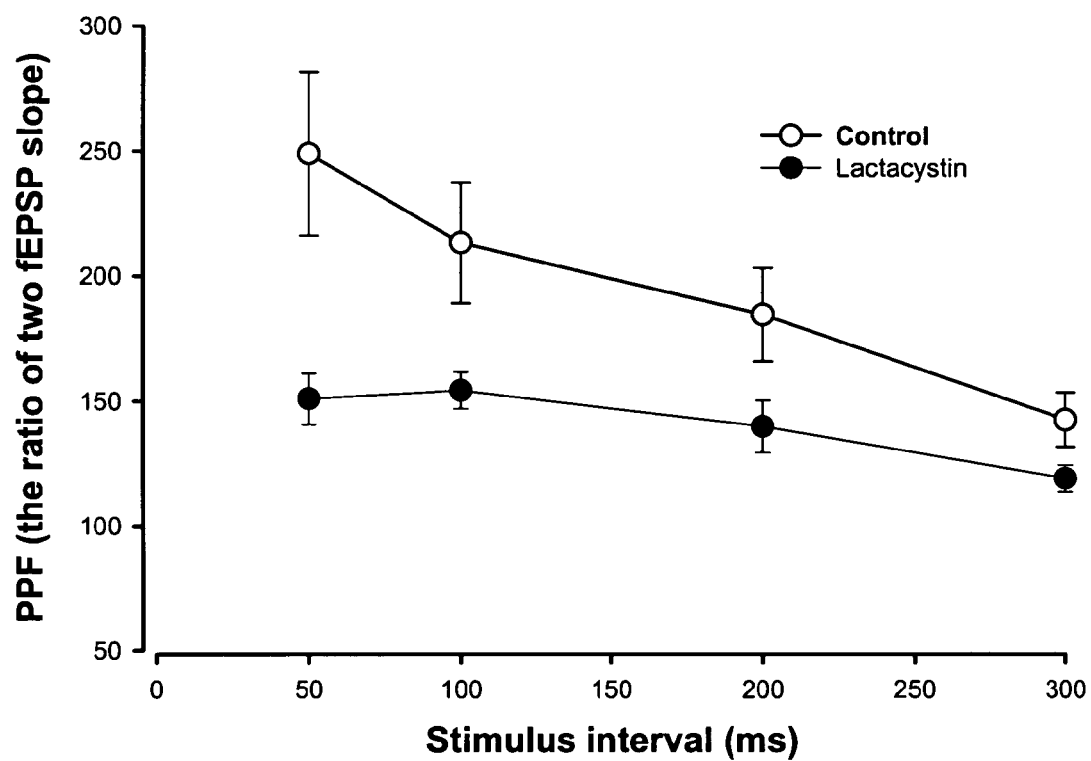
Figure 3A:
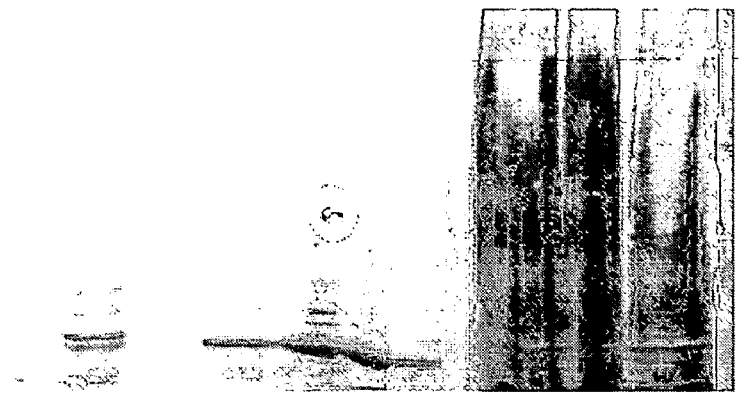
FIGS. 3A-3B. TAT-HA-Uch-L1 fusion protein purification was probed by Coomasie blue staining (FIG. 3A) and western blotting (FIG. 3B).
Figure 3B:
Figure 4A:
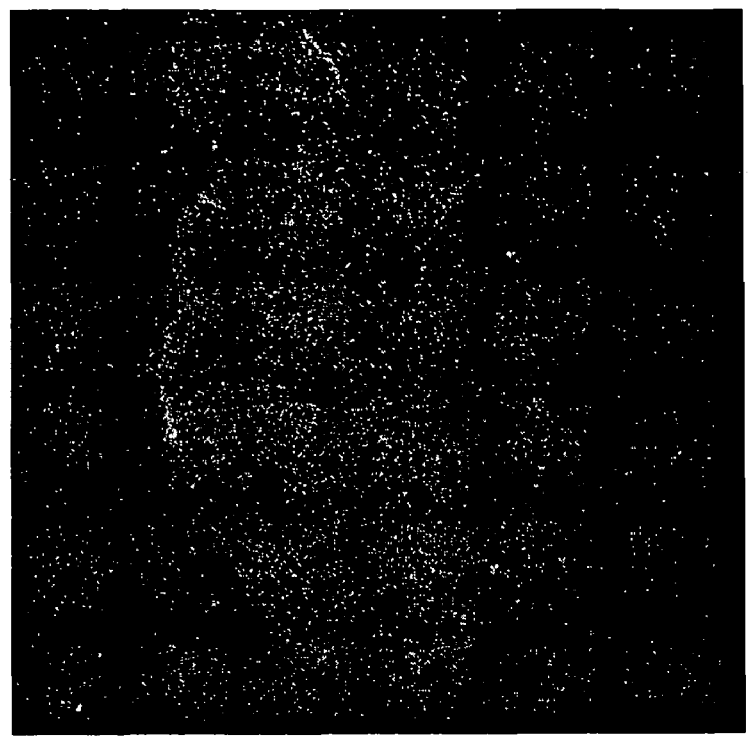
FIGS. 4A-4B. Immunohistochemical staining shows that TAT-HA-Uch-L1 fusion protein incubated slices (FIG. 4B) have more fluorescence intensity than vehicle treated slices (FIG. 4A) which only have weak background staining.
Figure 4B:
Figure 5A:
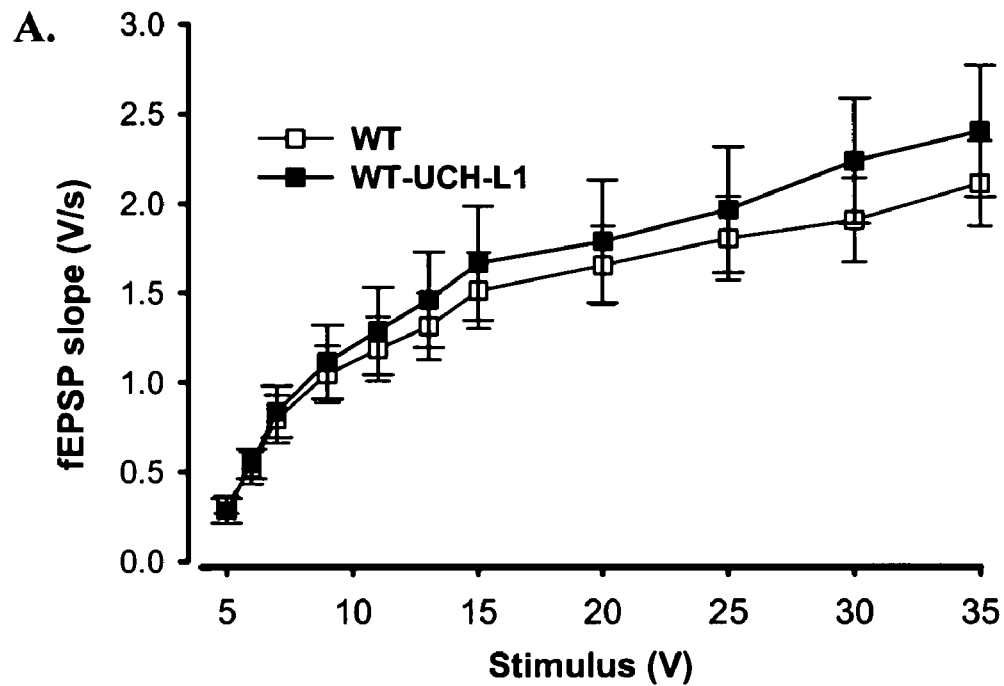
FIGS. 5A-5B. 20 nM Uch-L1 fusion protein does not affect BST (FIG. 5A) and LTP (FIG. 5B) in WT slices.
Figure 5B:
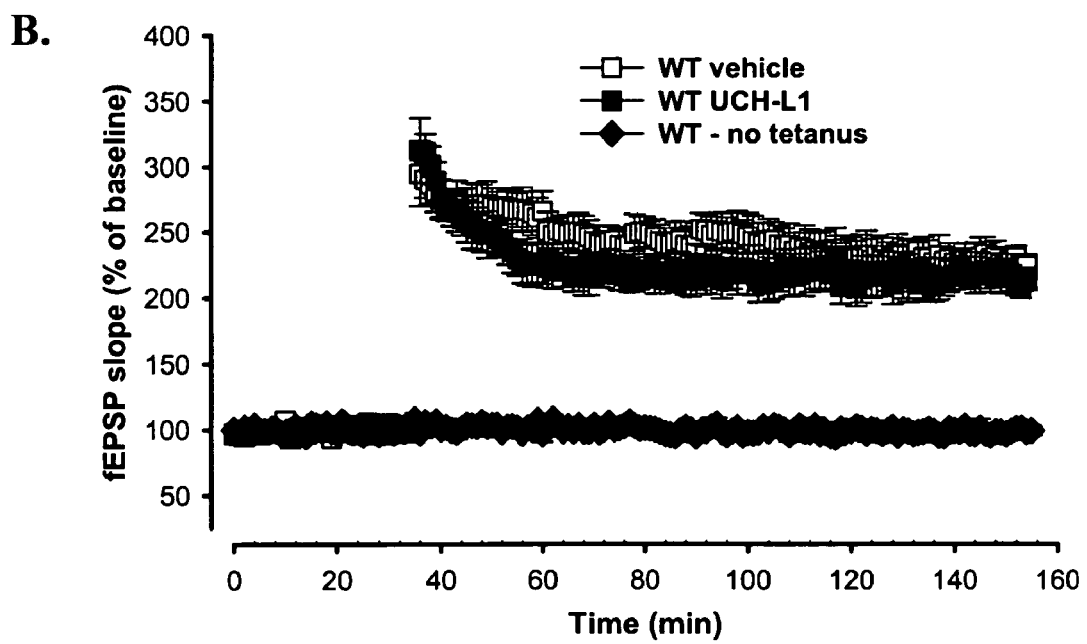
Figure 6A:
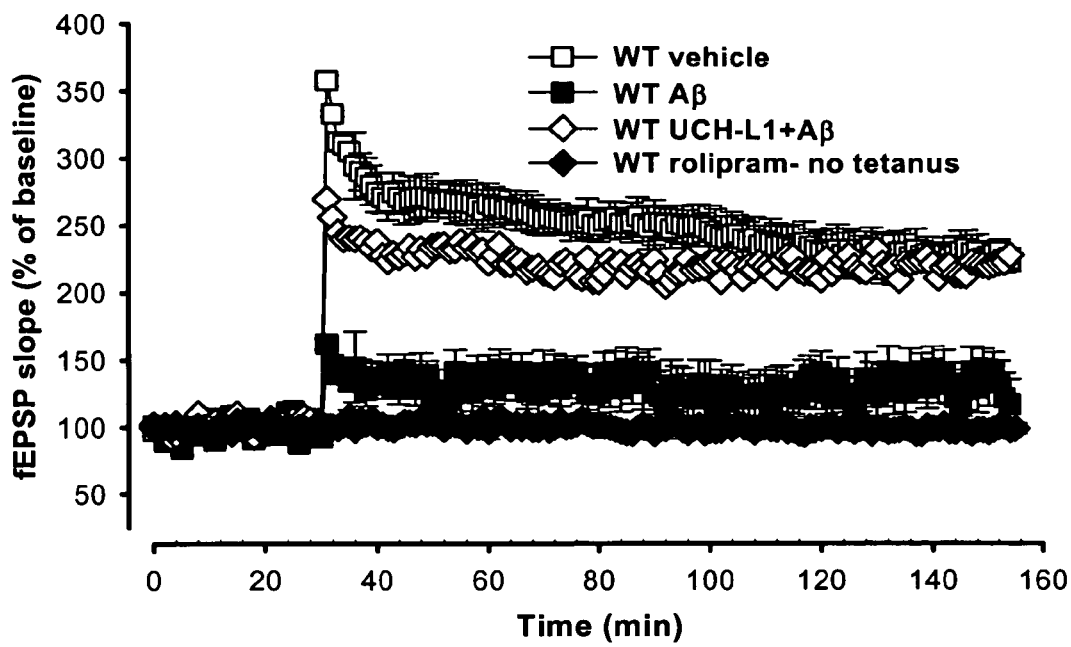
FIGS. 6A-6B. 20 nM Uch-L1 fusion protein reverses the deficits of LTP caused by 200 nM amyloid-beta (FIG. 6A). The PKA inhibitor KT5720 (1 µM) blocks the Uch-L1 fusion protein reversing effects on LTP (FIG. 6B).
Figure 6B:
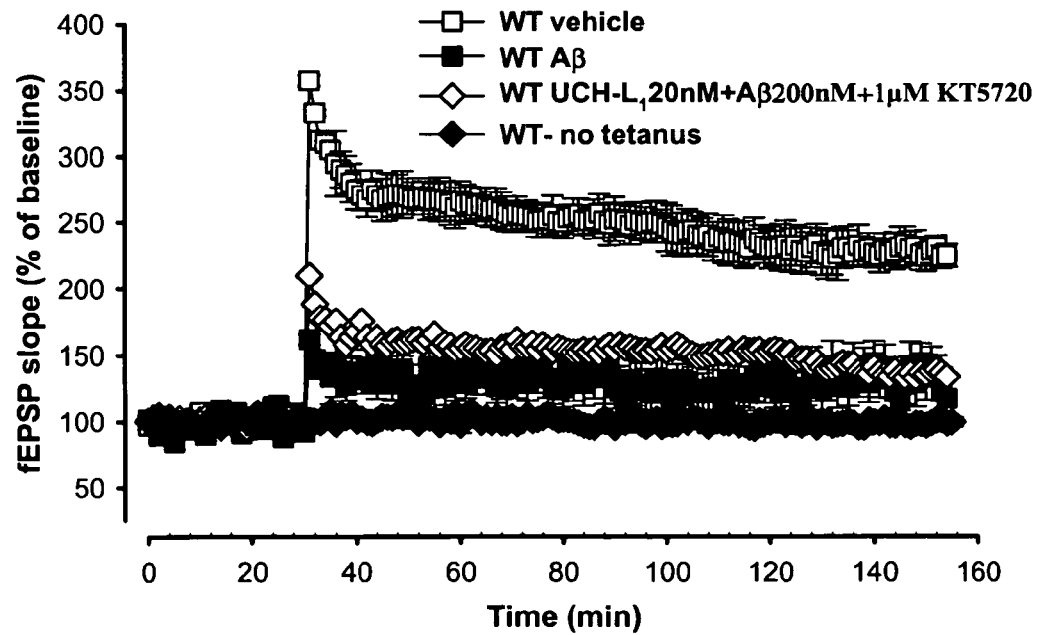
Figure 7:
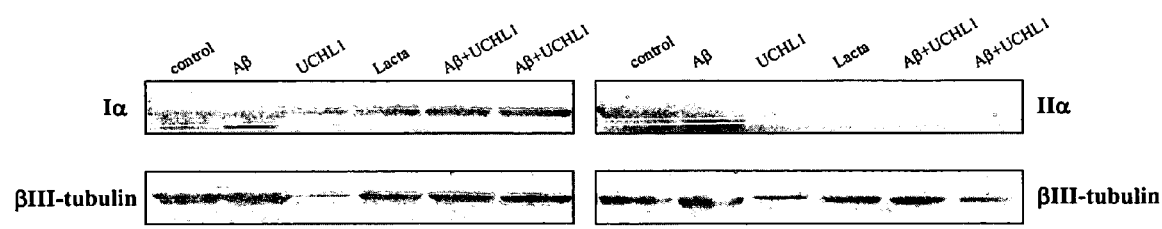
FIG. 7. PKA Regulatory subunit IIα level was increased by amyloid-beta. This increase was blocked by Uch-L1 fusion protein.
Figure 8:
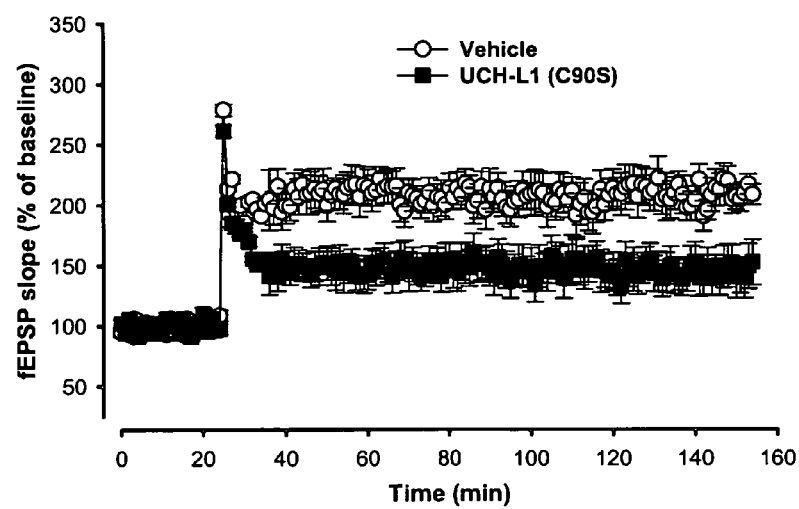
FIG. 8. Mutant (C90S) TAT-Uch-L1 fusion protein (20 nM) reduces LTP.
Figure 9A:
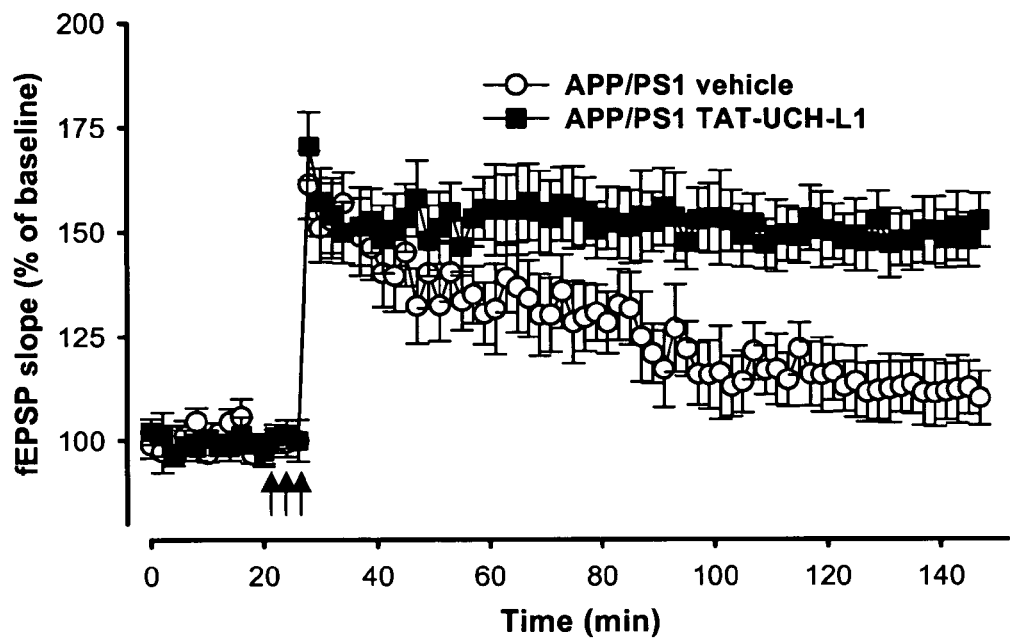
FIGS. 9A-9B.
Figure 9B:
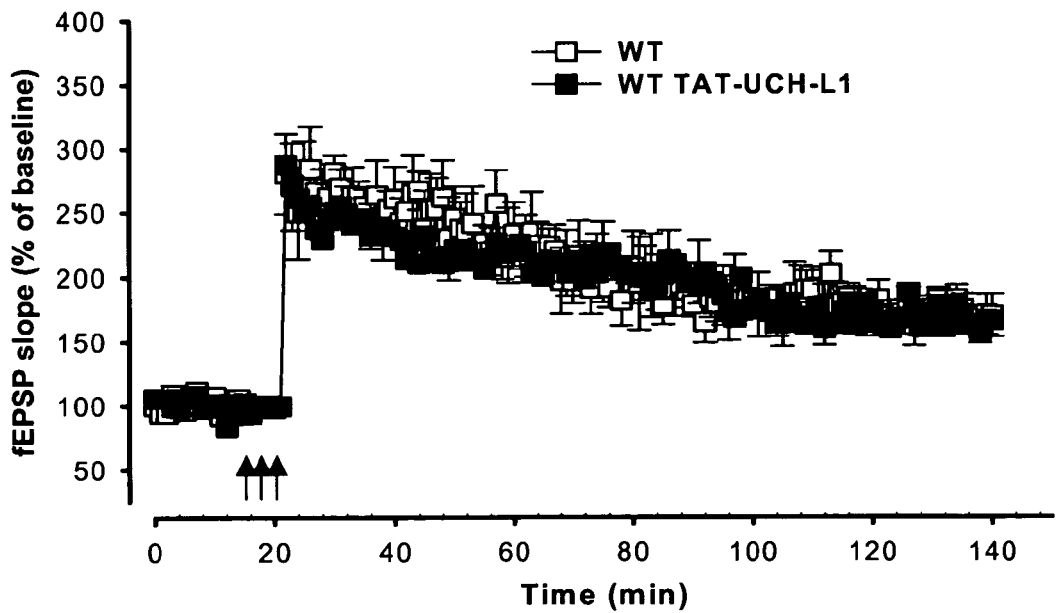
Figure 10:
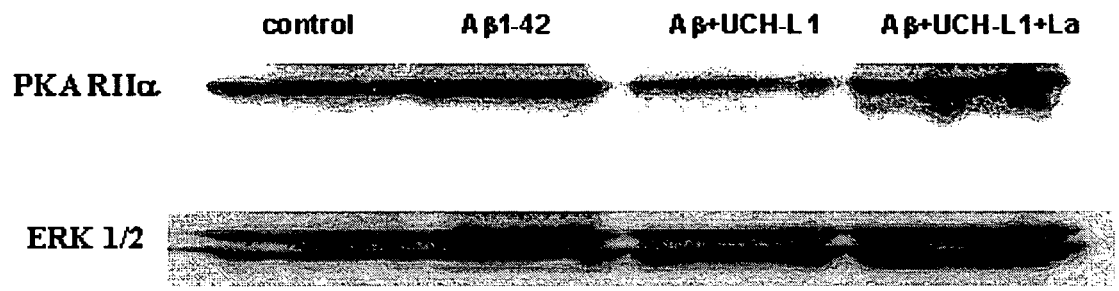
FIG. 10. TAT-Uch-L1 fusion protein (20 nM) blocks the increase in PKA RIIα levels induced by Aβ (200 nM) in hippocampal slices.
Figure 11:
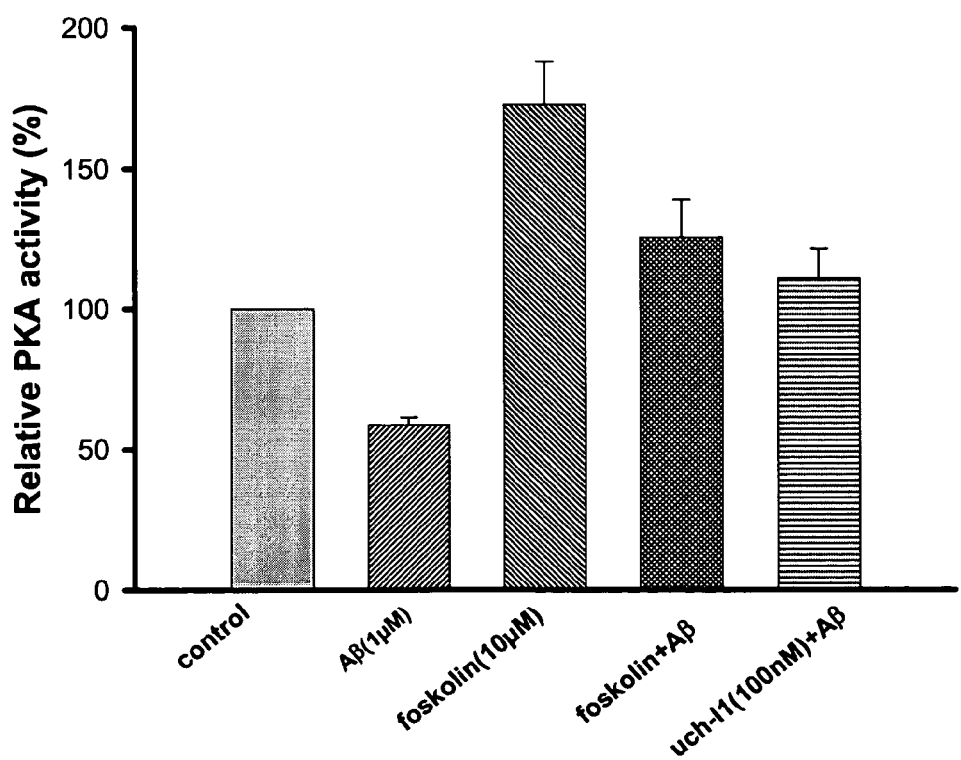
FIG. 11. TAT-Uch-L1 fusion protein re-establishes normal levels of PKA activity in Aβ-treated cultured hippocampal neurons. Cells were treated for 24 hrs with 1 µM Aβ with and without forskolin or TAT-Uch-L1.
Figure 16B:
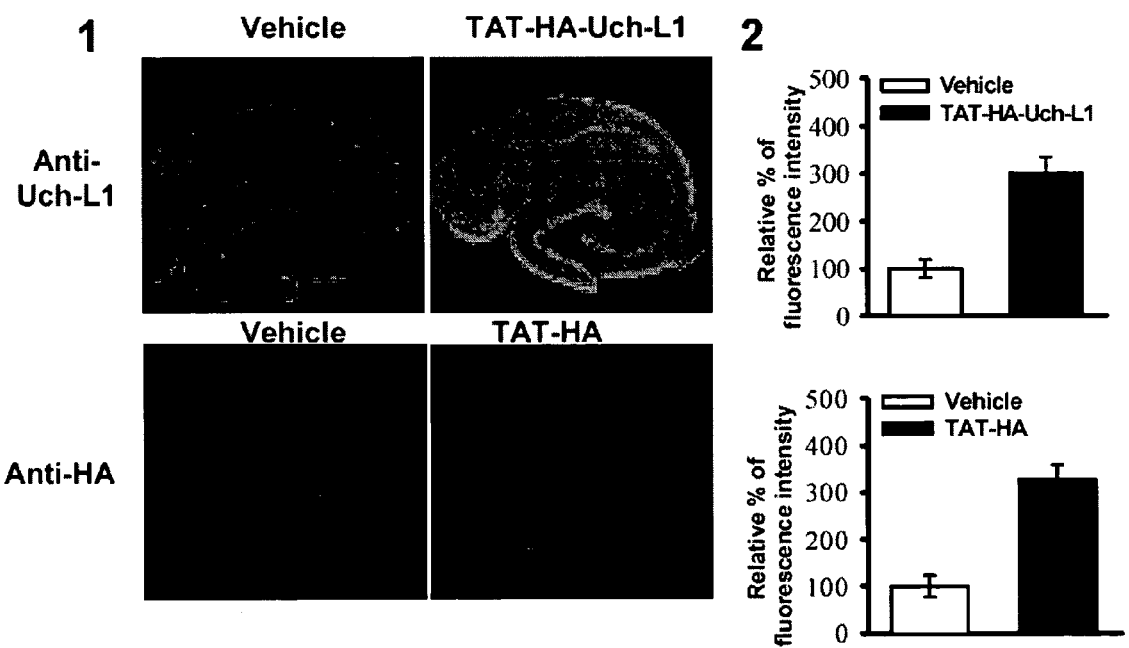
Figure 16C:
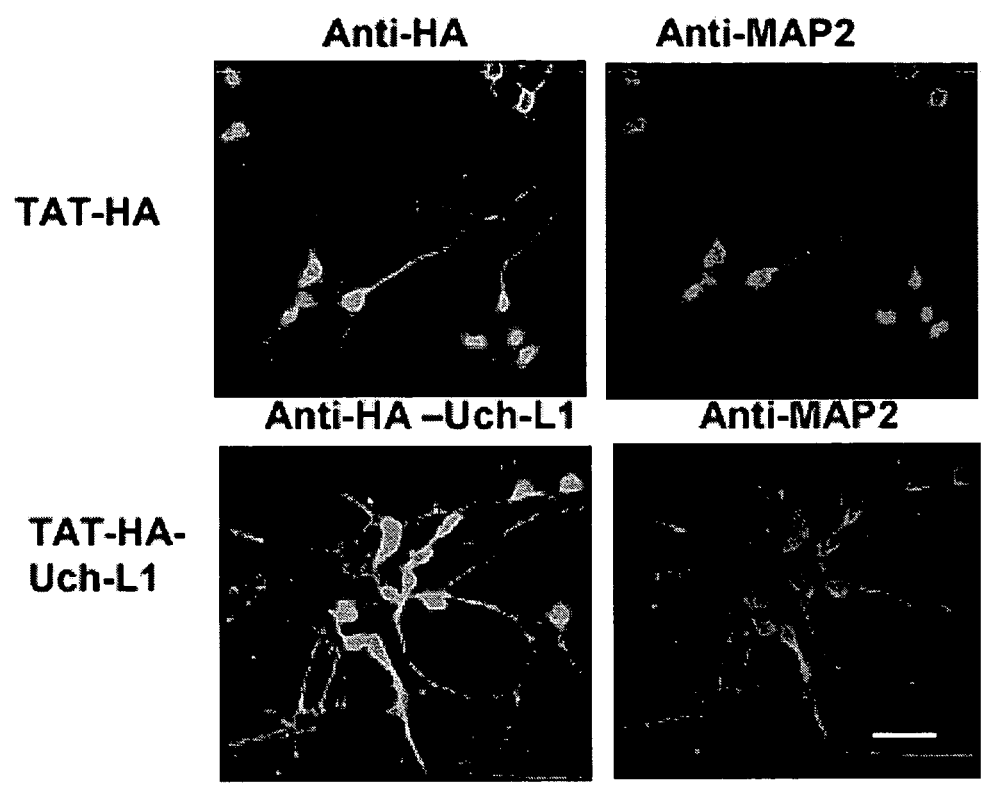
Figure 16D:
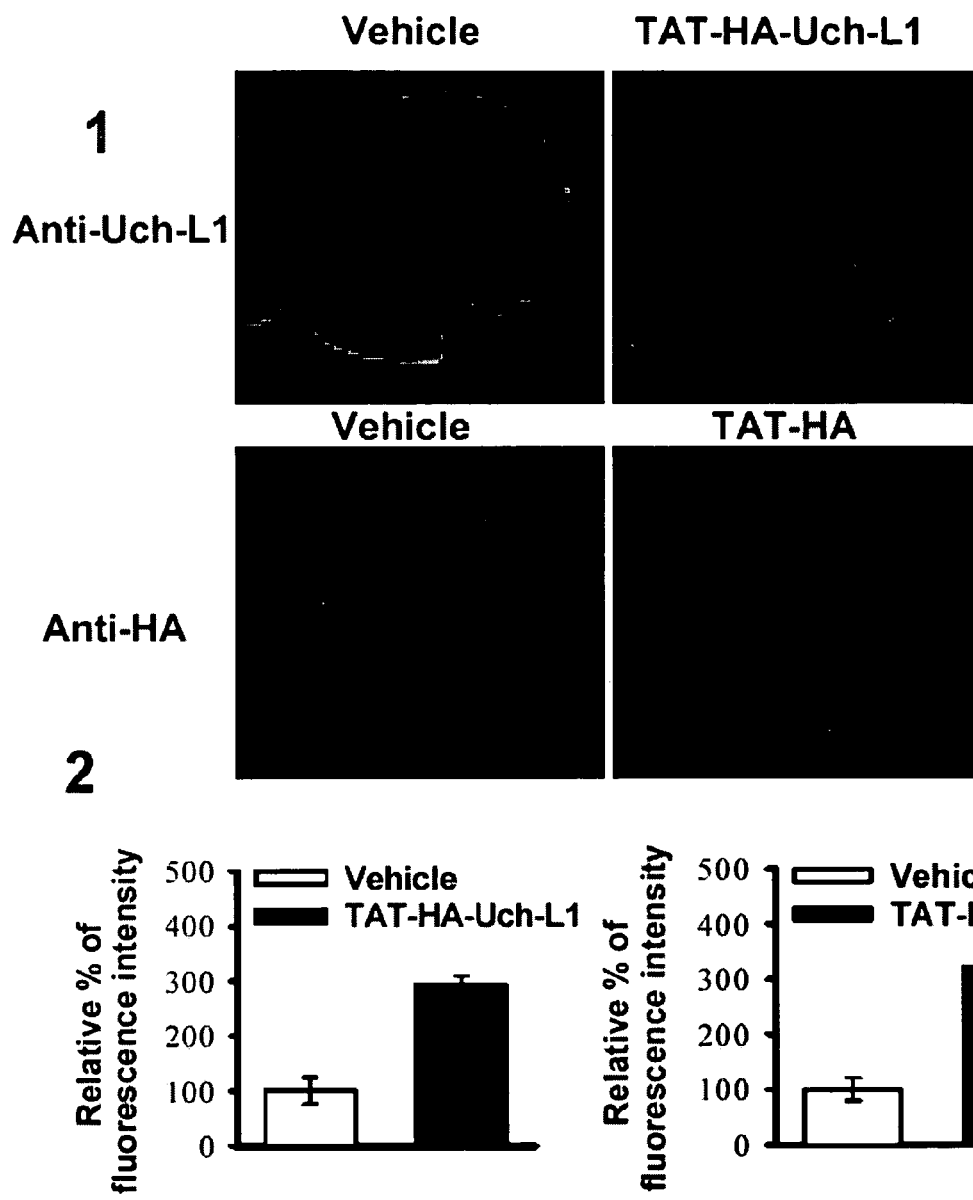

To show that TAT-HA-Uch-L1 enters cells, hippocampal slices were perfused with TAT-HA-Uch-L1 (20 nM) or TAT-HA (20 nM) or TAT-free vehicle solution for 1 hr. The slices were then fixed, stained with anti-Uch-L1 antibodies or HA antibodies, and viewed on a confocal microscope. There was an increase in the intensity of immunofluorescence after the perfusion with TAT-HA or TAT-HA-Uch-L1 compared to vehicle-treated control slices from the same animals (FIG. 16B1). Quantification of the immunofluorescence intensity in the CA1 region (same area LTP was recorded) revealed a three-fold increase in immunofluorescence in TAT-HA-Uch-L1 treated slices (FIG. 16B2). The intensity of staining was time-dependent with slices treated with TAT-HA-Uch-L1 showing a four-fold increase after 4 hrs. Penetration of TAT-HA-Uch-L1 or TAT-HA occurred also in primary hippocampal cultures. Dishes were treated with TAT-HA-Uch-L1 (100 nM) or TAT-HA (100 nM) or vehicle for 1 hr, fixed, co-labeled with antibodies against Uch-L1 and the specific neuronal marker MAP2 or antibodies against HA together with MAP2, and viewed on a confocal microscope. The same cells that showed positive immunoreactivity for TAT-HA-Uch-L1 or TAT-HA also double-labeled with MAP2 (FIG. 16C), confirming that the fusion proteins penetrate neurons. Finally, penetration of TAT-HA-Uch-L1 or TAT-HA occurred in live animals when they were administered TAT-HA-Uch-L1 or TAT-HA (0.02-0.04 g/kg, i.p.) and were sacrificed 4 or 8 hrs later. TAT-HA-Uch-L1- or TAT-HA-injected mice clearly showed an increase in immunofluorescence in the hippocampus when they were stained with antibodies against Uch-L1 or HA (FIG. 16D). In agreement with these results, Western blots from the hippocampi of mice injected with TAT-HA-Uch-L1 or TAT-HA (0.02-0.04 g/kg, i.p.) and sacrificed 4 hrs later showed the presence of TAT fusion protein as detected with anti-HA antibodies.

Figure 16E:
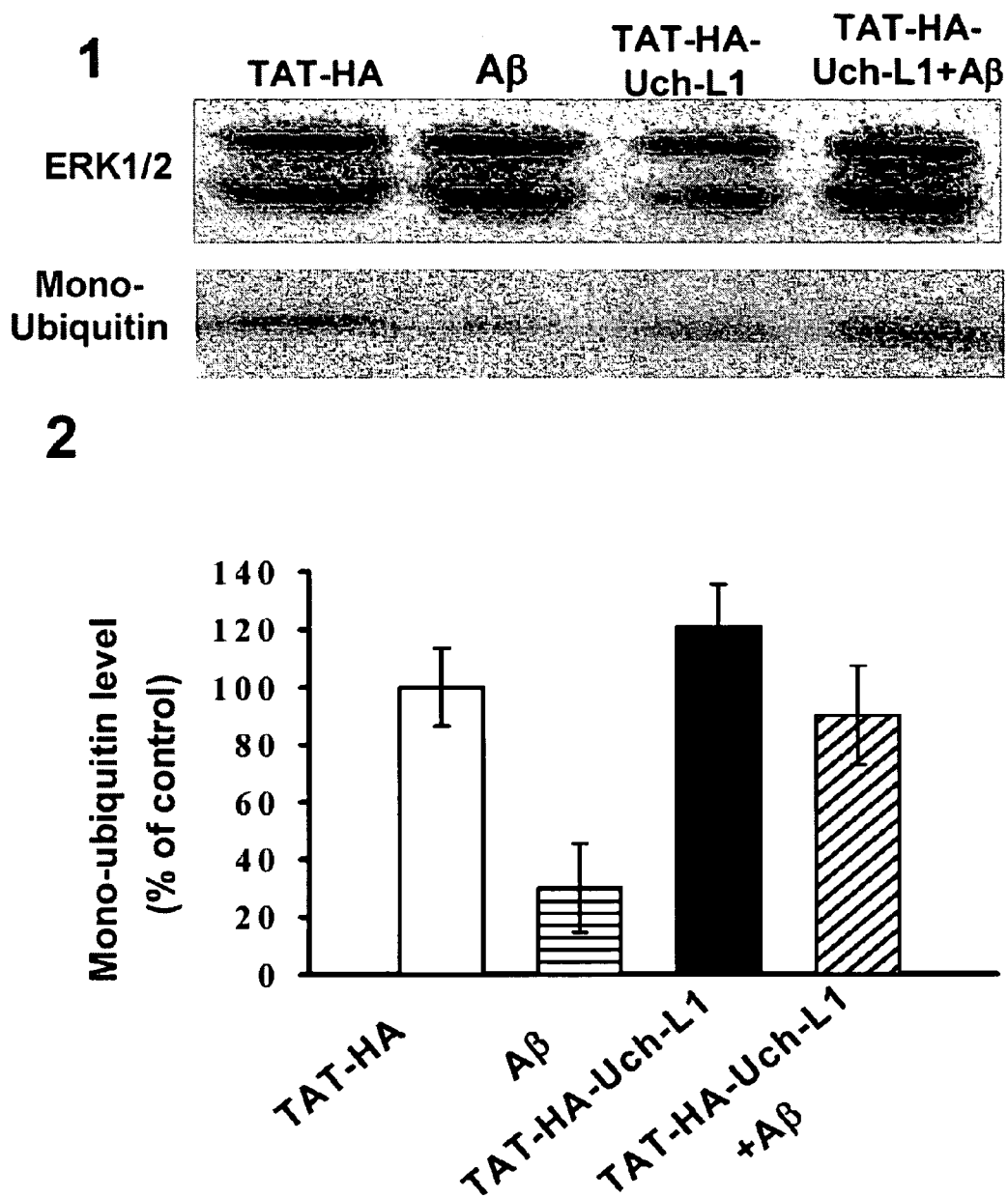
Figure 16F:
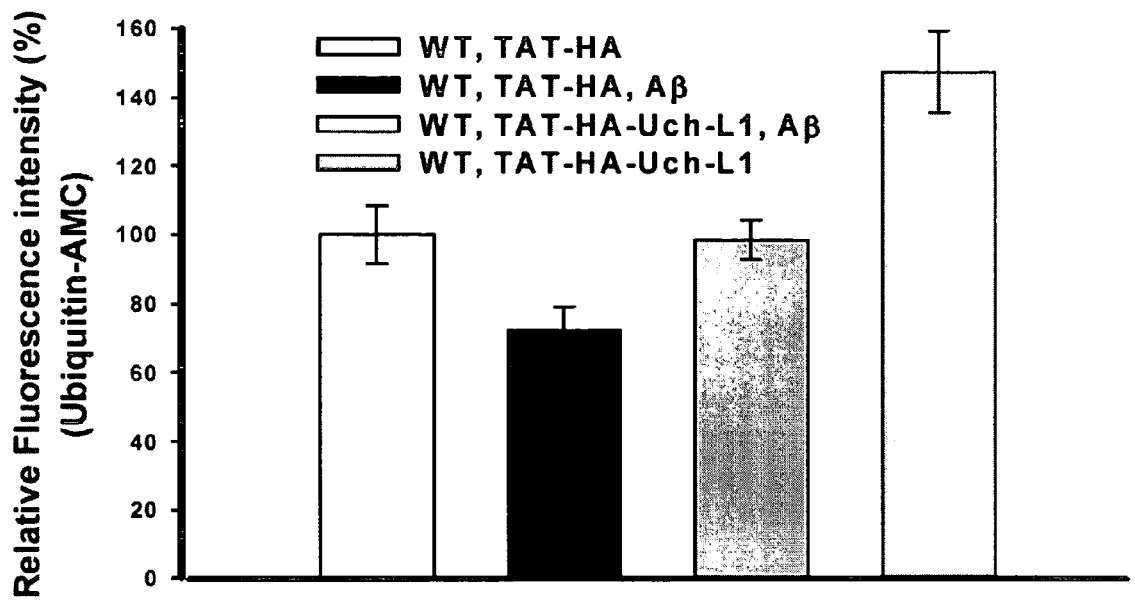

To determine if the exogenous TAT-HA-Uch-L1 protein is functional in the cell, the mono-ubiquitin levels were measured in Aβ-treated hippocampal cultures. Ubiquitin C-terminal hydrolases play an major role in the generation of monomeric ubiquitin (Wilkinson, 2000). Treatment with Aβ42 (200 nM for 20 min) markedly decreased the mono-ubiquitin levels to 30% of control values (FIG. 16E). Pre-incubation for 1 hour with TAT-HA-Uch-L1 peptide (20 nM) followed by perfusion with 200 nM oligomeric Aβ plus TAT-HA-Uch-L1 for 20 min re-established normal mono-ubiquitin levels (90.25±17.25% of control). TAT-HA-Uch-L1 peptide alone produced a slight increase in the mono-ubiquitin levels (121.03±14.69% of control). Treatment with 200 nM Aβ depressed the ubiquitin-c-terminal hydrolase enzymatic activity (72.36±6.81% of TAT-HA treated WT slices, FIG. 16F). This decrease was blocked by pre-incubation with 20 nM TAT-HA-Uch-L1 for 1 hr before applying 200 nM Aβ paired with TAT-HA-Uch-L1 (98.40±5.76% of TAT-HA treated WT slices). Incubation with TAT-HA-Uch-L1 alone for 1 hr increased the enzymatic activity to 148.63±12.01% of TAT-HA treated slices. These results show that the TAT-HA-Uch-L1 fusion protein is capable of re-establishing normal deubiquitination by ameliorating levels of enzymatic activity.

Figure 16G:
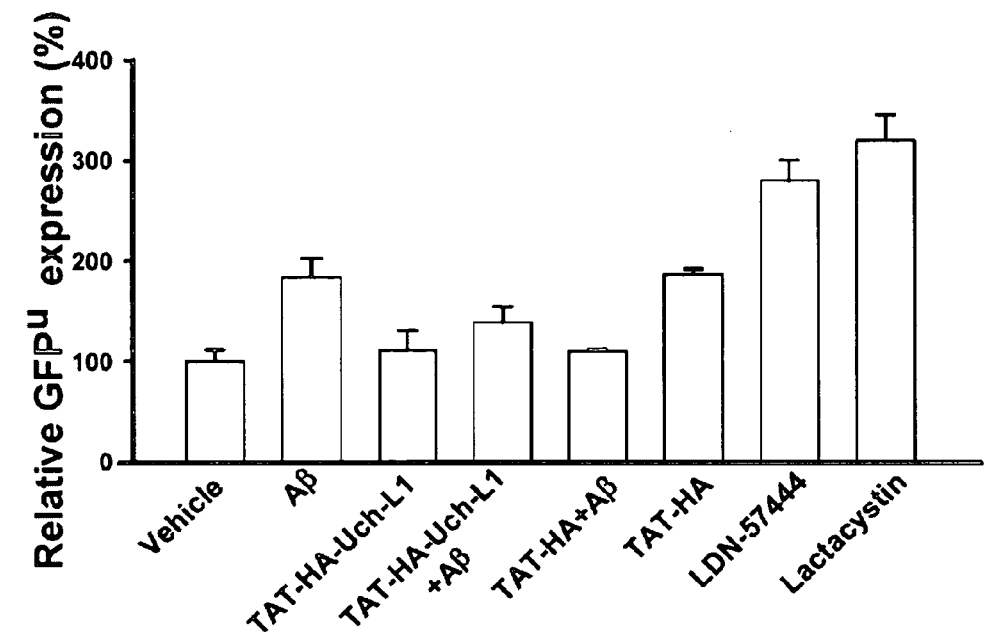

The effects of Aβ and TAT-HA-Uch-L1 on proteasome function were measured using a line of SY5Y neuroblastoma cells transfected with a degron CL1-GFP expression vector (Bence et al., 2001). These cells rapidly degrade the GFP produced, but in the presence of proteasome inhibitors, they become fluorescent and GFP is also detectable on western blots. When these cells were treated with oligomeric Aβ at concentrations as low as 200 µM, there is an increase in GFP levels as early as 20 minutes that persists for at least 24 hours (FIG. 16G). This inhibition is only partial as can be seen when compared to the much larger increase in GFP induced by either lactacystin or LDN-57444 (FIG. 16G). The Aβ inhibition can be reversed by incubation of the cells with TAT-HA-Uch-L1 at the same time as Aβ (FIG. 16G).

Figure 17A:
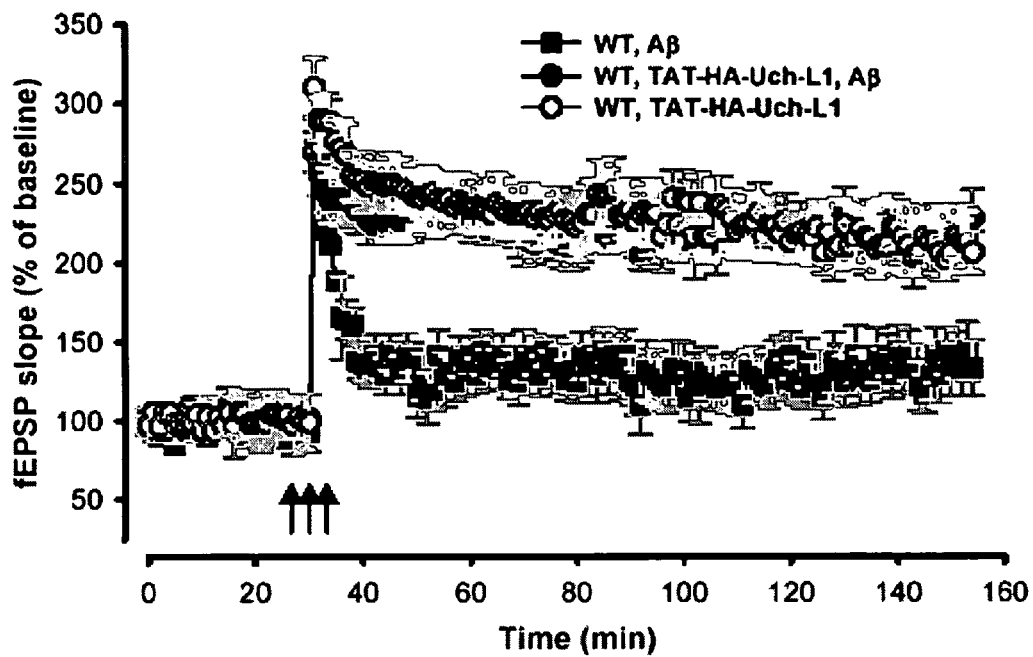
FIGS. 17A-17B. Exogenous Uch-L1 Rescues the Deficit of LTP by Aβ.
Figure 17B:
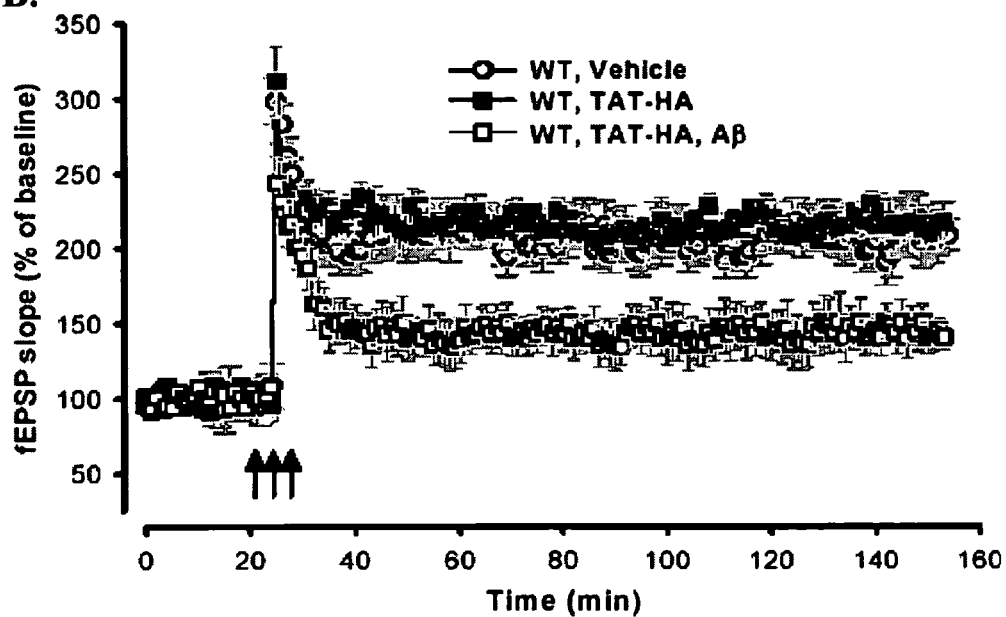
Figure 22:
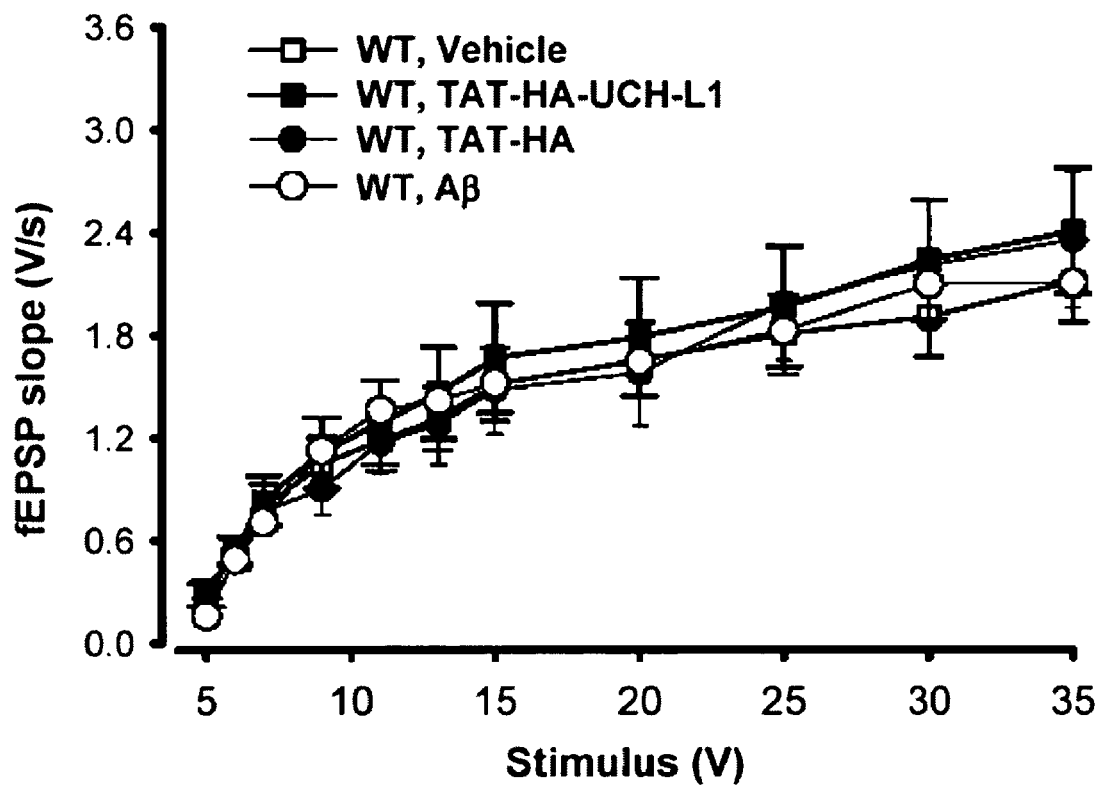
FIG. 22. Incubation of hippocampal slices for 1 hr with TAT-HA-Uch-L1 (20 nM) does not affect CA1-BST, nor incubation for 1 hr with TAT-HA-(20 nM) or 20 min $A\beta$ (200 nM) [TAT-HA-Uch-L1 n=9 slices from 9 mice; TAT-HA n=6 slices from 6 mice; $A\beta$ n=11 slices from 11 mice; vehicle n=10 slices from 10 mice; two-way ANOVA F(3, 33)=0.60, p>0.05].

Impairment of synaptic function is an important consequence of Aβ exposure (Cullen et al., 1997; Itoh et al., 1999; Vitolo et al., 2002; Walsh et al., 2002). To determine whether Uch-L1 plays a beneficial role in Aβ-induced synaptic dysfunction, hippocampal slices were treated with TAT-HA-Uch-L1 (20 nM) or TAT-HA (20 nM) or vehicle for 1 hr before evoking LTP with theta-burst stimulation. A 20 min perfusion with the oligomeric form of Aβ (200 nM) reduced LTP generation in the CA1 hippocampal region (136.34±13.40% of baseline slope at 120 min after tetanus) compared to control tetanized slices treated with vehicle alone (228.27±10.61%) (FIG. 17A). Pre-incubation (1 hr) with TAT-HA-Uch-L1 peptide (20 nM) followed by perfusion with 200 nM oligomeric Aβ plus TAT-HA-Uch-L1 for 20 min, prior to induction of LTP, protected against LTP suppression (FIG. 17A). On the other hand, pre-incubation (1 hr) with TAT-HA (20 nM) followed by perfusion with 200 nM oligomeric Aβ plus TAT-HA for 20 min, prior to induction of LTP, failed to protect (FIG. 17). TAT-HA-Uch-L1 and TAT-HA alone did not change the amplitude of LTP compared to that of slices treated with vehicle alone (FIG. 17). The protection by TAT-HA-Uch-L1 was not due to an effect of the peptide on baseline transmission because perfusion with the peptide alone did not modify the baseline. Moreover, assessment of the BST through measurement of the input/output curve in slices treated with TAT-HA-Uch-L1 or TAT-HA or vehicle or Aβ alone did not reveal any significant difference among treatments (FIG. 22).

Figure 18A:
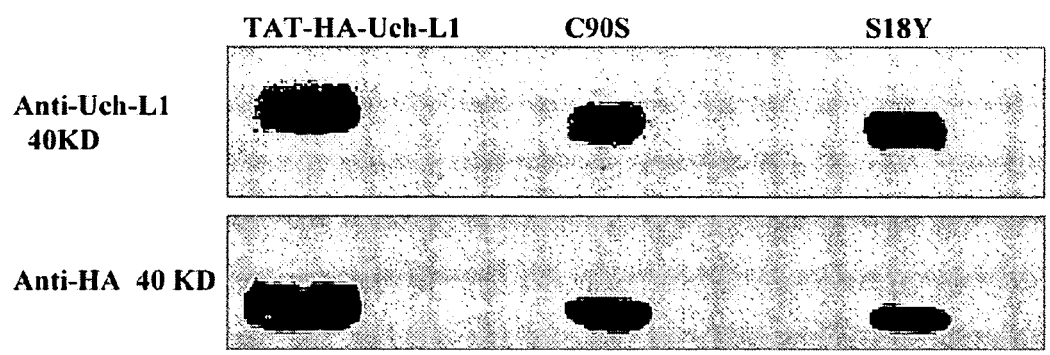
FIGS. 18A-18C. Hydrolase Function is Responsible for the Protective Effect of TAT-HA-Uch-L1 on LTP.
Figure 18B:
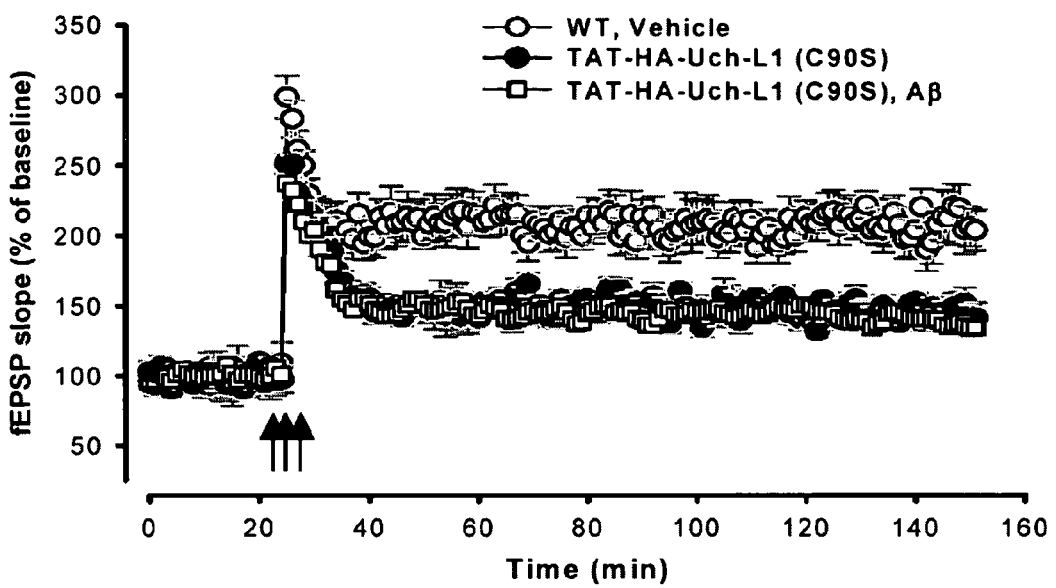
Figure 18C:
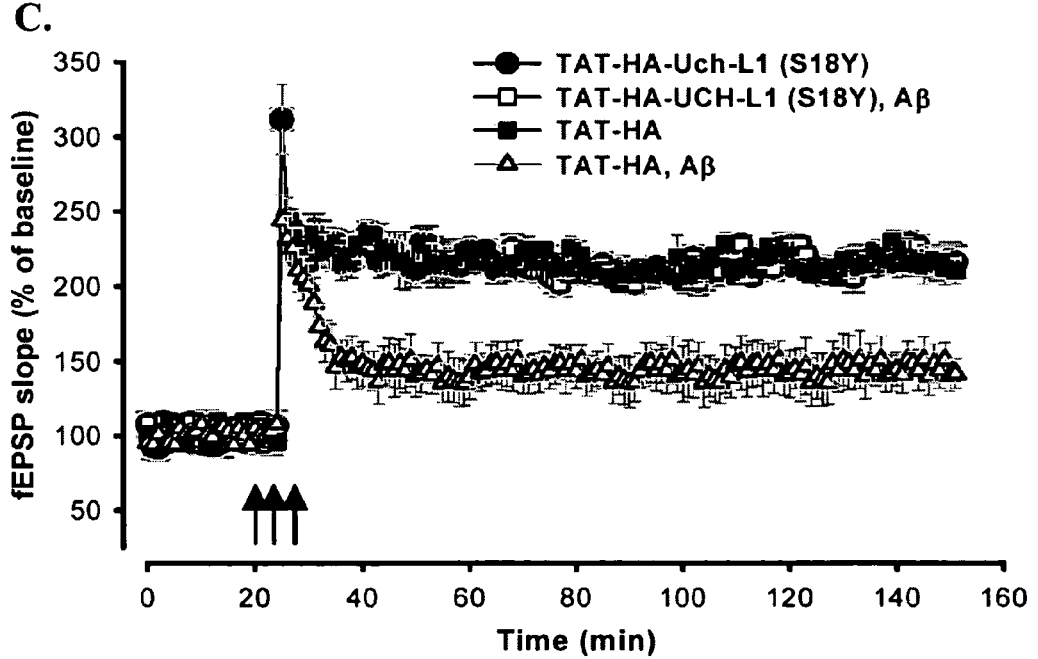

The Hydrolase Activity of Uch-L1 is Responsible for the Protective Effect of TAT-HA-Uch-L1 on LTP It has been shown that the Uch-L1 gene encodes two separate enzymatic activities (Liu et al., 2002). Both the C90 and H161 sites are involved in hydrolase function whereas the S18 site is involved in ligase function (Liu et al., 2002). To determine which function of Uch-L1 is involved in the beneficial effect of TAT-HA-Uch-L1 on Aβ-induced block of LTP, site-directed mutagenesis was used to produce two mutant constructs from the TAT-HA-Uch-L1 plasmid, TAT-HA-Uch-L1(C90S) and TAT-HA-Uch-L1(S18Y). When the mutant Uch-L1 fusion proteins were expressed and purified, their molecular weights were similar to that of Uch-L1 (~40 KD, FIG. 18A). Pre-incubation (1 hr) with TAT-HA-Uch-L1 (C90S) peptide (20 nM) followed by perfusion with 200 nM oligomeric Aβ plus TAT-HA-Uch-L1(C90S) for 20 min, prior to induction of LTP, did not protect against LTP suppression (FIG. 18B). TAT-HA-Uch-L1 (S18Y) significantly enhanced the amplitude of LTP in Aβ-treated slices compared to that of slices treated with TAT-HA plus Aβ (FIG. 18C). TAT-HA-Uch-L1(C90S) alone produced a significant decrease in the amounts of potentiation (152.38±10.90%) compared to slices treated with vehicle alone (219.42±15.60) (FIG. 18B) showing that Uch-L1(C90S) is a dominant negative inhibitor of LTP (see FIGS. 15G and 15D). Neither TAT-HA-Uch-L1 (C90S) nor TAT-HA-Uch-L1(S18Y) affected baseline. These results show that the Uch-L1 hydrolase function (but not the ligase function) is essential for the generation of LTP in the CA1 region. Proper function of the hydrolase domain is essential for the beneficial effect of Uch-L1. Administration of TAT-HA-Uch-L1(C90S) impaired both contextual learning and its decay in WT mice. Moreover, SY5Y neuroblastoma cells transfected with a degron CL1-GFP expression vector showed a decrease in proteasomal function following treatment with TAT-HA-Uch-L1(C90S) (20 nM for 2 hrs) as indicated by the increase in GFP$^u$.

Exogenous Uch-L1 has a Beneficial Effect on Synaptic and Cognitive Functions in APP/PS1 Mice.

Figures 19A, 19B:
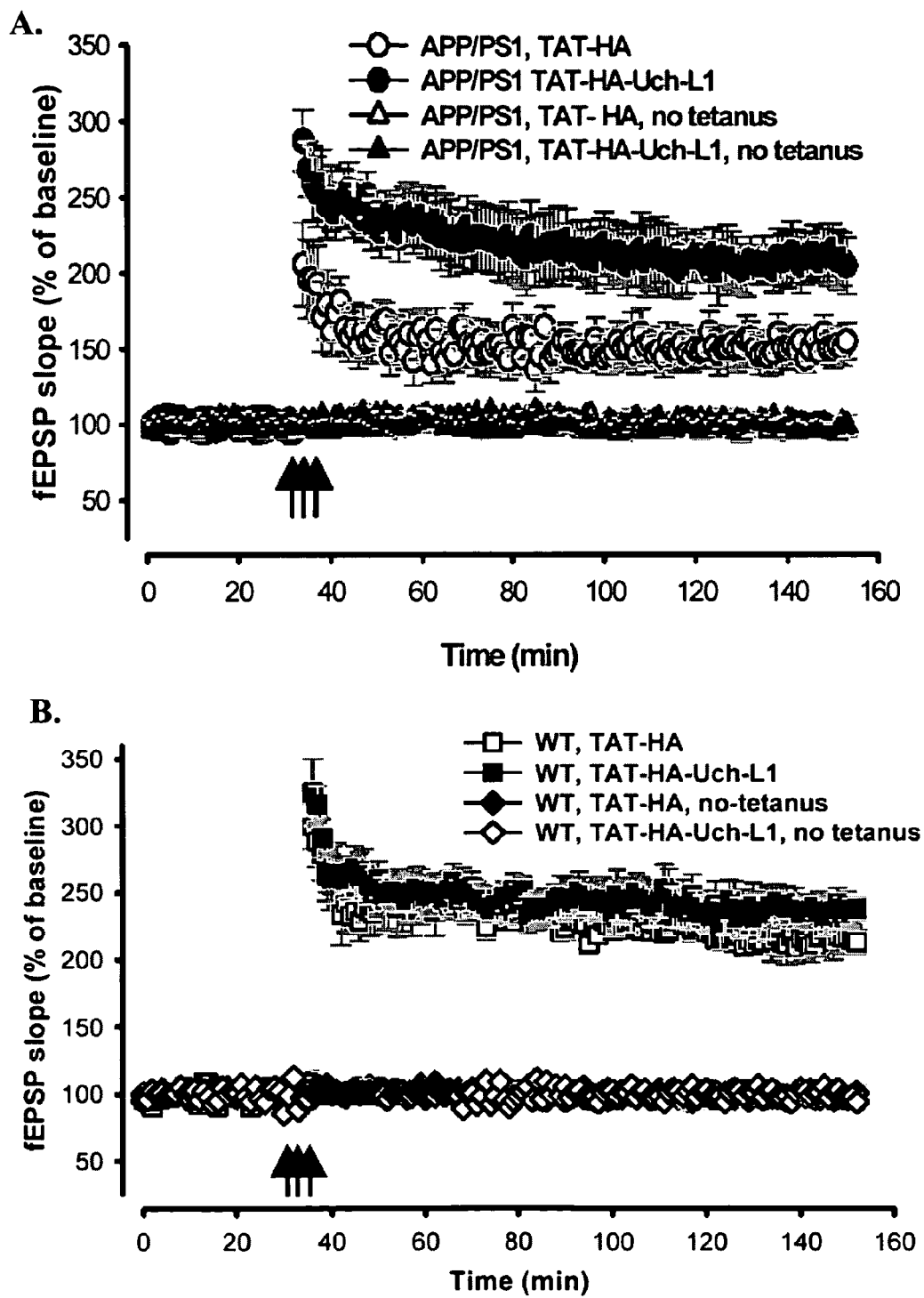
FIGS. 19A-19F. Exogenous Uch-L1 Plays a Beneficial Effect on Synaptic and Cognitive Functions in APP/PS1 Mice.

Based on the findings obtained in slices treated with Aβ and exogenous Uch-L1, experiments were designed to test whether TAT-HA-Uch-L1 could exert beneficial effects in the brains of mice carrying both the mutant amyloid precursor protein (APP) (K670N,M671L) and presenilin-1 (PS1) (M146L) transgenes (APP/PS1 mice). This animal model of amyloid deposition partially reproduces the cognitive deficits that occur in AD patients (Arendash et al., 2001). These mice display impaired LTP and contextual learning as early as 3-4 months of age, and they show deficits in BST after 5-6 months of age (Trinchese et al., 2004). When APP/PS1 mice were tested at 4 months (at this age synaptic plasticity impairment is just starting), hippocampal slices perfused with TAT-HA-Uch-L1 (20 nM) for 1 hr before induction of LTP displayed far greater potentiation than that in TAT-HA-treated APP/PS1 slices. Levels of LTP in TAT-HA-Uch-L1-treated APP/PS1 mice were equal to about 94% those of TAT-HA-treated WT littermates at 120 minutes after tetanus, versus about 66% for TAT-HA-treated APP/PS1 mice (FIGS. 19A and 19B). TAT-HA-Uch-L1 did not change the amplitude of LTP in hippocampal slices of WT mice compared with that of WT slices treated with TAT-HA alone (FIG. 19B). Levels of LTP at 120 minutes after tetanus were about 98% those of vehicle-treated WT slices (FIGS. 19A and 19B). TAT-HA-Uch-L1 had no effect on basal synaptic responses in slices from APP/PS1 mice or WT littermates either during its application or 120 minutes after the end of the application in experiments in which no tetanic stimulation was applied (FIGS. 19A and 19B). There was no difference in BST among the different groups. The slope of the input-output curve at a stimulation intensity equal to 35 V in APP/PS1 mice was about 94% that of WT littermates (APP/PS1 mice, 1.13±0.1 V/s, n=10 slices from 9 males; WT mice, 1.21±0.09 V/s, n=11 slices from 10 males). Two-way ANOVA showed no difference between double-transgenic mice and their littermate controls [$F(1, 19)=0.46$, $p>0.05$]. Similar results were obtained when the fEPSP slope was plotted versus the amplitude of the fiber afferent volley. Thus, exogenous Uch-L1 is capable of re-establishing normal synaptic plasticity following overexpression of the APP and PS1 transgenes.

Figure 19C:
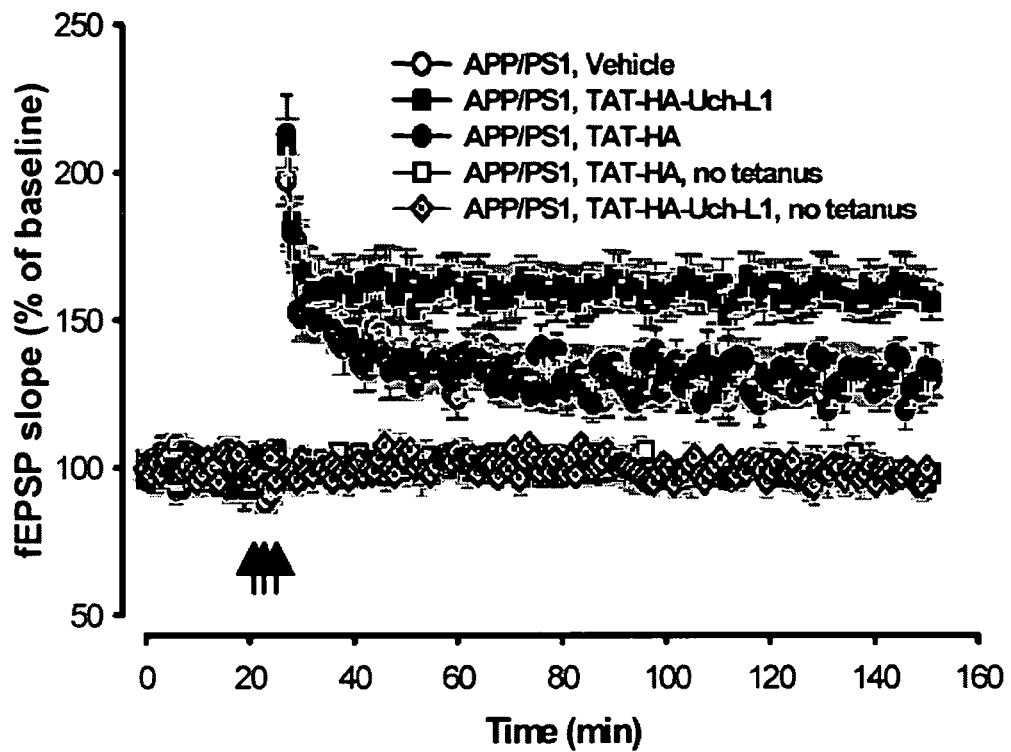
Figure 19D:
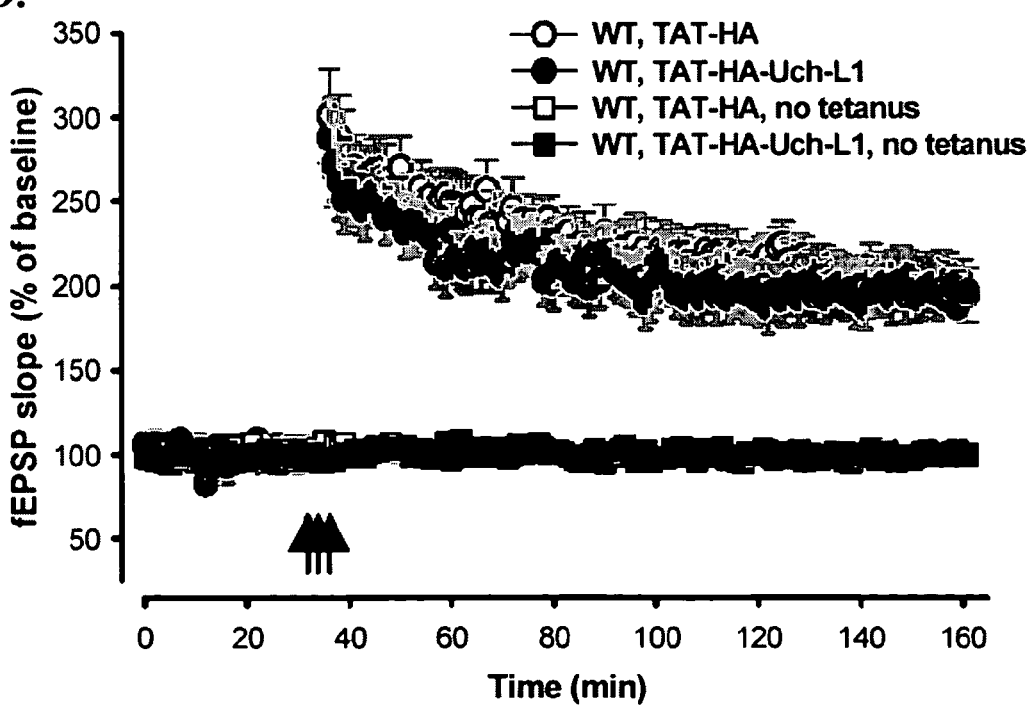
Figures 19E, 19F:
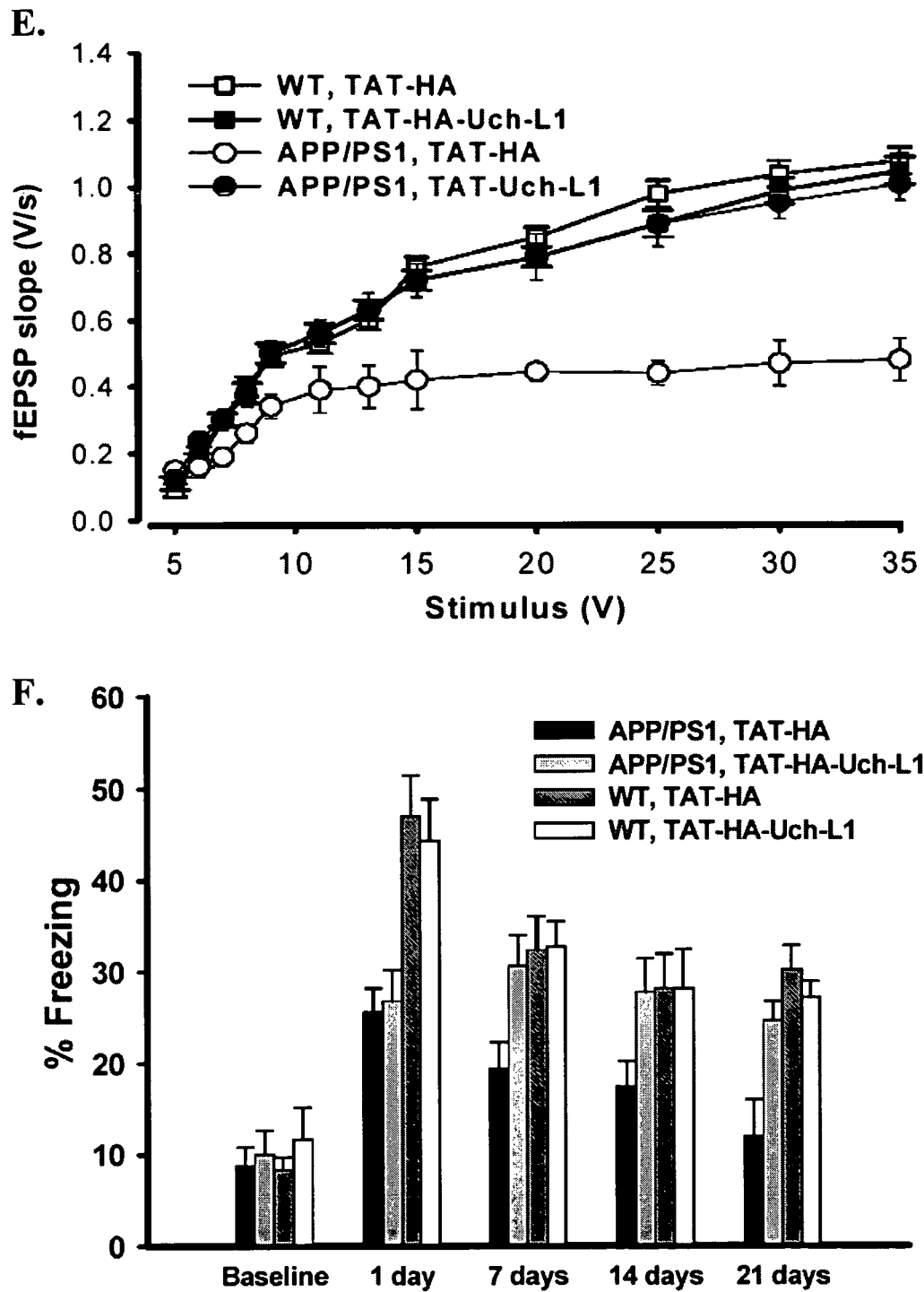

The beneficial effect of exogenous Uch-L1 on synaptic function is also present in older mice (12-18 months) with severe plaque load. APP/PS1 slices from these older animals treated with TAT-HA-Uch-L1 (20 nM) for 1 hr before induction of LTP displayed greater potentiation than TAT-HA-treated APP/PS1 slices (levels of LTP in TAT-HA-Uch-L1-treated APP/PS1 slices were equal to about 82% that of TAT-HA-treated WT littermates, versus about 65% for TAT-HA-treated APP/PS1 slices (FIGS. 19C and 19D). TAT-HA-Uch-L1 did not change the amplitude of LTP in hippocampal slices of WT mice compared with that of WT slices treated with TAT-HA alone (FIG. 19D). Levels of LTP at 120 minutes after tetanus were 98.5% of those of TAT-HA-treated WT slices. TAT-HA-Uch-L1 had no effect on basal synaptic responses in slices from APP/PS1 mice or WT littermates either during its application or 120 minutes after the end of the application in experiments in which no tetanic stimulation was applied (FIGS. 19C and 19D). BST was also improved in the TAT-HA-Uch-L1 group compared to the TAT-HA group in APP/PS1 mice (about 94% that of TAT-HA-treated WT mice) (FIG. 19E). TAT-HA-treated APP/PS1 animals had a significantly lower response than WT mice (about 44% that of TAT-HA-treated WT mice).

To address the question of whether treatment with exogenous Uch-L1 re-establishes normal cognition in APP/PS1 mice, 3-5 month-old mice were injected with TAT-HA-Uch-L1 or TAT-HA (0.02-0.04 g/kg, i.p.) 4 hrs before performing training for fear conditioning. No significant differences were seen during the training phase of fear conditioning in the freezing behavior of the 4 groups of mice. Treatment with TA-HA-Uch-L1 in APP/PS1 mice failed to re-establish normal freezing when the animals were reintroduced into the same context 1 day after training (FIG. 19F). There were no significant differences between the 4 groups in the cued conditioning test. However, treatment with TAT-HA-Uch-L1 greatly increased the freezing time in APP/PS1 mice compared to that of TAT-HA-treated APP/PS1 littermates during decay of contextual learning (TAT-HA-Uch-L1-treated APP/PS1 mice demonstrated about 85% freezing time of that of TAT-HA-treated WT mice, versus about 40% for TAT-HA-treated APP/PS1 mice at 21 days after training). TAT-HA-Uch-L1 did not change the freezing time in WT littermates compared with that of WT mice treated with TAT-HA (about 90% that of TAT-HA-treated WT mice) (FIG. 19F). Taken together, these results indicate that exogenous Uch-L1 plays a beneficial role during decay of the contextual learning in APP/PS1 mice.

Figures 23A, 23B:
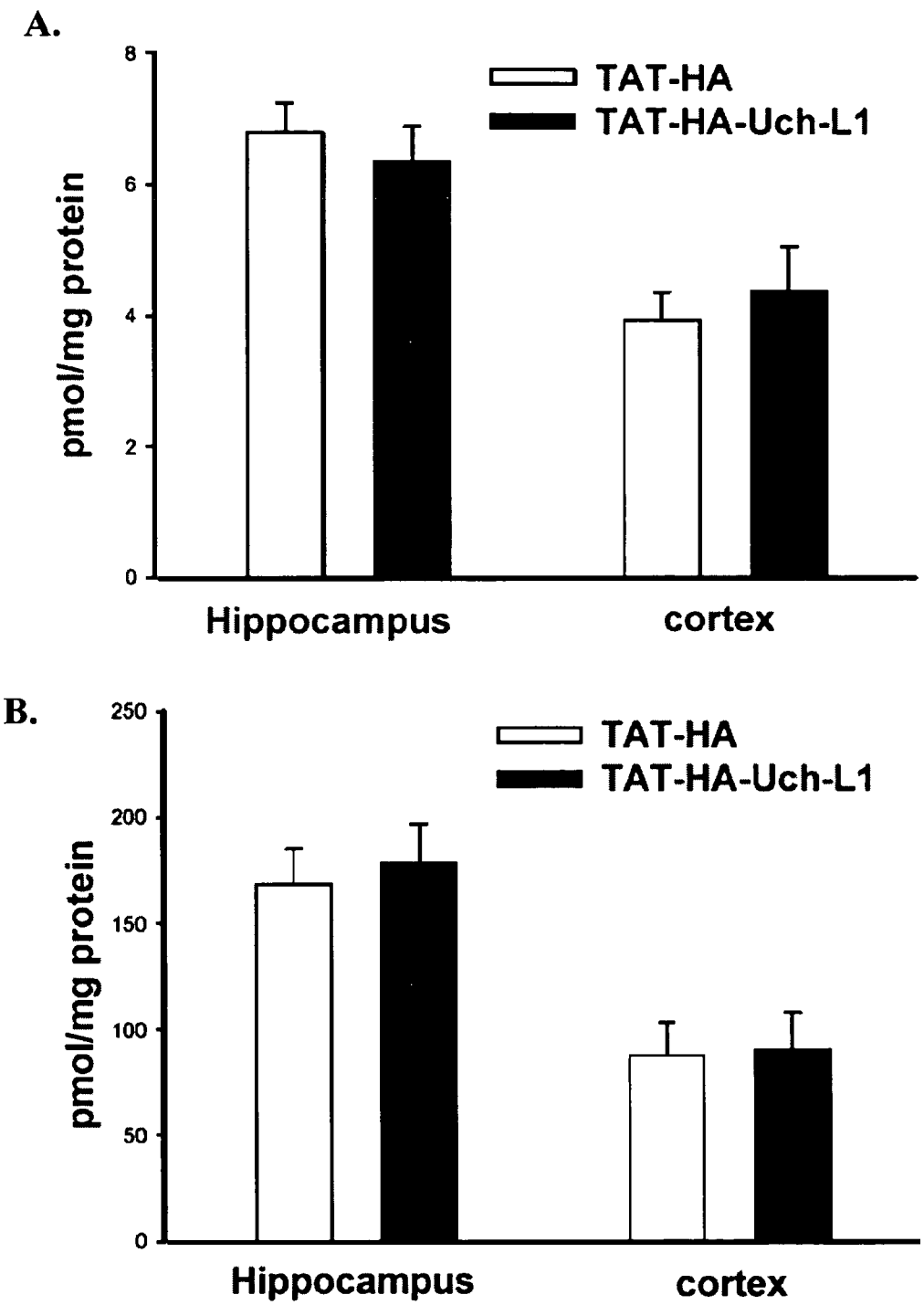
FIGS. 23A-23B. Injection of TAT-HA-Uch-L1 does not Affect $A\beta$ Levels in APP/PS1 Mice.

Given the physiological and behavioral effects of TAT-HA-Uch-L1 treatment in the double transgenic mice, experiments were carried out to determine whether treatment with the fusion protein affected Aβ levels, a hallmark of AD. ELISA of extracts of hippocampal and cerebral cortices revealed no difference in Aβ42 levels 4 hrs after injection of TAT-HA-Uch-L1 (0.02-0.04 g/kg, i.p.) in 4 month old APP/PS1 mice (hippocampal Aβ42, about 94% that of vehicle-treated APP/PS1 mice; cortical Aβ42, about 104%) (FIG. 23A). No Aβ was detected in WT littermates. Similar results were obtained by measurement of Aβ levels in mice that had been treated with TAT-HA-Uch-L1 and tested for fear conditioning over 21 days (hippocampal Aβ42, about 1-06% that of vehicle-treated APP/PS1 mice; cortical Aβ42, about 103%) (FIG. 23B). Thus, it is unlikely that TAT-HA-Uch-L1 produces its beneficial effects on learning and memory in the APP/PS1 mice by interference with Aβ production or clearance.

Figures 20A, 20B:
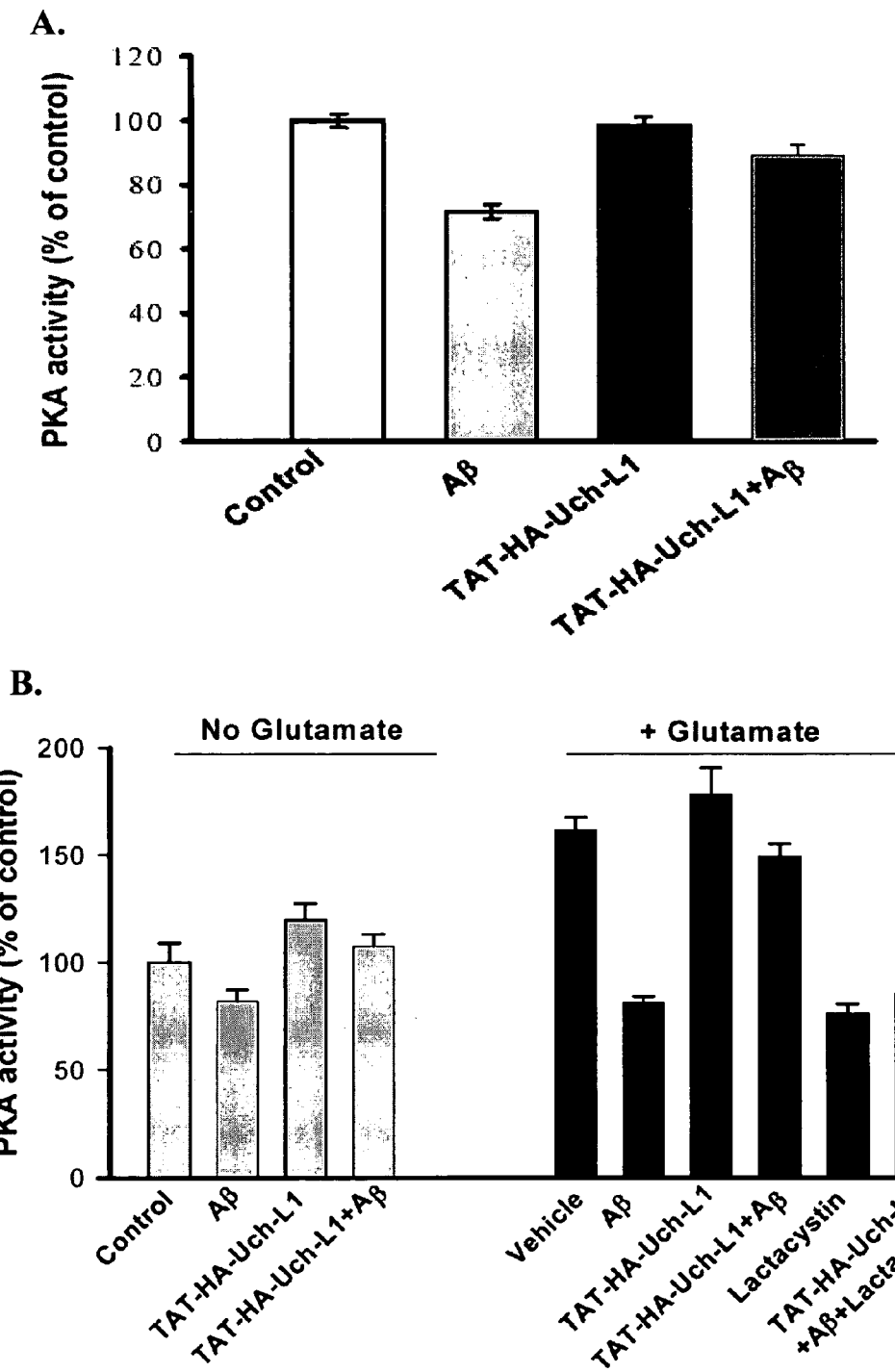
FIGS. 20A-20E. The Beneficial Effect of Uch-L1 on $A\beta$-induced Hippocampal Synaptic Dysfunction is Mediated through the PKA-CREB Pathway.

The Beneficial Effect of Uch-L1 on Aβ-Induced Hippocampal Synaptic Dysfunction is Mediated Through the PKA-CREB Pathway Proteolysis of the PKA regulatory (R) subunit by the ubiquitin-proteasome system coincides with the induction of Aplysia ubiquitin C-terminal hydrolase (Chain et al., 1999) and is likely to be involved in CREB-dependent long-term facilitation in Aplysia (Hegde et al., 1997). Experiments were carried out to determine whether the beneficial effect of exogenous TAT-HA-Uch-L1 fusion protein on Aβ-induced synaptic dysfunction is due to a rescue of the decrease in the degradation of the PKA-R subunit that results from Aβ treatment (Vitolo et al., 2002). This rescue would lead to the phosphorylation of CREB and increased transcription. Basal PKA phosphorylation activity was measured in hippocampal slices treated with 200 nM Aβ for 20 minutes and compared it to vehicle-treated control slices. A significant reduction in PKA activity was seen in the Aβ-treated slices as compared to controls (71.75±2.21% of control, FIG. 20A). When slices were pretreated with 20 nM TAT-HA-Uch-L1 for 1 hr before applying 200 nM Aβ paired with TAT-HA-Uch-L1 for 20 min PKA activity was significantly increased (89.21±3.21%, FIG. 20A). Inhibition of the ubiquitin-proteasome system through pretreatment with lactacystin (10 µM) for 1 hr suppressed the TAT-HA-Uch-L1 reversal of the Aβ effects (74.9±3.21%). Similar results were obtained when similar experiments were done in cultured hippocampal neurons (FIG. 20B). These findings show that Aβ reduces basal PKA activity (Vitolo et al., 2002). These results also show that exogenous Uch-L1 fusion protein acts through PKA to re-establish normal synaptic function.

Figure 20C:
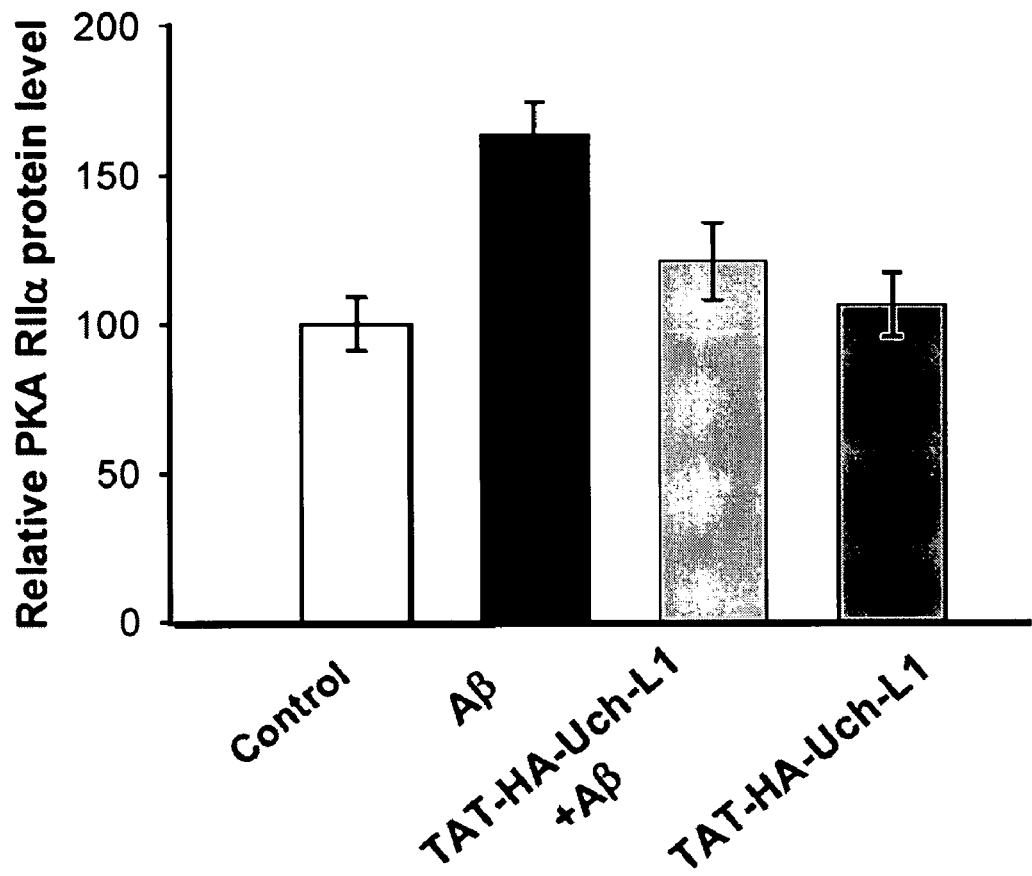

When the levels of the RIIα regulatory subunit of PKA were measured in hippocampal slices as a function of exposure to Aβ42 (200 nM for 20 minutes) and TAT-HA-Uch-L1 there was a marked increase in RIIα (163.68±10.51% of TAT-HA control slices, FIG. 20C). Pretreating the slices with 20 nM TAT-HA-Uch-L1 for 1 hr resulted in a reduction of the IIα regulatory subunit (121.03±14.10% of control; FIG. 20C). These data show that reduction of the regulatory subunit plays a role in re-establishing normal PKA activity following exposure of Aβ-treated slices to TAT-HA-Uch-L1.

Figure 24:
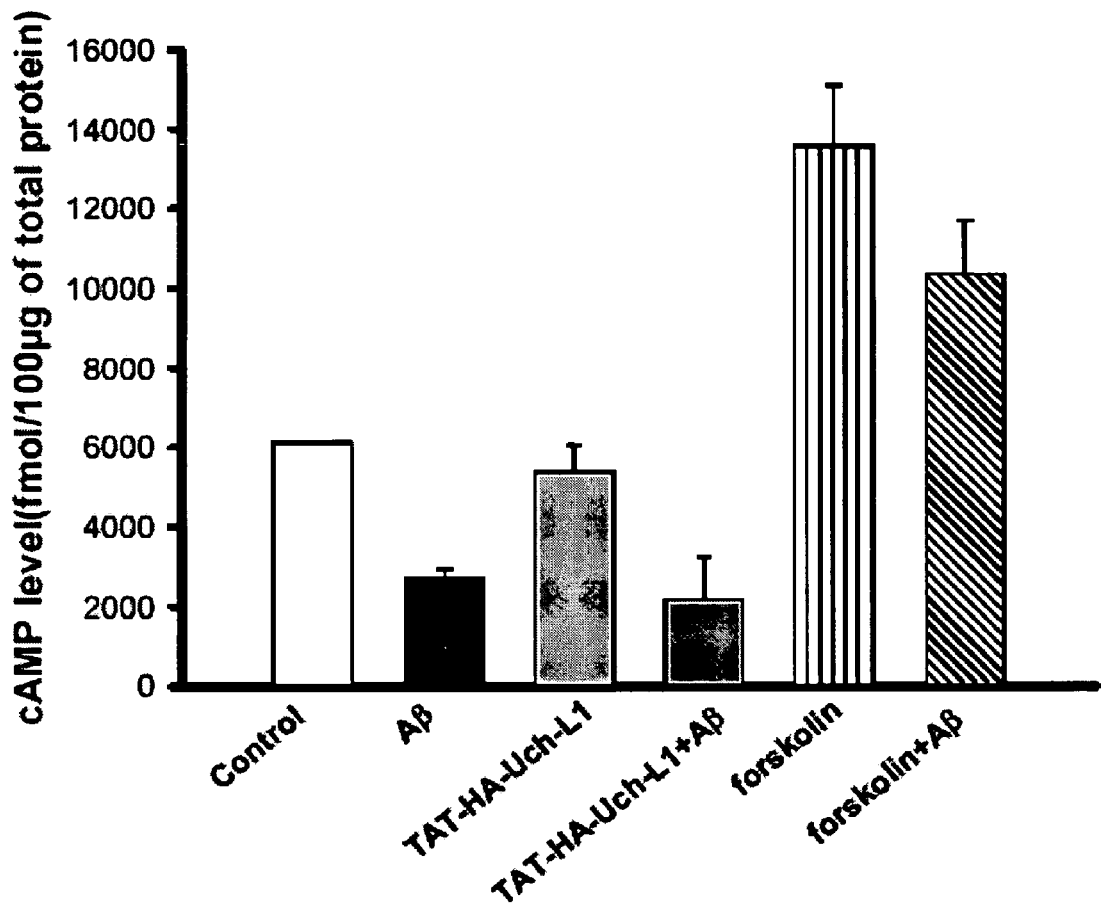
FIG. 24. TAT-HA-Uch-L1 (100 nM) for 24 hrs does not rescue the decrease in cAMP levels in cultured hippocampal neurons co-treated with 3 $\mu$M $A\beta$ (n=5 both for TAT-HA-Uch-L1 plus $A\beta$- and $A\beta$-alone-treated cultures). Addition of forskolin, a selective activator of adenylate cyclase, at 10 $\mu$M, showed a strong increase in cAMP levels in cultures treated with and without $A\beta$ (n=5).

The interaction of the two catalytic and two regulatory subunits of the PKA complex is controlled by cAMP. Cyclic AMP also regulates the proteasomal degradation of the PKA regulatory subunits (Chain et al., 1999). The cAMP levels were measured in cultured hippocampal neurons treated with A-beta 3 µM and TAT-HA-Uch-L1 (100 nM) for 24 hrs. Aβ alone reduced cAMP levels. However, the cAMP levels remained low in TAT-HA-Uch-L1 plus Aβ-treated cultures (FIG. 24). These results show that elevation of cAMP levels is not necessary for the rescue of PKA activity by TAT-HA-Uch-L1 to occur suggesting that the effect of Uch-L1 fusion protein in the presence of Aβ is downstream of cAMP.

Figure 20D:
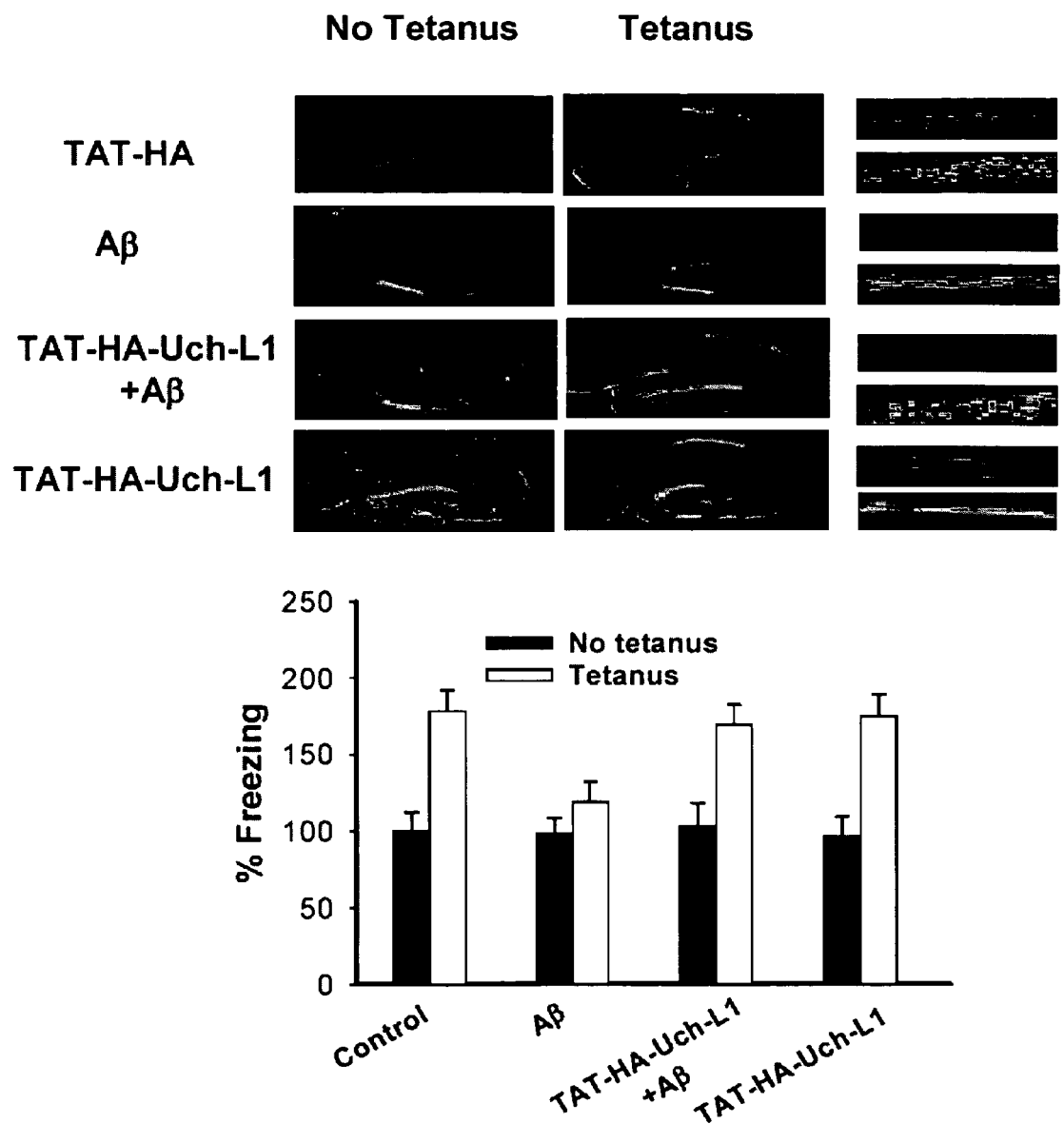
Figure 20E:
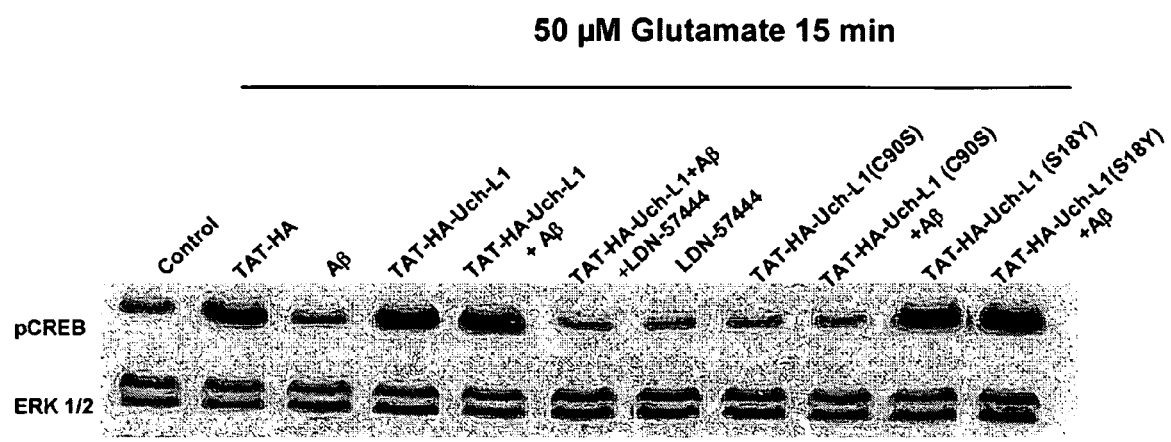

To determine if the beneficial effect of exogenous Uch-L1 fusion protein during Aβ-induced suppression of synaptic plasticity involves CREB phosphorylation, hippocampal slices were treated as described in the electrophysiological experiments, fixed 60 minutes after the treatment and stained with anti-phospho-CREB antibodies at Ser-133. There results show a significant increase in the intensity of immunofluorescence in CA1 cell bodies at 60 minutes after application of the tetanus in TAT-HA-treated slices compared to non-tetanized control TAT-HA slices from the same animals (FIG. 20D). Treatment with Aβ42 before the theta burst blocked the increase in CA1 immunofluorescence (Puzzo et al., 2005). Aβ42 alone without tetanization did not increase immunofluorescence (FIG. 20D). Pre-treatment with TAT-HA-Uch-L1 produced a significant protection against Aβ42 effects on phospho-CREB in tetanized slices. TAT-HA-Uch-L1 alone or TAT-HA-Uch-L1 paired with Aβ42 without theta-burst did not modify immunofluorescence (FIG. 20D). TAT-HA-Uch-L1 was also capable of reversing the Aβ-induced decrease in CREB phosphorylation in hippocampal cultures in which synaptic plasticity was induced through glutamate stimulation (Vitolo et al., 2002). Cultures pretreated for 24 hrs with 3 µM Aβ42 showed a strong decrease in CREB phosphorylation in response to treatment with 50 µM glutamate for 15 min (FIG. 20E). When 100 nM TAT-HA-Uch-L1 or TAT-HA-Uch-L1(S18Y) [but not TAT-HA-Uch-L1(C90S)] was added for 24 hrs, the exogenous protein totally blocked the effect of Aβ on CREB phosphorylation (FIG. 20E). Treatment with LDN-57444 blocked the beneficial effect of TAT-HA-Uch-L1, whereas the TAT-HA-Uch-L1(C90S) but not the TAT-HA-Uch-L1(S18Y) isoform blocked the glutamate-induced increase in CREB phosphorylation in cultures that were not treated with Aβ.

Although Uch-L1 has been implicated in familial Parkinson's disease, little is known on its role in sporadic AD. This Example shows a reduction of ubiquitin-C-terminal hydrolase enzymatic activity in the double transgenic APP/PS1 mouse model of AD. The invention provides for correction of this deficit by increasing Uch-L1 hydrolase activity by application of a fusion protein containing Uch-L1 not only rescues synaptic dysfunction in hippocampal slices treated with oligomeric Aβ, but also re-establishes normal synaptic and cognitive functions in the double transgenic mice. The beneficial effect of exogenously applied Uch-L1 is mediated, through the PKA/CREB pathway, via a reduction to normal levels of the PKA-RIIα subunit followed by re-establishment of normal PKA activity and CREB phosphorylation.

The neuron-specific Aplysia Uch regulates the switch from short to long-term facilitation (Hegde et al., 1997). Results shown in this Example demonstrate that Uch-L1 is also involved in hippocampal LTP, a synaptic phenomenon that is thought to be related to learning and memory, and in associative memory in vertebrates. Block of proteasomal function by the 20S proteasome inhibitor, lactacystin, or by the specific Uch-L1 inhibitor, LDN-57444, affected hippocampal synaptic function and contextual memory. It took a relatively long exposure of 2-4 hrs for the effect of the inhibitors to occur. It is likely that the prolonged exposure reflects the time necessary for the PKA regulatory subunit IIα to reach levels that effectively block the catalytic subunit such that CREB phosphorylation no longer occurs. DUNC-13, the *drosophila* homologue of the synaptic protein UNC-13 that similar to CREB is regulated by PKA, takes about 60-90 minutes to accumulate following block of the proteasome system with lactacystin (Aravamudan and Broadie, 2003).

Given that both synaptic dysfunction and memory loss are major hallmarks of AD, studies were designed to investigate whether an increase of Uch-L1 activity might re-establish normal synaptic and cognitive functions following Aβ elevation. The invention provides that transduction of Uch-L1 protein through the TAT system rescues the Aβ-induced damage of synaptic plasticity. The protein also re-establishes normal basal neurotransmission, synaptic plasticity and associative memory in APP/PS1 mice, an animal model that has revealed to be very useful for studies on consequences of altered amyloid deposition because it presents an early impairment of synaptic plasticity together with abnormal associative learning and spatial working memory, followed by a delayed impairment of basal neurotransmission and reference memory (Gong et al., 2004; Trinchese et al., 2004). Impairment of the ubiquitin-proteasome pathway might contribute to the early synaptic defects that characterize the disease (Masliah, 1995). If proper ubiquitin-proteasome mediated degradation at the synapse is required for plasticity and learning as well as maintaining the integrity of the synapse, perturbations in Uch-L1 function might lead to synaptic dysfunction and eventually loss of synapses together with memory loss.

This Example shows the occurrence of a beneficial effect of the treatment with exogenous Uch-L1 during decay of contextual learning over the three weeks after training, but not the day after training. Uch-L1 might stabilize synaptic circuitry via alterations in gene expression (Bourtchouladze et al., 2003), and that this synaptotrophic effect would take longer than one day to fully develop. It has been shown that the phosphodiesterase inhibitor, rolipram, plays a beneficial effect on synaptic and cognitive function of APP/PS1 mice (Gong et al., 2004). This effect lasted for several months (Gong et al., 2004) beyond the half-life of the drug which is 3 hrs (Krause and Kuhne, 1988). Moreover, a short treatment with the inhibitor stabilized phospho-CREB levels (Gong et al., 2004) and spine density. Formation of new synaptic connections probably underlies long-term memory formation in several vertebrate and invertebrate species with a mechanism that is dependent upon CREB gene expression (Tully et al., 2003). Thus, both formation of new synapses and consolidation of old ones are involved in the delayed and long-term effects of Uch-L1 treatment. As shown with rolipram (Gong et al., 2004), in addition to these mechanisms, proliferation and neurogenesis in the affected hippocampi may be induced by Uch-L1 (Nakagawa et al., 2002). As a result more mature neurons would be recruited by Uch-L1 through elevation of PKA activity, while the increased proliferation would preserve the progenitor pool, thus acting over the first week after training to re-establish the equilibrium with the synaptic dysfunction produced by Aβ. Molecules that are important in cortical neurogenesis, including P35, Notch, and Dab1, are ubiquitinated (Arnaud et al., 2003; Bock et al., 2004; Patrick et al., 1998; Qiu et al., 2000). Moreover, adult neurogenesis is required for long-term retention of spatial reference memory (Snyder et al., 2005).

Uch-L1 treatment did not improve contextual learning the day after training. It has been shown that rolipram ameliorates contextual learning the day after training (Gong et al., 2004). FIG. 24 shows that the treatment with Uch-L1 fusion protein does not rescue the decrease in cAMP levels caused by Aβ (but rather decreases PKA activity by reducing the cleavage of PKA-RIIα), whereas rolipram is known to increase cAMP levels and then PKA activity (Barad et al., 1998). Therefore, these findings show that retrieval of spatial memories is linked to elevation of cAMP levels, whereas proteasomal activity regulates decay of spatial memories.

Uch-L1 has been shown to cleave the PKA-RIIα subunit and increase levels of CREB phosphorylation (Chain et al., 1999). This Example shows that re-establishment of the normal levels of Uch-L1 hydrolase activity through application of exogenous Uch-L1 rescues the defect in PKA-RIIα cleavage normalizing PKA activity and CREB phosphorylation during synaptic plasticity. The dysfunction of the ubiquitin-proteasome system plays a major role in the pathogenesis of neurodegenerative diseases including Alzheimer's, Parkinson's, Huntington's, and Prion diseases as well as amyotrophic lateral sclerosis (Ciechanover and Brundin, 2003). In particular, ubiquitin has been detected in neurofibrillary tangles and senile plaque neurites of AD brains. Both PS1 and PS2 are targets for the ubiquitin system (Kim et al., 1997). Proteasome activity is inhibited by Aβ and exposure to oxidative stress (Gregori et al., 1995; Grune et al., 1995; Reinheckel et al., 1998), both of which are believed to contribute to the progression of AD (Markesbery, 1997; Mattson, 1997). Inhibition of proteasome activity without decrease in proteasome expression has been found in the hippocampus and parahippocampal gyrus, superior and middle temporal gyri, and inferior parietal lobule of AD patients (Keller et al., 2000; Lopez Salon et al., 2000). This effect was linked to binding of tau-based paired helical filaments to the 20S core proteasome (Keck et al., 2003). Finally, the most direct link between ubiquitin-proteasome and AD is the discovery of the frame-shift mutant form of ubiquitin (UBB$^{+1}$) which was first identified in neurons of Alzheimer's and Down patients as well as elderly non-demented individuals (>51 years) (van Leeuwen et al., 1998; van Leeuwen et al., 2000). That Aβ causes a decrease in proteasomal function as little as 20 minutes after exposure and at concentrations as low as 200 pM shows that proteasomal malfunction may be the result of a signalling pathway between Aβ and the proteasomal machinery that occurs in advance of protein binding to the proteasome or an excess of misfolded protein overwhelming the machinery.

A single injection of the Uch-L1 fusion protein did not change Aβ levels in APP/PS1 mice both at 4 hrs and at 3 weeks following the injection. This shows that the improvement of synaptic and memory deficits is not due to a reduction in Aβ production. Rolipram improves both synaptic and cognitive impairments in the double transgenic mice by acting downstream of Aβ production and ultimately affecting CREB phosphorylation through elevation of PKA activity (Gong et al., 2004). In addition, passive immunization with monoclonal anti-Aβ antibodies improved cognitive performance without affecting Aβ levels in PDAPP mice (Dodart et al., 2002). Moreover, correlation between Aβ pathology and memory impairment is disputed both in AD patients (Iwatsubo et al., 1995) and in the APP/PS1 mouse model of AD (Trinchese et al., 2004). However, it has been reported that the ubiquitin-proteasome system is involved in APP processing and Aβ production acting on the modifier of cell adhesion protein (MOCA), a DOCK-180-related molecule, which interacts with PS1 and PS2 (Chen et al., 2002).

The effect of Uch-L1 described in this Example represents an important mechanism for improving synaptic and memory deficits produced by Aβ. Transduction of fusion proteins has been widely used experimentally (Barka et al., 2000; Schwarze et al., 1999; Wadia et al., 2004) including for Uch-L1 (Wada et al, 2001). The discovery of the invention that Uch-L1 transduction can counteract both synaptic and cognitive abnormalities in an Alzheimer's model provides that this approach opens new avenues for the treatment of AD and other devastating diseases characterized by abnormal protein deposition.

Example 4

Uch-L1 is a Downstream Regulator of Synaptic Function and Contextual Memory Following Amyloid Elevation The development of AD is gradual, the early symptoms of memory loss are slight and AD can be difficult to differentiate from benign forms of memory loss. Memory deficits precede massive cell loss and are likely due to synaptic dysfunction (Masliah, 1995; Selkoe, 2002).

Cognitive deficits following Aβ elevation are seen in amyloid-depositing models such as double transgenic (Tg) mice overexpressing APP (K670N:M671L) together with PS1 (M146L). These mice overproduce Aβ and show inhibition of long-term potentiation (LTP), a type of synaptic plasticity related to memory, at young ages (Trinchese et al., 2004). Since application of Aβ to hippocampal slices from wild-type (WT) animals inhibits LTP, the deficit in Tg animals is likely to be due to Aβ rather than other changes in the brain (Cullen et al., 1997; Itoh et al., 1999; Walsh et al., 2002). LTP inhibition in slices is reversible by treatments that raise the intracellular concentration of cyclic AMP (cAMP) (Vitolo et al., 2002). It has been proposed that the effect of Aβ on LTP and memory is mediated by the inhibition of phosphorylation of the cAMP response element binding protein (CREB) (Dineley et al., 2001; Dineley et al., 2002; Gong et al., 2004; Vitolo et al., 2002), a transcription factor that is activated by cAMP-dependent protein kinase (PKA). PKA activity is regulated both by the dissociation of its catalytic and regulatory subunits and by the degradation of its regulatory subunits by the ubiquitin-proteasome system (UPS) (Chain et al., 1999). Moreover, long-term facilitation, a form of plasticity occurring in Aplysia, is mediated by a concurrent increase in cAMP and of a neuron-specific ubiquitin C-terminal hydrolase (Uch), an enzyme that enhances the recycling of ubiquitin (Hegde et al., 1997).

Uch-L1, a neuron and testis specific enzyme, is downregulated in AD brains. AD brains show prominent Uch-L1 immunostaining associated with neurofibrillary tangles and levels of soluble Uch-L1 inversely proportional to the number of tangles (Choi et al., 2004).

This Example investigates the effects of Uch-L1 inhibition on LTP and memory and whether increasing Uch activity by the application of a fusion protein containing Uch-L1 rescues synaptic dysfunction in hippocampal slices treated with oligomeric Aβ. These studies were validated on the APP/PS1 model of AD that allows the evaluation of the effects of Uch-L1 on synaptic function and on memory. Studies were also designed to determine whether Uch activity and levels of Uch-L1 are modified in the double Tg mice. The mechanism of action of exogenously applied Uch-L1, was studied by examining its effects on the components of the PKA/CREB pathway. The experimental procedures were carried out as described in Example 5.

TAT-HA-Uch-L1 Enters Cells and Retains Biological Activity

Penetration of TAT-HA-Uch-L1, TAT-HA-iUch-L1 or TAT-HA occurred both in brains of living animals and in neurons from primary hippocampal cultures. Animals were injected with TAT-HA-Uch-L1, TAT-HA-iUch-L1, and TAT-HA (0.02-0.04 g/kg, i.p.) and sacrificed 4 or 8 hrs later. Immunofluorescence for the fusion proteins was visible in the hippocampus with antibodies against Uch-L1 or HA (FIG. 33B). In agreement with these results, Western blots from the hippocampi of mice sacrificed 4 hrs after injection showed the presence of TAT fusion protein as detected with anti-HA antibodies. For experiments in cultures, dishes containing rat hippocampal neurons and devoid of non-neuronal cells were treated with TAT fusion proteins (100 nM) or vehicle for 1 hr, fixed, co-labeled with antibodies against Uch-L1 and the specific neuronal marker MAP2 or antibodies against HA together with MAP2. The same cells that showed positive immunoreactivity for TAT-HA-Uch-L1, TAT-HA-iUch-L1 or TAT-HA also double-labeled with MAP2 (FIG. 33C), confirming that the fusion proteins penetrate neurons.

Exogenous Uch-L1 Reduces Aβ-Induced Effects Through Up-Regulation of the PKA-CREB Pathway in Hippocampal Cell Cultures.

Figures 40A, 40B:
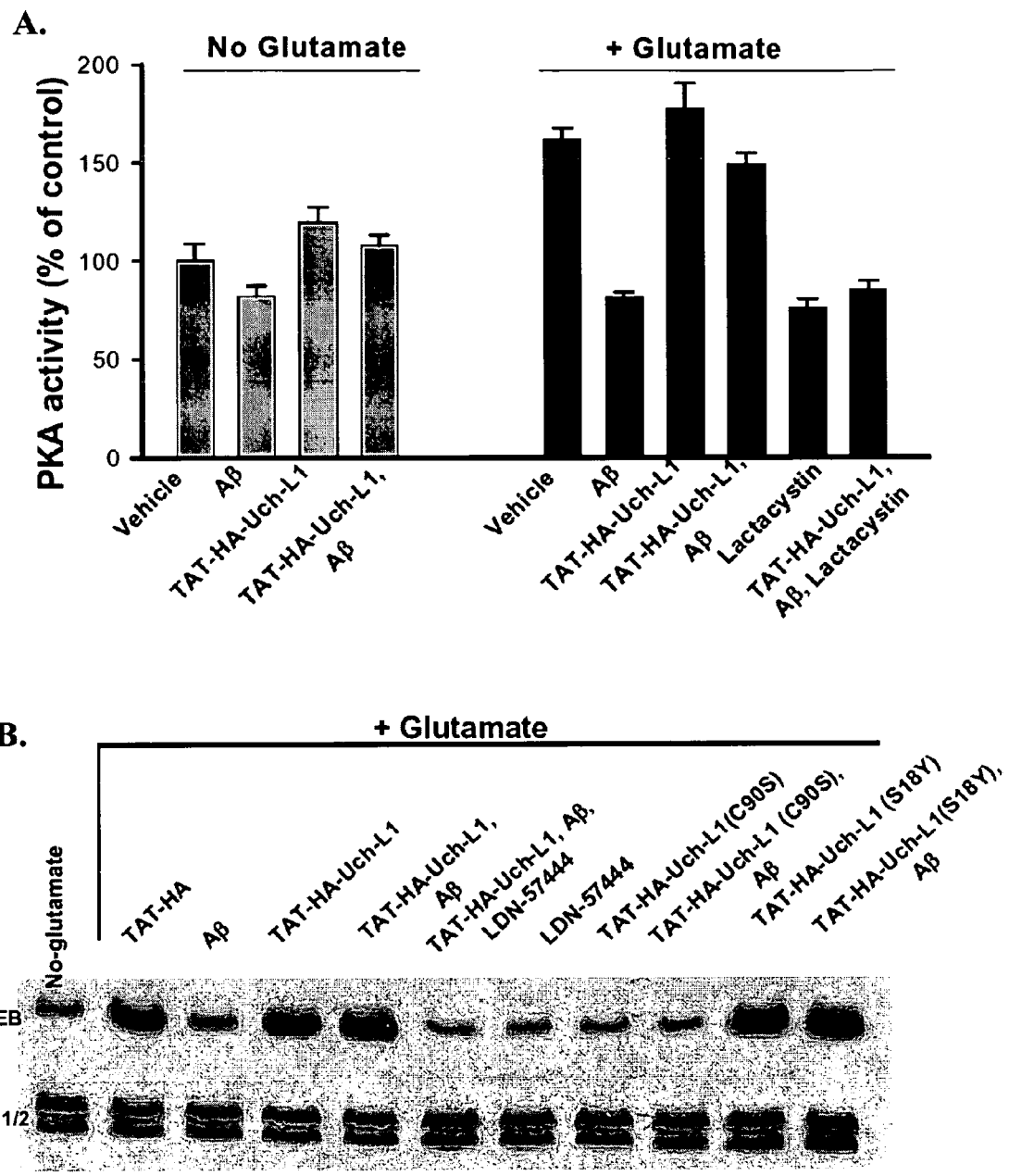
FIGS. 40A-40B. Exogenous Uch-L1 rescues Aβ-effects on the PKA-CREB pathway in rat hippocampal cell cultures.

To produce additional evidence of the involvement of the PKA-CREB pathway in the beneficial Uch-L1 effect independent of the type of preparation and animal species, the effect of exogenous Uch-L1 on rat hippocampal cultures exposed to 3 μM Aβ42 for 24 hrs was studied. Twenty-four hours pre-incubation with 100 mM TAT-HA-Uch-L1 was capable of reversing the Aβ-induced decrease in basal PKA activity in hippocampal cultures (Vitolo et al., 2002). TAT-HA-Uch-L1 rescued the increase in PKA activity in cultures in which synaptic plasticity was induced through glutamate stimulation (50 μM for 15 min) (Antonova et al., 2001; Malgaroli and Tsien, 1992) (FIG. 40A). By contrast, TAT-HA-Uch-L1 (100 nM for 24 hrs) did not affect the decrease in cAMP levels due to Aβ (3 μM for 24 hrs) (FIG. 24), demonstrating that elevation of cAMP levels is not necessary for the rescue of PKA activity by TAT-HA-Uch-L1 to occur and suggesting that the effect of Uch-L1 fusion protein is downstream of cAMP. Cultures pretreated for 24 hrs with 3 μM Aβ42 showed a strong decrease in CREB phosphorylation in response to a treatment with 50 μM glutamate for 15 min (FIG. 40B). However, exposure to 100 nM TAT-HA-Uch-L1 or TAT-HA-Uch-L1(S18Y) [but not TAT-HA-Uch-L1 (C90S)] for 24 hrs blocked the effect of Aβ on CREB phosphorylation. TAT-HA-Uch-L1(C90S) but not the TAT-HA-Uch-L1 (S18Y) isoform blocked the glutamate-induced increase in CREB phosphorylation in cultures that were not treated with Aβ. Treatment with LDN blocked the beneficial effect of TAT-HA-Uch-L1. Taken together, these results are consistent with findings on slices.

Uch-L1 Activity is Required for Normal Synaptic Function.

Figure 25A:
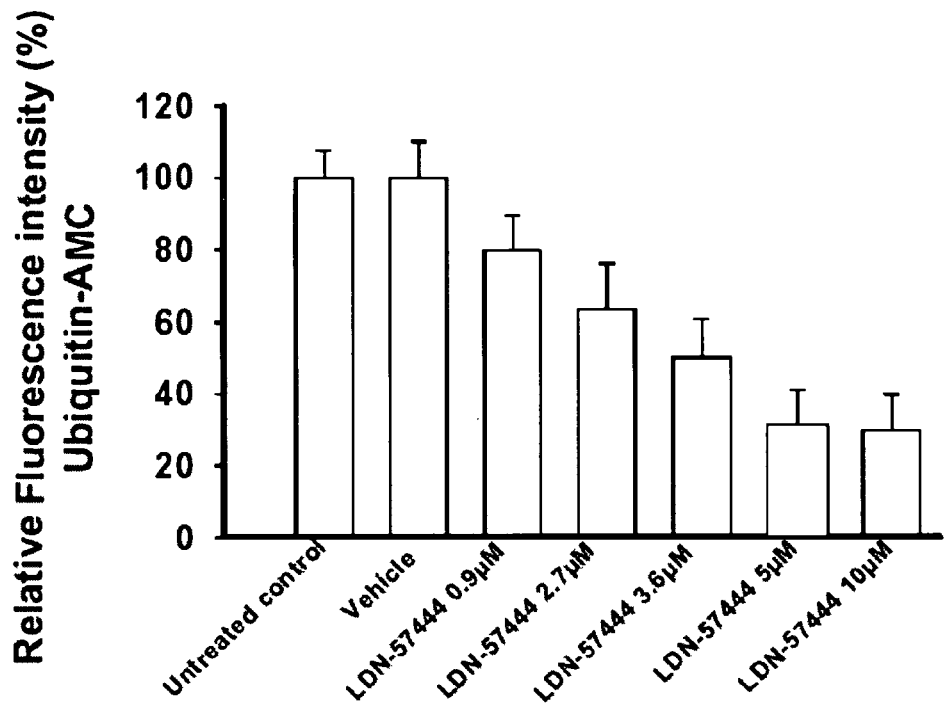
FIGS. 25A-25F. Activation of Uch-L1 is essential for synaptic function.
Figure 25B:
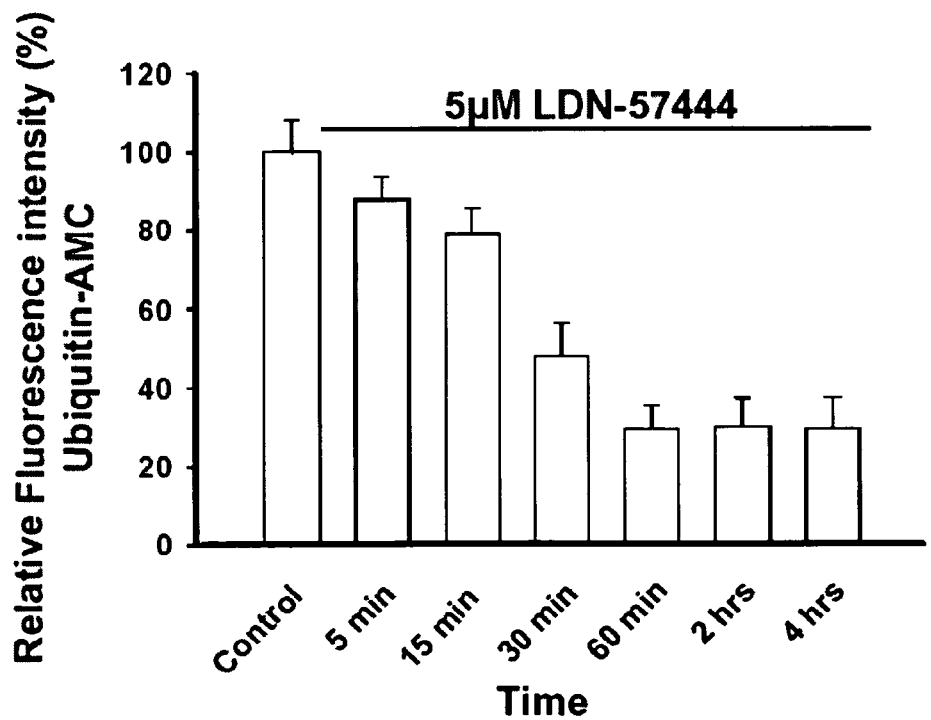
Figures 25C, 25D:
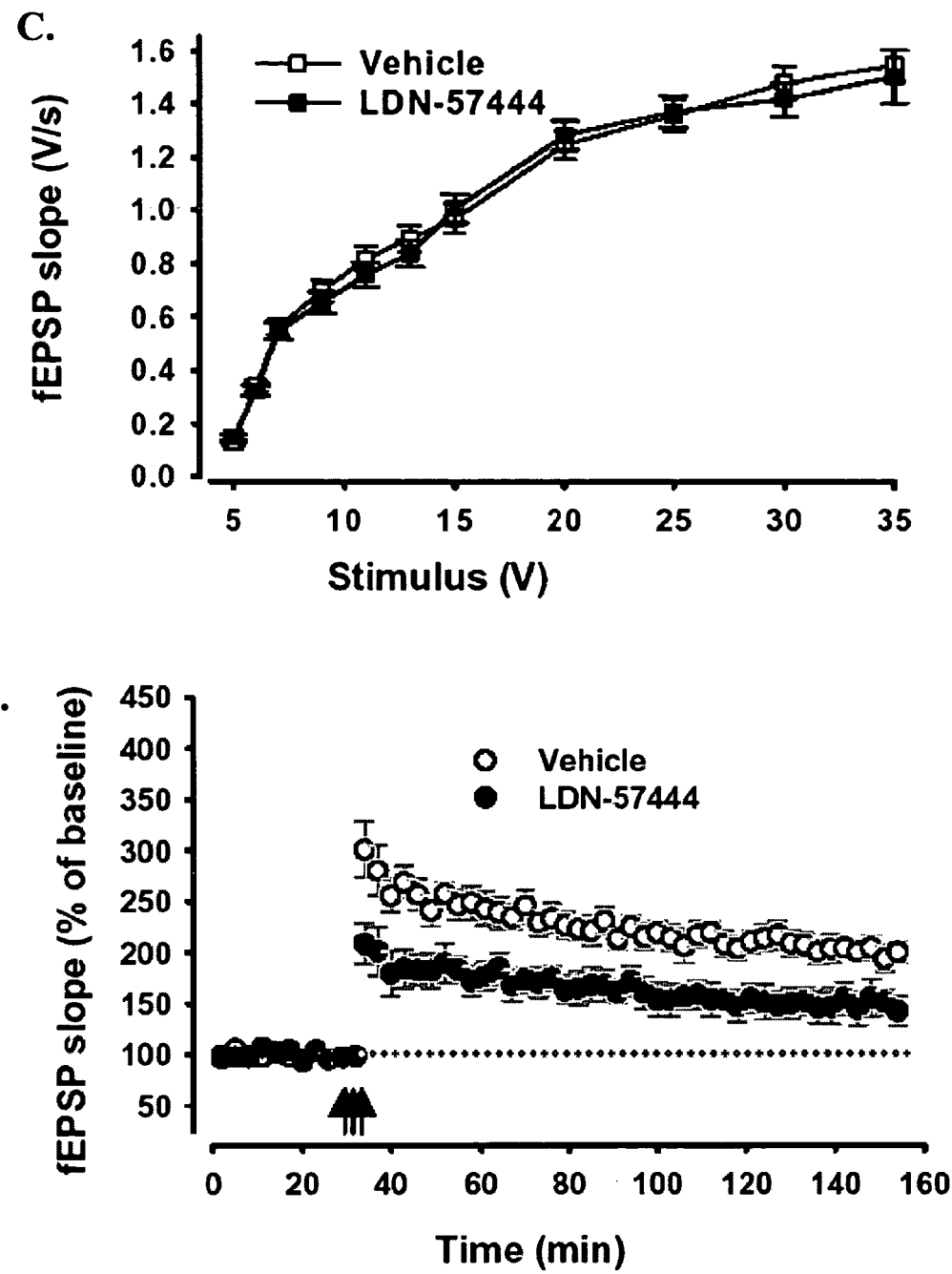
Figure 25E:
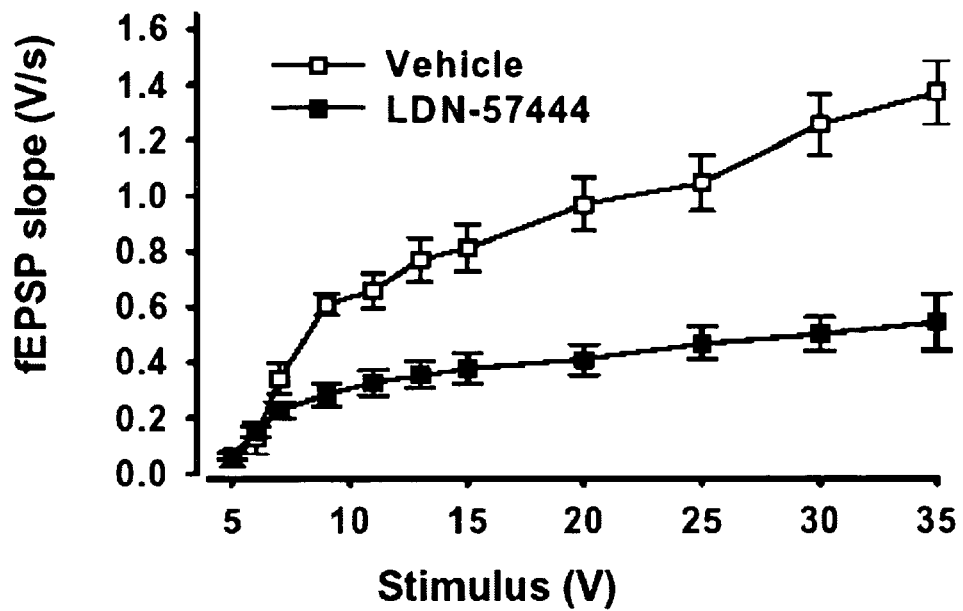
Figure 25F:
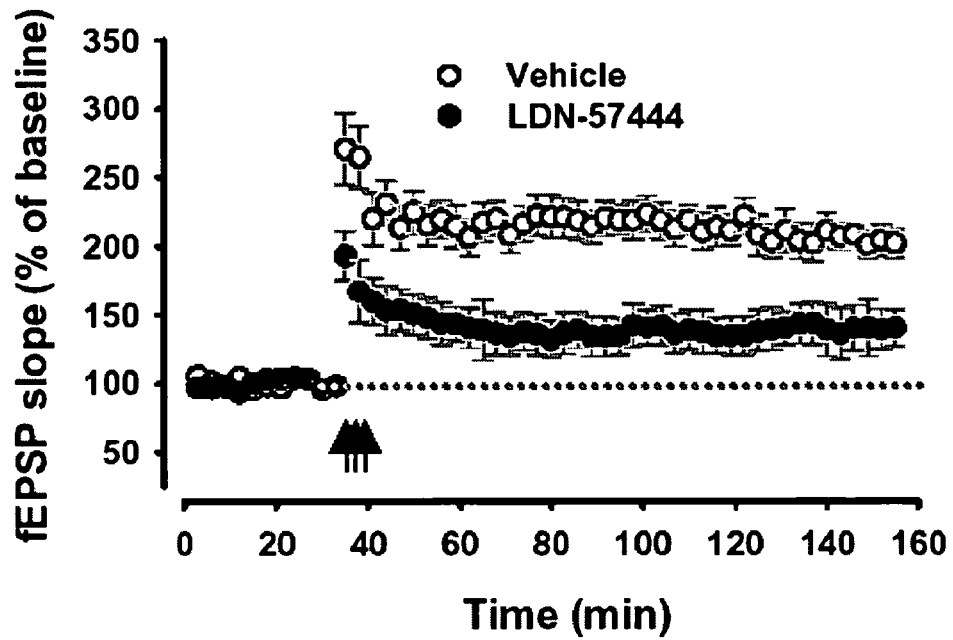
Figure 26A:
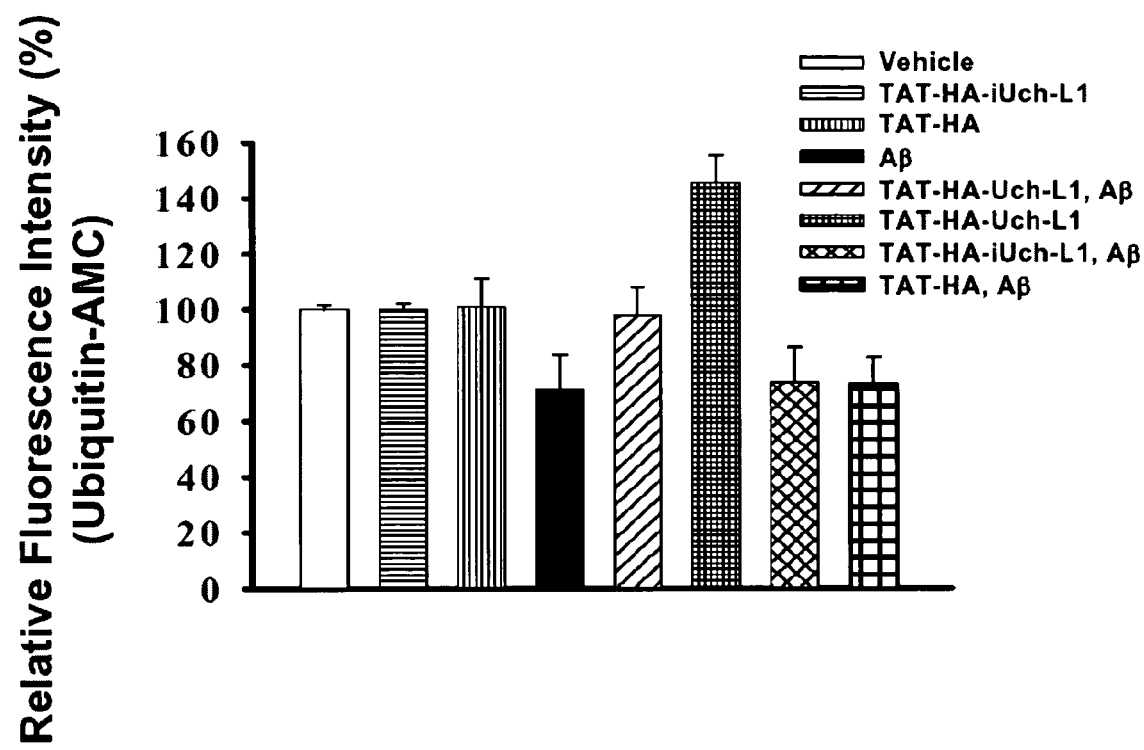
FIGS. 26A-26B. TAT-linked Uch-L1 retains biological activity.
Figure 28A:
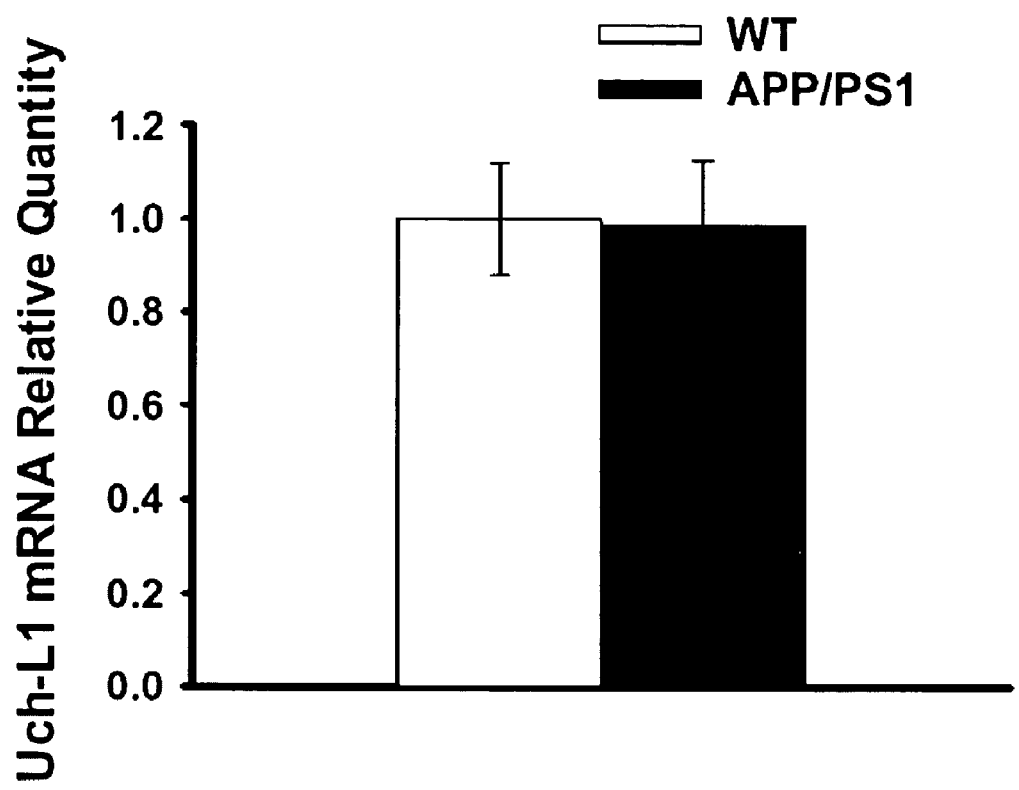
FIGS. 28A-28F. Uch-L1 activity is down-regulated in APP/PS1 Mice.
Figure 28B:
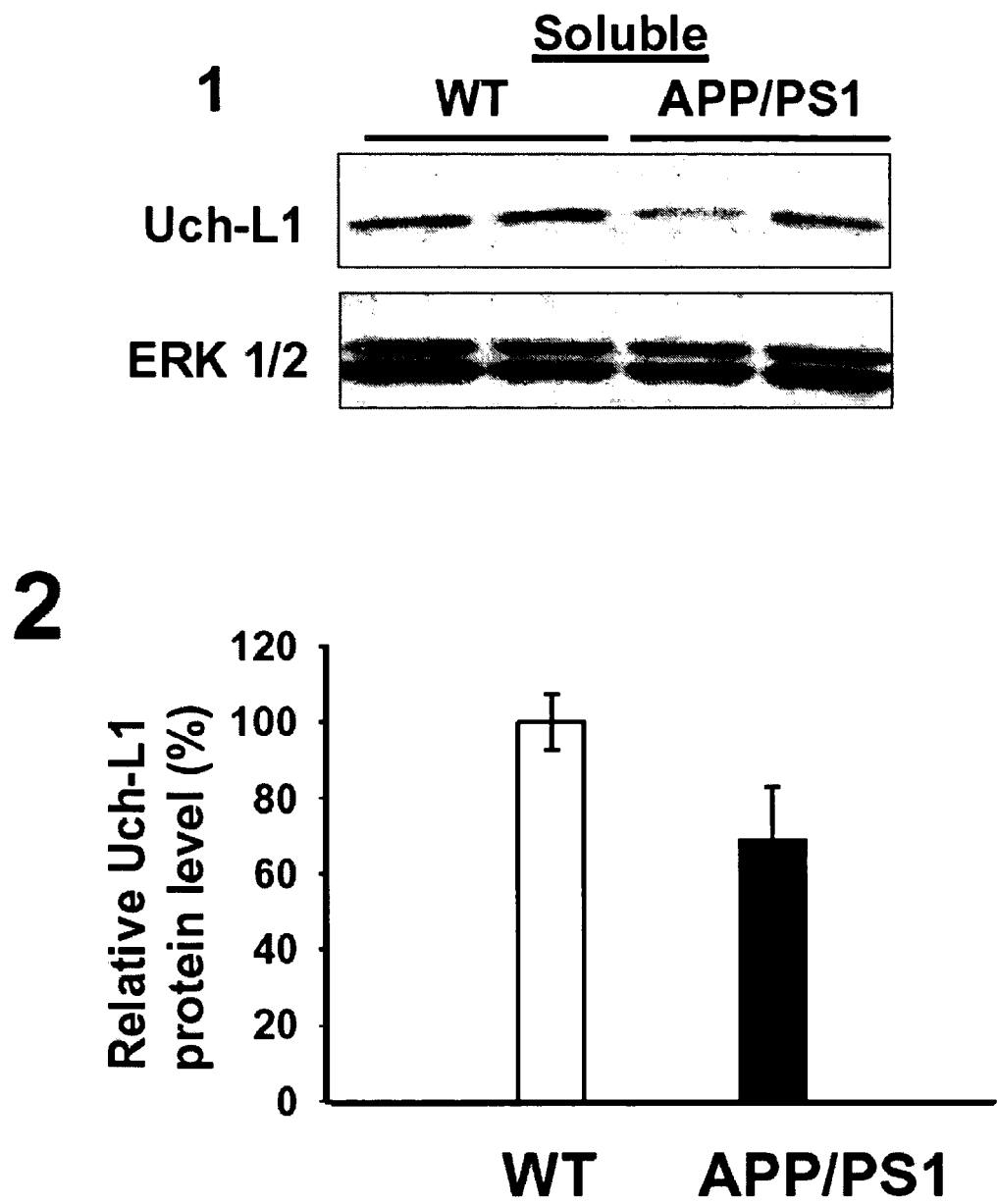
Figure 28C:
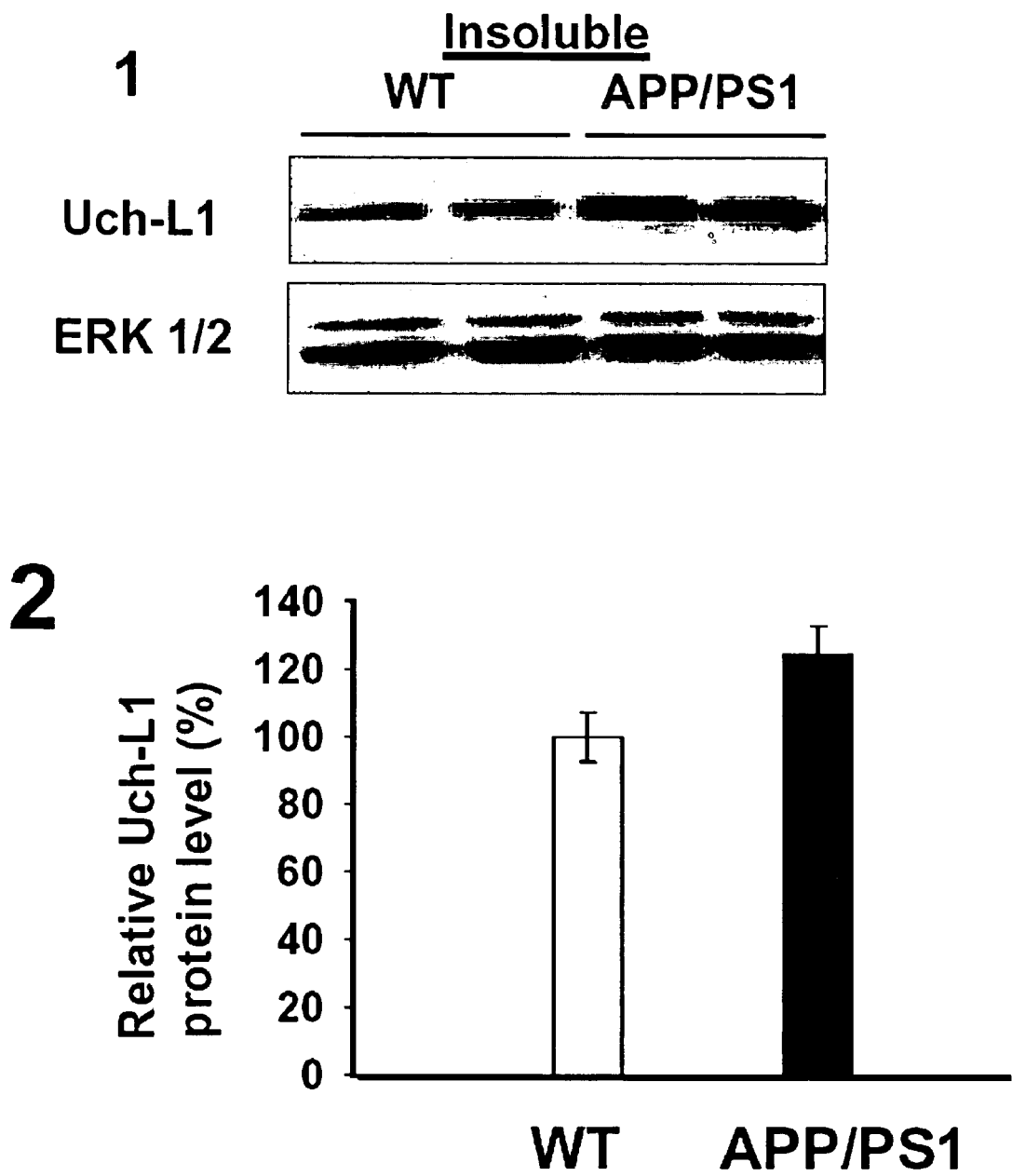
Figure 28D:
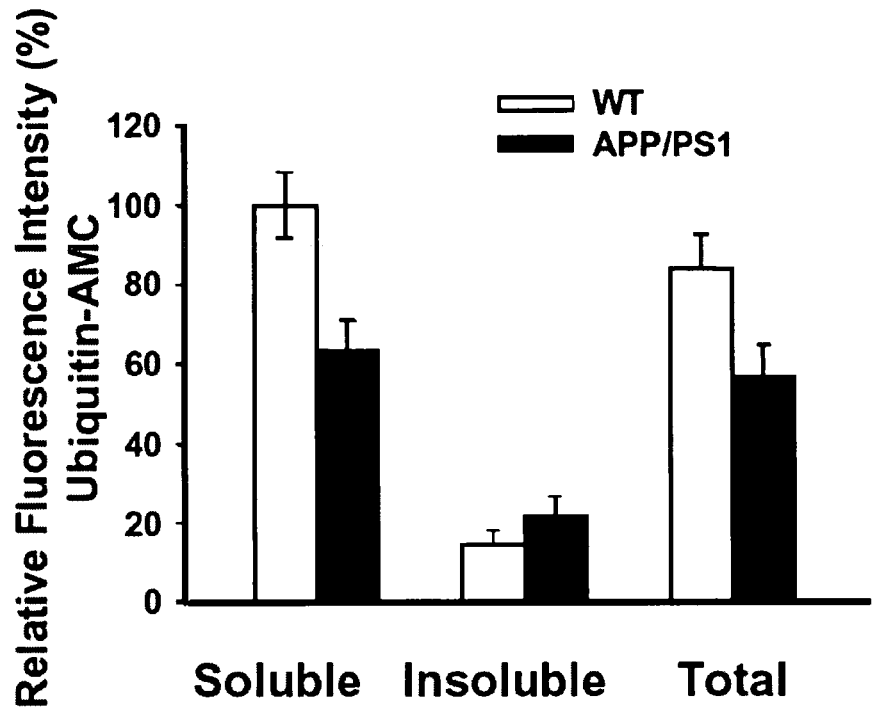
Figure 28E:
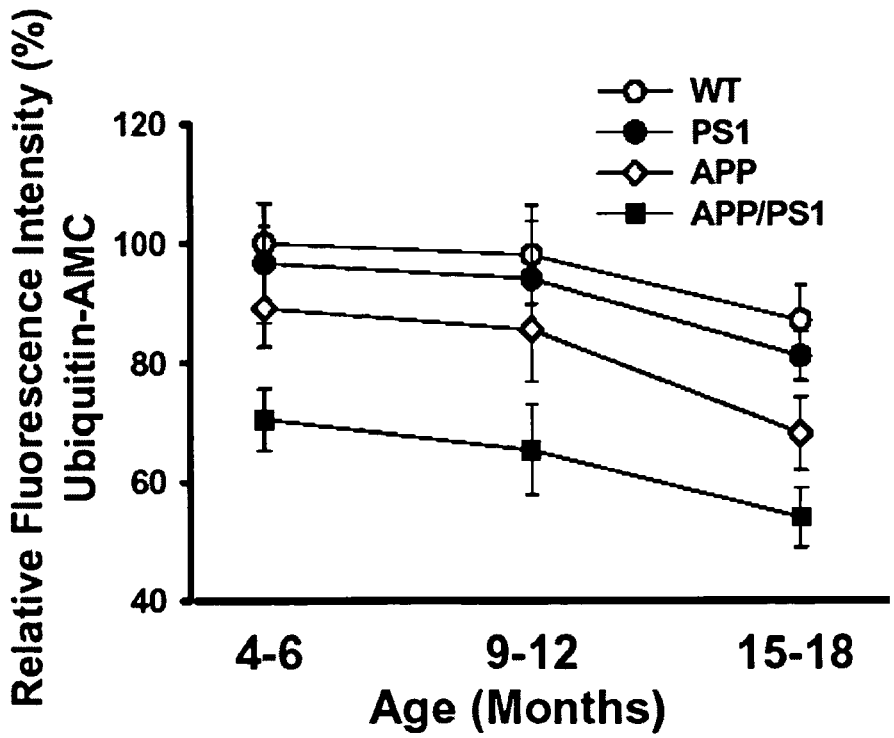
Figure 32A:
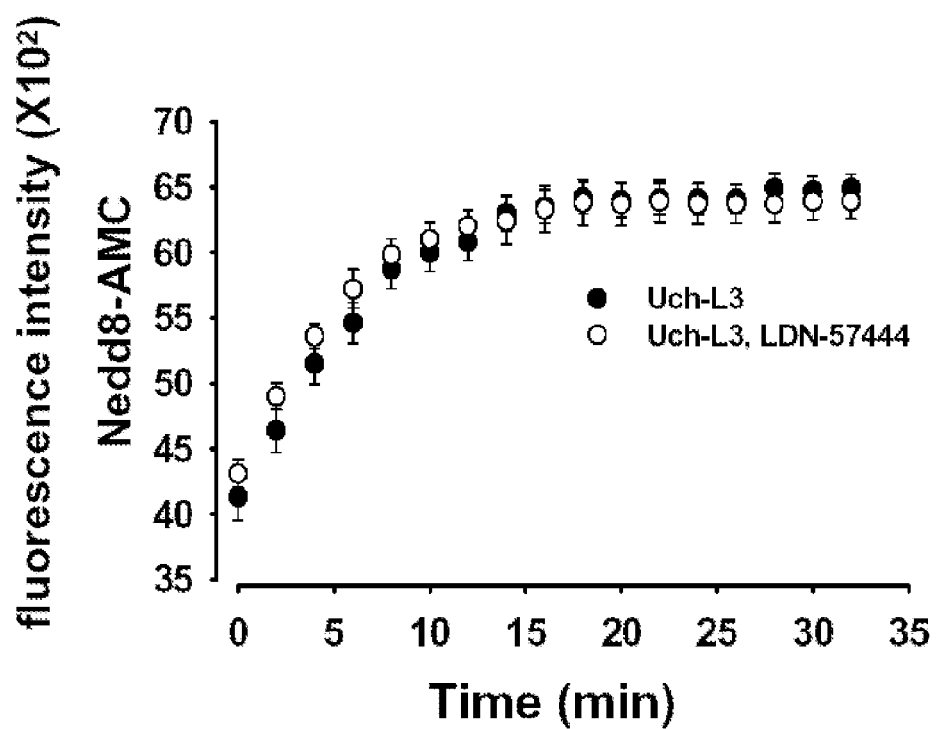
FIGS. 32A-32D. Effects of LDN-57444 on Uch-L3 and on synaptic function.
Figure 32B:
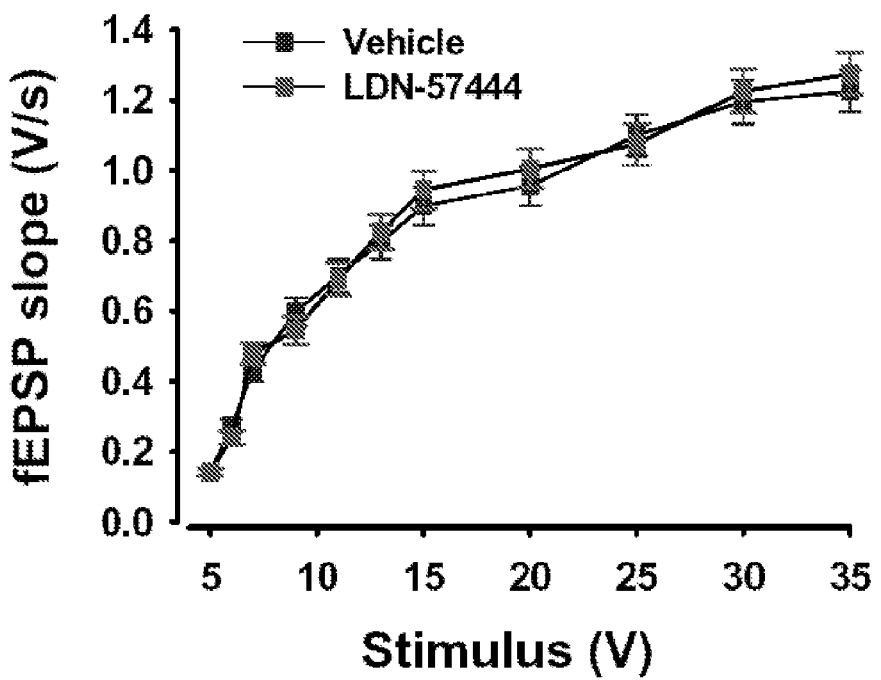
Figures 32C, 32D:
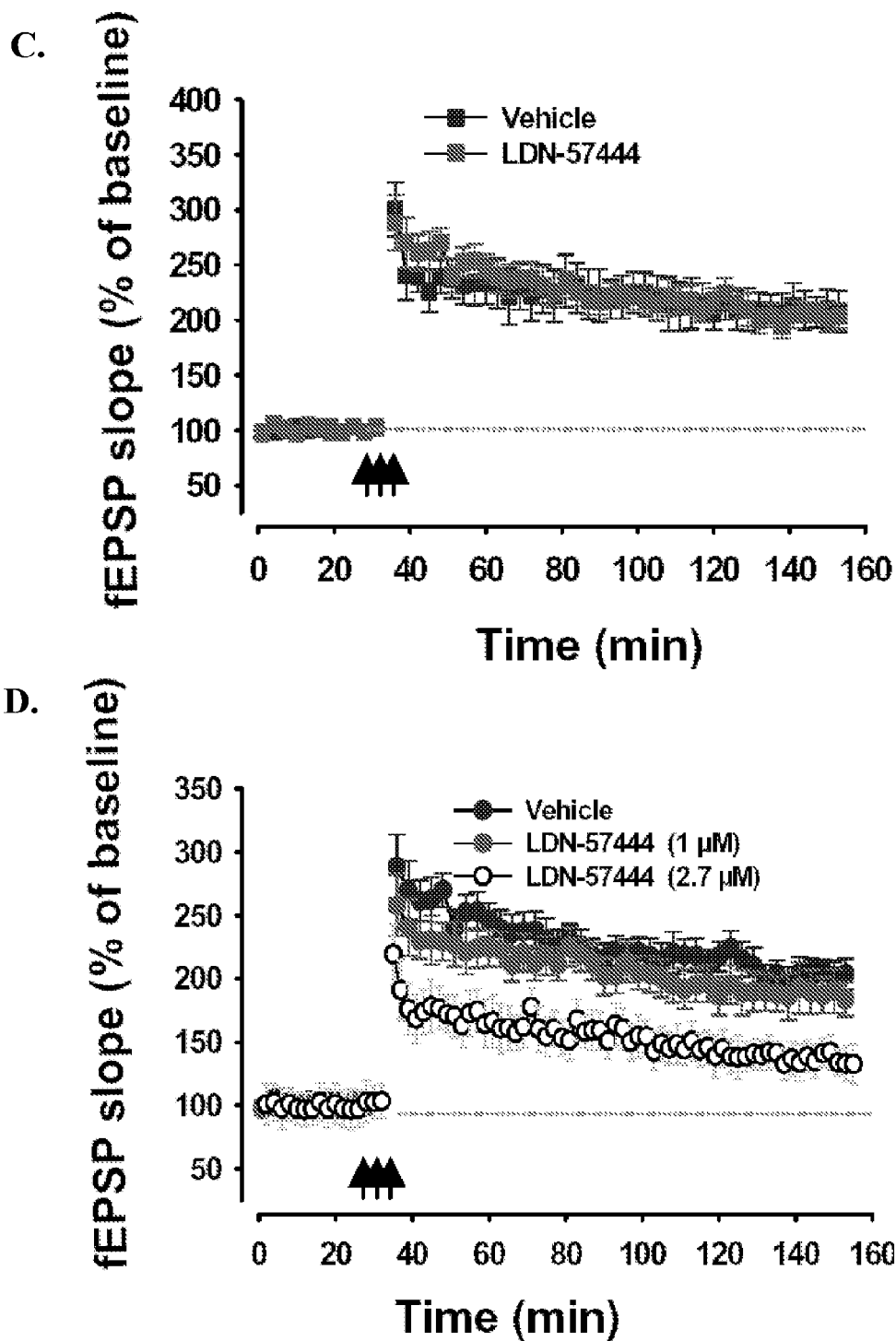

To test if Uch-L1 is required for synaptic function in the mammalian brain, hydrolase activity and LTP were measured in mouse hippocampal slices exposed to the specific Uch-L1 inhibitor, LDN-57444 (LDN), a reversible, competitive, active site directed isatin oxime with an $IC_{50}$ value of 0.88 μM for Uch-L1 and 25 μM for its systemic isoform, Uch-L3 (Liu et al., 2002). Maximal inhibition of Uch activity (70%) was obtained with 5 μM LDN in one hour (FIGS. 25A and 25B). This was not due to inhibition of Uch-L3 since there was no reduction in hydrolysis of Nedd8-AMC, a ubiquitin-like protein that binds to and is cleaved by Uch-L3, when 20 nM Uch-L3 was incubated with 5 μM LDN (Wada et al., 1998) (FIG. 32A). When the effect of LDN on synaptic function was examined, a 15 minute perfusion with 5 μM LDN was found to produce a 20% inhibition of enzymatic activity did not affect basal synaptic transmission (BST) or LTP at the CA3-CA1 connection (FIGS. 32B and 32C). In contrast, a 2 hour exposure reducing activity by 70%, diminished LTP without affecting BST (FIGS. 25C and 25D), and a 4 hour exposure reduced both BST (FIG. 25E) and LTP (FIG. 25). A similar reduction in LTP with normal BST was observed following 2-4 hour perfusion with 2.7 μM LDN (FIG. 32D) that reduced enzymatic activity by ~40%, but not with a concentration of 1 μM that produced only a 20% reduction (FIG. 25A). LDN at these concentrations did not inhibit Uch-L3 activity, thus synaptic dysfunction by LDN is due to Uch-L1 inhibition. These findings are consistent with recent work showing normal LTP, contextual learning and cued learning in Uch-L3 null mice (Wood et al., 2005). These alterations are similar to those induced by Aβ treatment and those seen in APP/PS1 mice where Uch-L1 activity was found to be decreased by approximately 30% (FIGS. 26A and 28E).

Restoration of Uch-L1 Levels Corrects Deficits in Synaptic Transmission in Aβ Treated Hippocampal Slices and in Slices from APP/PS1 Mice To manipulate the levels of Uch-L1, a fusion protein was produced in which the 11-amino acid transduction domain of the HIV-transactivator protein (TAT) was fused with an HA tag and Uch-L1 (TAT-HA-Uch-L1) (Wadia and Dowdy, 2003; Wadia et al., 2004). As controls, fusion proteins were produced between TAT and HA (TAT-HA) and between TAT and inactive Uch-L1 from which 57 amino acids (130 to 186) are deleted (TAT-HA-iUch-L1).

Figure 33A:
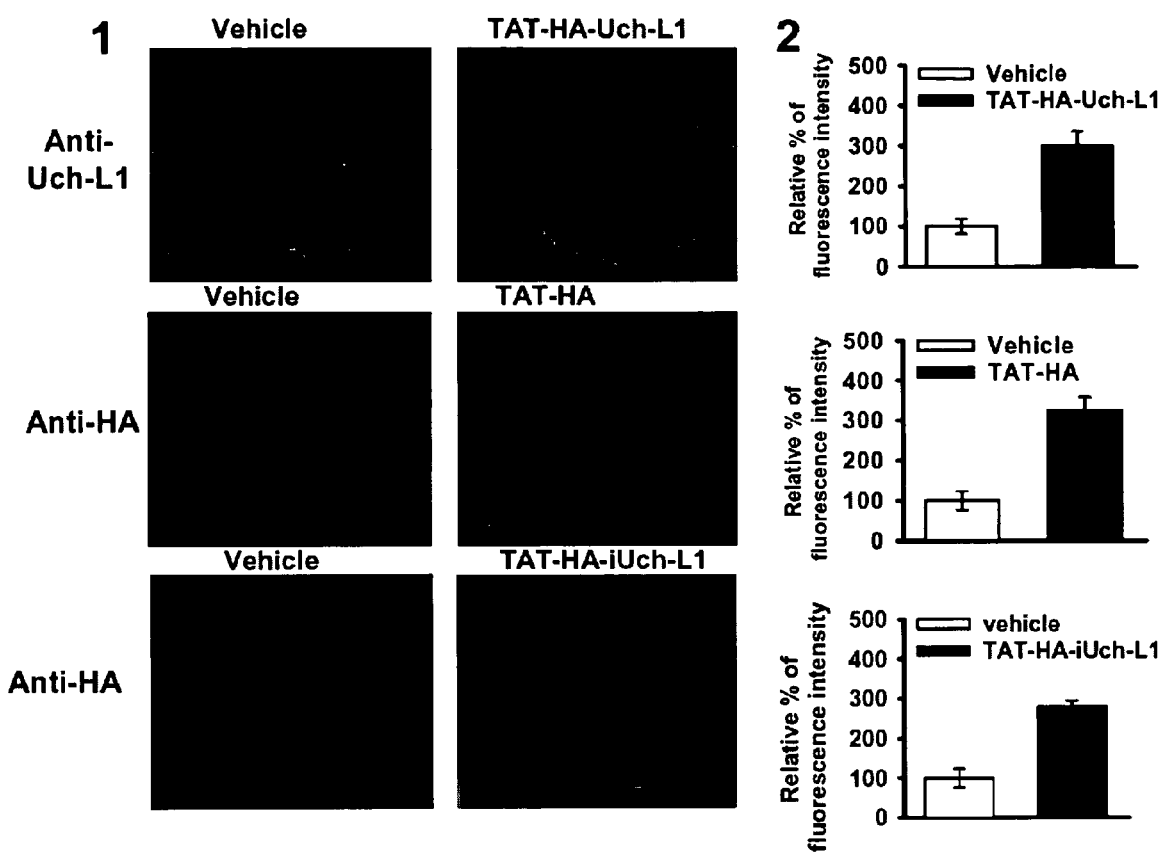
FIGS. 33A-33D. The 11-amino acid transduction domain of HIV-transactivator protein (TAT) carries Uch-L1 protein into tissue both in vitro and in vivo.
Figure 33B:
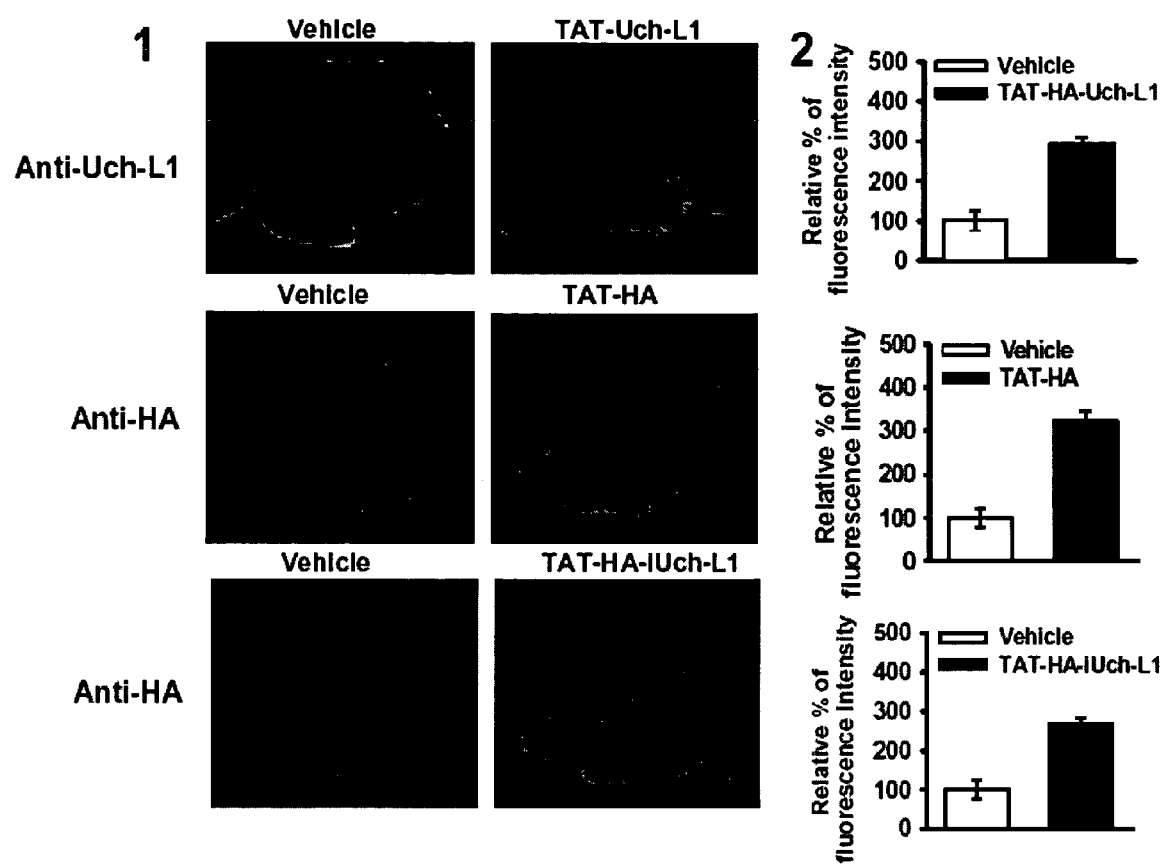
Figure 33C:
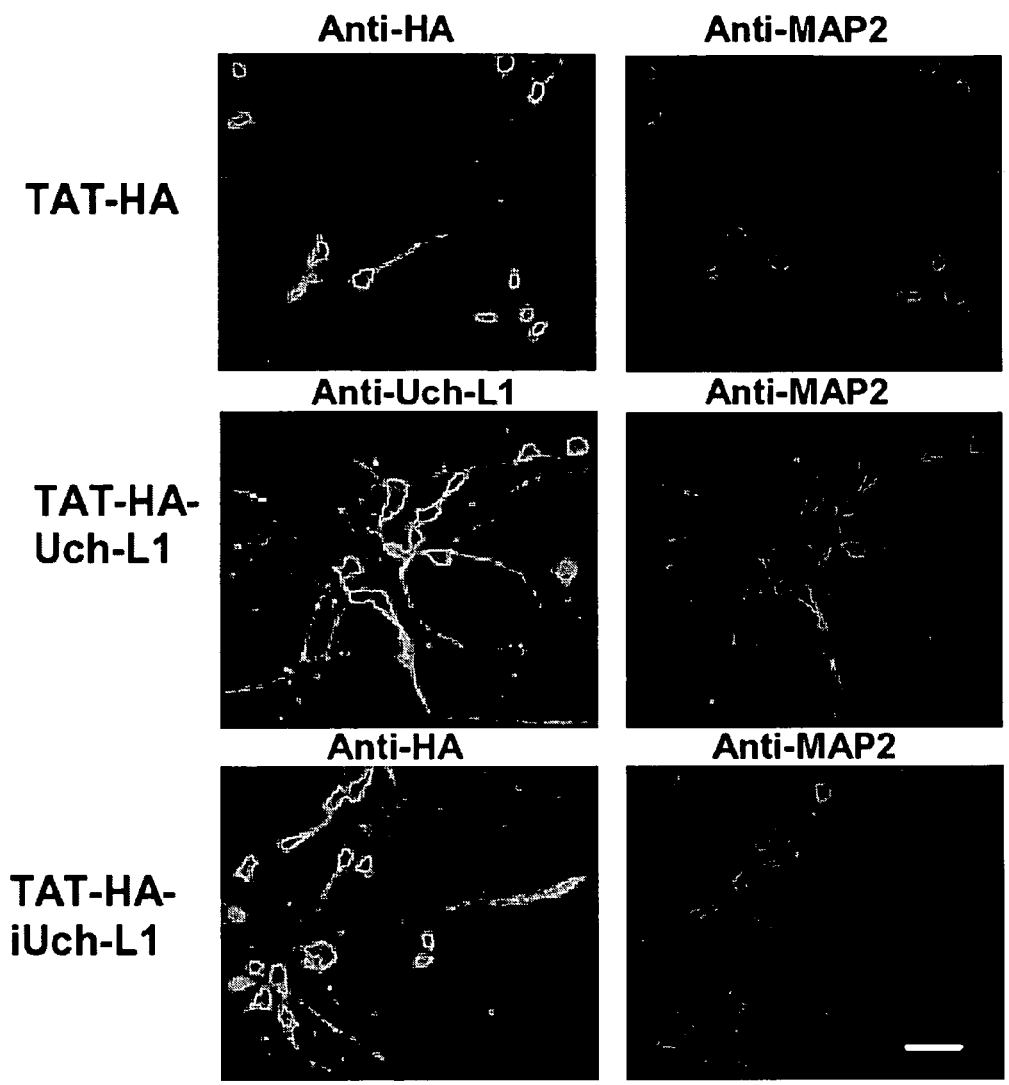
Figure 33D:
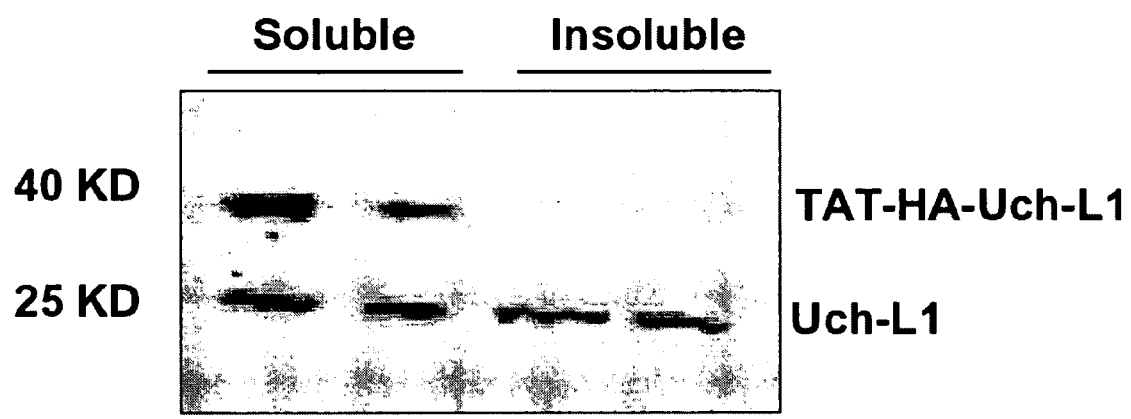

Hippocampal slices perfused with TAT-HA-Uch-L1 (20 nM), TAT-HA-iUch-L1 (20 nM), TAT-HA (20 nM) for 1 hr followed by fixation and staining with anti-Uch-L1 or anti-HA, as appropriate, showed a threefold increase in staining intensity as compared to vehicle-treated slices from the same animals (FIGS. 33A1 and 33A2). These proteins also enter the brains of living animals following i.p injection and neurons in primary hippocampal cultures (FIGS. 33B and 33C). TAT-HA-Uch-L1 was found to be localized to the soluble fraction of hippocampal homogenates 1 hr after its administration (FIG. 33D).

Figure 26B:
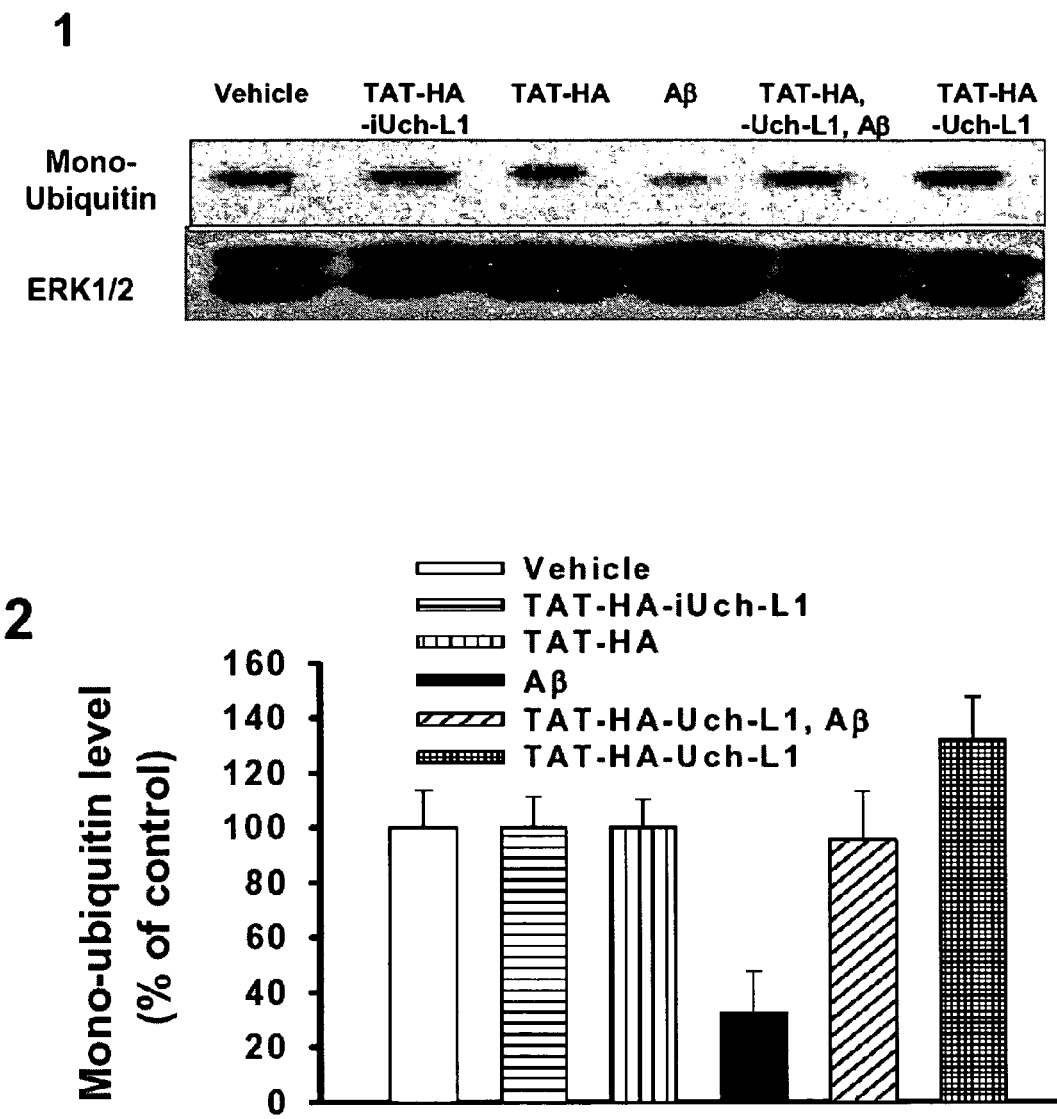

Uchs play a major role in the generation of monomeric ubiquitin (Wilkinson, 2000). Treatment with oligomeric Aβ42 (200 nM for 20 min) decreases monoubiquitin levels by ~70% (FIG. 26B). When slices are incubated for 1 hour with TAT-HA-Uch-L1 (20 nM) before Aβ treatment (20 min in the continued presence of TAT-HA-UchL1) normal monoubiquitin levels and Uch activity are maintained (FIGS. 26A and 26B). TAT-HA-Uch-L1 alone produced a slight increase in the monoubiquitin levels and in enzymatic activity while inactive TAT-HA-iUch-L1 and TAT-HA had no effect. These results show that the TAT-HA-Uch-L1 fusion protein enters cells, is enzymatically active and is capable of re-establishing normal hydrolase levels.

Figure 27A:
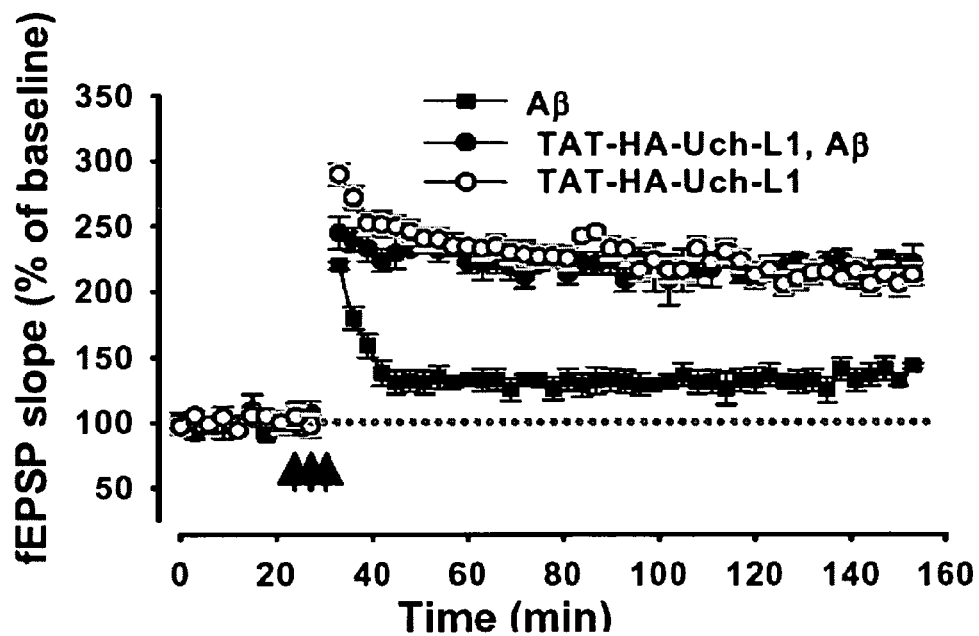
FIGS. 27A-27F. Exogenous Uch-L1 rescues the LTP deficit induced by Aβ.
Figure 27B:
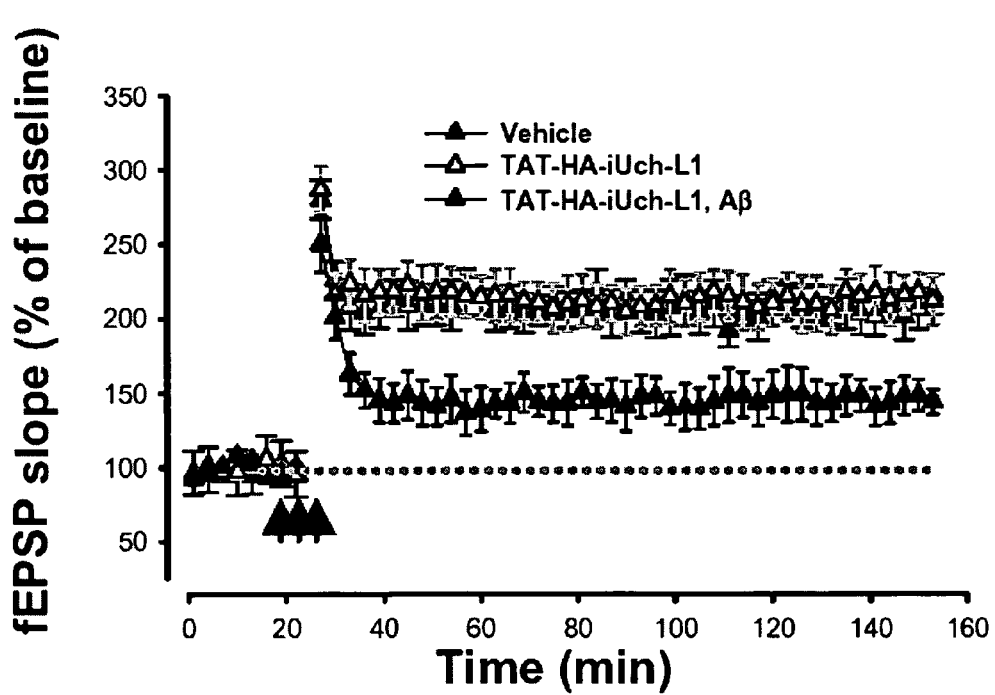
Figure 34:
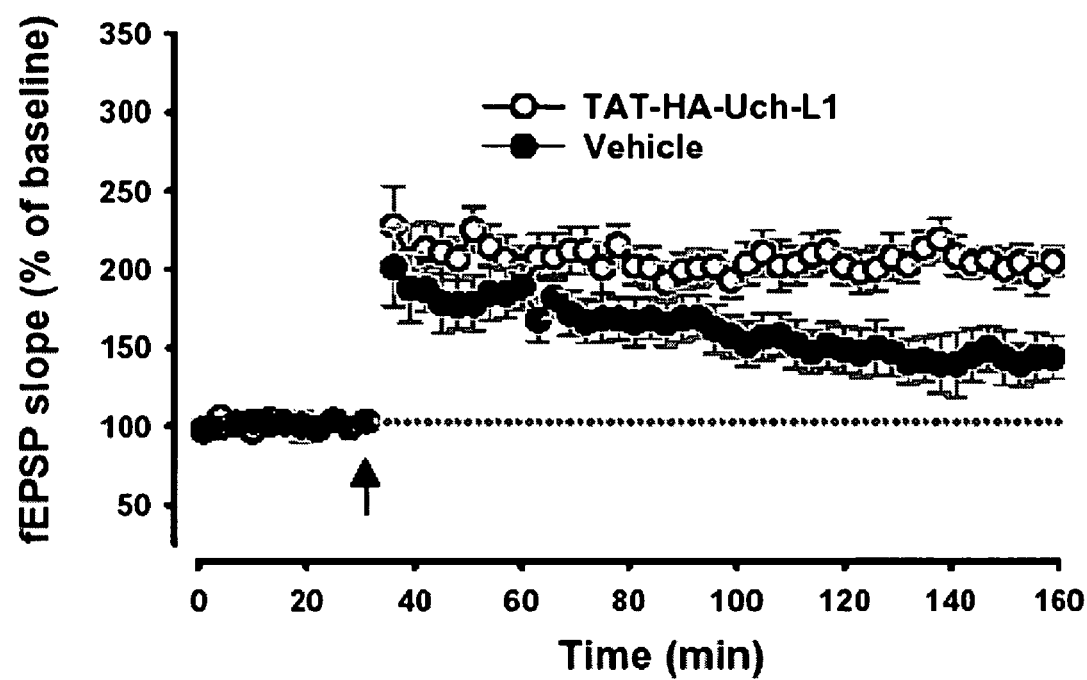
FIG. 34. Effect of TAT-HA-Uch-L1 on LTP induced through a weak tetanic stimulation. TAT-HA-Uch-L1 increases LTP in slices from WT mice that were stimulated with 1 theta-burst train instead of 3 (n=7 slices from 6 mice for both LDN- and vehicle-treated slices; two-way ANOVA F(1, 12)=10.35, p<0.01 and planned comparison showed that the groups were significantly different at each time point after tetanus, p<0.01).

Perfusion of hippocampal slices with oligomeric Aβ (200 nM) reduced LTP to ~60% in CA1 compared to control slices treated with vehicle alone (FIGS. 27A and 27B) (Cullen et al., 1997; Itoh et al., 1999; Vitolo et al., 2002; Walsh et al., 2002). Pretreatment with TAT-HA-Uch-L1 (20 nM) for 1 hr followed by perfusion with 200 nM oligomeric Aβ plus TAT-HA-Uch-L1 before theta-burst stimulation protected against LTP suppression (FIG. 27A). TAT-HA-iUch-L1 was not protective (FIG. 27B). TAT-HA-Uch-L1 alone had no effect on LTP evoked with 3 theta-burst trains but it enhanced LTP when applied prior to a weaker tetanus (1 theta-burst train instead of 3 trains) (FIG. 34), showing that the stronger tetanus produces maximal potentiation that cannot be further augmented by exogenous Uch-L1.

Figure 27C:
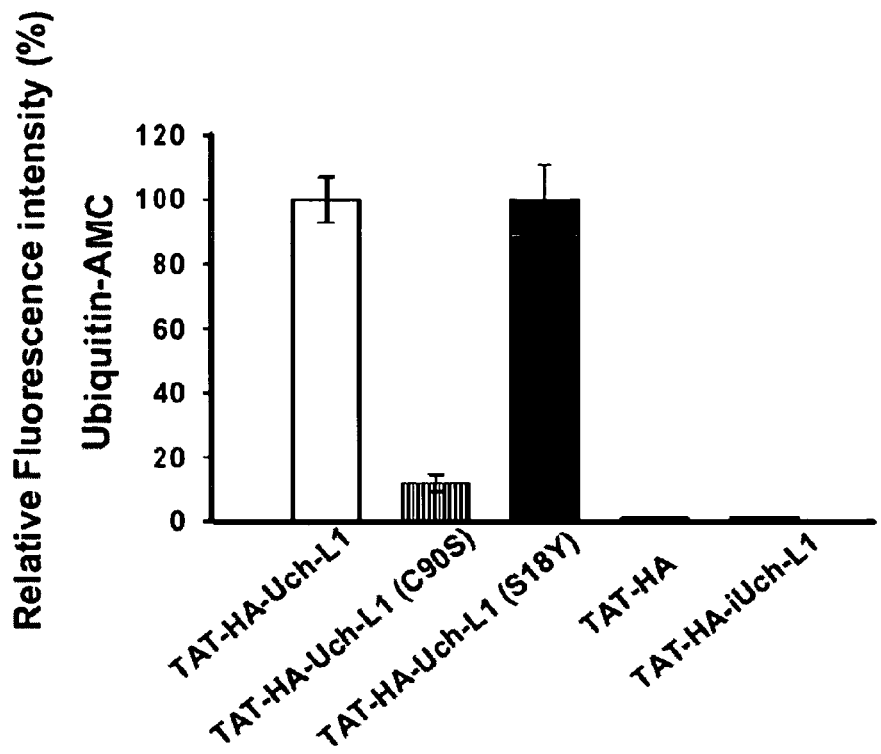
Figure 27D:
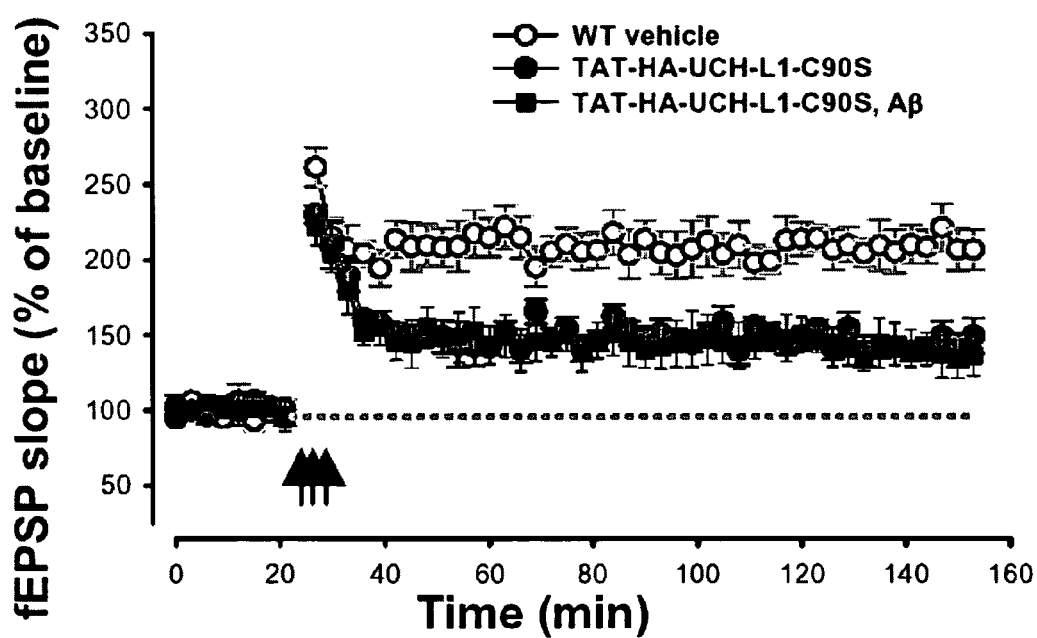

These results show parallels between the effect of TAT-HA-Uch-L1 on hydrolase activity in the slices and its ability to block deleterious actions of Aβ. However, Uch-L1 has two separate enzymatic activities. Both the C90 and H161 sites are involved in both hydrolase and ligase function whereas the S18 site modulates dimer formation that correlates with the ligase activity (Liu et al., 2002). To investigate which function of Uch-L1 is involved in its effect on Aβ-induced block of LTP, site-directed mutagenesis was used to produce three mutant constructs of TAT-HA-Uch-L1, TAT-HA-Uch-L1(C90S), TAT-HA-Uch-L1(S18Y) and TAT-HA-iUch-L1. The last of these has a 57 amino acid deletion (130-186) including the H161 site. TAT-HA-Uch-L1 and TAT-HA-Uch-L1 (S18Y) have similar hydrolase activity, while TAT-HA-Uch-L1(C90S), TAT-HA and TAT-HA-iUch-L1 have little or no activity (FIG. 27C). Pre-incubation (1 hr) with either TAT-HA-Uch-L1(C90S) or TAT-HA-iUch-L1 failed to protect against LTP suppression (FIGS. 27B and 27D) while TAT-HA-Uch-L1(S18Y) protected (FIG. 27E) to the same extend as unmodified construct (FIG. 27A). TAT-HA-Uch-L1 (C90S) alone produced a significant decrease (~60%) in potentiation compared to slices treated with vehicle or TAT-HA-iUch-L1 (FIGS. 27A and 27D) suggesting that it is a dominant negative inhibitor.

Figures 27E, 27F:
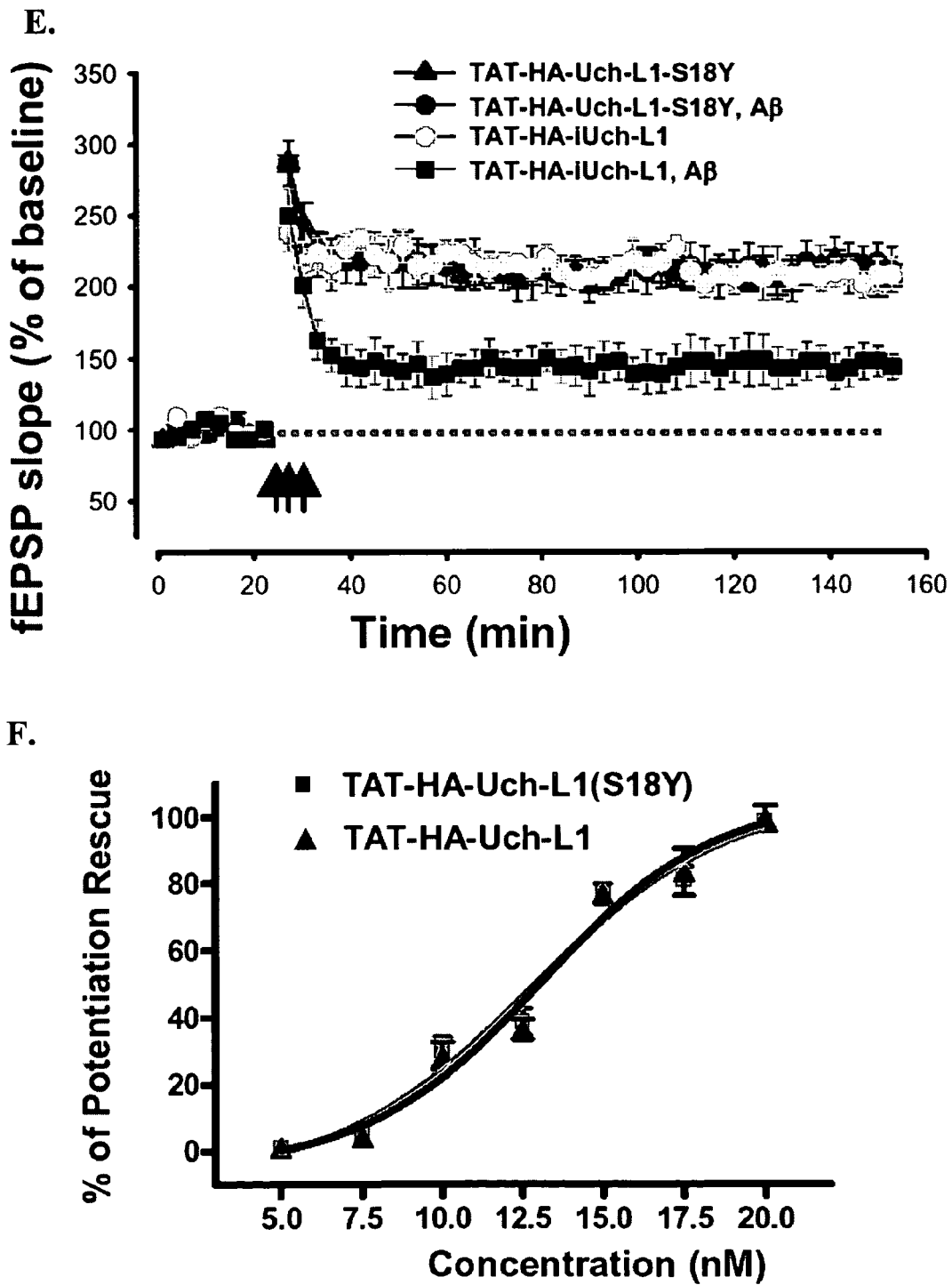
Figure 35:
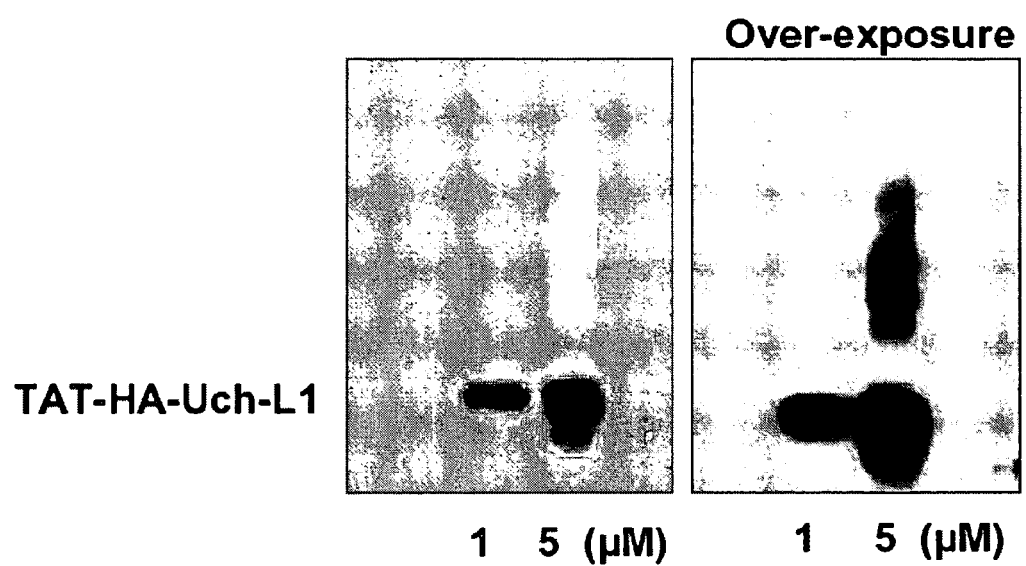
FIG. 35. Exogenous TAT-HA-Uch-L1 does not form dimers at low concentrations. Native gels of TAT-HA-Uch-L1 fusion protein at 1 and 5 μM concentrations. No dimers were detected at 1 μM. A weak band corresponding to dimers and other oligomeric species was detected at 5 μM. Overexposure confirmed results obtained with normal exposure.

Since the S18Y form dimerizes at higher concentrations than WT Uch-L1 (Liu et al., 2002), the effect of different concentrations of TAT-HA-Uch-L1 and TAT-HA-Uch-L1 (S18Y) on LTP rescue after Aβ was examined, reasoning that the lower ligase activity of the S18Y form at a given concentration should produce lower amounts of potentiation if ligase activity is relevant to the rescue effect. No difference was detected in the two (FIG. 27F). Dimer formation by TAT-HA-Uch-L1 was examined at concentrations of 1 μM and 5 μM—many times higher than that used in these experiments—no dimer formation was detected at 1 μM (FIG. 35).

Figure 36:
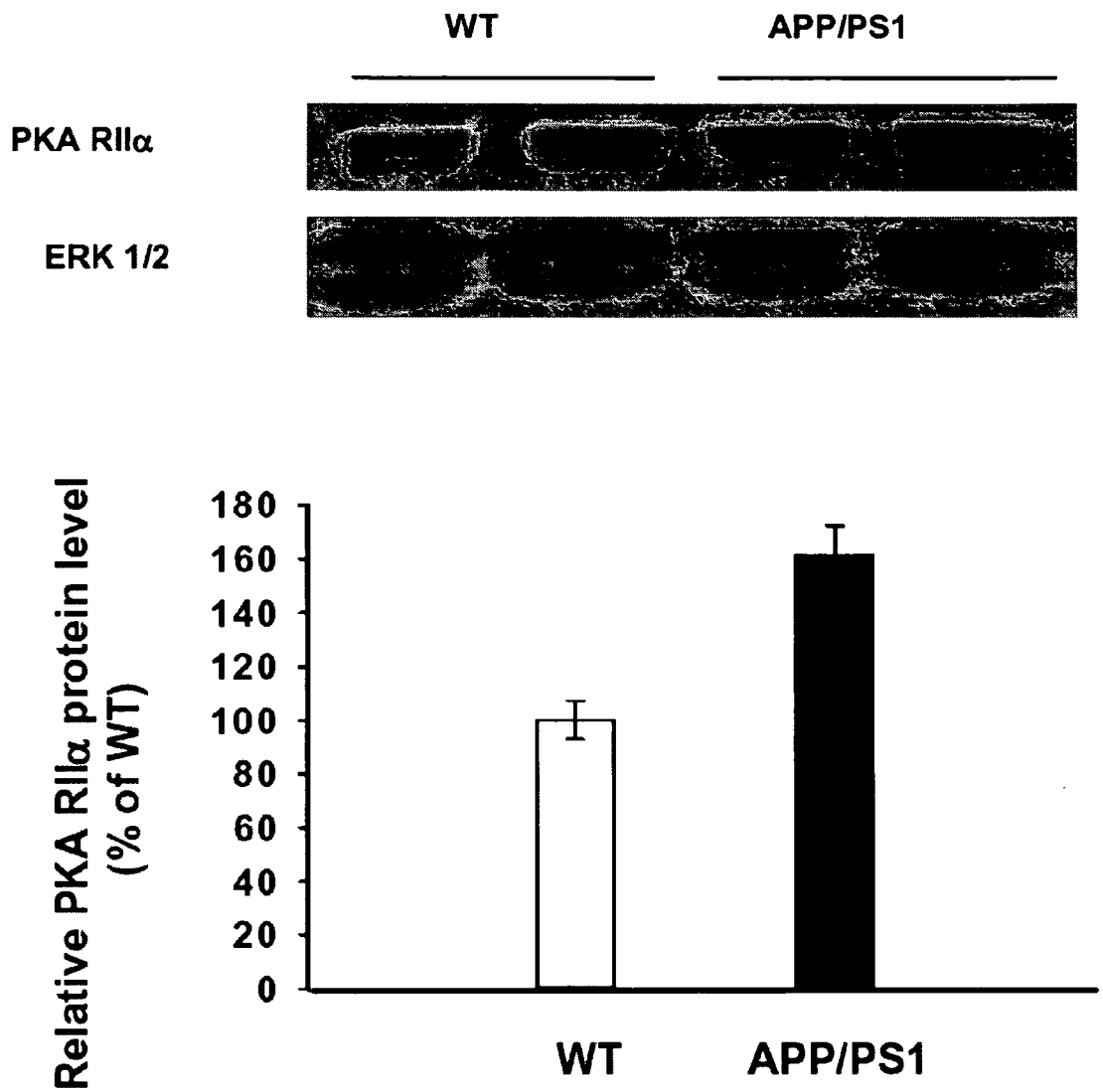
FIG. 36. PKA-RIIα levels are increased in APP/PS1 mice. Quantitative Western blot analysis of protein extracts from hippocampal slices showed an increase in PKA RIIα levels in APP/PS1 mice compared to WT littermates (n=5 in both groups, p<0.01). All samples are normalized against ERK1/2.
Figure 37A:
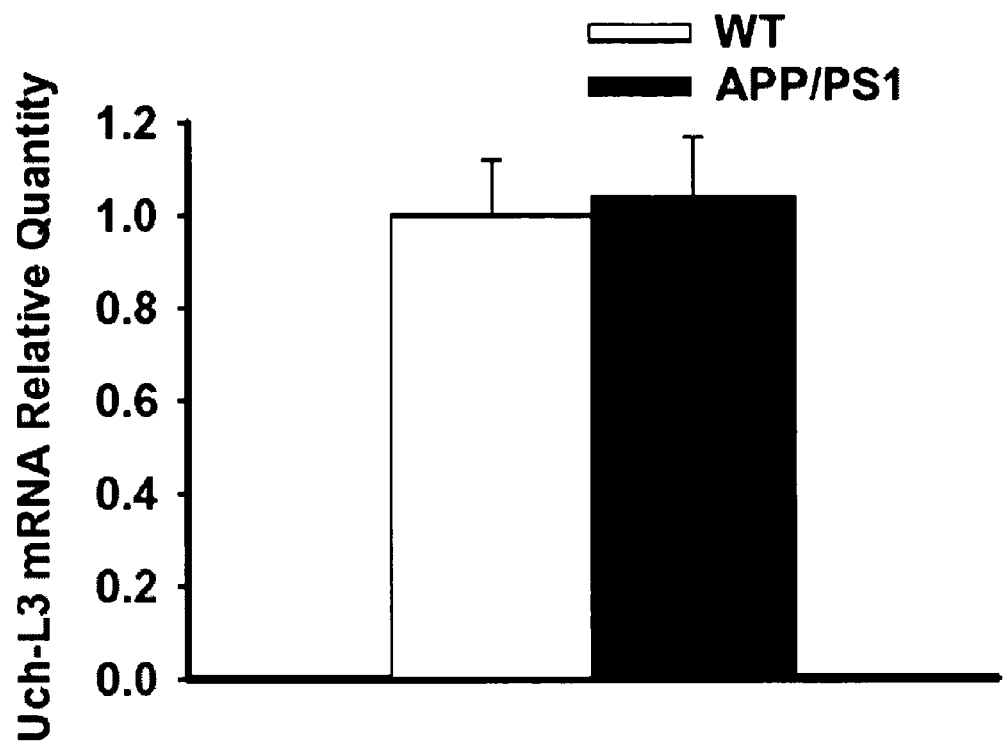
FIGS. 37A-37D. Uch-L3 mRNA levels and protein levels are normal in APP/PS1 mice.

Similar results were obtained in slices from double Tg animals carrying both the mutant amyloid precursor protein (APP) (K670N,M671L) and presenilin-1 (PS1) (M146L) transgenes (APP/PS1 mice) that were used to validate findings from Aβ treated slices. These mice start depositing Aβ at 8-10 weeks and partially reproduce the cognitive deficits that occur in AD patients. They display impaired LTP and contextual learning as early as 34 months of age, and deficits in BST at 5-6 months of age (Gong et al., 2004; Trinchese et al., 200-4). They also show a reduction of basal CREB levels (Gong et al., 2004) and an increase in PKA-RIIα subunit (FIG. 36). Examination of Uch-L1 in these animals revealed little difference between Tg and WT mice in mRNA levels for Uch-L1 (FIG. 28A) or Uch-L3 (FIG. 37A). There was no change in total Uch-L1 protein level in their hippocampi. However, there was a ~30% decrease of Uch-L1 protein in the soluble fraction of hippocampal homogenates from APP/PS1 mice compared to WT littermates (FIG. 28B) with a similar increase in the insoluble fraction (FIG. 28C). This reduction is reflected in the soluble Uch activity. The specific activity of the Uch-L1 in the insoluble fraction was very low, (~15% of the soluble enzyme). Thus, the total activity in the APP/PS1 mice was decreased (FIG. 28D). Double Tg APP/PS1 mice showed a 30% decrease in total hippocampal hydrolase activity at 4-6 months that increased to a 45% loss at 15-18 months. Single Tg APP mice showed only a slight decrease of activity at 4-6 months that increased to a 30% loss at 15-18 months.

Figure 28F:
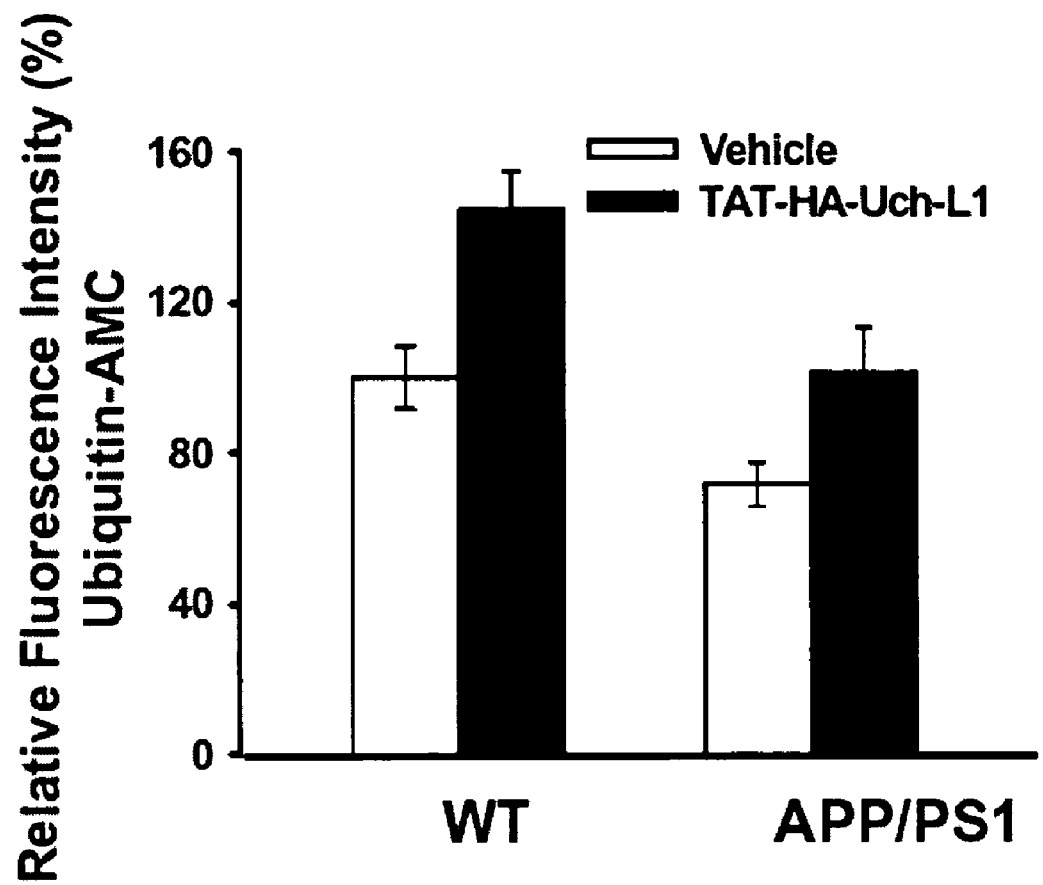
Figure 37B:
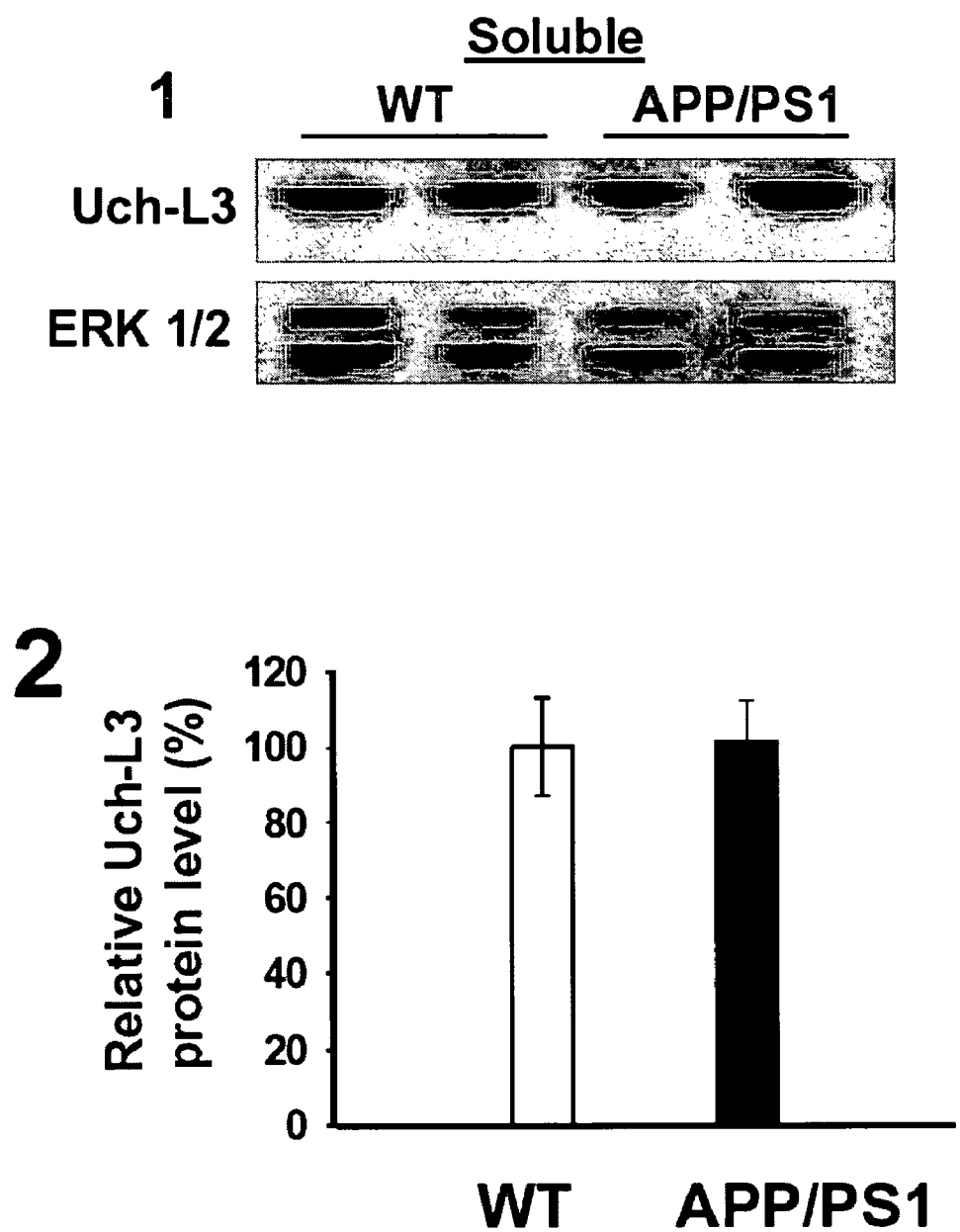
Figure 37C:
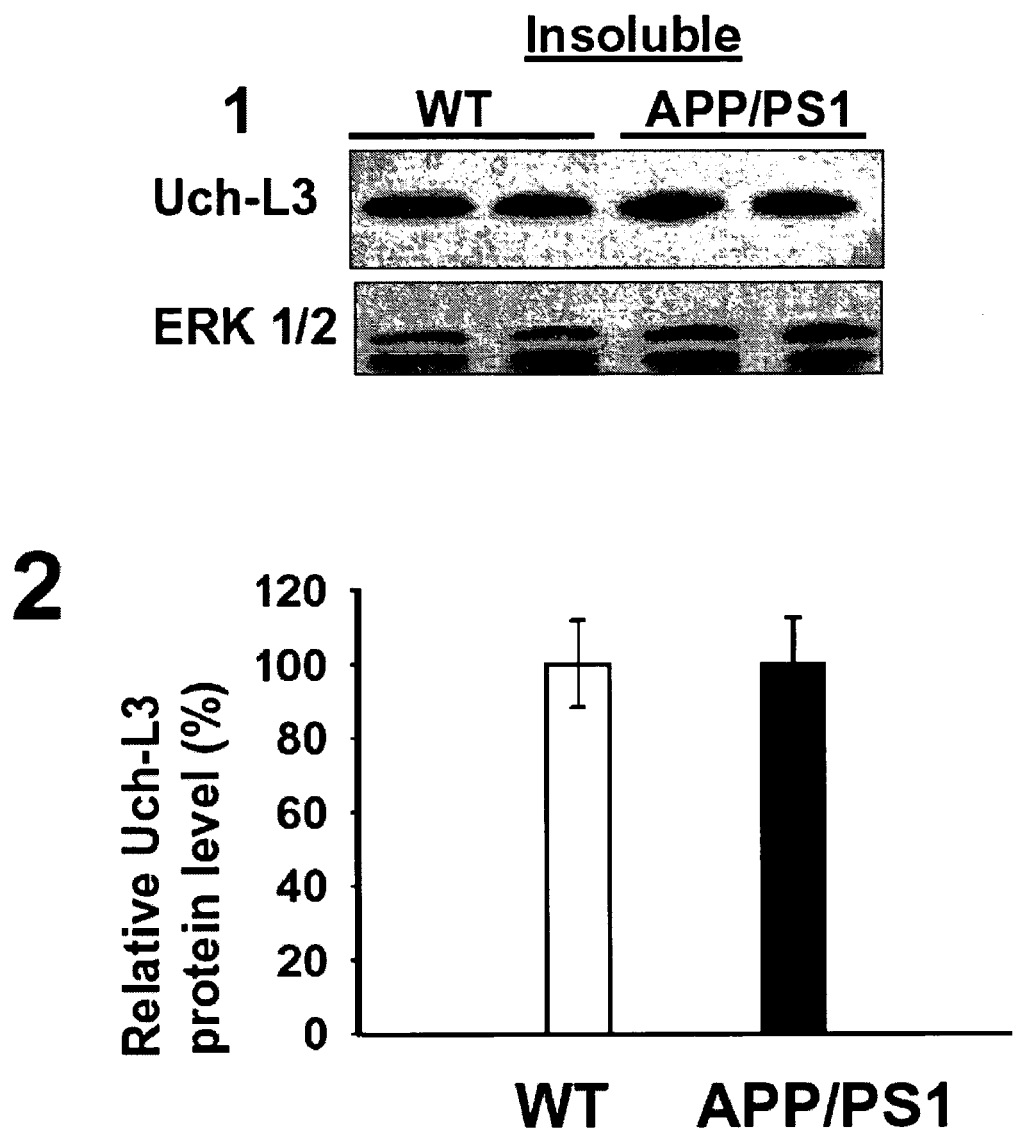
Figure 37D:
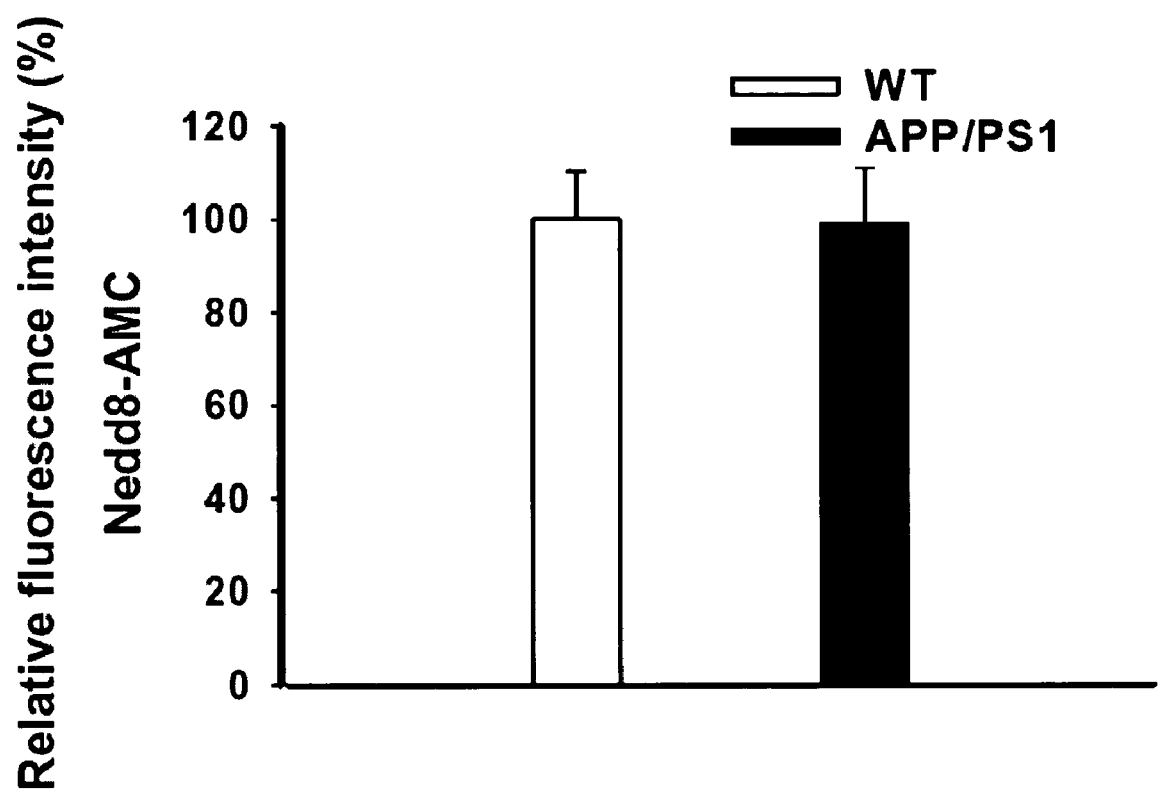
Figure 38A:
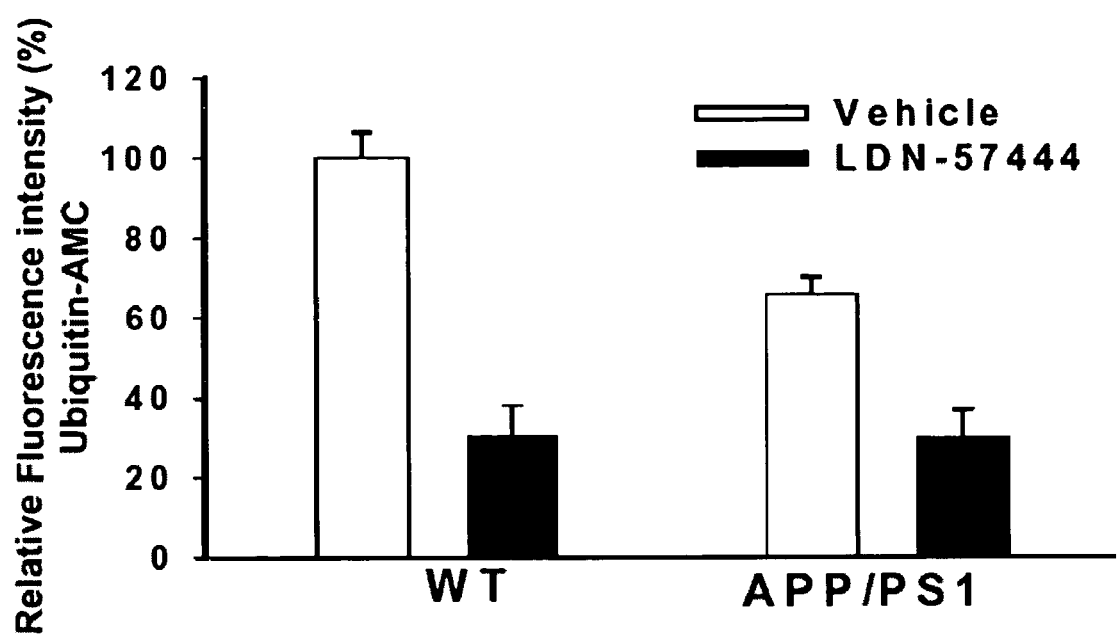
FIGS. 38A-38C. Inhibition of Uch-L1 activity by LDN-57444 decreases Uch-L1 activity but does not further reduce LTP following Aβ elevation.
Figure 38B:
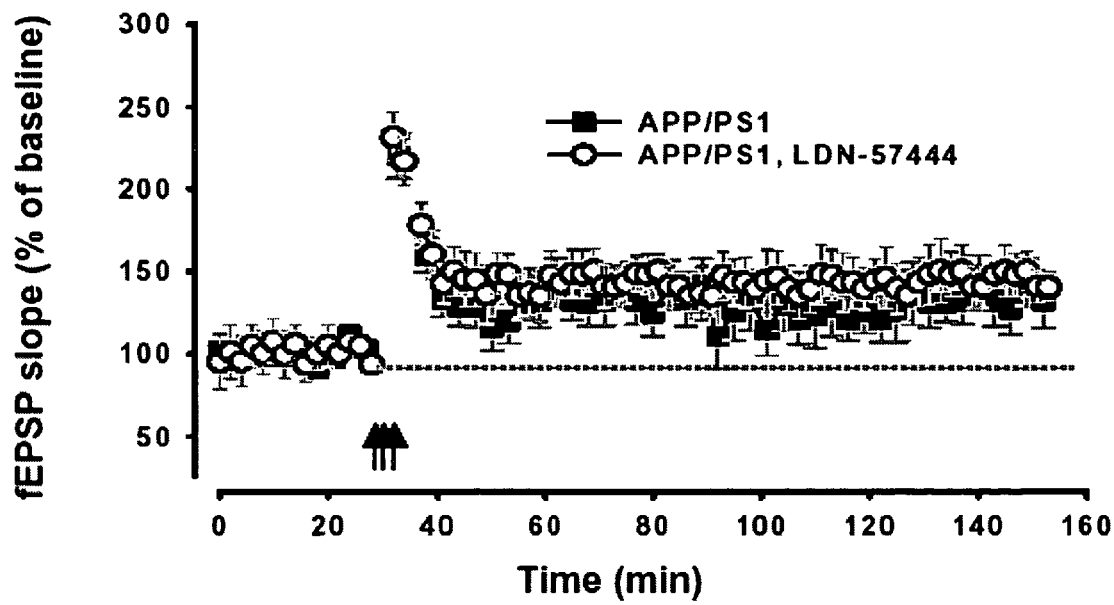
Figure 38C:
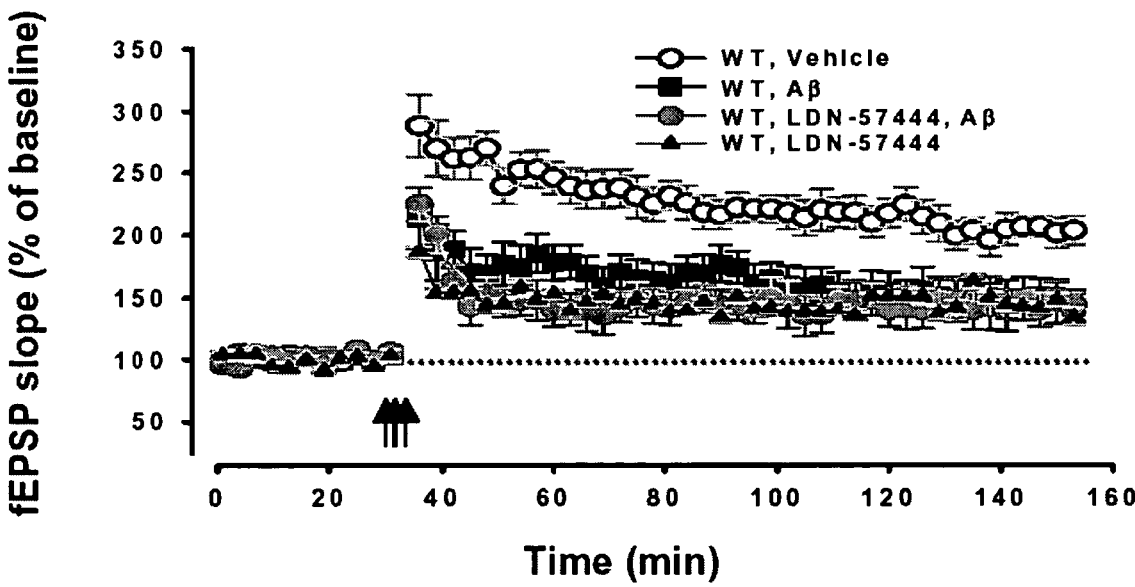

WT and single Tg PS1 mice did not differ significantly and showed a reduction of about 10% in activity at 15-18 months (FIG. 28E). When mice were injected with TAT-HA-Uch-L1 (0.02-0.04 g/kg, i.p.), Uch activity returned to control levels in APP/PS1 mice and increased above control level in WT mice (FIG. 28F). Since the Ub-AMC assay is not specific for Uch-L1, Uch-L3 protein was also measured in soluble and insoluble fractions of hippocampal tissue from APP/PS1 and WT littermates (FIGS. 37B and 37C) and used the Nedd8-AMC assay to examine total Uch-L3 activity (FIG. 37D). No difference was detected in either among genotypes, showing that Uch-L3 is not involved in the decrease of hydrolase activity. Taken together these findings support the hypothesis that a reduction in Uch-L1 protein levels leads to a lower hydrolase activity and the impairment of both synaptic function and cognition in the double Tg mice. The loss of hydrolase activity in the APP/PS1 mice is less than the reduction in slices treated with 5 µM LDN for 60 min (~30% vs ~70%) suggesting that Uch-L1 activity is not completely blocked in APP/PS1 mice. Indeed, if hippocampal slices of WT and APP/PS1 mice were exposed for 2 hours to 5 µM LDN, the inhibitor reduces enzymatic activity to the same level in the two genotypes (~70% of values in vehicle treated WT slices) (FIG. 38A). However, LDN (5 µM for 2 hrs) does not further reduce potentiation in APP/PS1 slices or in WT slices exposed to 200 nM Aβ (FIGS. 38B and 38C) suggesting that a 30% decrease of hydrolase activity is sufficient to produce maximal levels of LTP reduction.

Figure 29A:
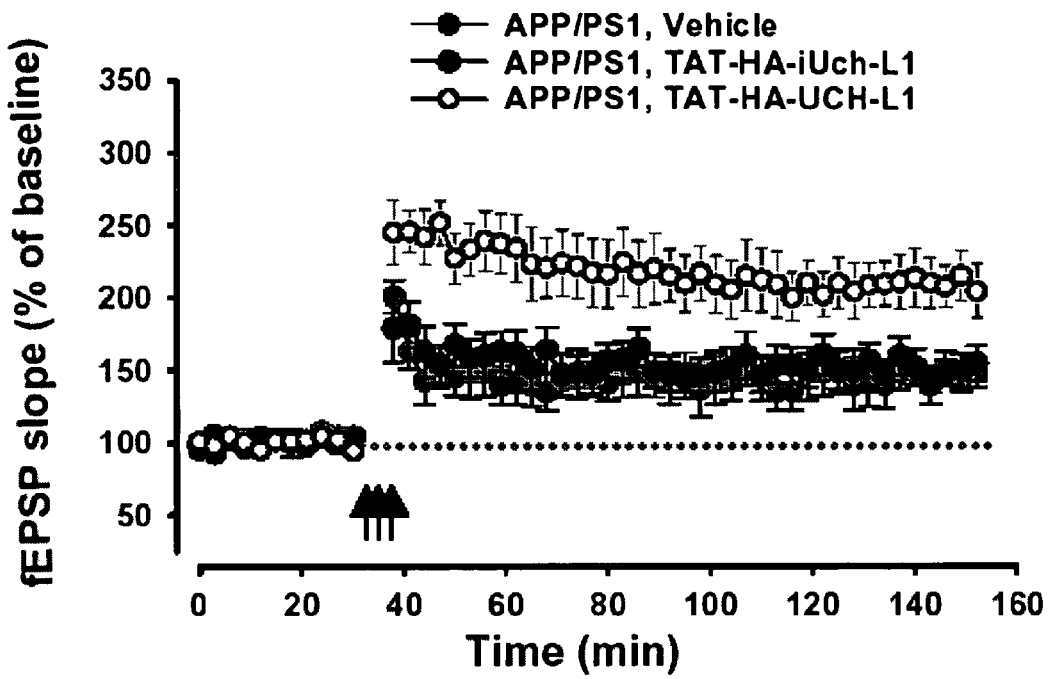
FIGS. 29A-29E. Uch-L1 effects on synaptic function in APP/PS1 mice.
Figure 29B:
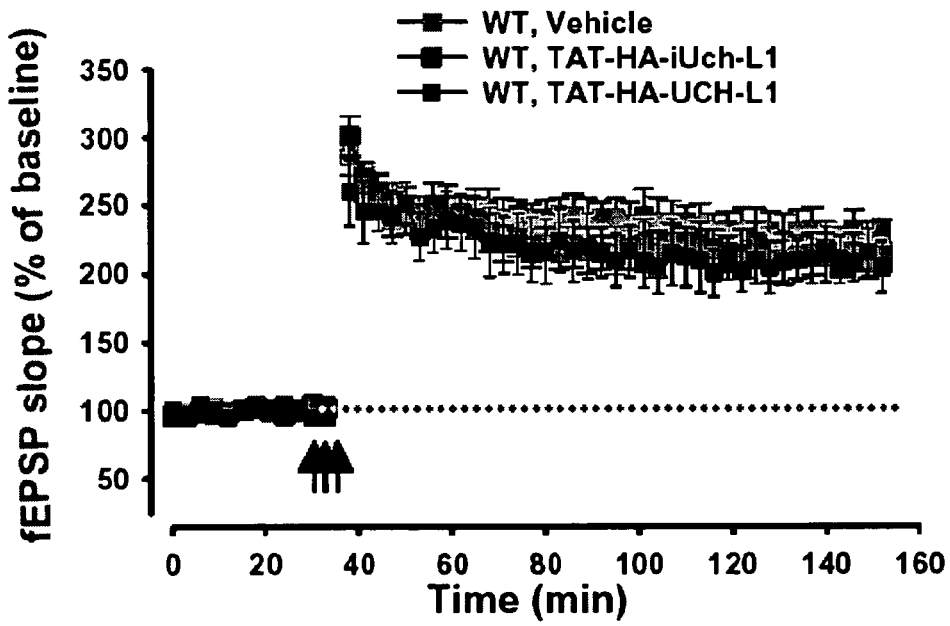
Figure 29C:
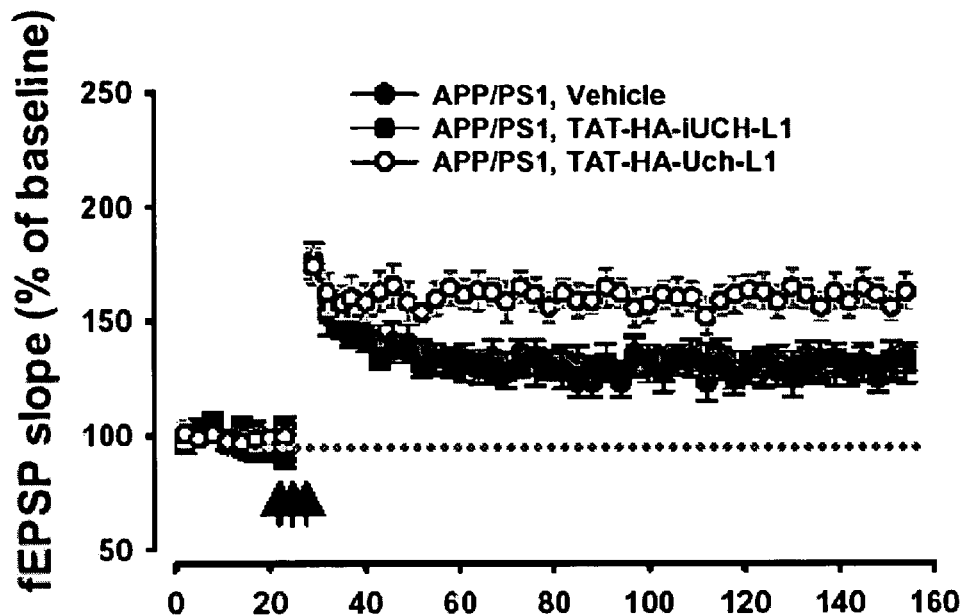
Figure 29D:
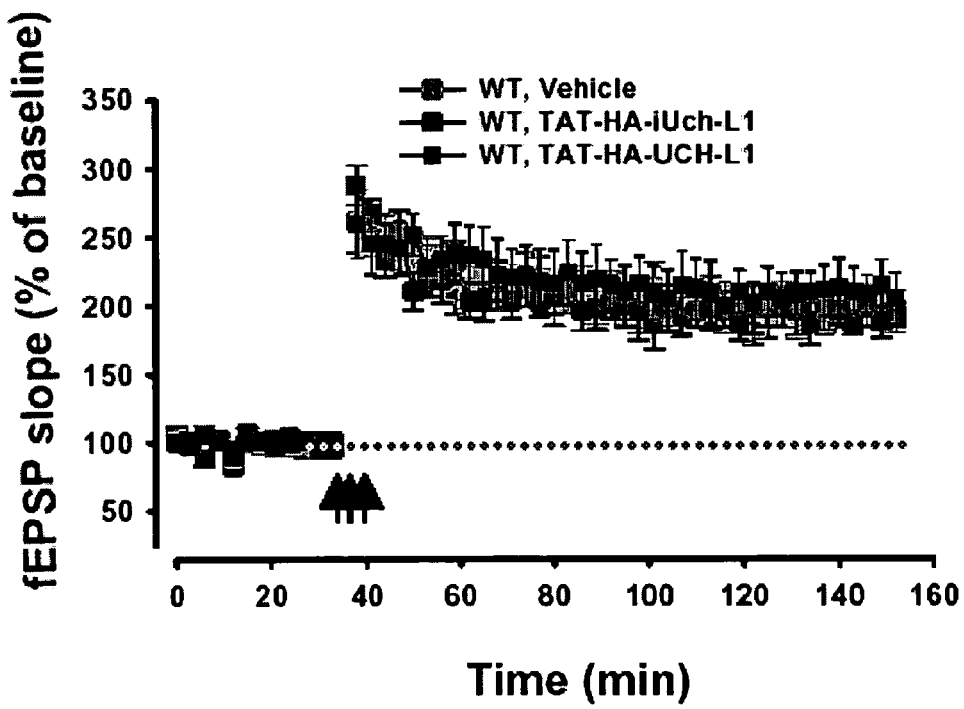
Figure 29E:
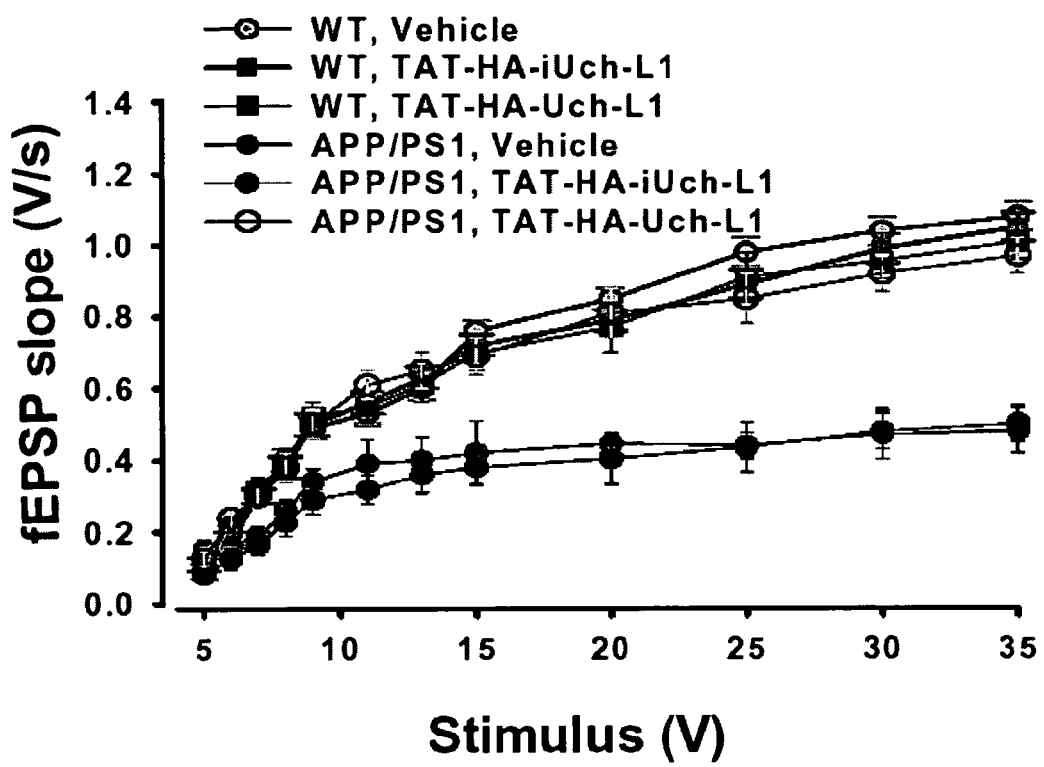

When hippocampal slices from 4 month APP/PS1 mice are perfused with TAT-HA-Uch-L1 (20 nM) for 1 hr Uch activity is restored and LTP amplitude following theta burst is elevated above vehicle treated slices and is similar to WT mice (FIGS. 29A and 29B). Neither TAT-HA nor TAT-HA-iUch-L1-treated slices differed from vehicle-treated slices. TAT-HA-Uch-L1 had no effect on LTP amplitude in hippocampal slices from WT mice (FIG. 29B). There was no difference in BST among the different groups as measured by plotting the fEPSP slope versus the stimulus intensity or versus the amplitude of the fiber afferent volley. Similar effects were seen in older APP/PS1 mice (12-18 months) with severe plaque load (FIGS. 29C and 29D). BST in APP/PS1 mice, initially lower than in WT mice, was also improved in the TAT-HA-Uch-L1 group as compared to vehicle or TAT-HA-iUch-L1 treated slices (FIG. 29E).

Exogenous Uch-L1 Improves Contextual Fear Learning in APP/PS1 Mice

Figure 30A:
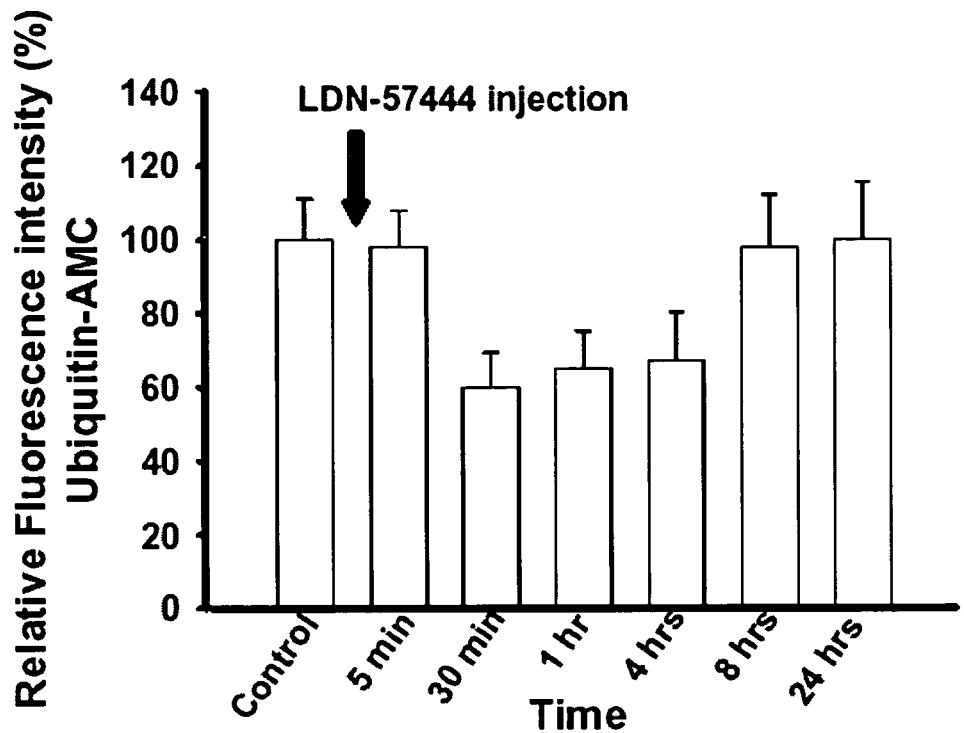
FIGS. 30A-30D. Exogenous Uch-L1 improves the retention of contextual memory in APP/PS1 mice over time.
Figure 30B:
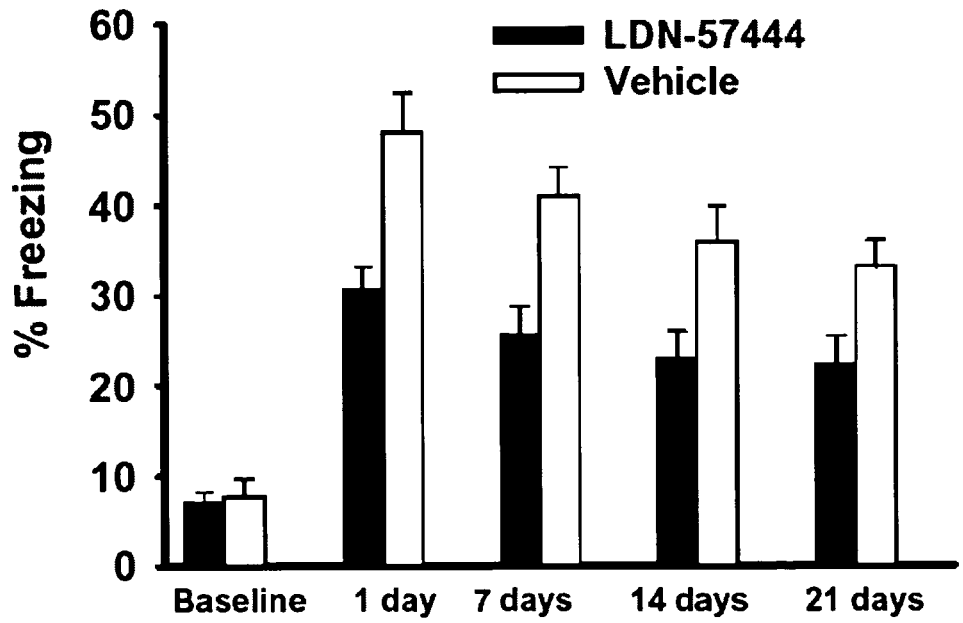
Figure 30C:
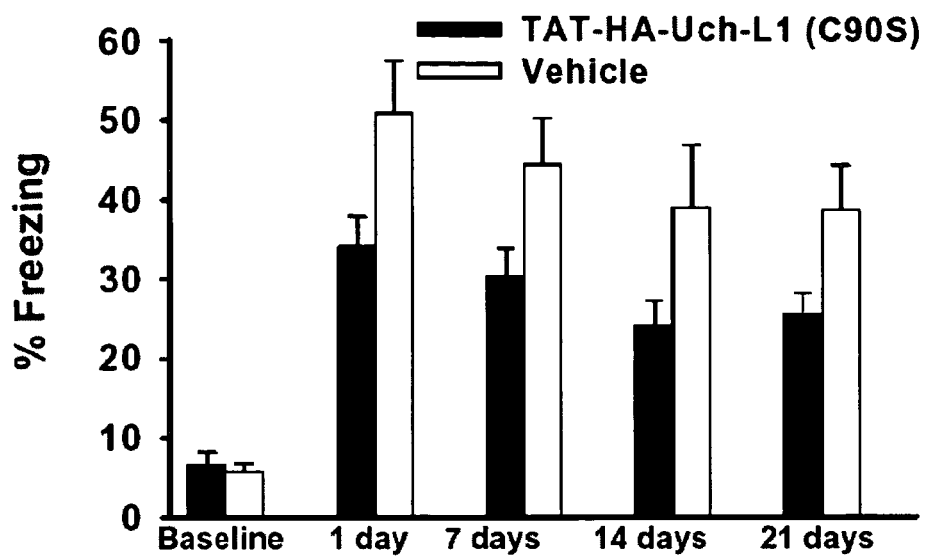

Fear-conditioning, a form of learning impaired in several AD mouse models (Dineley et al., 2002; Gong et al., 2004) was used to determine whether Uch-L1 is critical in this form of memory in mice. The fear-conditioning paradigm depends on the hippocampus and amygdala. The hippocampus is required for contextual fear learning (Phillips and LeDoux, 1992), a form of associative memory in which mice must associate a neutral stimulus with an aversive one. The inhibitor LDN was used to probe the role of Uch-L1 in this process. Assay of Uch in the hippocampus following a single i.p injection of inhibitor (0.4 mg/kg), revealed maximal inhibition of hydrolase activity (~40% of control) at 30 minutes post-injection with recovery by 8 hours (FIG. 30A). For fear-conditioning, LDN-treated and vehicle-treated mice were placed in a novel context (fear-conditioning box) and were exposed to a tone (conditioned stimulus [CS]) paired with a mild foot shock (unconditioned stimulus [US]) (training phase of the fear conditioning) (Bourtchuladze et al., 1994). Conditioning was assessed 24 hours later by measuring "freezing" behavior—the absence of all movement except respiration—in response to the context (contextual conditioning) or the auditory cue (CS) within a completely different context (cued conditioning). During the training phase, no difference in the freezing of LDN- or vehicle-injected mice was seen. Twenty-four hours later there was a decrease in the freezing time of LDN-treated mice to 65% of that of vehicle-treated mice in contextual conditioning (FIG. 30B). On the other hand, cued fear conditioning, did not show a difference in freezing behavior between the 2 groups showing that the amygdala, which is involved mainly in cued conditioning (Phillips and LeDoux, 1992), is not impaired by Uch-L1 inhibition. The difference in the freezing time persisted when contextual learning was assessed 7- 14- and 21 days following exposure to the electric shock with LDN-injected mice having values of 70% of vehicle-treated mice at 21 days (FIG. 30B). LDN failed to impair contextual learning when it was injected at 4 and 1 hour before the shock or at 1 hour after the shock, suggesting that there is a time-window at 4 hrs after the electric shock during which Uch-L1 is required for contextual fear memory processes in hippocampus. Similar to LDN, TAT-HA-Uch-L1(C90S) (0.04 g/kg i.p., injected 4 hrs after the electric shock) impaired contextual learning assessed at 1 day and at 7, 14 and 21 days compared to vehicle treated mice (FIG. 30C), suggesting that it is a dominant negative inhibitor as described above for the experiments on LTP (FIG. 27D). Taken together, these data strongly suggest that Uch-L1 activity plays a role in normal contextual fear learning.

Figure 30D:
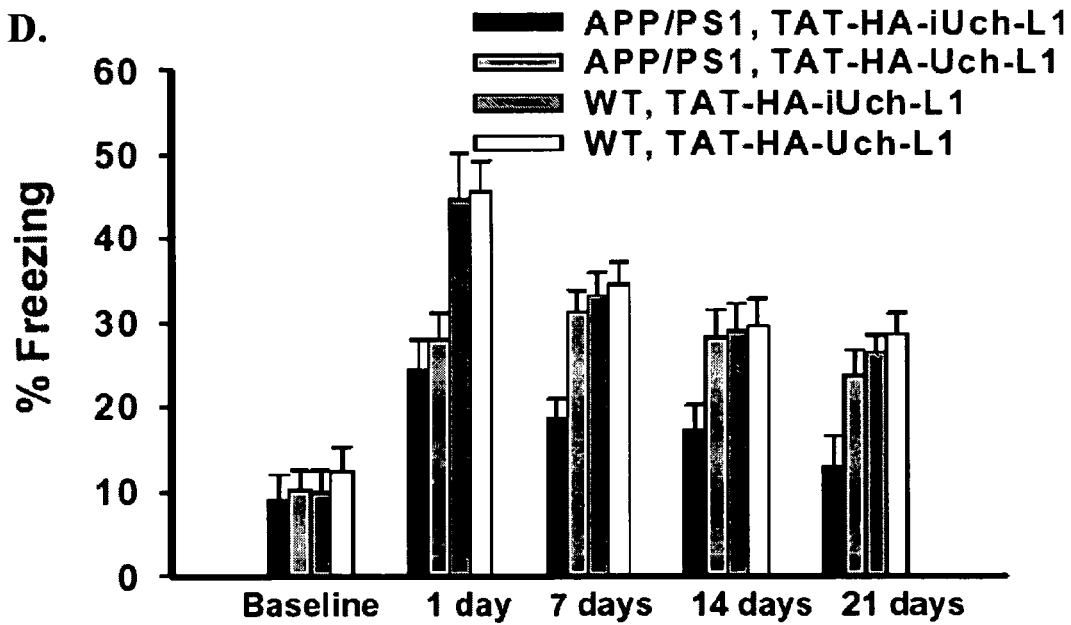

When 3-5 month-old APP/PS1 mice were injected with TAT-HA-Uch-L1 or TAT-HA-iUch-L1 or TAT-HA (0.02-0.04 g/kg, i.p.) 4 hrs before training for fear conditioning no significant differences in freezing behavior were seen between the groups in the training phase. Treatment with TAT-HA-Uch-L1 in APP/PS1 mice failed to re-establish normal freezing when the animals were reintroduced into the same context 1 day after training (FIG. 30D). There were also no differences between the 4 groups in cued conditioning. However, treatment with TAT-HA-Uch-L1 greatly increased the freezing time in APP/PS1 mice compared to that of TAT-HA-iUch-L1- and TAT-HA-treated APP/PS1 littermates when contextual learning was assessed over time. TAT-HA-Uch-L1-treated APP/PS1 mice demonstrated about 85% of the freezing time of WT mice, compared to ~40% for TAT-HA-iUch-L1-treated APP/PS1 mice at 21 days after training. TAT-HA-Uch-L1 did not change the freezing time in WT littermates compared with control WT mice (~95% that of TAT-HA-iUch-L1-treated WT mice) (FIG. 30D). Taken together, these results indicate that exogenous Uch-L1 improves the retention of contextual learning in APP/PS1 mice.

Figures 39A, 39B:
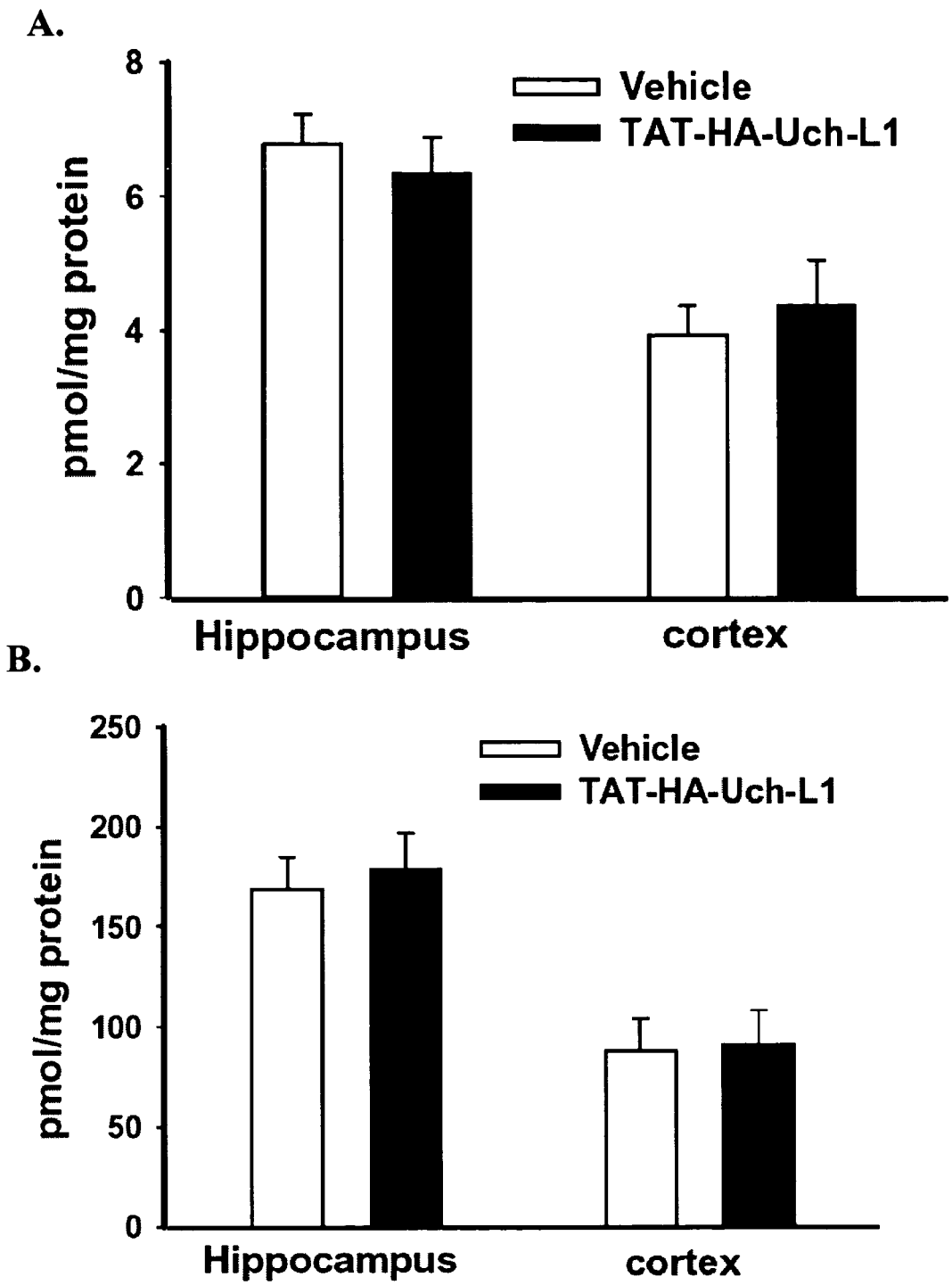
FIGS. 39A-39B. Injection of TAT-HA-Uch-L1 does not affect Aβ levels in APP/PS1 mice.

Given the physiological and behavioral effects of TAT-HA-Uch-L1 treatment in the double Tg mice experiments were designed to determine whether treatment with TAT-HA-Uch-L1 affected Aβ levels, a hallmark of AD. ELISA of extracts of hippocampal and cerebral cortices revealed no difference in Aβ42 levels 4 hrs after injection of TAT-HA-Uch-L1 (0.02-0.04 g/kg, i.p.) in 4 month old APP/PS1 mice (hippocampal Aβ42, about 94% that of vehicle-treated APP/PS1 mice; cortical Aβ42, about 104% (FIG. 39A). No Aβ was detected in WT littermates. Similar results were obtained by measuring Aβ levels in mice that received TAT-HA-Uch-L1 and were tested for fear conditioning over 21 days (hippocampal Aβ42, about 106% that of vehicle-treated APP/PS1 mice; cortical A42, about 103%; FIG. 39B).

Figure 31A:
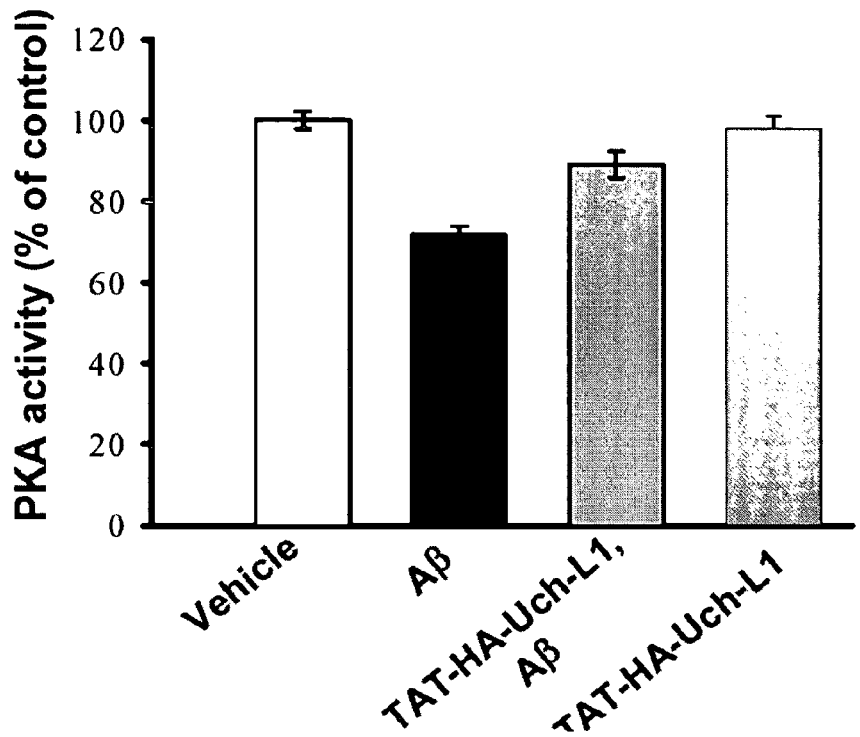
Figure 31B:
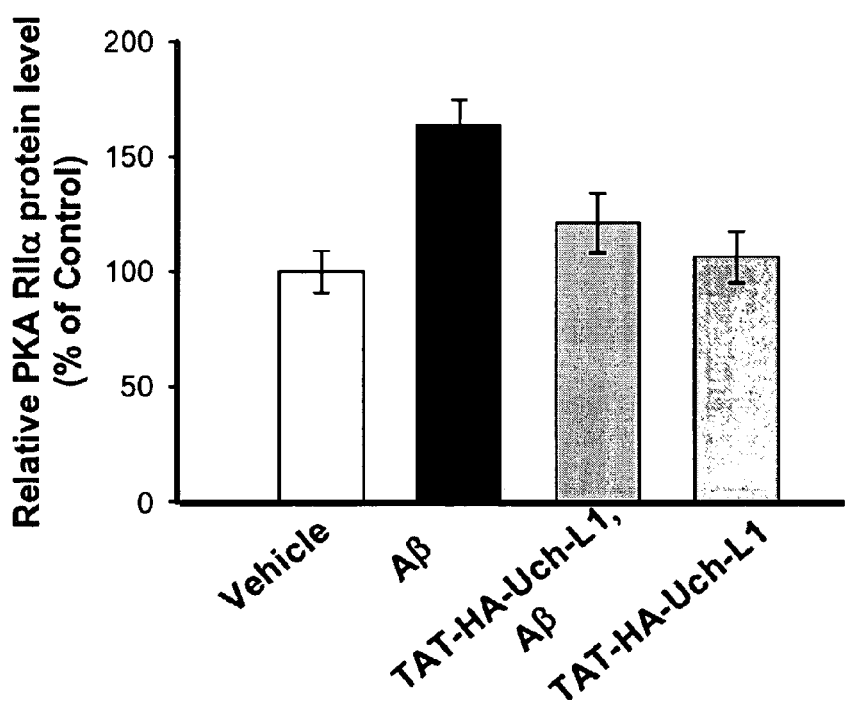
Figure 31D:
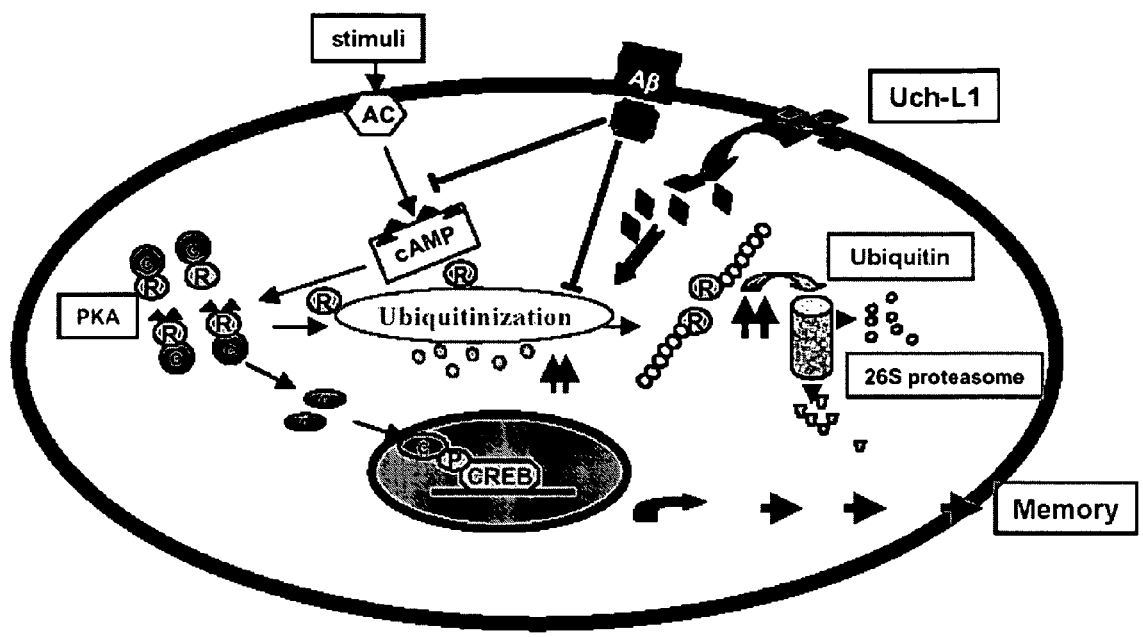

The Beneficial Effect of Exogenous Uch-L1 is Associated with Restoration of the PKA-CREB Pathway Proteolysis of the PKA regulatory (R) subunit coincides with Uch induction and CREB-dependent long-term facilitation in Aplysia (Chain et al., 1999; Hegde et al., 1997). Studies were carried out to determine whether the effect of TAT- HA-Uch-L1 on Aβ-induced synaptic dysfunction is associated with a reversal of the Aβ-induced block of PKA-R degradation (Vitolo et al., 2002). Treatment of hippocampal slices with 200 nM Aβ for 20 minutes reduced PKA activity by 30% (FIG. 31A). Pretreatment with 20 nM TAT-HA-Uch-L1 for 1 hr before applying Aβ blocked the reduction, while neither TAT-HA-iUch-L1 (20 nM) nor TAT-HA had any effect. Measurement of the PKA-RIIα subunit levels in hippocampal slices as a function of exposure to Aβ42 (200 nM for 20 minutes) showed a marked increase in RIIα that was blocked by pretreatment with 20 nM TAT-HA-Uch-L1 for 1 hr before the addition of 200 nM Aβ (FIG. 31B). Both TAT-HA-iUch-L1 and TAT-HA were without effect. Treatment with Aβ blocks the increase in phosphorylated CREB induced by theta burst in hippocampal slices as revealed by staining with an antibody specific to phosphoserine 133. This inhibition is reversed by TAT-HA-Uch-L1 pretreatment (FIG. 31C), but not by vehicle, TAT-HA or TAT-HA-iUCH-L1. Consistent with these findings suggesting that the PKA-CREB pathway mediates the effects of Uch-L1 on Aβ-induced synaptic dysfunction (FIG. 31D), the Aβ induced reduction in both PKA activity and glutamate-induced increase of CREB phosphorylation were re-established in hippocampal cell cultures treated with TAT-HA-Uch-L1 plus Aβ (FIGS. 40A and 40B).

It has been suggested that UPS dysfunction plays a major role in the pathogenesis of several neurodegenerative diseases (Ciechanover and Brundin, 2003). Ubiquitin has been detected in neurofibrillary tangles and senile plaque neurites of AD brains and both PS1 and PS2 are targets for the ubiquitin system (Kim et al., 1997). Proteasome activity is inhibited by Aβ and exposure to oxidative stress (Almeida et al., 2006; Gregori et al., 1995; Grune et al., 1995; Reinheckel et al., 1998), both of which are believed to contribute to the progression of AD (Markesbery, 1997; Mattson, 1997). A possible link between Uchs, memory and AD is suggested by the requirement for Uch in long-term facilitation in Aplysia (Chain et al., 1999), by reports of decreased levels of Uch-L1 in postmortem AD brain (Choi et al., 2004) and by Aβ aggregates and intraneuronal ubiquitin deposits in gracile axonal dystrophy (gad) mice that lack Uch-L1 activity (Ichihara et al., 1995; Saigoh et al., 1999). This Example shows a reduction of soluble Uch-L1 protein levels in the hippocampus of APP/PS1 mice. Inhibition of Uch-L1 activity by the specific Uch-L1 inhibitor LDN leads to the inhibition of hippocampal LTP. Transduction of Uch-L1 protein restores Aβ-induced inhibition of LTP and also re-establishes normal Uch activity, basal neurotransmission, synaptic plasticity and improves associative memory in APP/PS1 mice.

Since Uch-L1 has both hydrolase and ligase activity (Liu et al., 2002), studies were carried out to determine which function of Uch-L1 is involved in its effects on Aβ-induced synaptic dysfunction. Deletion of the H161 site in the TAT-HA-Uch-L1 protein or its mutation in C90S completely eliminates effects on LTP while mutation of the S18Y site has no effect. Given that ligase activity correlates with dimerization of Uch-L1, the formation of dimers and other aggregates were examined in the TAT-HA-Uch-L1 preparation. Dimers were seen at 5 µM but not at 1 µM (FIG. 35). In addition, since the S18Y form dimerizes only at higher concentrations than the WT form, attempts were made to rescue LTP using different concentrations of TAT-HA-Uch-L1 and TAT-HA-Uch-L1(S18Y). The less efficient ligase activity of the S18Y form (Liu et al., 2002) should produce lower amounts of potentiation if ligase activity is relevant to the rescue effect. Despite extending the concentration as low as 5 nM, there was no difference between the two forms (FIG. 27F). Since these concentrations are $1/250^{th}$-$1/1000^{th}$ of the dimer forming concentration in vitro, it is unlikely that the rescue of LTP is due to ligase activity. The main observations of this Example showing that exogenous Uch-L1 ameliorates Aβ-induced synaptic and memory dysfunction are clear and have important implications for the treatment of diseases characterized by abnormal Aβ elevation.

TAT-HA-Uch-L1 improves the retention of contextual fear conditioning over a three week period, but unlike rolipram, a PDE4 inhibitor, does not improve learning the day after training (Gong et al., 2004). One explanation is that Uch-L1 might stabilize synaptic circuitry via alterations in gene expression (Bourtchouladze et al., 2003) that take longer than one day to fully develop. Rolipram has a beneficial effect on synaptic and cognitive function of APP/PS1 mice that persists for several months after a brief course of treatment (Gong et al., 2004). These persistent effects are reflected in stabilization of phospho-CREB levels (Gong et al., 2004) and restoration of dendritic spine density to control levels in the APP/PS1 animals. The formation of new synaptic connections likely underlies long-term memory formation in several vertebrate and invertebrate species with a mechanism that is dependent upon CREB gene expression (Tully et al., 2003). It is likely that both formation of new synapses and consolidation of old ones are involved in the delayed and long-term effects of Uch-L1 treatment. The difference between rolipram and Uch-L1 effects may be linked to the differences in their mechanisms of action. Treatment with Uch-L1 fusion protein does not rescue the decrease in cAMP levels caused by Aβ (FIG. 24) (but rather decreases PKA activity by reducing the degradation of PKA-RIIα), whereas rolipram is known to increase cAMP levels and then PKA activity (Barad et al., 1998).

Uch-L1 is widely distributed in central neurons. However, this Example shows that Uch-L1 inhibition does not affect cued conditioning, whereas it impairs contextual learning. The amygdala is involved mainly in cued conditioning, while the hippocampus is required for contextual learning (Phillips and LeDoux, 1992). Thus, these data show that Uch-L1 is critical to learning and memory processes in the hippocampus but not amygdala, but memory processes in amygdala may also be sensitive to Uch-L1 in a time frame other than the one tested here. Similarly, inhibition of Uch-L1 activity during a narrow time window at 4 hrs after training (but not at 4 and 1 hr before training or at 1 hr after training) affected contextual learning. It is also possible that other pathways compensate for the Uch-L1 inhibition in amygdala, but not in hippocampus. For instance, there is a specific and critical activation of phosphatidylinositol 3-kinase in the amygdala after LTP induction and after fear conditioning (Lin et al., 2001). These findings show that inhibition of Uch-L1 can differentially affect multiple memory systems.

A significant difference between the effects of Aβ and Uch-L1 on LTP is that response to Aβ (20 min. or less) is more rapid than response to LDN (2 hrs). Examination of hippocampal slices from WT mice after 20 minutes of treatment with oligomeric Aβ shows a decrease of ~30% in Uch activity, a fall of ~70% in monoubiquitin levels, a fall of 30% in PKA activity and an increase in PKA-regulatory subunit levels within 20 minutes of exposure to Aβ. These data show that a fall in cAMP shifts the equilibrium of the PKA complex toward the inactive form resulting in decreased CREB phosphorylation and transcription (Vitolo et al. 2002). The current data shows that there is an equally rapid decrease in Uch-L1 and proteasome activity as reflected in monoubiquitin levels. The fact that, in cell culture, the glutamate-induced increase in CREB phosphorylation and PKA activity are restored by TAT-HA-Uch-L1 in the presence of Aβ without any alteration in cAMP levels suggests that Uch-L1 is downstream of cAMP in this pathway. Treatment with LDN also results in a rapid fall of Uch-L1 activity, but proteasome inhibition has no effect on cAMP levels over a period of several hours. Therefore, Uch-L1 does not directly affect the dissociation of the PKA complex and that inhibition of LTP does not occur until there has been accumulation of the PKA regulatory subunit (PKA-R) to levels sufficient to depress PKA activity and CREB phosphorylation. The rapid fall in Uch-L1 activity in response to Aβ raises the possibility that Aβ initiates a signaling cascade, perhaps mediated by cAMP that results in the partial inhibition of proteasome activity more rapidly than is likely as the result of the accumulation of misfolded or undigestable proteins.

This Example shows that Uch-L1 is an attractive target for the development of new therapeutic approaches to AD, either alone or in combination with therapies altering Aβ levels.

Example 5

Experimental Methods

Slice preparation. Mice were decapitated and their hippocampi removed. Transverse hippocampal slices (400 μm) were maintained in an interface chamber at 29° C. as previously described (Vitolo et al., 2002). Following decapitation and hippocampal removal, 400 μm hippocampal slices were maintained in an interface chamber at 29° C. and perfused with saline solution (124.0 mM NaCL, 4.4 mM KCL, 1.0 mM $Na_2HPO_4$, 25.0 mM $NaHCO_3$, 2.0 mM $CaCL_2$, 2.0 mM $MgSO_4$, and 10 mM glucose) continuously bubbled with 95% $O_2$ and 5% $CO_2$. Slices were permitted to recover from cutting for at least 90 min. before recordings. For experiments with lactacystin, slices were perfused with the drug or vehicle for 2 to 4 hrs in a small volume (10 ml) chamber.

Electrophysiological Recordings: The fEPSPs were recorded from the CA1 region of the hippocampus by placement of both the stimulating and the recording electrodes in the CA1 stratum radiatum, as previously described (Vitolo et al., 2002). The fEPSPs were recorded from the CA1 region of the hippocampus by placement of both the stimulating and the recording electrodes in the CA1 stratum radiatum. BST was assayed by plotting the stimulus voltage (V) against slopes of fEPSP to generate input-output relations or by plotting the peak amplitude of the fiber volley against the slope of the fEPSP to generate input-output relations. Paired pulse facilitation (PPF) was elicited by using three interstimulus intervals (200 ms, 100 ms and 50 ms). LTP was induced using theta-burst stimulation (4 pulses at 100 Hz, with the bursts repeated at 5 Hz, and each tetanus including three 10-burst trains separated by 15 seconds). Each point of the graphs represents the average of 3 successive events. In some experiments, oligomeric Aβ42 was added to the flowing bath solution, which was prepared as previously described (Puzzo et al., 2005; Stine et al., 2003; Trommer et al., 2005). Briefly, the lyophilized peptide (American Peptide) was resuspended in 100% 1,1,1,3,3,3-hexafluoro-2-propanol (HFIP; Sigma) to 1 mM. The solution was aliquoted, and the HFIP was allowed to evaporate in the fume hood. The resulting clear peptide film was dried under vacuum in a SpeedVac and stored at −20° C. Twenty-four hours before use, the aliquots were added to dimethylsulfoxide (DMSO; Sigma) and sonicated for 10 min. Oligomeric Aβ42 was obtained by diluting Aβ42-DMSO into ACSF concentration, vortexed for 30 sec, and incubated at 4° C. for 24 hrs. Before use, this compound was added to ACSF to obtain the final concentration. This synthetic Aβ has been extensively characterized biochemically and electrophysiologically. Similar to naturally secreted oligomers of Aβ has its biological effects at low nanomolar concentrations (Puzzo et al., 2005; Trommer et al., 2005; Walsh et al., 2002; Wang et al., 2004). In addition, its normal sequence but not the scrambled sequence (Puzzo et al., 2005) interrupts LTP rapidly, robustly and consistently (Trommer et al., 2005), indicating that the electrophysiological action of Aβ can be readily assayed before significant compensatory effects, inflammatory reaction, neuritic degeneration or apoptosis have occurred. In TAT-Uch-L1 protein experiments, 20 nM protein was added to the bath solution for 1 hr, 200 nM Ab was added 20 min, KT5720 1 μM 10 min respectively prior to the induction of LTP.

Preparation of TAT-HA-Uch-L1 constructs. Human Uch-L1 cDNA obtained by PCR with primers 5'-CCGCTC-GAGCGAGATATACATATGCAGC (SEQ ID NO:3), 5'-ACATGCATGCATGTAGAGCATTAGGCTGCC (SEQ ID NO:4) using pRSL1 vector containing human Uch-L1 cDNA as template. PCR products were purified, UchL1 cDNA was in frame ligated into TAT-HA vector Xho1 and Sph1 sites. *Ecoli*DH5a cells were used to TAT-HA-Uch-L1 vector expression and the Uch-L1 cDNA was confirmed by DNA sequencing. TAT-HA-iUch-L1 construct was generated by using restriction enzymes BbSI and SFOI to delete nucleotides of Uch-L1 cDNA from position 380 to 552.

Site-Directed Mutagenesis. Mutant TAT-Uch-L1 constructs, C90S and S18Y, were generated using PCR-based site-directed mutagenesis kit (Stratagene, Calif.) according to the manufacturer's instructions. The following primers were used: C90S, C90S-5 (5'-CAGA CCAT TGGG AATT CCAG CGGC ACAA TCGG ACTT ATT-3') (SEQ ID NO:7), and C90S-3 (5'-GACCA TTGG GAAT TCCA GTGG CACA ATCG GACT TA-3') (SEQ ID NO:8); S18Y, S18Y-5 (5'-CTGA ACAA AGTG CTGT ACCG GCTG GGGGT-3') (SEQ ID NO:9), and S18Y-3 (5'-ACCC CCAG CCGG TACA GCAC TTTG TTCAG-3') (SEQ ID NO:10).

Expression and Purification of Recombinant TAT Fusion Proteins: Following construct preparation, TAT-vectors were transformed into *E. Coli* BL21(DE3)pLysS competent cells (Novagen), independent colonies were grown as 1 ml overnight cultures in Luria broth (LB) medium (Sigma), with 100 μg ampicillin in the presence 100 μM IPTG. Then the cultures were transferred to 500 ml LB ampicillin plus 200 μM IPTG to make large scale preparations. Fusion proteins were purified by a standard 6-His fusion protein purification protocol using ProBond purification system (Invitrogen). Protein identity was confirmed by Western blotting using mouse anti-human monoclonal antibody against Uch-L1 (Novocastra Lab) and mouse monoclonal anti-HA (Santa Cruz Biotech).

Quantitative RT-PCR Analysis: Total RNAs were extracted using standard procedures. Total RNAs were extracted from hippocampi taken from APP/PS1 mice as well as their littermates and used for reverse transcription with SuperScript (Invitrogen) and PCR with GeneAmp2400 (Applied Biosystems) using the following synthetic oligonucleotides: Uch-L1-5 (5'-TGTCTGAAACGGAGAAGCTGT-3') (SEQ ID NO:5), and Uch-L1-3 (5'-TGAATTCTCTGC AGACCT-TGG-3') (SEQ ID NO:6). Each mRNA value was normalized to that of the housekeeping genes, GAPDH and β-actin.

Visualization of TAT-fusion Proteins: Immunocytochemistry of hippocampal slices was performed as previously described (Puzzo et al., 2005) with slight modifications. Hippocampal slices of 400 μm thickness were fixed in 4% paraformaldehyde/1×PBS after perfusion with the fusion protein or vehicle for 1 hr. After washing with 1×PBS, slices were treated with 0.2% Triton X-100 and incubated in 5% goat serum for 30 min. Slices were then incubated with primary antibodies (either anti-Uch-L1, anti-HA, or anti-PGP9.5) overnight at 4° C. Finally, slices were incubated with secondary antibodies (goat anti-mouse IgG FITC and TRITC, respectively), and examined with a confocal microscope (Nikon D-Eclipse C1) using a 4× and a 16× objective. In some experiments, slices were examined with a fluorescent microscope (Nikon Eclipse E600). Kalman averages of 4 scans were collected for each image. The analysis was performed using the NIH image software (Image J 1.33u) by an observer who was blind to the experimental treatment. The mean fluorescence intensity that exceeded a threshold set above background was determined for each slice in CA1 cell body area. The values were normalized to the values from vehicle-treated control slices from the same animal and expressed as mean percent of control±SEM. For these and all the other immunocytochemical experiments, the specificity of the immunofluorescence was confirmed by omitting the primary antibody, which resulted in a significant reduction in fluorescence intensity.

For in vivo experiments, TAT-HA-iUch-L1, TAT-HA and TAT-HA-Uch-L1 fusion proteins were i.p. injected into mice at 0.02-0.04 g/kg. After 4 or 8 hrs, mice were sacrificed, hippocampal slices were prepared and examined as described above.

For experiments on cell cultures, 5 DIV neurons were treated with fusion proteins or vehicle. After 2 hrs, cells were quickly washed with PBS and fixed in 4% paraformaldehyde, permeabilized with 0.1% Triton X-100, and incubated with anti-Uch-L1 or anti-HA antibodies paired with anti-MAP2 antibodies (Sigma). After reaction with FITC-conjugated or TRITC-conjugated secondary antibodies, cells were examined at the confocal microscope using a 20× objective and analyzed as described above.

Sections were then incubated with primary antibody (either anti-HA or anti-PGP9.5) overnight at 4° C. Slices were incubated with the secondary antibody (goat anti-mouse IgG FITC), slices were examined at the fluorescent microscope (Nikon Eclipse E600).

In a separate series of experiments the visualization approach consisted of labeling TAT-HA-Uch-L1 with Texas Red-X dye according to the instruction of manufacturer (Molecular Probe, Eugene, Oreg.) to facilitate visualization of exogenous Uch-L1 (but not endogenous) in the slice, culture or in vivo preparation. This approach confirmed findings with anti-Uch-L1 or anti-HA antibodies.

Western Blotting: Protein levels were assessed using standard procedures. Protein extraction was performed using buffer with and without detergent. For the extraction of protein using detergent, hippocampal tissues and cultured hippocampal neurons (5 DIV) were homogenized in RIPA buffer (50 mM Tris-HCl pH 7.4, 1% Triton X-100, 1% sodium deoxycholate, 0.1% SDS, 150 mM sodium chloride, 10 mM sodium fluoride, 30 mM sodium pyrophosphate, 50 mM sodium orthovanadate) containing 1× complete protease inhibitor (Roche) and 1 mM phenylmethylsulfonyl fluoride (PMSF). For extraction of proteins without detergent, hippocampal extracts were homogenized with disposable dounce homogenizers in buffer A, containing 10 mM HEPES pH 7.3, 300 mM sucrose, protease 1× complete protease inhibitor (Roche) and PMSF. After centrifugation at 10,000×g supernatant proteins were resolved on a 8% or 4-20% gradient Tris-Glycine gel, transferred onto PVDF or nitrocellulose membrane and blocked in 5% skim milk in PBS-Tween 0.1% (PBS-T). Membranes were probed with primary antibodies, and after washing with PBS-T incubated with an appropriate HRP-conjugated secondary antibody. The following antibodies were used: mouse monoclonal anti-ubiquitin (Chemicon), rabbit polyclonal anti-pCREB (Upstate Biotech.), rabbit polyclonal anti-PKA-RIIα (Santa Cruz Biotech. Inc), mouse monoclonal anti-Uch-L1 (Novocastra), monoclonal mouse anti-HA (Santa Cruz Biotech. Inc), and anti-PKA IIα. Detection was performed using HRP-conjugated secondary antibodies (Pierce, Rockford, Ill.). To control loading and transfer, protein immunoreactivities were normalized against total extracellular signal-regulated protein kinases (ERK1/2) levels with a rabbit analyzed using a rabbit polyclonal anti-ERK1/2 antibody (Cell Signaling Technology, Inc). NIH IMAGE was used to analyze the scanned blots and quantify the intensity of the protein signals.

Intracellular cAMP Enzyme Immunoassay. Hippocampal neurons from E18 rats were dissociated and plated on poly-L-lysine coated 6-well plates in minimum essential medium supplemented with N-2, glucose, albumin, pyruvic acid, antibiotics and antimycotics. Cells cultured for 7 days in vitro were then treated with 1 μM of oligomeric Aβ1-42 peptide and with or without 10 μM forskolin, 1 μM rolipram, 50 or 100 nM Uch-L1. After 24 hours, cell lysates were obtained and intracellular cAMP levels were measured using cAMP Biotrak Enzymeimmunoassay (EIA) System (Amersham) in accordance with manufacturer's instructions.

Proteasome reporter assays. In this cell line, human neuroblastoma SH-SY5Y cells were permanently transfected with reporter construct consisting of green fluorescent protein (GFP) conjugated at its C-terminus to a short degron sequence (CL-1) (Gilon et al., 1998). $GFP^u$ accumulation in cell lines treated with proteasome inhibitors has been previously demonstrated (Bence et al., 2001; Petrucelli et al., 2002). The SY5Y-$GFP^u$ cells were grown in 1×DMEM (Invitrogen) supplemented with 15% fetal bovine serum (JRH), 1× penicillin/streptomycin (Gibco). After indicated treatments, $GFP^u$ concentrations were assayed by densitometric analysis of immunoblots of total protein extracts (10 ug/lane) using monoclonal GFP antibodies (Santa Cruz Biotechnology) and visualized with HRP-conjugated secondary antibodies and ECL (Pierce). Loading equalization was normalized by probing blots with anti-ERK antibodies (Santa Cruz Biotechnology).

PKA Kinase Activity Measurement. Primary hippocampal neurons from E18 rats were dissociated and cultured as described (Vitolo et al, Proc Natl Acad Sci USA 99:13217-13221 (2002)). After 7 days in vitro, cultures were treated for 24 hours and cells were lysed with RIPA lysis buffer.

Hippocampal slices were lysed with RIPA lysis buffer and homogenized by Dounce homogenizer on ice. 5 DIV primary cultures were treated for 24 hrs and cells were lysed with RIPA lysis buffer.

Levels of intracellular PKA kinase activity were measured by PKA Kinase Activity Assay Kit (Stressxpress) according to manufacturer's instructions.

Animals. Either C57/BL6 mice or APP/PS1 mice were used. In some experiments fetuses at embryonic day 18 (E18) from timed pregnant Sprague-Dawley rats (Taconic Farms) were used. Transgenic mice expressing both human APP (K670N:M671L), and human PS1 (M146L) (line 6.2) were compared to their WT littermates, obtained by crossing heterozygous APP with PS1 animals, so that age and background strain were comparable. Genotype was identified through PCR as previously described (Di Rosa et al., 2002; Duff et al., 1996; Hsiao et al., 1996). The experimenter was blind to the genotype of the mice.

Measurement of Hydrolase Activity: The hydrolase assay was performed as previously described (Nishikawa et al., 2003) with slight modifications. Briefly, hippocampal tissue was treated with tissue protein extraction reagent (T-PER; Pierce) containing freshly added EDTA-free protease inhibitors. Homogenate was centrifuged at 10,000 rpm for 5 min. Protein concentration was measured in the supernatant using the BCA protein assay reagent. In some experiments hydrolysis was initiated by adding 10 μl of 20 nM Uch-L1 or Uch-L3 (Boston Biochem). The hydrolase assay was performed using fluorogenic ubiquitin-7-amino-4-methylcoumarin (ubiquitin-AMC) (Boston Biochem) as a substrate. The substrate was diluted in assay buffer (50 mM Tris-HCL, 0.5 mM EDTA, 5 mM dithiothreitol and 0.1 mg/ml ovalbumin, pH 7.6). Each reaction mixture containing 400 nM substrate and 100 μg enzyme sample was incubated for 5 min at room temperature. The reaction was monitored using a fluorescence spectrophotometer (CytoFluor Series 4000, ABI Inc) at 25° C. The free AMC fluorophore was excited at 380 nm and measured at 460 nm. Hydrolase activity was expressed as relative fluorescence intensity/min (Dang et al., 1998). In some experiments, hydrolysis was also measured on the soluble and insoluble fractions (FIG. 28D). In a group of experiments hydrolysis was measured by mixing ubiquitin-AMC with 20 nM TAT fusion proteins (FIG. 27C). In other experiments the substrate was Nedd8-AMC (Boston Biochem). LDN-57444 was purchased from Calbiochem.

Preparation of Cell Cultures. Hippocampal cell cultures were prepared as previously described (Vitolo et al., 2002). In cell culture experiments fetuses at embryonic day 18 from timed pregnant Sprague-Dawley rats (Taconic Farms) were used. Fetuses were sacrificed and the hippocampi removed. Neurons were then dissociated, plated on 6 well-plates coated with poly-L-lysine and maintained in a defined serum-free medium containing minimum essential medium supplemented with N-2, glucose, albumin, pyruvic acid, antibiotics and antimycotics. The obtained cultures resulted in a population enriched in large pyramidal neurons. 5 DIV cells were used for the experiments.

Behavioral Studies: Fear conditioning was performed in a conditioning chamber as previously described (Bourtchuladze et al., 1994; Gong et al., 2004). For contextual and cued fear conditioning mice were placed in the conditioning chamber for 2 min before the onset of a discrete tone (CS) (a 30 sec sound at 2800 Hz and 85 dB). In the last 2 sec of the CS, mice were given a foot shock (US) of 0.50 mA for 2 sec through the bars of the floor. After the CS/US pairing, the mice were left in the conditioning chamber for another 30 sec and then placed back in their home cages. Freezing behavior, defined as the absence of all movement except for that necessitated by breathing, was scored using Freezeview software. To evaluate contextual fear learning, freezing was measured for 5 min in the chamber in which the mice were trained 24 hrs after training. To evaluate cued fear conditioning, following contextual testing, the mice were placed in a novel context (triangular cage with smooth flat floor and with vanilla odorant) for 2 min (pre-CS test), after which they were exposed to the CS for 3 min (CS test), and freezing was measured. To evaluate the contextual fear over time, mice were placed for 5 min in the chamber in which the mice were trained 7- 14- 21-days after training. Sensory perception of the shock was determined through threshold assessment. Each animal was placed individually into the conditioning chamber. The electric current was gradually increased (0.1 mA for 1 sec. at 30 sec. intervals increasing the shock intensity by 0.1 mA to 0.7 mA). Animal behavior was evaluated for the first visible response to the shock (flinch), the first extreme motor response (run/jump), and the first vocalized distress (scream). Threshold to flinching, jumping, and screaming was quantified for each animal by averaging of the shock intensity at which each animal manifested a behavioral response of that type to the foot shock. Visual, motor, and motivation skills were also tested with visible platform training by measuring the time and the speed to reach a visible platform placed within a pool filled with water (Gong et al., 2004). Both time to reach the platform and swimming speed were recorded and analyzed with a video tracking system (HVS-2020, HVS Image, UK). No difference was observed among different groups of mice in the experiments in which fear conditioning was tested both in the presence of LDN and TAT fusion proteins. To decide the time of administration of LDN, experiments were performed in which the inhibitor was injected intra-peritoneally at different intervals (4 hrs before, 1 hr before, 1 hr after and 4 hrs after) from the electric shock. During the training phase, no difference was found in the freezing of LDN- or vehicle-injected mice. Twenty-four hours later, a decrease was found in the freezing time of LDN-treated mice compared with that of vehicle-treated mice in contextual conditioning only in the group that was treated 4 hrs after the electric shock (LDN-treated mice demonstrated a freezing time equal to ~72% that of vehicle-treated mice; n=5 males for both, $p<0.05$).

Quantification of amyloidpeptides by ELISA. Levels of human brain Aβ were determined by sandwich ELISA. Tissue samples of hippocampal and cerebral cortex from WT or APP/PS1 mice w/o TAT-HA-UCH-L1 treatment were homogenized in tissue homogenization buffer (250 mM sucrose, 20 mM tris base, 1 mM EDTA, 1 mM EGTA), followed by brief sonication and centrifugation at 4° C., 14,000 rpm for 15 min. Protein-containing supernatants were subjected to Aβ1-42 ELISA kit (Sigma BE0200). Signals were detected with a multiwell plate reader at 450 nm and reported as the mean±SEM of the results of 2 replica wells in picomoles of Aβ per milligram of protein (total protein concentration was determined with the BCA Protein Assay Reagent Kit).

Phospho-CREB Measurements: Hippocampal slices were fixed in ice-cold 4% paraformaldehyde at 60 minutes after the treatment, as previously described (Puzzo et al., 2005). Hippocampal slices were fixed in ice-cold 4% paraformaldehyde at 60 minutes after the treatment. Next, slices were washed 3 times in phosphate-buffered saline (PBS), treated with 0.3% Triton X-100 for 60 minutes, washed 3 times in PBS again, treated with 50 mM ammonium chloride for 20 minutes and incubated in 10% goat serum for 60 minutes. Slices were next incubated with the primary antibody (rabbit polyclonal anti-phospo-CREB from Upstate Biotechnology diluted 1:100 in 10% goat serum) for 36 hrs at 4° C. Then, slices were washed in PBS (6 times, 2 hrs each time), incubated with the secondary antibody (goat anti-rabbit antibody labelled with Alexa Fluor 488, from Molecular Probes), diluted 1:100 in 10% goat serum, for 12 hrs at 4° C. and washed in PBS again (6 times, 2 hrs each time). Finally, slices were examined with a confocal microscope (Nikon D-Eclipse C1) using a 4× and a 16× objective. Kalman averages of 4 scans were collected for each image. The analysis was performed using the NIH image software (Image J 1.33u) by an observer who was blind to the experimental treatment. The mean fluorescence intensity that exceeded a threshold set above background was determined for each slice in CA1 cell body area. The values were normalized to the values from untreated control slices from the same animal and expressed as mean percent of control±SEM.

Statistics: For all experiments mice were coded to "blind" investigators with respect to genotype and treatment. Data were expressed as mean±SEM. Data were analyzed by Student's t test (pairwise comparisons) or ANOVA with repeated measures (multiple comparisons) followed by Bonferroni's test for post-hoc analysis.

While the foregoing invention has been described in some detail for purposes of clarity and understanding, these particular embodiments and examples are to be considered as illustrative and not restrictive. It will be appreciated by one skilled in the art from a reading of this disclosure that various changes in form and detail can be made without departing from the true scope of the invention.

REFERENCES

Aarts, M., Liu, Y., Liu, L., Besshoh, S., Arundine, M., Gurd, J. W., Wang, Y. T., Salter, M. W., and Tymianski, M. (2002). Treatment of ischemic brain damage by perturbing NMDA receptor-PSD-95 protein interactions. Science 298, 846-850.

Almeida, C. G., Takahashi, R. H., and Gouras, G. K. (2006). Beta-amyloid accumulation impairs multivesicular body sorting by inhibiting the ubiquitin-proteasome system. J Neurosci 26, 4277-4288.

Antonova, I., Arancio, O., Trillat, A. C., Wang, H. G., Zablow, L., Udo, H., Kandel, E. R., and Hawkins, R. D. (2001). Rapid increase in clusters of presynaptic proteins at onset of long-lasting potentiation. Science 294, 1547-1550.

Aravamudan, B., and Broadie, K. (2003). Synaptic *Drosophila* UNC-13 is regulated by antagonistic G-protein pathways via a proteasome-dependent degradation mechanism. J Neurobiol 54, 417-438.

Arendash, G. W., King, D. L., Gordon, M. N., Morgan, D., Hatcher, J. M., Hope, C. E., and Diamond, D. M. (2001). Progressive, age-related behavioral impairments in transgenic mice carrying both mutant amyloid precursor protein and presenilin-1 transgenes. Brain Res 891, 42-53.

Arnaud, L., Ballif, B. A., and Cooper, J. A. (2003). Regulation of protein tyrosine kinase signaling by substrate degradation during brain development. Mol Cell Biol 23, 9293-9302.

Barad, M., Bourtchouladze, R., Winder, D. G., Golan, H., and Kandel, E. (1998). Rolipram, a type IV-specific phosphodiesterase inhibitor, facilitates the establishment of long-lasting long-term potentiation and improves memory. Proc Natl Acad Sci USA 95, 15020-15025.

Barka, T., Gresik, E. W., and van Der Noen, H. (2000). Transduction of TAT-HA-beta-galactosidase fusion protein into salivary gland-derived cells and organ cultures of the developing gland, and into rat submandibular gland in vivo. J Histochem Cytochem 48, 1453-1460.

Becker-Hapak, M., McAllister, S. S., and Dowdy, S. F. (2001). TAT-mediated protein transduction into mammalian cells. Methods 24, 247-256.

Bence, N. F., Sampat R. M., and Kopito, R. R. (2001). Impairment of the ubiquitin-proteasome system by protein aggregation. Science 292, 1552-1555.

Bock, H. H., Jossin, Y., May, P., Bergner, O., and Herz, J. (2004). Apolipoprotein E receptors are required for reelin-induced proteasomal degradation of the neuronal adaptor protein Disabled-1. J Biol Chem 279, 33471-33479.

Bourtchouladze, R., Lidge, R., Catapano, R., Stanley, J., Gossweiler, S., Romashko, D., Scott, R., and Tully, T. (2003). A mouse model of Rubinstein-Taybi syndrome: defective long-term memory is ameliorated by inhibitors of phosphodiesterase 4. Proc Natl Acad Sci USA 100, 10518-10522.

Bourtchuladze, R., Frenguelli, B., Blendy, J., Cioffi, D., Schutz, G., and Silva, A. J. (1994). Deficient long-term memory in mice with a targeted mutation of the cAMP-responsive element-binding protein. Cell 79, 59-68.

Cao, G., Pei, W., Ge, H., Liang, Q., Luo, Y., Sharp, F. R., Lu, A., Ran, R., Graham, S. H., and Chen, J. (2002). In Vivo Delivery of a Bcl-xL Fusion Protein Containing the TAT Protein Transduction Domain Protects against Ischemic Brain Injury and Neuronal Apoptosis. J Neurosci 22, 5423-5431.

Chain, D. G., Casadio, A., Schacher, S., Hegde, A. N., Valbrun, M., Yamamoto, N., Goldberg, A. L., Bartsch, D., Kandel, E. R., and Schwartz, J. H. (1999). Mechanisms for generating the autonomous cAMP-dependent protein kinase required for long-term facilitation in Aplysia. Neuron 22, 147-156.

Chen, Q., Kimura, H., and Schubert, D. (2002). A novel mechanism for the regulation of amyloid precursor protein metabolism. J Cell Biol 158, 79-89.

Choi, J., Levey, A. I., Weintraub, S. T., Rees, H. D., Gearing, M., Chin, L. S., and Li, L. (2004). Oxidative modifications and down-regulation of ubiquitin carboxyl-terminal hydrolase L1 associated with idiopathic Parkinson's and Alzheimer's diseases. J Biol Chem 279, 13256-13264.

Ciechanover, A., and Brundin, P. (2003). The ubiquitin proteasome system in neurodegenerative diseases: sometimes the chicken, sometimes the egg. Neuron 40, 427-446.

Cullen, W. K., Suh, Y. H., Anwyl, R., and Rowan, M. J. (1997). Block of LTP in rat hippocampus in vivo by beta-amyloid precursor protein fragments. Neuroreport 8, 3213-3217.

Dang, L. C., Melandri, F. D., and Stein, R. L. (1998). Kinetic and mechanistic studies on the hydrolysis of ubiquitin C-terminal 7-amido-4-methylcoumarin by deubiquitinating enzymes. Biochemistry 37, 1868-1879.

de Vrij, F. M., Fischer, D. F., van Leeuwen, F. W., and Hol, E. M. (2004). Protein quality control in Alzheimer's disease by the ubiquitin proteasome system. Prog Neurobiol 74, 249-270.

Di Rosa, G., Odrijin, T., Nixon, R. A., and Arancio, O. (2002). Calpain inhibitors: a treatment for Alzheimer's disease. J Mol Neurosci 19, 135-141.

Dineley, K. T., Westerman, M., Bui, D., Bell, K., Ashe, K. H., and Sweatt, J. D. (2001). Beta-amyloid activates the mitogen-activated protein kinase cascade via hippocampal alpha7 nicotinic acetylcholine receptors: In vitro and in vivo mechanisms related to Alzheimer's disease. J Neurosci 21, 4125-4133.

Dineley, K. T., Xia, X., Bui, D., Sweatt, J. D., and Zheng, H. (2002). Accelerated plaque accumulation, associative learning deficits, and up-regulation of alpha 7 nicotinic receptor protein in transgenic mice co-expressing mutant human presenilin 1 and amyloid precursor proteins. J Biol Chem 277, 22768-22780.

Dodart; J. C., Bales K. R., Gannon, K. S., Greene, S. J., DeMattos, R. B., Mathis, C., DeLong, C. A., Wu, S., Wu, X., Holtzman, D. M., and Paul, S. M. (2002). Immunization reverses memory deficits without reducing brain Abeta burden in Alzheimer's disease model. Nat Neurosci 5, 452-457.

Duff, K., Eckman, C., Zehr, C., Yu, X., Prada, C. M., Perez-tur, J., Hutton, M., Buee, L., Harigaya, Y., Yager, D., et al. (1996). Increased amyloid-beta42(43) in brains of mice expressing mutant presenilin 1. Nature 383, 710-713.

Fenteany, G., Standaert, R. F., Lane, W. S., Choi, S., Corey, E. J., and Schreiber, S. L. (1995). Inhibition of proteasome activities and subunit-specific amino-terminal threonine modification by lactacystin. Science 268, 726-731.

Gilon, T., Chomsky, O., and Kulka, R. G. (1998). Degradation signals for ubiquitin system proteolysis in *Saccharomyces cerevisiae*. Embo J 17, 2759-2766.

Gong, B., Vitolo, O. V., Trinchese, F., Liu, S., Shelanski, M., and Arancio, O. (2004). Persistent improvement in synaptic and cognitive functions in an Alzheimer mouse model following rolipram treatment. J Clin Invest 114, 1624-1634.

Gouras, G. K., Tsai, J., Naslund, J., Vincent, B., Edgar, M., Checler, F., Greenfield, J. P., Haroutunian, V., Buxbaum, J. D., Xu, H., et al. (2000). Intraneuronal Abeta42 accumulation in human brain. Am J Pathol 156, 15-20.

Gregori, L., Fuchs, C., Figueiredo-Pereira, M. E., Van Nostrand, W. E., and Goldgaber, D. (1995). Amyloid beta-protein inhibits ubiquitin-dependent protein degradation in vitro. J Biol Chem 270, 19702-19708.

Grune, T., Reinheckel, T., Joshi, M., and Davies, K. J. (1995). Proteolysis in cultured liver epithelial cells during oxidative stress. Role of the multicatalytic proteinase complex, proteasome. J Biol Chem 270, 2344-2351.

Hegde, A. N., Inokuchi, K., Pei, W., Casadio, A., Ghirardi, M., Chain, D. G., Martin, K. C., Kandel, E. R., and Schwartz, J. H. (1997). Ubiquitin C-terminal hydrolase is an immediate-early gene essential for long-term facilitation in Aplysia. Cell 89, 115-126.

Hsiao, K., Chapman, P., Nilsen, S., Eckman, C., Harigaya, Y., Younkin, S., Yang, F., and Cole, G. (1996). Correlative memory deficits, Abeta elevation, and amyloid plaques in transgenic mice. Science 274, 99-102.

Ichihara, N., Wu, J., Chui, D. H., Yamazaki, K., Wakabayashi, T., and Kikuchi, T. (1995). Axonal degeneration promotes abnormal accumulation of amyloid beta-protein in ascending gracile tract of gracile axonal dystrophy (GAD) mouse. Brain Res 695, 173-178.

Itoh, A., Akaike, T., Sokabe, M., Nitta, A., Iida, R., Olariu, A., Yamada, K., and Nabeshima, T. (1999). Impairments of long-term potentiation in hippocampal slices of beta-amyloid-infused rats. Eur J Pharmacol 382, 167-175.

Iwatsubo, T., Mann, D. M., Odaka, A., Suzuki, N., and Ihara, Y. (1995). Amyloid beta protein (A beta) deposition: A beta 42(43) precedes A beta 40 in Down syndrome. Ann Neurol 37, 294-299.

Keck, S., Nitsch, R., Grune, T., and Ullrich, O. (2003). Proteasome inhibition by paired helical filament-tau in brains of patients with Alzheimer's disease. J Neurochem 85, 115-122.

Keller, J. N., Hanni, K. B., and Markesbery, W. R. (2000). Impaired proteasome function in Alzheimer's disease. J Neurochem 75, 436-439.

Kim, T. W., Pettingell, W. H., Hallmark, O. G., Moir, R. D., Wasco, W., and Tanzi, R. E. (1997) Endoproteolytic cleavage and proteasomal degradation of presenilin 2 in transfected cells. J Biol Chem 272, 11006-11010.

Krause, W., and Kuhne, G. (1988). Pharmacokinetics of rolipram in the rhesus and cynomolgus monkeys, the rat and the rabbit. Studies on species differences. Xenobiotica 18, 561-571.

LaFerla, F. M., Troncoso, J. C., Strickland, D. K., Kawas, C. H., and Jay, G. (1997). Neuronal cell death in Alzheimer's disease correlates with apoE uptake and intracellular Abeta stabilization. J Clin Invest 100, 310-320.

Leroy, E., Boyer, R., Auburger, G., Leube, B., Ulm, G., Mezey, E., Harta, G., Brownstein, M. J., Jonnalagada, S., Chernova, T., et al. (1998). The ubiquitin pathway in Parkinson's disease. Nature 395, 451-452.

Lin, C. H., Yeh, S. H., Lin, C. H., Lu, K. T., Leu, T. H., Chang, W. C., and Gean, P. W. (2001). A role for the PI-3 kinase signaling pathway in fear conditioning and synaptic plasticity in the amygdala. Neuron 31, 841-851.

Lissy, N. A., Davis, P. K., Irwin, M., Kaelin, W. G., and Dowdy, S. F. (2000). A common E2F-1 and p73 pathway mediates cell death induced by TCR activation. Nature 407, 642-645.

Liu, Y., Fallon, L., Lashuel, H. A., Liu, Z., and Lansbury, P. T., Jr. (2002). The UCH-L1 gene encodes two opposing enzymatic activities that affect alpha-synuclein degradation and Parkinson's disease susceptibility. Cell 111, 209-218.

Lopez Salon, M., Morelli, L., Castano, E. M., Soto, E. F., and Pasquini, J. M. (2000). Defective ubiquitination of cerebral proteins in Alzheimer's disease. J Neurosci Res 62, 302-310.

Lu, Y. F., Kandel, E. R., and Hawkins, R. D. (1999). Nitric oxide signaling contributes to late-phase LTP and CREB phosphorylation in the hippocampus. J Neurosci 19, 10250-10261.

Malgaroli, A., and Tsien, R. W. (1992). Glutamate-induced long-term potentiation of the frequency of miniature synaptic currents in cultured hippocampal neurons. Nature 357, 134-139.

Markesbery, W. R. (1997). Oxidative stress hypothesis in Alzheimer's disease. Free Radic Biol Med 23, 134-147.

Masliah, E. (1995). Mechanisms of synaptic dysfunction in Alzheimer's disease. Histol Histopathol 10, 509-519.

Mattson, M. P. (1997). Cellular actions of beta-amyloid precursor protein and its soluble and fibrillogenic derivatives. Physiol Rev 77, 1081-1132.

Morgan, D., Diamond, D. M., Gottschall, P. E., Ugen, K. E., Dickey, C., Hardy, J., Duff, K., Jantzen, P., DiCarlo, G., Wilcock, D., et al. (2000). A beta peptide vaccination prevents memory loss in an animal model of Alzheimer's disease. Nature 408, 982-985.

Nakagawa, S., Kim, J. E., Lee, R., Malberg, J. E., Chen, J., Steffen, C., Zhang, Y. J., Nestler, E. J., and Duman, R. S. (2002). Regulation of neurogenesis in adult mouse hippocampus by cAMP and the cAMP response element-binding protein. J Neurosci 22, 3673-3682.

Nishikawa, K., Li, H., Kawamura, R., Osaka, H., Wang, Y. L., Hara, Y., Hirokawa, T., Manago, Y., Amano, T., Noda, M., et al. (2003). Alterations of structure and hydrolase activity of parkinsonism-associated human ubiquitin carboxyl-terminal hydrolase L1 variants. Biochem Biophys Res Commun 304, 176-183.

Oddo, S., Caccamo, A., Shepherd, J. D., Murphy, M. P., Golde, T. E., Kayed, R., Metherate, R., Mattson, M. P., Akbari, Y., and LaFerla, F. M. (2003). Triple-transgenic model of Alzheimer's disease with plaques and tangles: intracellular Abeta and synaptic dysfunction. Neuron 39, 409-421.

Patrick, G. N., Zhou, P., Kwon, Y. T., Howley, P. M., and Tsai, L. H. (1998). p35, the neuronal-specific activator of cyclin-dependent kinase 5 (Cdk5) is degraded by the ubiquitin-proteasome pathway. J Biol Chem 273, 24057-24064.

Petrucelli, L., O'Farrell, C., Lockhart, P. J., Baptista, M., Kehoe, K., Vink, L., Choi, P., Wolozin, B., Farrer, M., Hardy, J., and Cookson, M. R. (2002). Parkin protects against the toxicity associated with mutant alpha-synuclein: proteasome dysfunction selectively affects catecholaminergic neurons. Neuron 36, 1007-1019.

Phillips, R. G., and LeDoux, J. E. (1992). Differential contribution of amygdala and hippocampus to cued and contextual fear conditioning. Behav Neurosci 106, 274-285.

Puzzo, D., Vitolo, O., Trinchese, F., Jacob, J. P., Palmeri, A., and Arancio, O. (2005). Amyloid-beta peptide inhibits activation of the nitric oxide/cGMP/cAMP-responsive element-binding protein pathway during hippocampal synaptic plasticity. J Neurosci 25, 6887-6897.

Qiu, L., Joazeiro, C., Fang, N., Wang, H.Y., Elly, C., Altman, Y., Fang, D., Hunter, T., and Liu, Y. C. (2000). Recognition and ubiquitination of Notch by Itch, a hect-type E3 ubiquitin ligase. J Biol Chem 275, 35734-35737.

Reinheckel, T., Sitte, N., Ullrich, O., Kuckelkorn, U., Davies, K. J., and Grune, T. (1998). Comparative resistance of the 20S and 26S proteasome to oxidative stress. Biochem J 335 (Pt 3), 637-642.

Saigoh, K., Wang, Y. L., Suh, J. G., Yamanishi, T., Sakai, Y., Kiyosawa, H., Harada, T., Ichihara, N., Wakana, S., Kikuchi, T., and Wada, K. (1999). Intragenic deletion in the gene encoding ubiquitin carboxy-terminal hydrolase in gad mice. Nat Genet 23, 47-51.

Schwarze, S. R., Ho, A., Vocero-Akbani, A., and Dowdy, S. F. (1999). In vivo protein transduction: delivery of a biologically active protein into the mouse. Science 285, 1569-1572.

Selkoe, D. J. (2002). Alzheimer's disease is a synaptic failure. Science 298, 789-791.

Snyder, J. S., Hong, N. S., McDonald, R. J., and Wojtowicz, J. M. (2005). A role for adult neurogenesis in spatial long-term memory. Neuroscience 130, 843-852.

Stine, W. B., Jr., Dahlgren, K. N., Krafft, G. A., and LaDu, M. J. (2003). In vitro characterization of conditions for amyloid-beta peptide oligomerization and fibrillogenesis. J Biol Chem 278, 11612-11622.

Tanaka, K. (1998). Proteasomes: structure and biology. J Biochem (Tokyo) 123, 195-204.

Trinchese, F., Liu, S., Battaglia, F., Walter, S., Mathews, P. M., and Arancio, O. (2004). Progressive age-related development of Alzheimer-like pathology in APP/PS1 mice. Ann Neurol 55, 801-814.

Trommer, B. L., Shah, C., Yun, S. H., Gamkrelidze, G., Pasternak, E. S., Blaine Stine, W., Manelli, A., Sullivan, P., Pasternak, J. F., and LaDu, M. J. (2005). ApoE isoform-specific effects on LTP: blockade by oligomeric amyloid-beta1-42. Neurobiol Dis 18, 75-82.

Tully, T., Bourtchouladze, R., Scott, R., and Tallman, J. (2003). Targeting the CREB pathway for memory enhancers. Nat Rev Drug Discov 2, 267-277.

van Leeuwen, F. W., de Kleijn, D. P., van den Hurk, H. H., Neubauer, A., Sonnemans, M. A., Sluijs, J. A., Koycu, S., Ramdjielal, R. D., Salehi, A., Martens, G. J., et al. (1998). Frameshift mutants of beta amyloid precursor protein and ubiquitin-B in Alzheimer's and Down patients. Science 279, 242-247.

van Leeuwen, F. W., Fischer, D. F., Benne, R., and Hol, E. M. (2000). Molecular misreading. A new type of transcript mutation in gerontology. Ann N Y Acad Sci 908, 267-281.

Vitolo, O. V., Sant'Angelo, A., Costanzo, V., Battaglia, F., Arancio, O., and Shelanski, M. (2002). Amyloid beta-peptide inhibition of the PKA/CREB pathway and long-term potentiation: reversibility by drugs that enhance cAMP signaling. Proc Natl Acad Sci USA 99, 13217-13221.

Wada, K., Osaka, H., Aoki, S., and Wang, Y. L. (2001). [The ubiquitin-proteasome system and neurodegeneration]. Rinsho Shinkeigaku 41, 1072-1074.

Wada, H., Kito, K., Caskey, L. S., Yeh, E. T., and Kamitani, T. (1998). Cleavage of the C-terminus of NEDD8 by UCH-L3. Biochem Biophys Res Commun 251, 688-692.

Wadia, J. S., and Dowdy, S. F. (2002). Protein transduction technology. Curr Opin Biotechnol 13, 52-56.

Wadia, J. S., and Dowdy, S. F. (2003). Modulation of cellular function by TAT mediated transduction of full length proteins. Curr Protein Pept Sci 4, 97-104.

Wadia, J. S., Stan, R. V., and Dowdy, S. F. (2004). Transducible TAT-HA fusogenic peptide enhances escape of TAT-fusion proteins after lipid raft macropinocytosis. Nat Med 10, 310-315.

Walsh, D. M., Klyubin, I., Fadeeva, J. V., Cullen, W. K., Anwyl, R., Wolfe, M. S., Rowan, M. J., and Selkoe, D. J. (2002). Naturally secreted oligomers of amyloid beta protein potently inhibit hippocampal long-term potentiation in vivo. Nature 416, 535-539.

Wang, Q., Walsh, D. M., Rowan, M. J., Selkoe, D. J., and Anwyl, R. (2004). Block of long-term potentiation by naturally secreted and synthetic amyloid beta-peptide in hippocampal slices is mediated via activation of the kinases c-Jun N-terminal kinase, cyclin-dependent kinase 5, and p38 mitogen-activated protein kinase as well as metabotropic glutamate receptor type 5. J Neurosci 24, 3370-3378.

Wilkinson, K. D. (2000). Ubiquitination and deubiquitination: targeting of proteins for degradation by the proteasome. Semin Cell Dev Biol 11, 141-148.

Wilkinson, K. D., Lee, K. M., Deshpande, S., Duerksen-Hughes, P., Boss, J. M., and Pohl, J. (1989). The neuron-specific protein PGP 9.5 is a ubiquitin carboxyl-terminal hydrolase. Science 246, 670-673.

Wood, M. A., Kaplan, M. P., Brensinger, C. M., Guo, W., and Abel, T. (2005). Ubiquitin C-terminal hydrolase L3 (Uchl3) is involved in working memory. Hippocampus 15, 610-621.

---

What is claimed is:

1. A composition comprising a peptide having hydrolase activity, wherein the peptide consists of consecutive amino acids of SEQ ID NO:2 starting at an amino acid from amino acid 53 to 90 of SEQ ID NO:2 and terminating at an amino acid from amino acid 161 to 196 of SEQ ID NO:2.

2. A composition comprising a peptide having hydrolase activity, wherein the peptide consists of consecutive amino acids of SEQ ID NO:2 starting at amino acid 73 of SEQ ID NO:2 and terminating at amino acid 176 of SEQ ID NO:2.

3. The composition of claim 1 or 2, wherein the peptide is linked to a carrier.

4. The composition of claim 3, wherein the carrier comprises a peptide transduction signal, a non-protein molecule, or any combination thereof.

5. The composition of claim 4, wherein the peptide transduction signal comprises an HIV-transactivator protein (TAT) domain, a penetratin 1 protein, a penetratin 1 protein transducing domain, an HSV VP22 protein, or a VP22 protein transducing domain.

6. The composition of claim 2, wherein the peptide is linked to a carrier.

7. The composition of claim 6, wherein the carrier comprises a peptide transduction signal, a non-protein molecule, or any combination thereof.

8. The composition of claim 7, wherein the peptide transduction signal comprises an HIV-transactivator protein (TAT) domain, a penetratin 1 protein, a penetratin 1 protein transducing domain, an HSV VP22 protein, or a VP22 protein transducing domain.

* * * * *